US008124610B2

(12) United States Patent
Fulp et al.

(10) Patent No.: US 8,124,610 B2
(45) Date of Patent: Feb. 28, 2012

(54) SODIUM CHANNEL INHIBITORS

(75) Inventors: Alan Bradley Fulp, Williow Spring, NC (US); Matthew Scott Johnson, Durham, NC (US); Christopher John Markworth, Durham, NC (US); Brian Edward Marron, Durham, NC (US); Darrick Conway Seconi, Cary, NC (US); Christopher William West, Cary, NC (US); Xiaodong Wang, Chapel Hill, NC (US); Shulan Zhou, Chapel Hill, NC (US)

(73) Assignee: Icagen Inc., Durham, NC (US)

( * ) Notice: Subject to any disclaimer, the term of this patent is extended or adjusted under 35 U.S.C. 154(b) by 602 days.

(21) Appl. No.: 12/173,012

(22) Filed: Jul. 14, 2008

(65) Prior Publication Data
US 2009/0023740 A1    Jan. 22, 2009

Related U.S. Application Data

(60) Provisional application No. 60/949,745, filed on Jul. 13, 2007, provisional application No. 60/954,980, filed on Aug. 9, 2007.

(51) Int. Cl.
*C07D 409/12* (2006.01)
*A61K 31/44* (2006.01)

(52) U.S. Cl. ........ 514/275; 514/342; 514/370; 544/322; 546/270.7; 548/197

(58) Field of Classification Search .......... None
See application file for complete search history.

(56) References Cited

U.S. PATENT DOCUMENTS

| | | | |
|---|---|---|---|
| 6,172,085 B1 | 1/2001 | Ohkawa et al. | |
| 2006/0079543 A1 * | 4/2006 | Sum et al. | 514/275 |
| 2009/0163545 A1 | 6/2009 | Goldfarb | |

FOREIGN PATENT DOCUMENTS

| | | | |
|---|---|---|---|
| WO | WO 9609294 A1 * | 3/1996 | |
| WO | WO 2005/013914 A2 | 2/2005 | |
| WO | WO 2005/013914 A3 | 2/2005 | |
| WO | WO 2005/026129 A1 | 3/2005 | |
| WO | WO 2006/042638 A1 | 4/2006 | |
| WO | 2009/012242 A2 | 1/2009 | |

OTHER PUBLICATIONS

Phillips et al, Journal of the Chemical Society (1941) 9-15.*
El-Gaby et al, Journal of the Chinese Chemical Society, (2004), 51(2), 327-333.*
West, Anthony R., Solid State Chemistry and its Applications, Wiley, New York, 1988, pp. 358 & 365.*
El-Mouafi, Bulletin of the Faculty of Pharmacy (Cairo University) (1974), 13(1), pp. 111-115.*
Abdel-Monem, W.R., "Synthesis and biological evaluations of sulfa derivatives bearing heterocyclic moieties," *Bolletino Chimico Framaceutico*, 2004, vol. 142, No. 6, pp. 239-247.
Database Chemcats, Chemical Abstracts, CAS Registry No. RN: 914217-53-1, Nov. 20, 2007, 2 pages.
El-Basil, S. et al., "Synthesis of Certain $N^1$- and $N^4$-(5-Nitro-2-pyridiyl)-Substituted Sulfonamides," *Journal of Pharmaceutical Sciences*, Jul. 1969, vol. 58, No. 7, pp. 907-909.
International Search Report mailed on Jan. 7, 2009, for International Patent Application No. PCT/US2008/070019, filed on Jul. 14, 2008, 5 pages.
Maggiolo, A. et al., "Synthesis of 2-Methyl-4-amino-6-substiuted Aminopyrimidines," *Journal of the American Chemical Society*, 1951, vol. 73, pp. 106-107.
Saved, G.H. et al., "Synthesis and Reactions of 4-(p-BromophenyI)-4-Oxo-2-(4-Antipyriny1)-Butanoic Acid and Some Unexpected Products," *Egyptian Journal of Chemistry*, 2000, vol. 43, No. 1, pp. 17-29.

* cited by examiner

*Primary Examiner* — Zinna Northington Davis
(74) *Attorney, Agent, or Firm* — Gregg C. Benson; Richard V. Zanzalari

(57) ABSTRACT

Compounds, compositions and methods are provided which are useful in the treatment of diseases through the inhibition of sodium ion flux through voltage-gated sodium channels. More particularly, the invention provides substituted sulfonamides, compositions comprising these compounds, as well as methods of using these compounds or compositions in the treatment of central or peripheral nervous system disorders, particularly pain and chronic pain by blocking sodium channels associated with the onset or recurrence of the indicated conditions. The compounds, compositions and methods of the present invention are of particular use for treating neuropathic or inflammatory pain by the inhibition of ion flux through a voltage-gated sodium channel.

47 Claims, No Drawings

SODIUM CHANNEL INHIBITORS

CROSS-REFERENCES TO RELATED APPLICATIONS

This application claims priority to U.S. Provisional Patent Application No. 60/949,745 filed Jul. 13, 2007 and U.S. Provisional Patent Application No. 60/954,980 filed Aug. 9, 2007, which applications are incorporated herein by reference in its entirety and for all purposes.

BACKGROUND OF THE INVENTION

Voltage-gated sodium channels are found in all excitable cells including myocytes of muscle and neurons of the central and peripheral nervous system. In neuronal cells sodium channels are primarily responsible for generating the rapid upstroke of the action potential. In this manner sodium channels are essential to the initiation and propagation of electrical signals in the nervous system. Proper and appropriate function of sodium channels is therefore necessary for normal function of the neuron. Consequently, aberrant sodium channel function is thought to underlie a variety of medical disorders (See Hubner C A, Jentsch T J, *Hum. Mol. Genet.*, 11(20): 2435-45 (2002) for a general review of inherited ion channel disorders) including epilepsy (Yogeeswari et al., *Curr. Drug Targets*, 5(7): 589-602 (2004)), arrhythmia (Noble D., *Proc. Natl. Acad. Sci. USA*, 99(9): 5755-6 (2002)) myotonia (Cannon, S C, *Kidney Int.* 57(3): 772-9 (2000)), and pain (Wood, J N et al., *J. Neurobiol.*, 61(1): 55-71 (2004)). See Table I, below.

Human genetic variants of these channels have not been associated with any inherited clinical disorder. However, aberrant expression of $Na_V1.8$ has been found in the CNS of human multiple sclerosis (MS) patients and also in a rodent model of MS (Black, J A, et al., *Proc. Natl. Acad. Sci. USA*, 97(21): 11598-602 (2000)). Evidence for involvement in nociception is both associative (preferential expression in nociceptive neurons) and direct (genetic knockout). $Na_V1.8$-null mice exhibited typical nociceptive behavior in response to acute noxious stimulation but had significant deficits in referred pain and hyperalgesia (Laird J M, et al., *J. Neurosci.*, 22(19): 8352-6 (2002)).

The TTX-sensitive subset of voltage-gated sodium channels is expressed in a broader range of tissues than the TTX-resistant channels and has been associated with a variety of human disorders. The $Na_V1.1$ channel well exemplifies this general pattern, as it is expressed in both the central and peripheral nervous system and has been associated with several seizure disorders including Generalized Epilepsy with Febrile Seizures Plus, types 1 and 2 (GEFS+1, GEFS+2), Severe Myoclonic Epilepsy of Infancy (SMEI), and others (Claes, L, et al., *Am. J. Hum. Genet.*, 68:1327-1332 (2001); Escayg, A., *Am. J. Hum. Genet.*, 68: 866-873 (2001); Lossin, C, *Neuron*, 34: 877-884 (2002)). The $Na_V1.2$ channel is largely, if not exclusively, expressed in the central nervous system and quantitative studies indicate it is the most abundant VGSC of the CNS. Mutations of $Na_V1.2$ are also associated with seizure disorders (Berkovic, S. F., et al., *Ann. Neurol.*, 55: 550-557 (2004)) and $Na_V1.2$-null "knockout" mice exhibit perinatal lethality (Planells-Cases R et al., *Bio-*

TABLE I

| Type | Gene Symbol | Primary tissue | TTX IC-50 | Disease association | Indications |
|---|---|---|---|---|---|
| $Na_V1.1$ | SCN1A | CNS/PNS | 10 | Epilepsy | Pain, seizures, neurodegeneration |
| $Na_V1.2$ | SCN2A | CNS | 10 | Epilepsy | Epilepsy, neurodegeneration |
| $Na_V1.3$ | SCN3A | CNS | 15 | — | Pain |
| $Na_V1.4$ | SCN4A | Sk. muscle | 25 | Myotonia | Myotonia |
| $Na_V1.5$ | SCN5A | Heart | 2000 | Arrhythmia | Arrhythmia |
| $Na_V1.6$ | SCN8A | CNS/PNS | 6 | — | Pain, movement disorders |
| $Na_V1.7$ | SCN9A | PNS | 25 | Erythermalgia | Pain |
| $Na_V1.8$ | SCN10A | PNS | 50000 | — | Pain |
| $Na_V1.9$ | SCN11A | PNS | 1000 | — | Pain |

There are currently 9 known members of the family of voltage-gated sodium channel (VGSC) alpha subunits. Names for this family include SCNx, SCNAx, and $Na_x$x.x. The VGSC family has been phylogenetically divided into two subfamilies $Na_V1.x$ (all but SCN6A) and $Na_V2.x$ (SCN6A). The $Na_V1.x$ subfamily can be functionally subdivided into two groups, those which are sensitive to blocking by tetrodotoxin (TTX-sensitive or TTX-s) and those which are resistant to blocking by tetrodotoxin (TTX-resistant or TTX-r).

There are three members of the subgroup of TTX-resistant sodium channels. The SCN5A gene product ($Na_V1.5$, H1) is almost exclusively expressed in cardiac tissue and has been shown to underlie a variety of cardiac arrhythmias and conduction disorders (Liu H, et al., *Am. J. Pharmacogenomics*, 3(3): 173-9 (2003)). Consequently, blockers of $Na_V1.5$ have found clinical utility in treatment of such disorders (Srivatsa U, et al., *Curr. Cardiol. Rep.*, 4(5): 401-10 (2002)). The remaining TTX-resistant sodium channels, $Na_V1.8$ (SCN10A, PN3, SNS) and $Na_V1.9$ (SCN11A, NaN, SNS2) are expressed in the peripheral nervous system and show preferential expression in primary nociceptive neurons.

*phys. J.*, 78(6):2878-91 (2000)). Expression of the $Na_V1.4$ gene is largely restricted to skeletal muscle and, accordingly, mutations of this gene are associated with a variety of movement disorders (Ptacek, L. J., *Am. J. Hum. Genet.*, 49: 851-854 (1991); Hudson A J, *Brain*, 118(2): 547-63 (1995)). The majority of these disorders are related to hyperactivity or "gain-of-function" and have been found to respond to treatment with sodium channel blockers (Desaphy J F, et al., *J. Physiol.*, 554(2): 321-34 (2004)).

Neither the SCN3A nor the SCN8A VGSC genes have been conclusively linked to heritable disorders in humans. Loss-of-function mutations of the SCN8A gene are known in mice and yield increasingly debilitating phenotypes, dependent upon the remaining functionality of the gene products (Meisler M H, *Genetica*, 122(1): 37-45 (2004)). Homozygous null mutations cause progressive motor neuron failure leading to paralysis and death, while heterozygous null animals are asymptomatic. Homozygous $med^J$ mice have nearly 90% reduction in functional $Na_V1.6$ current and exhibit dystonia and muscle weakness but are still viable. Evidence for $Na_V1.6$ being important for nociception is largely associative as $Na_V1.6$ is expressed at high levels in dorsal root ganglia and can be found in spinal sensory tracts (Tzoumaka E, *J. Neurosci. Res.*, 60(1): 37-44 (2000)). It should be noted however that expression of $Na_V1.6$ is not restricted to sensory neurons of the periphery. Like the $Na_V1.6$ channel, expression of the $Na_V1.3$ VGSC can also be detected in both the central and peripheral nervous system, though levels in the adult CNS are generally much higher than PNS. During development and the early postnatal period $Na_V1.3$ is expressed in peripheral neurons but this expression wanes as the animal matures (Shah B S, *Physiol.*, 534(3): 763-76 (2001); Schaller K L, *Cerebellum*, 2(1): 2-9 (2003)). Following neuronal insult $Na_V1.3$ expression is upregulated, more closely mimicking the developmental expression patterns (Hains B C, *J. Neurosci.*, 23(26): 8881-92 (2003)). Coincident with the recurrence of $Na_V1.3$ expression is the emergence of a rapidly re-priming sodium current in the injured axons with a biophysical profile similar to $Na_V1.3$ (Leffler A, et al., *J. Neurophysiol.*, 88(2): 650-8 (2002)). Treatment of injured axons with high levels of GDNF has been shown to diminish the rapidly repriming sodium current and reverses thermal and mechanical pain-related behaviors in a rat model of nerve injury, presumably by down-regulating the expression of $Na_V1.3$ (Boucher T J, *Curr. Opin. Pharmacol.*, 1(1): 66-72 (2001)). Specific down-regulation of $Na_V1.3$ via treatment with antisense oligonucle-otides has also been shown to reverse pain-related behaviors following spinal cord injury (Hains B C, *J. Neurosci.*, 23(26): 8881-92 (2003)).

The $Na_V1.7$ (PN1, SCN9A) VGSC is sensitive to blocking by tetrodotoxin and is preferentially expressed in peripheral sympathetic and sensory neurons. The SCN9A gene has been cloned from a number of species, including human, rat, and rabbit and shows ~90% amino acid identity between the human and rat genes (Toledo-Aral et al., *Proc. Natl. Acad. Sci. USA*, 94(4): 1527-1532 (1997)).

An increasing body of evidence suggests that $Na_V1.7$ may play a key role in various pain states, including acute, inflammatory and/or neuropathic pain. Deletion of the SCN9A gene in nociceptive neurons of mice led to a reduction in mechanical and thermal pain thresholds and reduction or abolition of inflammatory pain responses (Nassar et al., *Proc Natl Acad Sci USA*, 101(34): 12706-11 (2004)). In humans, $Na_V1.7$ protein has been shown to accumulate in neuromas, particularly painful neuromas (Kretschmer et al., *Acta. Neurochir. (Wien)*, 144(8): 803-10 (2002)). Mutations of $Na_V1.7$, both familial and sporadic, have also been linked to primary erythermalgia, a disease characterized by burning pain and inflammation of the extremities (Yang et al., *J. Med. Genet.*, 41(3): 171-4 (2004)). Congruent with this observation is the report that the non-selective sodium channel blockers lidocaine and mexiletine can provide symptomatic relief in cases of familial erythermalgia (Legroux-Crepel et al., *Ann. Dermatol Venereol.*, 130: 429-433).

Sodium channel-blocking agents have been reported to be effective in the treatment of various disease states, and have found particular use as local anesthetics and in the treatment of cardiac arrhythmias. It has also been reported that sodium channel-blocking agents may be useful in the treatment of pain, including acute, chronic, inflammatory and/or neuropathic pain; see, for example, Wood, J N et al., *J. Neurobiol.*, 61(1): 55-71 (2004). Preclinical evidence demonstrates that sodium channel-blocking agents can suppress neuronal firing in peripheral and central sensory neurons, and it is via this mechanism that they may be useful for relieving pain. In some instances abnormal or ectopic firing can originate from injured or otherwise sensitized neurons. For example, it has been shown that sodium channels can accumulate in peripheral nerves at sites of axonal injury and may function as generators of ectopic firing (Devor et al. *J. Neurosci.*, 132: 1976 (1993)). Changes in sodium channel expression and excitability have also been shown in animal models of inflammatory pain where treatment with proinflammatory materials (CFA, Carrageenan) promoted pain-related behaviors and correlated with increased expression of sodium channel subunits (Gould et al., *Brain Res.*, 824(2): 296-9 (1999); Black et al., *Pain*, 108(3): 237-47 (2004)). Alterations in either the level of expression or distribution of sodium channels, therefore, may have a major influence on neuronal excitability and pain-related behaviors.

Many patients with either acute or chronic pain disorders respond poorly to current pain therapies and resistance or insensitivity to opiates is common. In addition, many of the currently available treatments have undesirable side effects. It has been reported that there is no treatment to prevent the development of neuropathic pain or to control established neuropathic pain. Mannion et al., *Lancet*, 353: 1959-1964 (1999).

Ohkawa et al. have described a class of cyclic ethers that are of use as sodium channel blockers (U.S. Pat. No. 6,172, 085).

Currently, gabapentin is the principal treatment for neuropathic pain. As with epilepsy, its mechanism of action for pain is unknown. However, as little as only 30% of patients respond to gabapentin treatment for neuropathic pain.

In view of the limited number of agents presently available and the low levels of efficacy of the available agents, there is a pressing need for compounds that are potent, specific inhibitors of ion channels implicated in neuropathic pain. The present invention provides such compounds, methods of using them, and compositions that include the compounds.

SUMMARY OF THE INVENTION

The present invention relates to the use of certain compounds as sodium channel blockers and to the treatment of pain by the inhibition of sodium channels. Additionally, this invention relates to novel compounds that are useful as sodium channel blockers.

It has now been discovered that various substituted aryl sulfonamides are potent modulators of sodium channels. In the discussion that follows, the invention is exemplified by reference to the inhibition of sodium channels that are localized in the peripheral nervous system, and in particular those compounds that are selective inhibitors of TTX-s sodium channels, and are useful for treating pain through the inhibition of sodium ion flux through channels that include a TTX-s sodium channel subunit. The compounds, compositions and methods of the present invention are useful for treating diseases in which modulating one or more TTX-s sodium channels provides relief from the disease. Of particular interest is the use of the compounds, compositions and methods of the invention for treating pain and central or peripheral nervous system disorders, preferably peripheral nervous system disorders. The present invention is of use for treating acute, chronic, inflammatory, and/or neuropathic pain.

The present invention provides compounds that are useful in the treatment of diseases through the modulation of sodium ion flux through voltage-dependent sodium channels. More particularly, the invention provides compounds, compositions and methods that are useful in ameliorating or alleviating conditions susceptible to such ion channel modulation as more fully described below.

In one aspect, the present invention provides compounds of Formula (I):

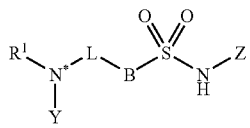

(I)

or pharmaceutical acceptable salts or solvates thereof, wherein Y is a member selected from substituted or unsubstituted five or six-membered heteroaryl and substituted or unsubstituted aryl; $R^1$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; with the proviso that Y, N* and $R^1$ can be optionally joined to form a member selected from a 5 to 8 membered substituted or unsubstituted heteroaryl or heterocycloalkyl moiety; B is a member selected from substituted or unsubstituted cycloalkyl, substituted or unsubstituted heterocycloalkyl, substituted or unsubstituted aryl and substituted or unsubstituted heteroaryl and fused combinations thereof wherein if B is a fused ring system, one of said fused rings optionally contains N* or is substituted by N*; L is a member selected from a bond and a ring system that optionally contains N* or is substituted by N*; Z is a member selected from substituted or unsubstituted five or six-member heteroaryl. In one embodiment, L is a bond.

In one group of embodiments, the present invention provides compounds having Formula (II):

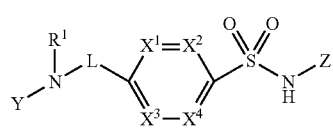

(II)

or pharmaceutical acceptable salts or solvates thereof, wherein Z is 5-membered heteroaryl having from 1 to 4 heteroatoms as ring members selected from N, O or S or 6-membered heteroaryl having from 1 to 3 nitrogen heteroatoms as ring members; Y is 5-membered heteroaryl having from 1 to 4 heteroatoms as ring members selected from N, O or S, 6-membered heteroaryl having from 1 to 3 nitrogen heteroatoms as ring members, or aryl optionally fused with a 5-membered heteroaryl having 1 to 2 heteroatoms as ring members selected from O, N or S; or Y and $X^1$ are taken together to form a 5-membered fused heteroaryl ring having from 0-2 additional nitrogen atoms as ring members and $R^1$ is a lone pair, wherein the fused heteroaryl ring is optionally substituted with a $R^b$ group;
wherein the heteroaryl and aryl of Y and Z substituents are each optionally substituted with from 1 to 3 $R^a$ substituents, at each occurrence, each $R^a$ is independently selected from the group consisting of $C_{1-8}$alkyl-NH—, $(C_{1-8}$alkyl$)_2$N—, aryl, $R^b$, $C_{1-8}$haloalkyl, aryl-$C_{3-8}$cycloalkyl, $C_{3-8}$cycloalkyl, heterocycloalkyl, arylsulfonyl, arylsulfinyl and $R^f$, wherein $R^b$ is $C_{1-8}$alkyl optionally substituted with from 1-3 members independently selected from the group consisting of aryl, aryl-(CO)—, aryloxy, $(R^c)(R^d)$N—, $C_{3-5}$cycloalkyl, hetero-$C_{4-5}$cycloalkyl, arylthio and heteroaryl; wherein $R^c$ is —H or $C_{1-6}$alkyl and $R^d$ is $C_{3-7}$cycloalkyl or $C_{1-8}$alkyl optionally substituted with from 1-2 aryl groups, or optionally $R^c$ and $R^d$ together with the nitrogen atom to which they are attached form a 5 or 6-membered ring having 0-2 additional heteroatoms as ring members selected from N, O or S; wherein the aryl portion of each $R^a$ substituent is further optionally substituted with from 1-3 substituents independently selected from the group consisting of $C_{1-4}$haloalkyl, $C_{1-4}$haloalkoxy and $R^f$, and the heterocycloalkyl of the $R^b$ group is further optionally substituted with a hetero-$C_{4-5}$cycloalkyl-$C_{1-6}$alkyl; or any two adjacent $R^a$ substituents together with the atoms to which they are attached form a 5- or 6-membered carbocyclic ring, wherein 1-2 ring carbon atoms of the carbocyclic ring are optionally replaced by a carbonyl and the carbocyclic ring is optionally substituted with 1-2 members independently selected from an halogen, aryl or $C_{1-8}$alkyl; wherein $R^f$ is halogen, —OH, —$OR^g$, —$OC(O)O$—$R^g$, —$OC(O)R^g$, —$OC(O)NHR^g$, —$OC(O)N(R^g)_2$, —SH, —$SR^g$, —$S(O)R^g$, —$S(O)_2R^g$, —$SO_2NH_2$, —$S(O)_2NHR^g$, —$S(O)_2N(R^g)_2$, —$NHS(O)_2R^g$, —$NR^gS(O)_2R^g$, —$C(O)NH_2$, —$C(O)NHR^g$, —$C(O)N(R^g)_2$, —$C(O)R^g$, —$C(O)H$, —$C(=S)R^g$, —$NHC(O)R^g$, —$NR^gC(O)R^g$, —$NHC(O)NH_2$, —$NR^gC(O)NH_2$, —$NR^gC(O)NHR^g$, —$NHC(O)NHR^g$, —$NR^gC(O)N(R^g)_2$, —$NHC(O)N(R^g)_2$, —$CO_2H$, —$CO_2R^g$, —$NHCO_2R^g$, —$NR^gCO_2R^g$, —CN, —$NO_2$, —$NH_2$, —$NR^gS(O)NH_2$, —$NR^gS(O)NHR^g$, —$NHC(=NR^g)NH_2$, —$N=C(NH_2)NH_2$, —$C(=NR^g)NH_2$, —NH—OH, —$NR^g$—OH, —$NR^g$—$OR^g$, —N=C=O and —N=C=S; wherein each $R^g$ is independently a $C_{1-8}$alkyl; $X^1$, $X^2$, $X^3$ and $X^4$ are each independently —N=, or $C(R^2)$=, wherein $R^2$ is selected from the group consisting of —H, halogen, $C_{1-8}$alkyl, —CN, —OH, $C_{1-6}$haloalkyl and $C_{1-6}$haloalkoxy; or any two adjacent $R^2$ substituents together with the atoms to which they are attached form a fused benzene ring, optionally substituted with a $C_{1-6}$alkyl, with the proviso that not more than three of $X^1$, $X^2$, $X^3$ and $X^4$ are —N=;
L is a bond or i) L, the aromatic carbon atom to which L is attached, and $X^1$ taken together form a fused 5- or 6-membered carbocyclic ring, wherein 1-2 ring carbon atoms of the fused carbocyclic ring are optionally replaced with —C(O)— or —S(O)$_2$— group; or ii) L, the two atoms to which L is attached, and $X^1$ taken together form a 5- or 6-membered fused heterocyclic ring having from 0-2 additional heteroatoms selected from N, O or S, wherein 1-2 ring carbon atoms of the fused heterocyclic ring are optionally replaced with —C(O)— or —S(O)$_2$— group; and $R^1$ is —H, a lone pair or $C_{1-8}$alkyl, with the proviso that the compound is other than 4-(4-methylphthalazin-1-ylamino)-N-(thiazol-2-yl)benzenesulfonamide; 4-(4-(4-chlorophenyl)phthalazin-1-ylamino)-N-(thiazol-2-yl)benzenesulfonamide; N-(thiazol-2-yl)-4-(4-p-tolylphthalazin-1-ylamino) benzenesulfonamide; and 4-(4-phenylphthalazin-1-ylamino)-N-(thiazol-2-yl)benzenesulfonamide, with the proviso the compounds are other than 4-(4-methylphthalazin-1-ylamino)-N-(thiazol-2-yl)benzenesulfonamide; 4-(4-(4-chlorophenyl)phthalazin-1-ylamino)-N-(thiazol-2-yl)benzenesulfonamide; N-(thiazol-2-yl)-4-(4-p-tolylphthalazin-1-ylamino)benzenesulfonamide; and 4-(4-phenylphthalazin-1-ylamino)-N-(thiazol-2-yl)benzenesulfonamide. In Formula (II), at each occurrence, alkyl by itself or as part of another substituent, is an unsubstituted, fully saturated, straight or branched chain hydrocarbon radical; at each occurrence, cycloalkyl by itself or as part of another substituent is an unsubstituted, fully saturated, cyclic hydrocarbon radical; and at each occurrence, aryl by itself or as part of another substituent is a monovalent monocyclic, bicyclic or polycyclic polyunsaturated aromatic hydrocarbon radical.

In another aspect, the present invention provides a method of modulating the activity of a sodium channel in a subject. The method includes administering to a subject an amount of a compound according to the formulas described herein sufficient to modulate the activity.

In yet another aspect, the present invention provides a method of ameliorating or alleviating a condition in a subject. The method includes administering to the subject an amount of a compound according to the formulas described herein sufficient to ameliorate or alleviate the condition.

Additional aspects, advantages and objects of the present invention will be apparent from the detailed description that follows.

DETAILED DESCRIPTION OF THE INVENTION

Abbreviations

The abbreviations used herein generally have their conventional meaning within the chemical and biological arts. For example: CHO, Chinese hamster ovary; EBSS, Earl's Balanced Salt Solution; SDS, sodium dodecyl sulfate; $Et_3N$, triethylamine; MeOH, methanol; and DMSO, dimethylsulfoxide.

Definitions

The term "pain" refers to all categories of pain, including pain that is described in terms of stimulus or nerve response, e.g., somatic pain (normal nerve response to a noxious stimulus) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic neuropathy (see, e.g., Harrison's Principles of Internal Medicine, pp. 93-98 (Wilson et al., eds., 12th ed. 1991); Williams et al., *J. of Med. Chem.* 42: 1481-1485 (1999), herein each incorporated by reference in their entirety).

"Somatic" pain, as described above, refers to a normal nerve response to a noxious stimulus such as injury or illness, e.g., trauma, burn, infection, inflammation, or disease process such as cancer, and includes both cutaneous pain (e.g., skin, muscle or joint derived) and visceral pain (e.g., organ derived).

"Neuropathic" pain, as described above, refers to pain resulting from injury to or chronic changes in peripheral and/or central sensory pathways, where the pain often occurs or persists without an obvious noxious input.

"Acute pain", as described above, refers to pain which is marked by short duration or a sudden onset.

"Chronic pain", as described above, refers to pain which is marked by long duration or frequent recurrence.

"Inflammatory pain", as described above, refers to pain which is produced as a symptom or a result of inflammation or an immune system disorder.

"Visceral pain", as described above, refers to pain which is located in an internal organ.

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

"Lone pair" as used herein refers to a pair of electrons on the heteroatoms not involved in bond formation. Exemplary lone pair includes a nitrogen lone pair.

"Compound of the invention," as used herein refers to the compounds discussed herein, pharmaceutically acceptable salts, solvates and prodrugs of these compounds.

"Inhibiting" and "blocking," are used interchangeably herein to refer to the partial or full blockade of a voltage sodium gated channel by a compound of the invention, which leads to a decrease in ion flux either into or out of a cell in which a voltage-gated sodium channel is found.

Where substituent groups are specified by their conventional chemical formulae, written from left to right, they equally encompass the chemically identical substituents, which would result from writing the structure from right to left, e.g., —$CH_2O$— is preferably intended to also recite —$OCH_2$—.

The term "alkyl," by itself or as part of another substituent, means, unless otherwise stated, a straight- or branched-chain, or cyclic hydrocarbon radical, or combination thereof, which may be fully saturated, mono- or polyunsaturated and can include mono-, di- and multivalent radicals, having the number of carbon atoms designated (i.e. $C_{1-10}$ or $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, also preferably include those derivatives of alkyl defined in more detail below, such as "heteroalkyl." Alkyl groups that are limited to hydrocarbon groups are termed "homoalkyl". The term "alkyl", as used herein refers to alkyl, alkenyl and alkynyl moieties, each of which can be mono-, di- or polyvalent species. Alkyl groups are preferably substituted, e.g., with one or more group referred to herein below as an "alkyl group substituent." In one embodiment, alkyl includes a straight or branched chain fully saturated aliphatic hydrocarbon radicals having the number of carbon atoms designated. For example, $C_{1-8}$alkyl refers to a hydrocarbon radical straight or branched having 1, 2, 3, 4, 5, 6, 7 or 8 carbon atoms and includes, but are not limited to, $C_{1-2}$alkyl, $C_{1-4}$alkyl, $C_{2-6}$alkyl, $C_{2-4}$alkyl, $C_{1-6}$alkyl, $C_{2-8}$alkyl, $C_{1-7}$alkyl, $C_{2-7}$alkyl and $C_{3-8}$ alkyl.

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight- or branched-chain, or cyclic alkyl radical consisting of the stated number of carbon atoms and at least one heteroatom selected from the group consisting of B, O, N, Si and S, wherein the heteroatom may optionally be oxidized and the nitrogen atom may optionally be quaternized. The heteroatom(s) may be placed at any internal position of the heteroalkyl group or at a terminus of the chain, e.g., the position through which the alkyl group is attached to the remainder of the molecule. Examples of "heteroalkyl" groups include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Two or more heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent refers to a substituted or unsubstituted divalent heteroalkyl radical, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents —C(O)$_2$R'— and, preferably, —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Preferably, "cycloalkyl" refers to hydrocarbon rings having the indicated number of ring atoms (e.g., $C_{3-6}$ cycloalkyl) and being fully saturated or having no more than one double bond between ring vertices. One or two C atoms may optionally be replaced by a carbonyl. "Cycloalkyl" is also meant to refer to bicyclic and polycyclic hydrocarbon rings such as, for example, bicyclo[2.2.1]heptane, bicyclo[2.2.2]octane, etc. The term "heterocycloalkyl" refers to a cycloalkyl group that contain from one to five heteroatoms selected from N, O, and S, wherein the nitrogen and sulfur atoms are optionally oxidized, and the nitrogen atom(s) are optionally quaternized, the remaining ring atoms being C, where one or two C atoms may optionally be replaced by a carbonyl. The heterocycloalkyl may be a monocyclic, a bicyclic or a polycylic ring system of 3 to 12, preferably 5 to 8, ring atoms in which one to five ring atoms are heteroatoms. The heterocycloalkyl can also be a heterocyclic alkyl ring fused with an aryl or a heteroaryl ring. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, pyrrolidinyl, piperidinyl, imidazolidinyl, pyrazolidinyl, butyrolactam radical, valerolactam radical, imidazolidinone radical, hydantoin, dioxolane radical, phthalimide radical, piperidine, 1,4-dioxane radical, morpholinyl, thiomorpholinyl, thiomorpholinyl-5-oxide, thiomorpholinyl-S, S-oxide, piperazinyl, pyranyl, pyridine radical, 3-pyrrolinyl, thiopyranyl, pyrone radical, tetrahydrofuranyl, tetrahydrothiophenyl, quinuclidinyl, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" or "$C_{1-8}$haloalkyl" is mean to include, but not be limited to, trifluoromethyl, 2,2,2-trifluoroethyl, 4-chlorobutyl, 3-bromopropyl, and the like. The term "haloalkoxy" refers to an alkoxy radical substituted with one or more halogen atoms. $C_{1-4}$haloalkoxy is meant to include $CF_3O$—, $CF_3(CH_2)_3O$—, $Cl(CH_2)_4O$—, and the like.

The term "aryl" means, unless otherwise stated, a polyunsaturated, aromatic, substituent that can be a single ring or multiple rings (preferably from 1 to 3 rings, one or more of which is optionally a cycloalkyl or heterocycloalkyl), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of "aryl group substituents" described below.

For brevity, the term "aryl" when used in combination with other terms (e.g., aryloxy, arylthioxy, arylalkyl) preferably includes both homoaryl and heteroaryl rings as defined above. Thus, the term "arylalkyl" optionally includes those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR'", —NR—C(NR'R")=NR'", —S(O)R', —S(O)$_2$R', —S(O)$_2$NR'R", —$NRSO_2$R', —CN and —$NO_2$ in a number ranging from zero to (2m'+1), where m' is the total number of carbon atoms in such radical. R', R", R'" and R'''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" includes groups with carbon atoms bound to groups other than hydrogen, such as haloalkyl (e.g., —$CF_3$ and —$CH_2CF_3$) and acyl (e.g., —$C(O)CH_3$, —$C(O)CF_3$, —$C(O)CH_2OCH_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R"' and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R"' and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer from 0 to 3. Alternatively, two of the substituents on adjacent atoms of the aryl or heteroaryl ring may optionally be replaced with a substituent of the formula -A-($CH_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R"')$_d$—, where s and d are independently integers of from 0 to 3, and X is —O—, —NR'—, —S—, —S(O)—, —S(O)$_2$—, or —S(O)$_2$NR'—. The substituents R, R', R" and R"' are preferably independently selected from hydrogen or substituted or unsubstituted ($C_1$-$C_6$)alkyl.

As used herein, the term "heteroatom" includes oxygen (O), nitrogen (N), sulfur (S) and silicon (Si).

The term "arylsulfonyl" means a radical —$SO_2$R, where R is an aryl as defined above, e.g. phenylsulfonyl and the like.

The term "arylsulfinyl" means a radical —S(=O)R, where R is an aryl as defined above, e.g., phenylsulfinyl and the like. The term "arylthio" means a radical —SR, where R is an aryl as defined above, e.g., phenylthio and the like.

The term "heterocycloalkylalkyl" means a radical —R'R, where R' is an alkyl and R is a heterocycloalkyl as defined above. Exemplary heterocycloalkylalkyl includes pyrrolidinyl, piperidinyl, imidazolidinyl, pyrazolidinyl, and the like.

The term "arylcycloalkyl" means a radical —R'R, where R' is a cycloalkyl and R is a aryl as defined above. Exemplary arylcycloalkyl includes 2-phenylcyclopropyl, 1-phenylcyclopentyl, 1-phenylcyclohexyl, 1-phenylcyclopropyl, and the like.

The term "carbocyclic ring" means a saturated, unsaturated or partially saturated, mono-, bicyclic or polycyclic ring (preferably 1-3 rings), which contains only carbon ring atoms (preferably 3-14 ring carbon atoms). The carbocyclic ring can be non-aromatic or aromatic ring. Exemplary carbocyclic rings include cyclopentane ring, cyclohexane ring, benzene ring, naphthalene ring, and the like.

"Tautomer" refers to alternate forms of a molecule that differ in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. Where the compound contains, for example, a keto or oxime group or an aromatic moiety, tautomeric isomerism ('tautomerism') can occur. It follows that a single compound may exhibit more than one type of isomerism. A person of ordinary skill in the art would recognize that other tautomeric ring atom arrangements are possible.

The term "salt(s)" includes salts of the compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, butyric, maleic, malic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts.

When the compound prepared by a method of the invention is a pharmacological agent, the salt is preferably a pharmaceutically acceptable salt. Examples of pharmaceutically acceptable salts are presented hereinabove, and are generally known in the art. See, for example, Wermuth, C., PHARMACEUTICAL SALTS: PROPERTIES, SELECTION AND USE—A HANDBOOK, Verlag Helvetica Chimica Acta (2002)

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds that are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

As used herein, and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include compounds that comprise NO, $NO_2$, —ONO, or —$ONO_2$ moieties. The term "prodrug" is accorded a meaning herein such that prodrugs do not encompass the parent compound of the prodrug. When used to describe a compound of the invention, the term "prodrug" may also to be interpreted to exclude other compounds of the invention.

As used herein, and unless otherwise indicated, the terms "biohydrolyzable carbamate," "biohydrolyzable carbonate," "biohydrolyzable ureide" and "biohydrolyzable phosphate" mean a carbamate, carbonate, ureide and phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, and unless otherwise indicated, the term "biohydrolyzable ester" means an ester of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, alkoxyacyloxy esters, alkyl acylamino alkyl esters, and choline esters.

As used herein, and unless otherwise indicated, the term "biohydrolyzable amide" means an amide of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable amides include, but are not limited to, lower alkyl amides, alpha.-amino acid amides, alkoxyacyl amides, and alkylaminoalkylcarbonyl amides.

Certain compounds of the present invention can exist in unsolvated forms as well as solvated forms, including hydrated forms. "Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention. These isomers can be resolved or asymmetrically synthesized using conventional methods to render the isomers "optically pure", i.e., substantially free of its other isomers. If, for instance, a particular enantiomer of a compound of the present invention is desired, it may be prepared by asymmetric synthesis, or by derivation with a chrial auxilliary, where the resulting diastereomeric mixture is separated and the auxilliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diasteromers thus formed by fractional crystallization or chromatographic means well known in the art, and subsequent recovery of the pure enantiomers.

As used herein, and unless otherwise indicated, a composition that is "substantially free" of a compound means that the composition contains less than about 20% by weight, more preferably less than about 10% by weight, even more preferably less than about 5% by weight, and most preferably less than about 3% by weight of the compound.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

Description of the Embodiments

I. The Compounds

In one aspect, the present invention provides compounds of Formula (I):

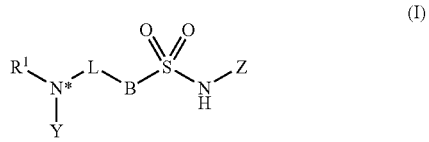

or pharmaceutical acceptable salts or solvates thereof, wherein Y is a member selected from substituted or unsubstituted five or six-membered heteroaryl and substituted or unsubstituted aryl; $R^1$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; with the proviso that Y, N* and $R^1$ can be optionally joined to form a member selected from a 5 to 8 membered substituted or unsubstituted heteroaryl or heterocycloalkyl moiety; B is a member selected from substituted or unsubstituted cycloalkyl, substituted or unsubstituted heterocycloalkyl, substituted or unsubstituted aryl and substituted or unsubstituted heteroaryl and fused combinations thereof wherein if B is a fused ring system, one of said fused rings optionally contains N* or is substituted by N*; L is a member selected from a bond and a ring system that optionally contains N* or is substituted by N*; Z is a member selected from substituted or unsubstituted five or six-member heteroaryl. In one group of embodiments, L is a bond.

In one group of embodiments, the present invention provides compounds having the formula selected from the group consisting of:

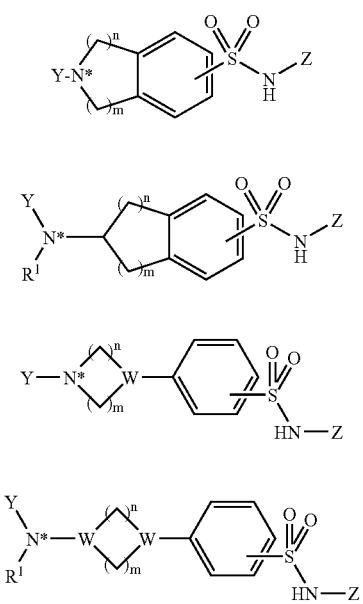

wherein Y is a member selected from substituted or unsubstituted five or six-member heteroaryl and substituted or unsubstituted aryl; Z is a member selected from substituted or unsubstituted five or six-member heteroaryl; W is a member selected from C, substituted carbon and nitrogen; n is an integer selected from 0, 1, 2, 3, 4 and 5; and m is an integer selected from 0, 1, 2, 3, 4 and 5.

In a group of embodiments, the present invention provides compounds of Formula (IA):

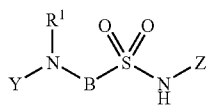

or pharmaceutical acceptable salts thereof, wherein Y is a member selected from substituted or unsubstituted five or six-member heteroaryl; $R^1$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; B is a member selected from substituted or unsubstituted cycloalkyl, substituted or unsubstituted heterocycloalkyl, substituted or unsubstituted aryl and substituted or unsubstituted heteroaryl and fused combinations thereof; wherein if B is a fused ring system, one of said fused rings optionally contains N. In one group embodiments of compounds having Formulas (I) or (IA), Z is substituted or unsubstituted thiazoyl. In certain instances, the moiety through which Y and $R^1$ are covalently attached to the N* is not a carbonyl or an ester moiety. In some instances, Y is 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, or 6-quinolyl. In other instances, Z is 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, or 6-quinolyl. In yet other instances, B is 1-naphthyl, 2-naphthyl, 4-biphenyl.

In a group of embodiments of compounds having Formulas (I) or (IA), Z is substituted or unsubstituted thiazoyl.

In one group of embodiments of compounds of Formulas (I) or (IA), B is a divalent radical member derived from substituted or unsubstituted phenyl, halogen-substituted phenyl, substituted or unsubstituted 2-pyridinyl, substituted or unsubstituted 3-pyridinyl, substituted or unsubstituted pyrimidinyl, substituted or unsubstituted naphthyl, substituted or unsubstituted 2,3-dihydro-1H-indene, substituted or unsubstituted indolin-2-one, substituted or unsubstituted 2,3-dihydro-1H-inden-1-one, substituted or unsubstituted isoindolin-1-one, substituted or unsubstituted 3-sulfonyl isoindolin-1-one, substituted or unsubstituted 1,2,3,4-tetrahydroisoquinoline and substituted or unsubstituted 2,3-dihydroisoquinolin-4(1H)-one.

In another group of embodiments of compounds having Formula (I) or (IA), B is a member selected from

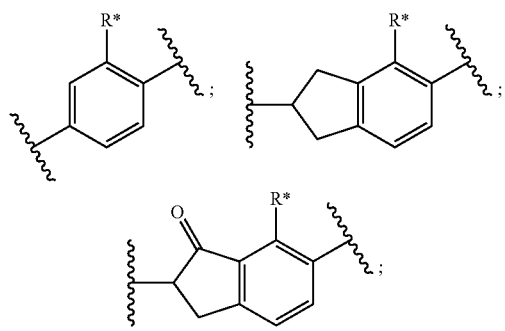

wherein R* is a member selected from OR, SR, NRR, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl, wherein each R** is a member selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl.

In yet another group of embodiments of compounds having Formula (I) or (IA), B is a member selected from the group consisting of:

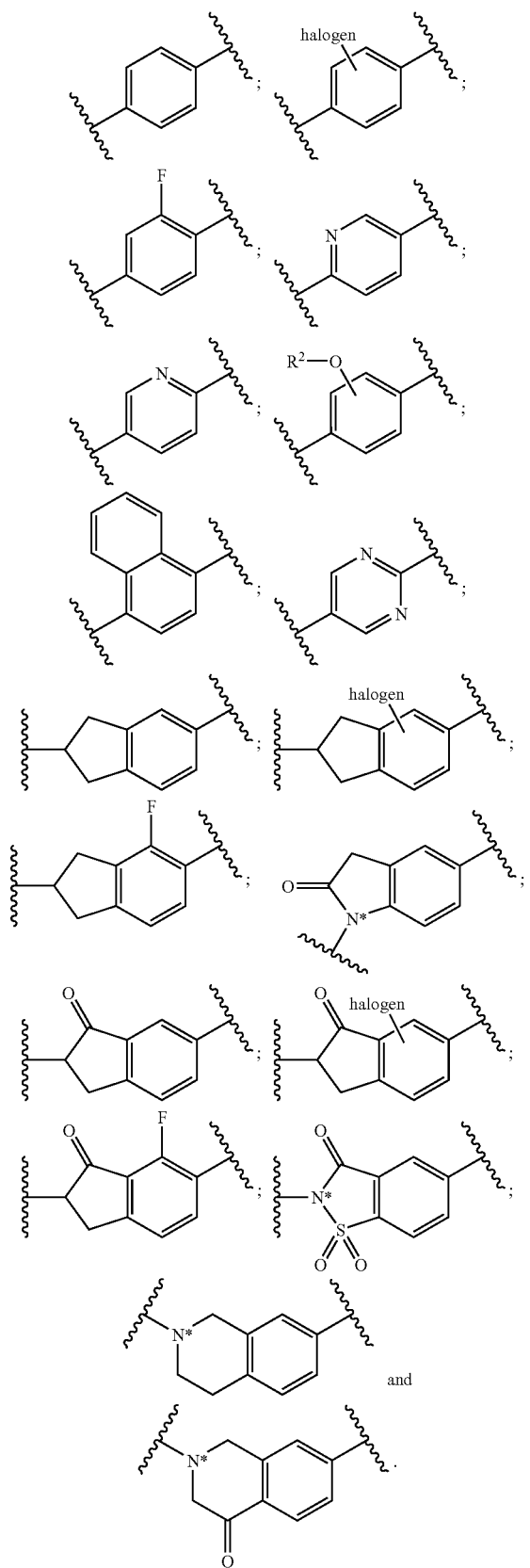

In certain instances, B is a member selected from the group consisting of:

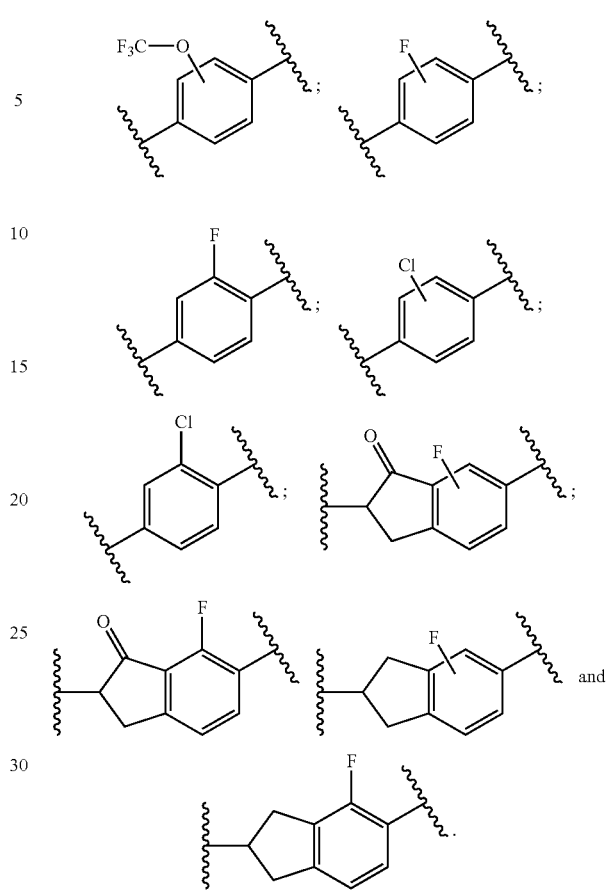

In one group of embodiments of compounds having Formula (I) or (IA), Y is a member selected from substituted or unsubstituted thiazoyl, substituted or unsubstituted pyrimidine, substituted or unsubstituted oxazolyl, substituted or unsubstituted isoxazolyl, substituted or unsubstituted imidazolyl, substituted or unsubstituted pyrazolyl, substituted or unsubstituted triazolyl, substituted or unsubstituted azathiazoyl and substituted or unsubstituted azaisoxazolyl. In certain instances, Y is substituted with at least one member selected from:

$C(CH_3)_3$, methyl, $C(O)CH_3$, $NH_2$, $C(O)NH_2$, cyclopropyl

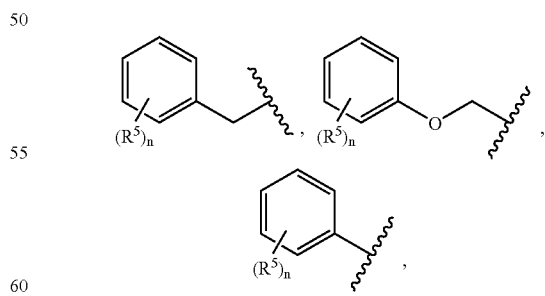

wherein $R^5$ is a member selected from halogen, $C(CH_3)_3$, $OCH_3$, $S(O)(O)CH_3$, —CN, $CF_3$ and cyclopropyl; n is a member selected from 0 to 5. In other instances, Y is substituted with at least one member selected from the group consisting of:

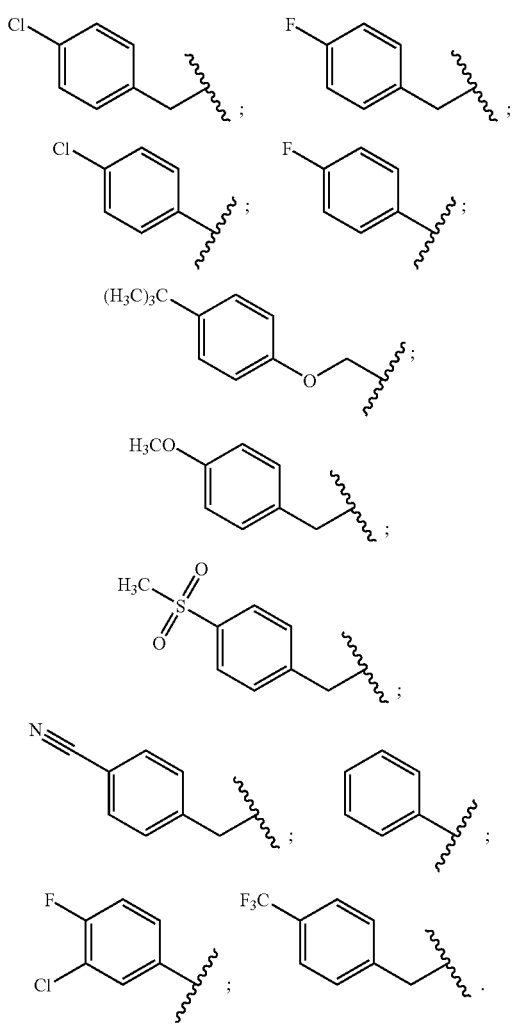
In yet other instances, Y is a member selected from:
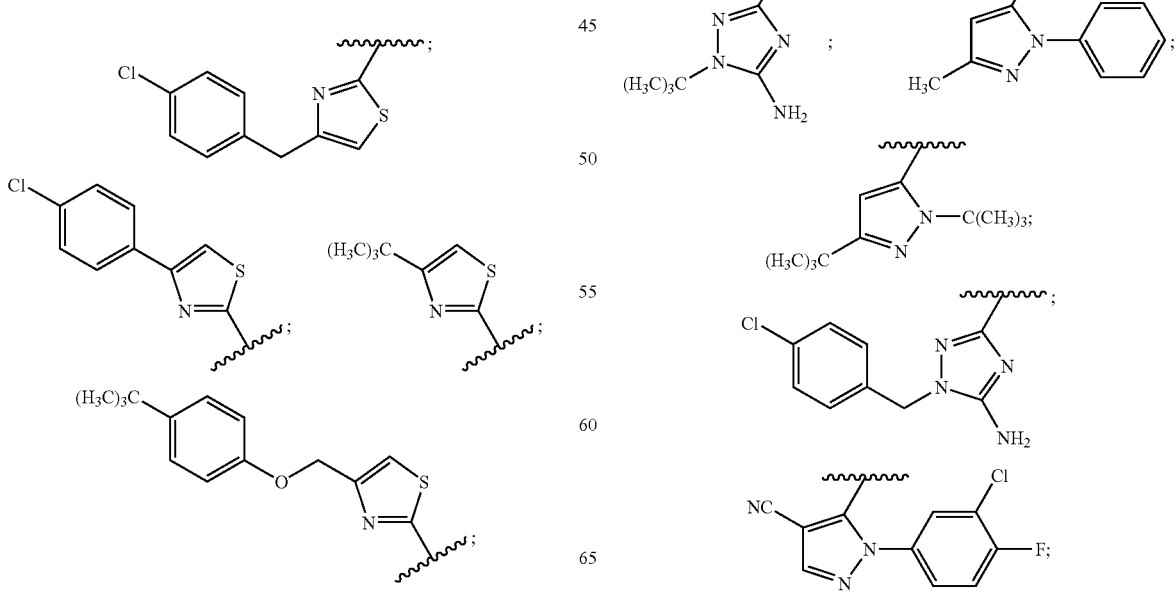
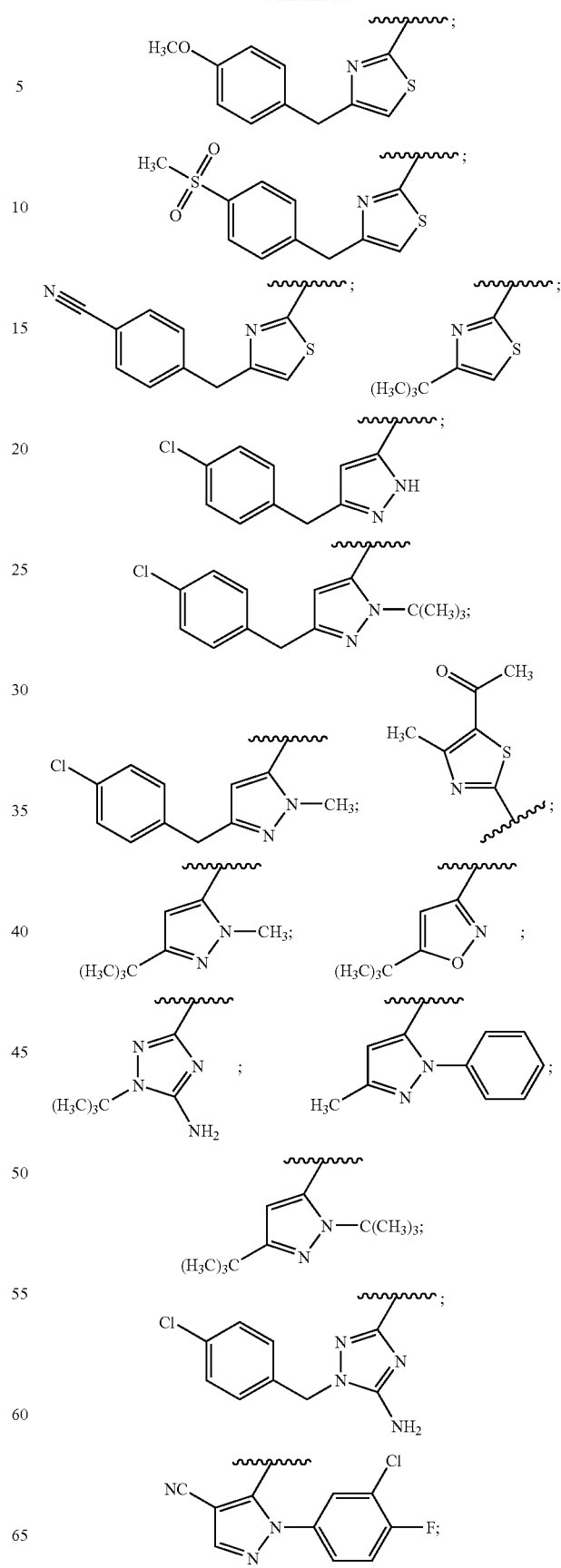

-continued

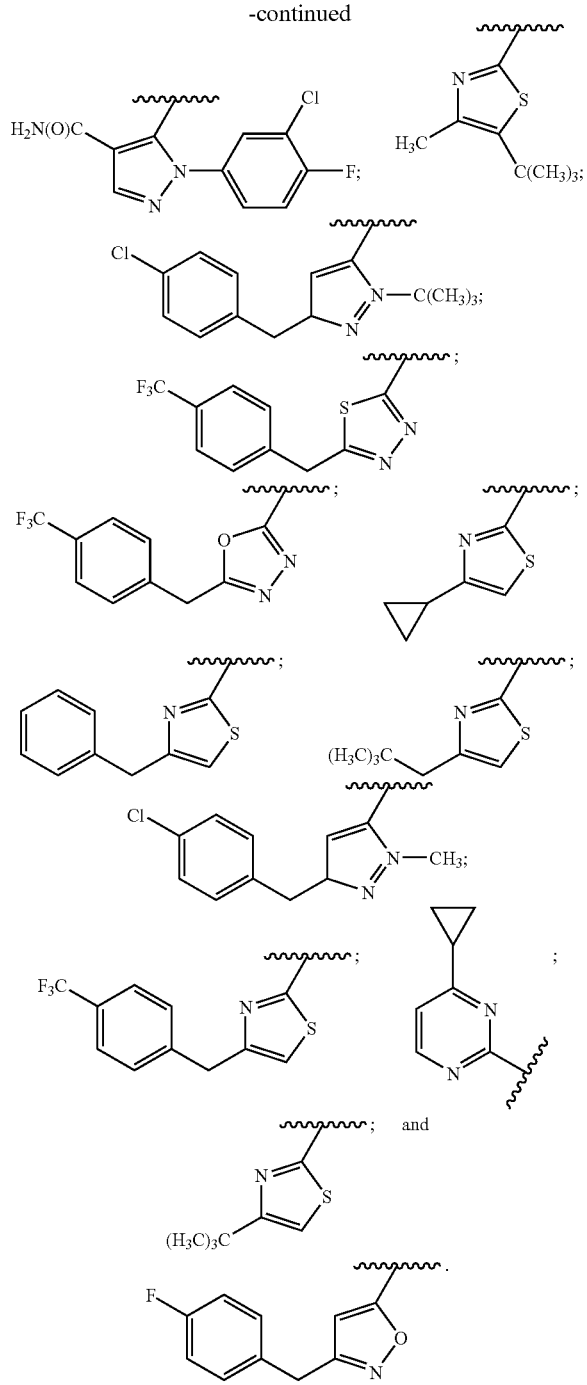

In some embodiments, $R^1$ is —H, —$CH_2C(O)NH_2$ and —$CH_3$.

In one group of embodiments, the present invention provides compounds having Formula (II):

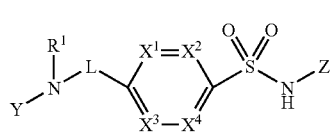

or pharmaceutically acceptable salts or solvates thereof.

Z is 5-membered heteroaryl having from 1 to 4 heteroatoms as ring members selected from N, O or S or 6-membered heteroaryl having from 1 to 3 nitrogen heteroatoms as ring members; Y is 5-membered heteroaryl having from 1 to 4 heteroatoms as ring members selected from N, O or S, 6-membered heteroaryl having from 1 to 3 nitrogen heteroatoms as ring members, or aryl optionally fused with a 5-membered heteroaryl having 1 to 2 heteroatoms as ring members selected from O, N or S; or Y and $X^1$ taken together to form a 5-membered fused heteroaryl ring having from 0-2 additional nitrogen atoms as ring members, wherein the fused heteroaryl ring is optionally substituted with a $R^b$ group; wherein the heteroaryl and aryl of Y and Z substituents are each optionally substituted with from 1 to 3 $R^a$ substituents, at each occurrence, each $R^a$ is independently selected from the group consisting of $C_{1-8}$alkyl-NH—, $(C_{1-8}$alkyl$)_2$N—, aryl, $R^b$, $C_{1-8}$haloalkyl, aryl-$C_{3-8}$cycloalkyl, $C_{3-8}$cycloalkyl, heterocycloalkyl, arylsulfonyl, arylsulfinyl and $R^f$, wherein $R^b$ is $C_{1-8}$alkyl optionally substituted with from 1-3 members independently selected from the group consisting of aryl, aryl-(CO)—, aryloxy, $(R^c)(R^d)$N—, $C_{3-5}$cycloalkyl, hetero-$C_{4-5}$cycloalkyl, arylthio and heteroaryl; wherein $R^c$ is —H or $C_{1-6}$alkyl and $R^d$ is $C_{3-7}$cycloalkyl or $C_{1-8}$alkyl optionally substituted with from 1-2 aryl groups, or optionally $R^c$ and $R^d$ together with the nitrogen atom to which they are attached form a 5 or 6-membered ring having 0-2 additional heteroatoms as ring members selected from N, O or S; wherein the aryl portion of each $R^a$ substituent is further optionally substituted with from 1-3 substituents independently selected from the group consisting of $C_{1-4}$haloalkyl, $C_{1-4}$haloalkoxy and $R^f$, and the heterocycloalkyl of the $R^b$ group is further optionally substituted with a hetero-$C_{4-5}$cycloalkyl-$C_{1-6}$alkyl; or any two adjacent $R^a$ substituents together with the atoms to which they are attached form a 5- or 6-membered carbocyclic ring, wherein 1-2 ring carbon atoms of the carbocyclic ring are optionally replaced by a carbonyl and the carbocyclic ring is optionally substituted with 1-2 members independently selected from an halogen, aryl or $C_{1-8}$alkyl; wherein $R^f$ is halogen, —OH, —$OR^g$, —OC(O)O—$R^g$, —OC(O)$R^g$, —OC(O)NH$R^g$, —OC(O)N($R^g$)$_2$, —SH, —S$R^g$, —S(O)$R^g$, —S(O)$_2R^g$, —SO$_2$NH$_2$, —S(O)$_2$NH$R^g$, —S(O)$_2$N($R^g$)$_2$, —NHS(O)$_2R^g$, —N$R^g$S(O)$_2R^g$, —C(O)NH$_2$, —C(O)NH$R^g$, —C(O)N($R^g$)$_2$, —C(O)$R^g$, —C(O)H, —C(=S)$R^g$, —NHC(O)$R^g$, —N$R^g$C(O)$R^g$, —NHC(O)NH$_2$, —N$R^g$C(O)NH$_2$, —N$R^g$C(O)NH$R^g$, —NHC(O)NH$R^g$, —N$R^g$C(O)N($R^g$)$_2$, —NHC(O)N($R^g$)$_2$, —CO$_2$H, —CO$_2R^g$, —NHCO$_2R^g$, —N$R^g$CO$_2R^g$, —CN, —NO$_2$, —NH$_2$, —N$R^g$S(O)NH$_2$, —N$R^g$S(O)$_2$NH$R^g$, —NHC(=N$R^g$)NH$_2$, —N=C(NH$_2$)NH$_2$, —C(=N$R^g$)NH$_2$, —NH—OH, —N$R^g$—OH, —N$R^g$—O$R^g$, —N=C=O and —N=C=S; wherein each $R^g$ is independently a $C_{1-8}$alkyl.

$X^1$, $X^2$, $X^3$ and $X^4$ are each independently —N=, or C($R^2$)=, wherein $R^2$ is selected from the group consisting of —H, halogen, $C_{1-8}$alkyl, —CN, $C_{1-6}$haloalkyl, —OH and $C_{1-6}$haloalkoxy; or any two adjacent $R^2$ substituents together with the atoms to which they are attached form a fused benzene ring, optionally substituted with a $C_{1-6}$alkyl, with the proviso that not more than three of $X^1$, $X^2$, $X^3$ and $X^4$ are —N=.

L is a bond or i) L, the aromatic carbon atom to which L is attached, and $X^1$ taken together form a fused 5- or 6-membered carbocyclic ring, wherein 1-2 ring carbon atoms of the fused carbocyclic ring are optionally replaced with —C(O)— or —S(O)$_2$— group; or ii) L, the two atoms to which L is attached, and $X^1$ taken together form a 5- or 6-membered fused heterocyclic ring having from 0-2 additional heteroatoms selected from N, O or S, wherein the fused heterocyclic ring is optionally substituted with a $R^b$ group and 1-2 ring carbon atoms of the fused heterocyclic ring are optionally replaced with —C(O)— or —S(O)$_2$— group.

$R^1$ is —H or $C_{1-8}$alkyl.

In Formula (II), at each occurrence, alkyl by itself or as part of another substituent, is an unsubstituted, fully saturated, straight or branched chain hydrocarbon radical; at each occurrence, cycloalkyl by itself or as part of another substituent is an unsubstituted, fully saturated, cyclic hydrocarbon radical; and at each occurrence, aryl by itself or as part or another substituent is a monovalent monocyclic, bicyclic or polycyclic polyunsaturated aromatic hydrocarbon radical of 5 to 16 ring atoms, which can be a single ring or multiple rings (up to three rings) which are fused together or linked covalently.

In a group of embodiments of the compounds having Formula (II), Z is: i) 5-membered heteroaryl having from 1-3 heteroatoms as ring members selected from N, O or S, wherein the heteroaryl is optionally substituted with from 1 to 2 substituents selected from the group consisting of $C_{1-8}$haloalkyl, —CN, halogen, $C_{3-7}$cycloalkyl, aryl, substituted and unsubstituted $C_{1-8}$alkyl, aryl-NH—$C_{1-6}$alkyl and $C_{1-8}$alkoxy-$C_{1-4}$alkyl; or ii) 6-membered heteroaryl having from 1-2 nitrogen atoms as ring members, wherein the heteroaryl is optionally substituted with 1-3 unsubstituted $C_{1-8}$alkyl;

$X^1, X^2, X^3$ and $X^4$ are each independently —N=, or C($R^2$)=, wherein $R^2$ is selected from the group consisting of —H, halogen, $C_{1-8}$alkyl, —CN, $C_{1-6}$haloalkyl and $C_{1-6}$haloalkoxy; or any two adjacent $R^2$ substituents together with the atoms to which they are attached form a fused benzene ring, optionally substituted with a $C_{1-6}$alkyl, with the proviso that not more than three of $X^1, X^2, X^3$ and $X^4$ are —N=. L is a bond or i) L, the aromatic carbon atom to which L is attached, and $X^1$ taken together form a fused 5- or 6-membered carbocyclic ring, wherein 1-2 ring carbon atoms of the fused carbocyclic ring are optionally replaced with —C(O)— or —S(O)$_2$— group; or ii) L, the two atoms to which L is attached, and $X^1$ taken together form a 5- or 6-membered fused heterocyclic ring having from 0-2 additional heteroatoms selected from N, or S, wherein 1-2 ring carbon atoms of the fused heterocyclic ring are optionally replaced with —C(O)— or —S(O)$_2$— group. Y is i) 5-membered heteroaryl having from 1-4 heteroatoms as ring members selected from N, O or S, wherein the heteroaryl is optionally substituted with 1-3 $R^a$ members, at each occurrence, each $R^a$ is independently selected from the group consisting of $C_{1-8}$alkyl-NH—, ($C_{1-8}$alkyl)$_2$N—, aryl, $R^b$, $C_{1-8}$haloalkyl, aryl-$C_{3-8}$cycloalkyl, $C_{3-5}$-cycloalkyl, heterocycloalkyl, arylsulfonyl, arylsulfinyl and $R^f$, wherein $R^b$ is $C_{1-8}$alkyl optionally substituted with from 1-3 members independently selected from the group consisting of aryl, aryloxy, ($R^c$)($R^d$)N—, $C_{3-5}$cycloalkyl, hetero-$C_{4-5}$cycloalkyl, arylthio and heteroaryl; wherein $R^c$ is —H or $C_{1-6}$alkyl and $R^d$ is $C_{3-7}$cycloalkyl or $C_{1-8}$alkyl optionally substituted with from 1-2 aryl groups; wherein the aryl portion of each $R^a$ substituent is further optionally substituted with from 1-3 substituents independently selected from the group consisting of $C_{1-4}$haloalkyl, $C_{1-4}$haloalkoxy and $R^f$, and the heterocycloalkyl of the $R^b$ group is further optionally substituted with a hetero-$C_{4-5}$cycloalkyl-$C_{1-6}$alkyl; or any two adjacent $R^a$ substituents together with the atoms to which they are attached form a 5- or 6-membered carbocyclic ring, wherein 1-2 ring carbon atoms of the carbocyclic ring are optionally replaced by a carbonyl and the carbocyclic ring is optionally substituted with 1-2 members independently selected from an halogen, aryl or $C_{1-8}$alkyl; wherein $R^f$ is halogen, —OH, —OR$^g$, —OC(O)O—R$^g$, —OC(O)R$^g$, —OC(O)NHR$^g$, —OC(O)N(R$^g$)$_2$, —SH, —SR$^g$, —S(O)R$^g$, —S(O)$_2$R$^g$, —SO$_2$NH$_2$, —S(O)$_2$NHR$^g$, —S(O)$_2$N(R$^g$)$_2$, —NHS(O)$_2$R$^g$, —NR$^g$S(O)$_2$R$^g$, —C(O)NH$_2$, —C(O)NHR$^g$, —C(O)N(R$^g$)$_2$, —C(O)R$^g$, —C(O)H, —C(=S)R$^g$, —NHC(O)R$^g$, —NR$^g$C(O)R$^g$, —NHC(O)NH$_2$, —NR$^g$C(O)NH$_2$, —NR$^g$C(O)NHR$^g$, —NHC(O)NHR$^g$, —NR$^g$C(O)N(R$^g$)$_2$, —NHC(O)N(R$^g$)$_2$, —CO$_2$H, —CO$_2$R$^g$, —NHCO$_2$R$^g$, —NR$^g$CO$_2$R$^g$, —CN, —NO$_2$, —NH$_2$, —NR$^g$S(O)NH$_2$, —NR$^g$S(O)$_2$NHR$^g$, —NH$_2$C(=NR$^g$)NH$_2$, —N=C(NH$_2$)NH$_2$, —C(=NR$^g$)NH$_2$, —NH—OH, —NR$^g$—OH, —NR$^g$—OR$^g$, —N=C=O and —N=C=S; wherein each $R^g$ is independently a $C_{1-8}$alkyl; or ii) 6-member heteroaryl having from 1-3 nitrogen atoms as ring members, wherein the heteroaryl is optionally substituted with 1-3 $R^e$ substituents independently selected from the group consisting of —OH, aryl, aryl-$C_{1-6}$alkyl, aryl-$C_{1-6}$alkoxy, $C_{3-6}$cycloalkyl-$C_{1-6}$alkoxy and $C_{1-8}$alkoxy, wherein the aliphatic portion of the $R^e$ group is further optionally substituted with an aryl and the aromatic portion of the $R^e$ group is further optionally substituted with from 1-2 members independently selected from $C_{1-6}$haloalkyl, halogen or $C_{1-6}$alkyl; or any two adjacent $R^e$ substituents together with the atoms to which they are attached form a 6-membered fused benzene ring, optionally substituted with a halogen or $C_{1-6}$ alkyl; or iii) aryl optionally substituted with an aryl or $C_{1-6}$alkyl. $R^1$ is —H or $C_{1-6}$alkyl. In certain instances, L is a bond.

In one embodiment of the compounds having Formula (II), $R^1$ is —H. In another embodiment, $R^1$ is $C_{1-8}$alkyl. In yet another embodiment, $R^1$ is a lone pair.

In one group of embodiments of the compounds having Formula (II), Z is a 5-membered heteroaryl having from 1-3 heteroatoms as ring members independently selected from N, O or S, wherein the heteroaryl is optionally substituted with 1-3 substituents (1, 2, or 3) selected from the group consisting of $C_{1-8}$haloalkyl, —CN, halogen, $C_{3-7}$cycloalkyl, aryl, substituted or unsubstituted $C_{1-8}$alkyl, aryl-NH—$C_{1-6}$alkyl and $C_{1-8}$alkoxy-$C_{1-4}$alkyl. In certain instances, Z is selected from the group consisting of thiazolyl, isothiazolyl, isoxazoly, oxazolyl, 1,3,4-thiadiazoly, 1,2,3-thiadiazoly, 1,2,4-thiadiazoly, 1,3,4-oxadiazoly, 1,2,3-oxadiazoly, 1,2,4-oxadiazoly, 1,2,5-thiadiazolyl, pyrazolyl, 1,2,5-oxadiazolyl, 1,2,3,5-thiatriazolyl, 1,2,3,4-thiatriazolyl, 1,2,3,5-oxatriazolyl, 1,2,3,4-oxatriazolyl and imidazoly, each of which is optionally substituted with a member selected from the group consisting of $C_{1-8}$haloalkyl, —CN, halogen, $C_{3-7}$cycloalkyl, aryl, substituted and unsubstituted $C_{1-8}$alkyl, aryl-NH—$C_{1-6}$alkyl and $C_{1-8}$alkoxy-$C_{1-4}$alkyl. In other instances, Z is selected from the group consisting of thiazol-2-yl, 4-thiazolyl, 5-thiazolyl, isoxazol-3-yl, 2-oxazolyl, 1,3,4-thiadiazol-2yl, 1,2,3-thiadiazol-4-yl, 1,2,3-thiadiazol-5-yl, 1,2,4-thiazol-3-yl, 1,2,4-thiadiazol-5-yl, 1,3,4-oxadiazol-2yl, 1,2,5-thiadiazol-4-yl, pyrazolyl, 1,2,5-oxadiazol-4-yl, 1,2,3,5-thiatriazol-4-yl, 1,2,3,4-thiatriazol-5-yl, 1,2,3,5-oxatriazol-4-yl, 1,2,3,4-oxatriazol-5-yl and 2-imidazolyl, each of which is optionally substituted with a member selected from the group consisting of $C_{1-8}$haloalkyl, —CN, halogen, $C_{3-7}$cycloalkyl, aryl, substituted and unsubstituted $C_{1-8}$alkyl, aryl-NH—$C_{1-6}$alkyl and $C_{1-8}$alkoxy-$C_{1-4}$alkyl. In yet other instances, Z is substituted with a member selected from the group consisting of 3-chloropropyl, phenylaminomethyl, —CH$_3$, CH$_2$CH$_3$, —Cl, —CF$_3$, —CF$_2$H, CH$_3$OCH$_2$—, cyclopropyl, isopropyl and —CN. In still other instances, Z is thiazolyl, isothiazolyl, isoxazoly, oxazolyl, 1,3,4-thiadiazoly, 1,2,3-thiadiazoly, 1,2,4-thiadiazoly, 1,3,4-oxadiazoly, 1,2,3-oxadiazoly, 1,2,4-oxadiazoly, 1,2,5-thiadiazolyl, pyrazolyl, 1,2,5-oxadiazolyl, 1,2,3,5-thiatriazolyl, 1,2,3,4-thiatriazolyl, 1,2,3,5-oxatriazolyl, 1,2,3,4-oxatriazolyl and imidazoly, each of which is optionally substituted with a group as set forth in paragraphs [0043] and [0044].

In a second group of embodiments of the compounds having Formula (II), Z is 6-membered heteroaryl having from 1-2 nitrogen atoms as ring members, wherein the heteroaryl is optionally substituted with 1-3 $C_{1-8}$alkyl. In certain instances, Z is selected from the group consisting of pyridyl, pyridazinyl, primidinyl or pyrizinyl, each of which is optionally substituted with from 1-3 $C_{1-6}$alkyl or substituted with a group as set forth in paragraphs [0043] and [0044]. In one occurrence, Z is selected from the group consisting of 2-pyridyl, 3-pyridazinyl, 4-primidinyl and 2-pyrizinyl, each of which is optionally substituted with from 1-3 $C_{1-6}$alkyl. In one embodiment, the unsubstituted $C_{1-6}$alkyl is —$CH_3$, -Et, i-Pr, Butyl, pentyl or hexyl.

In one group of embodiments of the compounds having Formula (II), Y is selected from the group consisting of thiazolyl, pyrazolyl, isoxazolyl, imidazolyl, 1,2,4-triazolyl, 1,2,3-thiadiazolyl, 1,3,4-thiadiazolyl, 1,3,4-oxadiazolyl, 1,2,5-thiadiazol-4-yl, 1,2,5-oxadiazol-4-yl, 1,2,3,5-thiatriazol-4-yl, 1,2,3,4-thiatriazol-5-yl, 1,2,3,5-oxatriazol-4-yl, 1,2,3,4-oxatriazol-5-yl, benzimidazolyl, benzoxazolyl, benzthiazolyl, tetrahydrobenzothiazolyl and dihydrobenzothiazolone, each of which is optionally substituted with 1-3 $R^a$ members or substituted with a group as set forth in paragraphs [0043] and [0044]. In other instances, Y is selected from the group consisting of thiazolyl, pyrazolyl, isoxazolyl, imidazolyl, 1,2,4-triazolyl, 1,2,3-thiadiazolyl, 1,3,4-thiadiazolyl, 1,3,4-oxadiazolyl, benzimidazolyl, benzoxazolyl, benzthiazolyl, tetrahydrobenzothiazolyl and dihydrobenzothiazolone. The pyrozolyl can be pyrozol-1yl, pyrazol-3-yl, pyrazol-4-yl or pyrazol-4-yl. In some occurrences, Y is selected from the group consisting of thiazol-2-yl, pyrazol-3-yl, pyrazol-4-yl, pyrazol-4-yl, isoxazol-3-yl, 1,2,4-triazol-1yl, 1,2,4-triazol-3-yl, 1,3,4-thiadiazol-2-yl, 1,3,4-oxadiazol-2-yl, benzimidazol-2-yl, benzoxazol-2-yl, benzthiazol-2-yl, tetrahydrobenzothiazol-2-yl and dihydrobenzothiazol-2-yl-7-one, each of which is optionally substituted with 1-3 $R^a$ members. In certain instances, $R^a$ is selected from the group consisting of —CN, —$NO_2$, -Ph, $Ph_2CH$—, $PhOCH_2$—, $Ph_2CHCH_2$—, Ph-O$(CH_2)_3$—, cyclopentylethyl, 4-chlorophenoxymethyl, 2-phenylcyclopropyl, $Ph_2CHCH_2NHCH_2$—, $PhOCH_2CH_2NHCH_2$—, 2-(pyrrolidin-1-ylmethyl)pyrrolidin-1-yl, (S)-2-(pyrrolidin-1-ylmethyl)pyrrolidin-1-yl, $Ph_2NHCH_2$—, $Ph_2CHCH_2CH_2NHCH_2$—, 4-t-butyl-phenoxymethyl, PhO$(CH_3)CH$—, 1-(4-chlorophenyl)cyclopentyl, 4-chlorophenyl-$CH_2NHCH_2$—, 3,4-dimethoxyphenyl-$(CH_2)_2NHCH_2$—, $Ph(CH_2)_2N(CH_3)CH_2$—, $(CH_3CH_2)_2NCH_2$—, $Ph(CH_2)_4NHCH_2$—, $Ph_2CHN(CH_3)CH_2$—, 4-$CF_3$-Ph-$CH_2NHCH_2$—, 4-$NO_2$-Ph-$CH_2NHCH_2$—, 4-dimethylaminophenyl-$CH_2NHCH_2$—, 4-pyridyl-$CH_2CH_2N(CH_3)CH_2$—, 3,5-dimethoxyphenyl-$CH_2NH$—$CH_2$—, —$CH_3$, $CH_3OC(O)$—, 2,4-difluorobenzyl, 4-fluoro-Ph-$SCH_2$—, —$CF_3$, 4-trifluoromethylphenyl, 4-fluorophenylsulfinylmethyl, 4-chlorophenylsulfinylmethyl, 2-fluoro-4-trifluoromethylphenyl, 4-chlorobenzyl, 4-chlorophenoxypropyl, 2,4-dichlorophenoxymethyl, 2-methyl-4-chlorophenoxymethyl, 4-chlorophenoxy-$C(CH_3)_2$—, t-butoxyphenoxymethyl, 4-chlorophenyl, t-butyl, 4-methoxybenzyl, 4-methylsulfonylbenzyl, 4-cyanobenzyl, 4-chlorophenylsulfonyl, acetyl, —$NH_2$, 3-chloro-4-fluoro-phenyl, 4-trifluoromethylbenzyl, neopentyl, 4-methoxybenzyl, 2-methoxybenzyl, 1-(4-chlorophenyl)cyclopropyl, $CF_3CH_2$—, 4-pyridylmethyl, cyclohexylmethyl, cyclopropyl, isopropyl, 2-methylphenyl, 4-methylphenyl, 2-chlorophenyl, 3-chlorophenyl, 4-methylbenzyl, 2-fluoro-4-chlorobenzyl, cylopentyl, 2-fluorophenyl, cyclopropyl-$(CH_3)CH$—, 3-methylphenyl, 3-fluorophenyl, 4-fluorophenyl, 2-trifluoromethylphenyl, 2-chloro-4-fluorophenyl, 2-methyl-4-fluoro-phenyl, 2-trifluoromethyl-4-fluorophenyl, 2-methoxyphenyl, 2,6-dichlorophenyl, 2,6-difluororophenyl, 2,6-dimethylphenyl, 2,4-difluorobenzyl, 3-trifluoromethylphenyl, 1-methypiperidinyl, 2-chloro-4-fluorobenzyl, 2-chlorobenzyl, 3-fluoro-4-chlorobenzyl, benzyl, $(CH_3CH_2)_2NC(O)$—$CH_2$—, 4-fluorobenzyl, 3-chlorobenzyl, 2-methoxy-4-chlorobenzyl, 2-methoxyphenyl, 4-methoxybenzyl, 3-trifluoromethyl-4-chlorobenzyl, 2-methoxy-4-chlorobenzyl, 3-methoxyphenyl, 4-methoxybenzyl, 3-trifluormethyl-4-chlorobenzyl, 2-methoxy-5-trifluoromethoxybenzyl and $NH_2C(O)$—.

In another group of embodiments of the compounds having Formula (II), Y is selected from the group consisting of primidinyl, pyridazinyl, prazinyl, triazinyl and phthalazinyl, each of which is optionally substituted with from 1-3 $R^e$ substituents. In other instances, Y is selected from the group consisting of 2-primidinyl, 4-pyrimidinyl, pyridazinyl, 3-prazinyl, 1,2,4-triazin-3-yl and 1-phthalazinyl, each of which is optionally substituted with from 1-3 $R^e$ substituents. In one occurrence, $R^e$ is selected from the group consisting of 4-chlorophenyl, 4-methylphenyl, Ph-, benzyloxy, $Ph_2CHCH_2O$—, 4-trifluoromethylbenzyloxy, cyclohexylmethyloxy, methoxy, $Ph_2CH$—, —OH, and 3,5-difluorobenzyl.

In yet another group of embodiments of compounds having Formula (II), Y is an aryl, optionally substituted with an aryl or $C_{1-6}$alkyl. In certain instances, Y is an aryl, optionally substituted with phenyl or —$CH_3$. In other instances, Y is phenyl, optionally substituted with phenyl or —$CH_3$.

In still another group of embodiments of compounds having Formula (II), Y and $X^1$ taken together to form a 5-membered fused heteroaryl ring having from 0-2 additional nitrogen atoms as ring members, wherein the fused heteroaryl ring is optionally substituted with a R group. In certain instances, the fused heteroaryl ring is a pyrazolyl ring or a triazolyl ring, each of which is optionally substituted with a $R^b$. In some occurrences, $R^b$ is aryl-$C_{1-8}$alkyl or aryl-C(O)—$C_{1-8}$alkyl, the aryl moiety of the aryl-$C_{1-8}$alkyl and aryl-C(O)—$C_{1-8}$alkyl groups is optionally substituted with 1-2 members selected from $C_{1-4}$haloalkoxy, $C_{1-8}$alkoxy, $CF_3O$— or $CH_3O$—.

In one group of embodiments of the compounds having Formula (II), $X^1$, $X^2$, $X^3$ and $X^4$ are each independently —N=, —CH=, —C($C_{1-8}$alkyl)=, —C(CN)=, —(C(CF_3)=, —(C(OCF_3)=, =C(OH)— or —C(halo)=. In a first embodiment, $X^1$, $X^2$, $X^3$ and $X^4$ are =CH—. In a second embodiment, $X^1$ is —N=, and $X^2$, $X^3$ and $X^4$ are =CH—. In a third embodiment, $X^2$ is —N=, and $X^1$, $X^3$ and $X^4$ are =CH—. In a fourth embodiment, $X^1$ is =CF—, =CCl—, =C(OCF_3)—, =C(CH_3)—, =C(OH)— or —C(CH)= and $X^2$, $X^3$ and $X^4$ are =CH—. In a fifth embodiment, $X^2$ is =CF—, =CCl—, =C(OCF_3)—, =C(CN)—, =C(CF_3)—, =C(CH_3)—, =C(OH)— or —C(CH)= and $X^1$, $X^3$ and $X^4$ are =CH— or =C(CH_3)—. In a sixth embodiment, $X^2$ and $X^3$ are =CH—. In a seventh embodiment, $X^3$ and $X^4$ are =CH—. In an eighth embodiment, $X^2$, $X^3$ and $X^4$ are =CH—. In a ninth embodiment, $X^1$, $X^2$ and $X^3$ are =CH—. In a tenth embodiment, $X^2$ is =CF— and $X^3$ is =C(CH_3)—.

In a second group of embodiments of the compounds having Formula (II), $X^1$, $X^2$, $X^3$ and $X^4$ are each independently —N= or C($R^2$) and $R^2$ is selected from the group consisting of —H, halogen, $C_{1-8}$alkyl, —CN, —OH, $C_{1-6}$haloalkyl and $C_{1-6}$haloalkyoxy; or any two adjacent $R^2$ substituents together with the atoms to which they are attached form a fused benzene ring, optionally substituted with a $C_{1-6}$alkyl. In certain instances, $R^2$ is selected from the group consisting of —H, —Cl, —F, —$CF_3$, —$OCF_3$, —$CH_3$ and —CN. In other instances, two adjacent $R^2$ substituents together with the atoms to which they are attached form a fused benzene ring, optionally substituted with a halogen or $C_{1-6}$alkyl, such as a methyl. In one instance, the

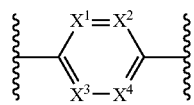

moiety is

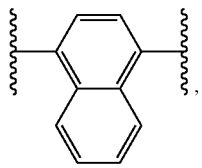

the wavy line represents the point of attachment to the rest of the molecule.

In one group of embodiments of the compounds having Formula (II), Z is 2-thiazolyl or 3-isoxazolyl, each of which is optionally substituted with a member selected from the group consisting of $C_{1-8}$haloalkyl, —CN, halogen, $C_{3-7}$cycloalkyl, aryl, unsubstituted $C_{1-8}$alkyl, aryl-NH—$C_{1-6}$alkyl and $C_{1-8}$alkoxy-$C_{1-4}$alkyl; and Y is 3-pyrazolyl, 4-pyrazolyl, 5-pyrazolyl, 2-thiazolyl, imidazoly or 1,2,4-triazol-3-yl, each of which is optionally substituted with from 1-3 $R^a$ groups, wherein any two adjacent $R^a$ substituents together with the atoms to which they are attached optionally form a 5- or 6-membered carbocyclic ring, wherein one of the ring carbon atom is optionally replaced by a carbonyl and the carbocyclic ring is optionally substituted with 1-2 members independently selected from an halogen, aryl or $C_{1-8}$alkyl. In one occurrence, Z is 2-thiazolyl, optionally substituted with a member selected from the group consisting of $C_{1-8}$haloalkyl, —CN, halogen, $C_{3-7}$cycloalkyl, aryl, unsubstituted $C_{1-8}$alkyl, aryl-NH—$C_{1-6}$alkyl and $C_{1-8}$alkoxy-$C_{1-4}$alkyl. In other occurrences, the carbocyclic ring is a benzene ring, a cyclopentane ring or cyclohexane ring, each of which is optionally substituted with a halogen or $C_{1-6}$alkyl.

In the above embodiments of compounds having Formula (II), at each occurrence, alkyl by itself or as part of another substituent, is an unsubstituted, fully saturated, straight or branched chain hydrocarbon radical; at each occurrence, cycloalkyl by itself or as part of another substituent is an unsubstituted, fully saturated, cyclic hydrocarbon radical; and at each occurrence, aryl by itself or as part or another substituent is a monovalent monocyclic, bicyclic or polycyclic polyunsaturated aromatic hydrocarbon radical of 5 to 16 ring atoms, which can be a single ring or multiple rings (up to three rings) which are fused together or linked covalently.

Subformula of Formula II

In one group of embodiments, the compounds of Formula II, or pharmaceutically acceptable salts or solvates thereof, have a subformula (IIa):

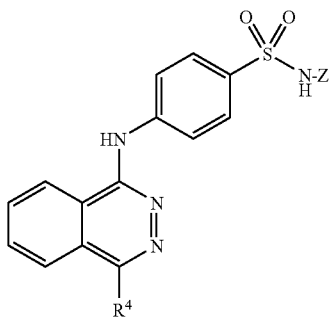

wherein Z is 2-thiazoly, 4-thiazolyl, 5-thiazolyl, 1,2,3-thiadiazol-4-yl, 1,2,3-thiadiazol-5-yl, 1,3,4-thiadiazol-2-yl, 1,2,5-thiadiazol-4-yl, 1,2,4-thiazol-3-yl or 1,2,4-thiazol-5-yl, each of which is optionally substituted with from 1-2 $R^3$ substituents selected from the group consisting of $C_{1-8}$haloalkyl, —CN, —OH, halogen, $C_{3-7}$cycloalkyl, aryl, $C_{1-8}$alkyl, aryl-NH—$C_{1-6}$alkyl and $C_{1-8}$alkoxy-$C_{1-4}$alkyl; and $R^4$ is selected from the group consisting of —H, —OH, $C_{0-6}$alkylaryl, aryl-$C_{1-6}$alkyl, aryl-$C_{1-6}$alkoxy, $C_{3-6}$cycloalkyl-$C_{1-6}$alkoxy and $C_{1-6}$alkoxy, wherein the aryl group is optionally substituted with from 1-3 $R^f$ substituents. In certain instances, Z is 2-thiazolyl, 1,3,4-thiadiazol-2-yl or 1,2,4-thiazol-5-yl, each of which is optionally substituted with from 1-2 $R^3$ substituents selected from —OH, —F, —Cl, —$CF_3$, $C_{1-8}$alkyl.

In a second embodiment, the compounds of Formula II, or pharmaceutically acceptable salts or solvates thereof, have a subformula (IIb):

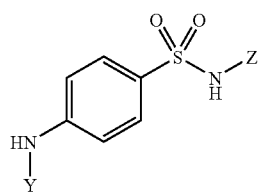

wherein Y is 2-pyrimidinyl, 4-pyrimidinyl, 2-pyrazinyl, pyridyl or 1,2,4-triazin-3-yl, each of which is optionally substituted with a member selected from the group consisting of —H, $C_{1-8}$haloalkyl, —CN, halogen, $C_{3-7}$cycloalkyl, aryl, unsubstituted $C_{1-8}$alkyl, aryl-NH—$C_{1-6}$alkyl and $C_{1-8}$alkoxy-$C_{1-4}$alkyl; and Z is 2-thiazolyl, oxazoly, imidazoly, or 3-isoxazolyl, each of which is optionally substituted with a member selected from the group consisting of —H, —OH, aryl, aryl-$C_{1-6}$alkyl, aryl-$C_{1-6}$alkoxy, $C_{3-6}$cycloalkyl-$C_{1-6}$alkoxy and $C_{1-6}$alkoxy.

In a third embodiment, compounds of Formula II, or pharmaceutically acceptable salts or solvates thereof, have a subformula (IIc):

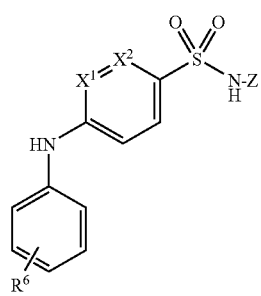

wherein Z is 2-thiazoly, 4-thiazolyl, 5-thiazolyl, 1,2,3-thiadiazol-4-yl, 1,2,3-thiadiazol-5-yl, 1,3,4-thiadiazol-2-yl, 1,2,5-thiadiazol-4-yl, 1,2,4-thiazol-3-yl or 1,2,4-thiazol-5-yl, each of which is optionally substituted with from 1-2 $R^5$ substituents selected from the group consisting of $C_{1-8}$haloalkyl, —CN, halogen, —OH, $C_{3-7}$cycloalkyl, aryl, $C_{1-8}$alkyl, aryl-NH—$C_{1-6}$alkyl and $C_{1-8}$alkoxy-$C_{1-4}$alkyl; $R^6$ is —H, aryl or $C_{1-6}$alkyl; and $X^1$ and $X^2$ are each independently —CH=, —C(CH$_3$)=, —C(CN)=, —C(OH)= or —C(halo)=. In one instance, $X^1$ and $X^2$ are each independently —CH= or —C(halo)=. In certain instances, Z is 2-thiazolyl, 1,3,4-thiadiazol-2-yl or 1,2,4-thiazol-5-yl, each of which is optionally substituted with from 1-2 $R^5$ substituents selected from —OH, —F, —Cl, —CF$_3$, $C_{1-8}$alkyl.

In a fourth embodiment, the compounds of Formula II, or pharmaceutically acceptable salts or solvates thereof, have a subformula (IId):

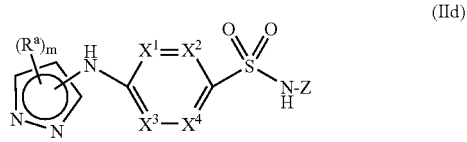

wherein Z is 2-thiazoly, 4-thiazolyl, 5-thiazolyl, 1,2,3-thiadiazol-4-yl, 1,2,3-thiadiazol-5-yl, 1,3,4-thiadiazol-2-yl, 1,2,5-thiadiazol-4-yl, 1,2,4-thiazol-3-yl or 1,2,4-thiazol-5-yl, each of which is optionally substituted with from 1-2 $R^7$ substituents selected from the group consisting of $C_{1-8}$haloalkyl, —CN, halogen, —OH, $C_{3-7}$cycloalkyl, aryl, $C_{1-8}$alkyl, aryl-NH—$C_{1-6}$alkyl and $C_{1-8}$alkoxy-$C_{1-4}$alkyl. m is an integer of from 0-3. In certain instances, Z is 2-thiazolyl, 1,3,4-thiadiazol-2-yl or 1,2,4-thiadiazol-5-yl, each of which is optionally substituted with from 1-2 $R^5$ substituents selected from —OH, —F, —Cl, —CF$_3$, $C_{1-8}$alkyl. In certain instances, $R^7$ is —H, —CF$_3$, —CN, —Cl, —F, -Ph, —CH$_3$, Ph-NH—CH$_2$—, or CH$_3$OCH$_2$—. $X^1$, $X^2$, $X^3$ and $X^4$ are as defined above in compounds of Formula (II). In certain instances, $X^1$, $X^2$, $X^3$ and $X^4$ are —CH=. In other instances, $X^1$, $X^2$ and $X^3$ are —CH= and $X^4$ is —CF=, —C(CN)=, —C(CH$_3$)=, —C(OH)= or —N=. In yet other instances, $X^1$, $X^2$ and $X^4$ are —CH= and $X^3$ is —CF=, —C(CN)=, —C(CH$_3$)=, —C(OH)= or —N=. $R^a$ is as defined above.

In certain instances, the compounds of Formula (IId), or pharmaceutically acceptable salts or solvates thereof, have a subformula (IId-1):

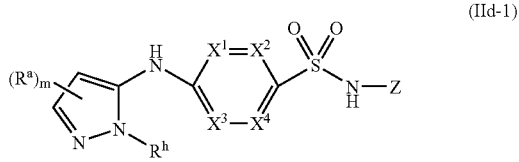

wherein m is an integer from 0-2. $R^h$ is H or $R^a$. Substituents $R^a$, $R^7$, $X^1$, $X^2$, $X^3$, $X^4$ and Z are as defined above in Formula (IId). In one group of embodiments of compounds having Formula (IId-1), Z is 2-thiazoly, 4-thiazolyl, 5-thiazolyl, 1,2,3-thiadiazol-4-yl, 1,2,3-thiadiazol-5-yl, 1,3,4-thiadiazol-2-yl, 1,2,5-thiadiazol-4-yl, 1,2,4-thiazol-3-yl or 1,2,4-thiazol-5-yl, each of which is optionally substituted with from 1-2 $R^7$ substituents selected from the group consisting of $C_{1-8}$haloalkyl, —CN, halogen, —OH, $C_{3-7}$cycloalkyl, aryl, $C_{1-8}$alkyl, aryl-NH—$C_{1-6}$alkyl and $C_{1-8}$alkoxy-$C_{1-4}$alkyl.

In other instances, compounds of Formula (IId), or pharmaceutically acceptable salts or solvates thereof, have a subformula (IId-2):

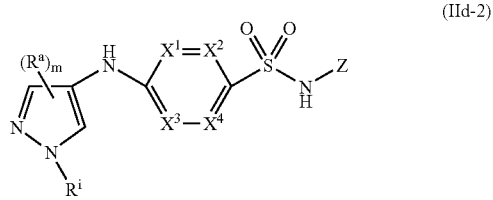

wherein m is an integer from 0-2. $R^i$ is H or $R^a$. Substituents $R^a$, $X^1$, $X^2$, $X^3$, $X^4$ and Z are as defined above in Formula (IId). In one group of embodiments of compounds having Formula (IId-2), Z is 2-thiazoly, 4-thiazolyl, 5-thiazolyl, 1,2,3-thiadiazol-4-yl, 1,2,3-thiadiazol-5-yl, 1,3,4-thiadiazol-2-yl, 1,2,5-thiadiazol-4-yl, 1,2,4-thiazol-3-yl or 1,2,4-thiazol-5-yl, each of which is optionally substituted with from 1-2 $R^7$ substituents selected from the group consisting of $C_{1-8}$haloalkyl, —CN, halogen, —OH, $C_{3-7}$cycloalkyl, aryl, $C_{1-8}$alkyl, aryl-NH—$C_{1-6}$alkyl and $C_{1-8}$alkoxy-$C_{1-4}$alkyl.

In yet other instances, the compounds of Formula (IId), or pharmaceutically acceptable salts or solvates thereof, have a subformula (IId-3):

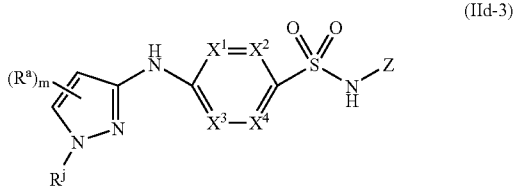

wherein m is an integer from 0-2. $R^j$ is H or $R^a$. Substituents $R^a$, $X^1$, $X^2$, $X^3$, $X^4$ and Z are as defined above in Formula (IId). In one group of embodiments of compounds having Formula (IId-2), Z is 2-thiazoly, 4-thiazolyl, 5-thiazolyl, 1,2,3-thiadiazol-4-yl, 1,2,3-thiadiazol-5-yl, 1,3,4-thiadiazol-2-yl, 1,2,5-thiadiazol-4-yl, 1,2,4-thiazol-3-yl or 1,2,4-thiazol-5-yl, each of which is optionally substituted with from 1-2 $R^7$ substituents selected from the group consisting of $C_{1-8}$haloalkyl, —CN, halogen, —OH, $C_{3-7}$cycloalkyl, aryl, $C_{1-8}$alkyl, aryl-NH—$C_{1-6}$alkyl and $C_{1-8}$alkoxy-$C_{1-4}$alkyl.

In a fifth embodiment, the compounds of Formula II, or pharmaceutically acceptable salts or solvates thereof, have a subformula (IIe):

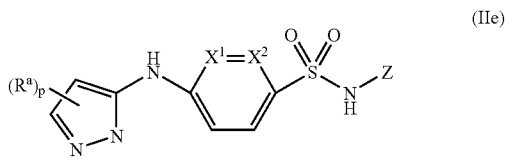

wherein Z is pyridyl, pyridazinyl, primidinyl or pyrizinyl, each of which is optionally substituted with from 1-3 unsubstituted $C_{1-6}$alkyl. In certain instances, $X^1$ is —CH= and $X^2$ is —CF=. In other instances, $X^1$ is —CF= and $X^2$ is —CH=. In yet other instances, $X^1$ and $X^2$ are —CH= or —CF=. The subscript p is an integer of 0-3. $R^a$ is as defined above.

In sixth embodiment, compounds of Formula II, or pharmaceutically acceptable salts or solvates thereof, have a subformula (IIf):

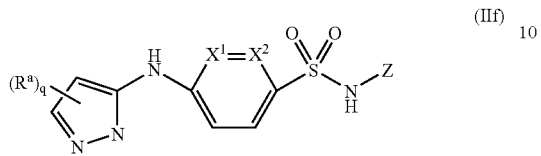

wherein Z is 1,3,4-thiadiazol-2-yl, 1,2,3-thiadiazol-4-yl, 1,2, 3-thiadiazol-5-yl, 1,2,4-thiazol-3-yl, 1,2,4-thiadiazol-5-yl, 1,3,4-oxadiazol-2yl, 1,2,5-thiadiazol-4-yl, pyrazolyl, 1,2,5-oxadiazol-4-yl, 1,2,3,5-thiatriazol-4-yl, 1,2,3,4-thiatriazol-5-yl, 1,2,3,5-oxatriazol-4-yl or 1,2,3,4-oxatriazol-5-yl. In certain instances, Z is 1,3,4-thiadiazolyl, 1,3,4-triazolyl, 1,3, 4-oxadiazolyl. The subscript q is an integer from 0-3. The substituents $R^a$, $X^1$ and $X^2$ are as defined above for compounds of Formula (II). In other instances, $X^1$ is —CH= and $X^2$ is —CF=. In yet other instances, compounds of Formula (IIf) have a subformula (IIf-1):

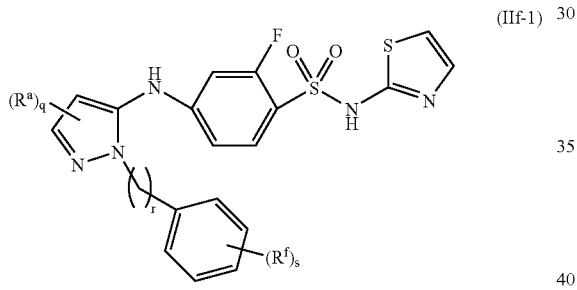

wherein the subscript r is 0 or 1. The subscript s is an integer of from 0-3. The subscript q is an integer of from 0-2. $R^a$ is $C_{1-8}$alkyl or aryl optionally substituted with from 1-3 $R^f$ substituents. $R^f$ is as defined above.

In a seventh embodiment, the compounds of Formula II, or pharmaceutically acceptable salts or solvates thereof, have a subformula (IIg):

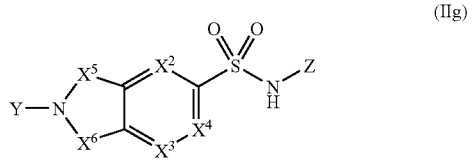

$X^5$ and $X^6$ are each independently —S(O)$_2$—, —C(O)— or —CHR$^2$—. In one instance, $X^5$ and $X^6$ are —CH$_2$—. In another instance, $X^5$ and $X^6$ are each independently —S(O)$_2$— or —C(O)—. The substituents Y, Z, $R^2$, $X^2$, $X^3$ and $X^4$ are as defined above for compounds of Formula (II).

In an eighth embodiment, the compounds of Formula II, or pharmaceutically acceptable salts or solvates thereof, have a subformula (IIh):

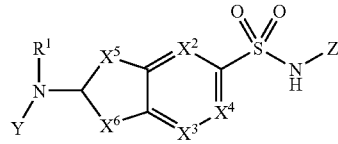

$X^5$ and $X^6$ are each independently —S(O)$_2$—, —C(O)— or —CHR$^2$—. In one instance, $X^5$ and $X^6$ are —CH$_2$—. In another instance, $X^5$ and $X^6$ are each independently —CH$_2$ or —C(O)—. In yet another instance, $X^5$ and $X^6$ are each independently —S(O)$_2$— or —C(O)—. The substituents Y, Z, $R^1$, $R^2$, $X^2$, $X^3$ and $X^4$ are as defined above for compounds of Formula (II).

In a ninth embodiment, the compounds of Formula II, or pharmaceutically acceptable salts or solvates thereof, have a subformula (IIi):

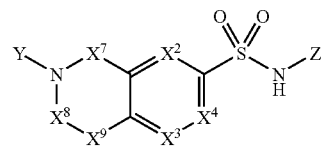

$X^7$, $X^8$ and $X^g$ are each independently CHR$^2$—, —S(O)$_2$— or —C(O)—. In one instance, $X^7$, $X^8$ and $X^g$ are —CH$_2$—. In another instance, $X^7$, $X^8$ and $X^g$ are each independently —CH$_2$ or —C(O)—. In yet another instance, $X^7$, $X^8$ and $X^g$ are each independently —S(O)$_2$— or —C(O)—. The substituents Y, Z, $R^2$, $X^2$, $X^3$ and $X^4$ are as defined above for compounds of Formula (II).

In a tenth embodiment, the compounds of Formula II, or pharmaceutically acceptable salts or solvates thereof, have a subformula (IIj):

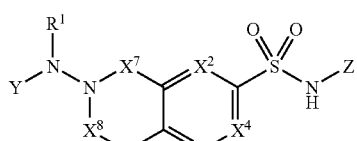

$X^7$, $X^8$ and $X^g$ are each independently CHR$^2$—, —S(O)$_2$— or —C(O)—. In one instance, $X^7$, $X^8$ and $X^g$ are —CH$_2$—. In another instance, $X^7$, $X^8$ and $X^g$ are each independently —CH$_2$ or —C(O)—. In yet another instance, $X^7$, $X^8$ and $X^g$ are each independently —S(O)$_2$— or —C(O)—. The substituents Y, Z, $R^1$, $R^2$, $X^2$, $X^3$ and $X^4$ are as defined above for compounds of Formula (II).

In an eleventh embodiment, the compounds of Formula II, or pharmaceutically acceptable salts or solvates thereof, have a subformula (IIk):

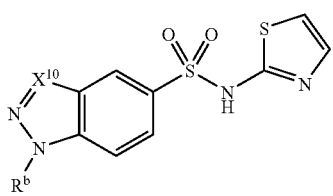

(IIk)

where $X^{10}$ is —N═, —CH═ or —C($R^a$)═. In certain instances, $X^{10}$ is —CH═. $R^b$ is as defined above for compounds of Formula (II). In certain instances, $R^b$ is aryl or aryl-(CO)—, each of which is optionally substituted with from 1-2 substituents independently selected from $C_{1-8}$alkoxy, $C_{1-4}$haloalkyl, $C_{1-4}$haloalkoxy or halogen. In one occurrence, the halogen is —F, haloalkyl is —$CF_3$ and $C_{1-4}$haloalkoxy is $CF_3O$—.

In a twelfth embodiment, the compounds of Formula II, or pharmaceutically acceptable salts or solvates thereof, have a subformula (III):

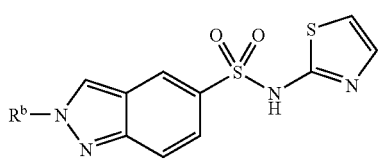

(III)

where $R^b$ is as defined above for compounds of Formula (II). In certain instances, $R^b$ is aryl or aryl-(CO)—, each of which is optionally substituted with from 1-2 substituents independently selected from $C_{1-8}$alkoxy, $C_{1-4}$haloalkyl, $C_{1-4}$haloalkoxy or halogen. In one occurrence, the halogen is —F, haloalkyl is —$CF_3$ and $C_{1-4}$haloalkoxy is $CF_3O$—.

In each of the above embodiments of the subformulas IIa-III, at each occurrence, alkyl by itself or as part of another substituent, is an unsubstituted, fully saturated, straight or branched chain hydrocarbon radical; at each occurrence, cycloalkyl by itself or as part of another substituent is an unsubstituted, fully saturated, cyclic hydrocarbon radical; and at each occurrence, aryl by itself or as part or another substituent is a monovalent monocyclic, bicyclic or polycyclic polyunsaturated aromatic hydrocarbon radical.

Also within the scope of the present invention are compounds of the invention that are poly- or multi-valent species, including, for example, species such as dimers, trimers, tetramers and higher homologs of the compounds of the invention or reactive analogues thereof. The poly- and multi-valent species can be assembled from a single species or more than one species of the invention. For example, a dimeric construct can be "homo-dimeric" or "heterodimeric." Moreover, poly- and multi-valent constructs in which a compound of the invention or a reactive analogue thereof, can be attached to an oligomeric or polymeric framework (e.g., polylysine, dextran, hydroxyethyl starch and the like) are within the scope of the present invention. The framework is preferably polyfunctional (i.e. having an array of reactive sites for attaching compounds of the invention). Moreover, the framework can be derivatized with a single species of the invention or more than one species of the invention.

Moreover, the present invention includes compounds within a motif described herein, which are functionalized to afford compounds having water-solubility that is enhanced relative to analogous compounds that are not similarly functionalized. Thus, any of the substituents set forth herein can be replaced with analogous radicals that have enhanced water solubility. For example, it is within the scope of the invention to, for example, replace a hydroxyl group with a diol, or an amine with a quaternary amine, hydroxy amine or similar more water-soluble moiety. In a preferred embodiment, additional water solubility is imparted by substitution at a site not essential for the activity towards the ion channel of the compounds set forth herein with a moiety that enhances the water solubility of the parent compounds. Methods of enhancing the water-solubility of organic compounds are known in the art. Such methods include, but are not limited to, functionalizing an organic nucleus with a permanently charged moiety, e.g., quaternary ammonium, or a group that is charged at a physiologically relevant pH, e.g. carboxylic acid, amine. Other methods include, appending to the organic nucleus hydroxyl- or amine-containing groups, e.g. alcohols, polyols, polyethers, and the like. Representative examples include, but are not limited to, polylysine, polyethyleneimine, poly(ethyleneglycol) and poly(propyleneglycol). Suitable functionalization chemistries and strategies for these compounds are known in the art. See, for example, Dunn, R. L., et al., Eds. *Polymeric Drugs and Drug Delivery Systems*, ACS Symposium Series Vol. 469, American Chemical Society, Washington, D.C. 1991.

II. Preparation of the Compounds

Compounds of the present invention can be prepared using readily available starting materials or known intermediates. The synthetic schemes set forth below provide exemplary synthetic pathways for the preparation of compounds of the invention.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1967-2004, Volumes 1-22; *Rodd's Chemistry of Carbon Compounds*, Elsevier Science Publishers, 1989, Volumes 1-5 and Supplementals; and *Organic Reactions*, Wiley & Sons: New York, 2005, Volumes 1-65. The following synthetic reaction schemes are merely illustrative of some methods by which the compounds of the present invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., and more preferably from about −20° C. to about 80° C.

II.a. General Procedure for Synthesizing Sulfonamide-Containing Compounds

A general route to the compounds of the invention is shown in Scheme A.

Scheme A

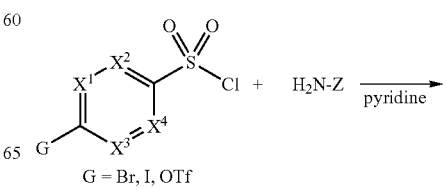

G = Br, I, OTf

-continued

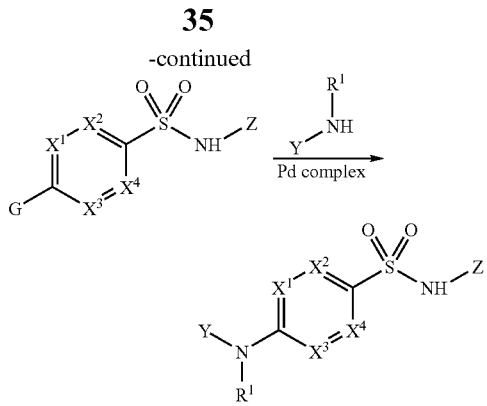

Scheme A describes a method of preparing a compound of Formulas I and II, wherein the symbols are as defined before.

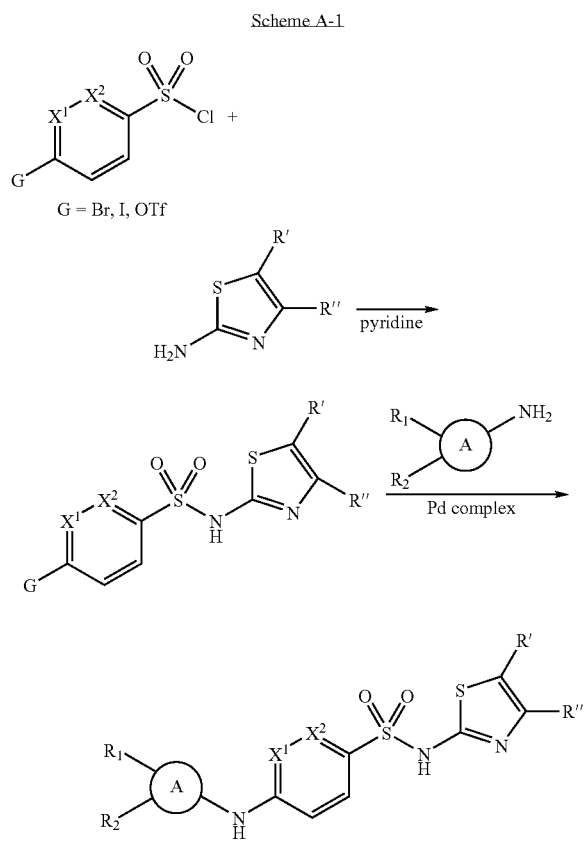

Scheme A-1 shows a synthetic approach for the preparation of certain compounds of Formulas I and II. R', R", $R_1$ and $R_2$ are non-interfering substituents, which include protected functional groups. The choice of a suitable protecting group is within the ability of a person of skill in the art. Symbol A represents an aryl or an heteroaryl.

An alternate route to the compounds of the present invention is provided in Scheme B.

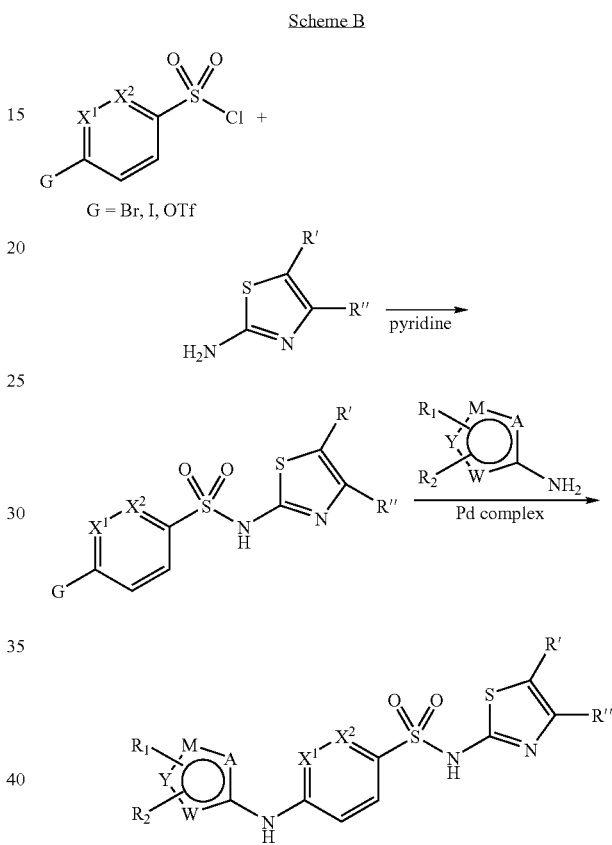

Scheme B shows the synthesis of certain compounds of Formulas I and II, where Y and Z are 5-membered heteroaryls. R', R", $R_1$ and $R_2$ are non-interfering substituents, which include protected functional groups. Symbols A, M, W and Y represent carbon or heteroatoms selected from N, O or S, wherein at least one of A, M, W and Y is a heteroatom.

Another synthetic route to the compounds of the present invention is set forth in Scheme B-1.

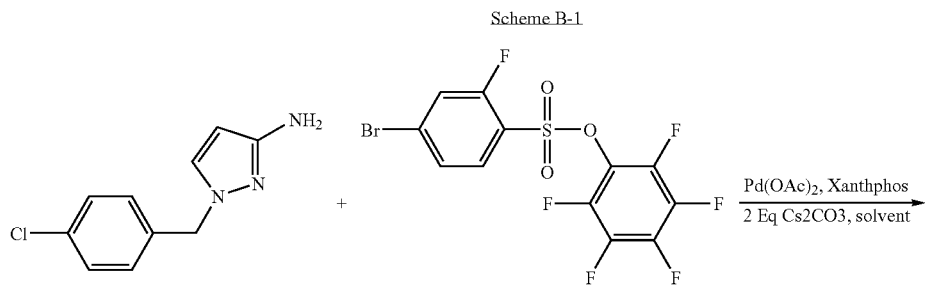

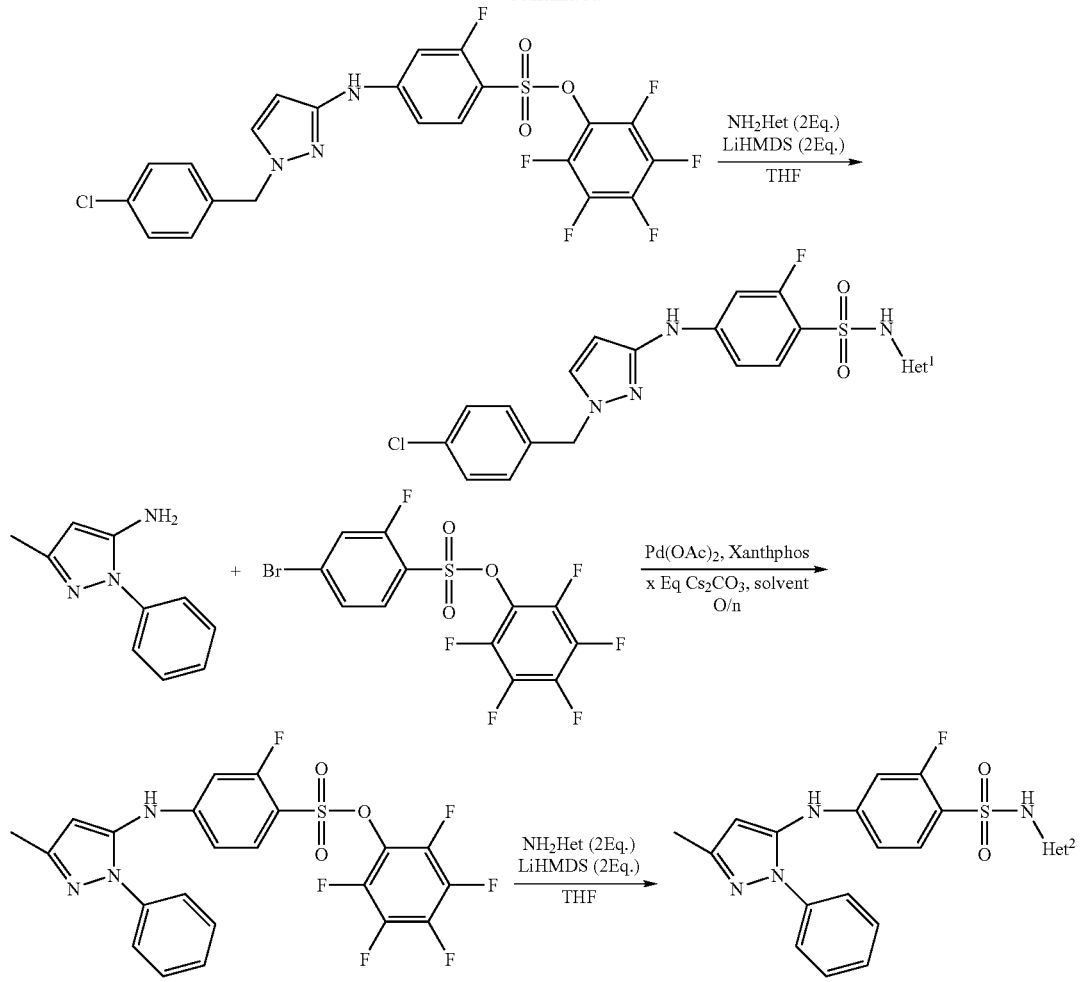
In Scheme B-1, exemplary NH₂Het¹ aminoheterocycles include:
Exemplary NH₂Het² aminoheterocycle include:
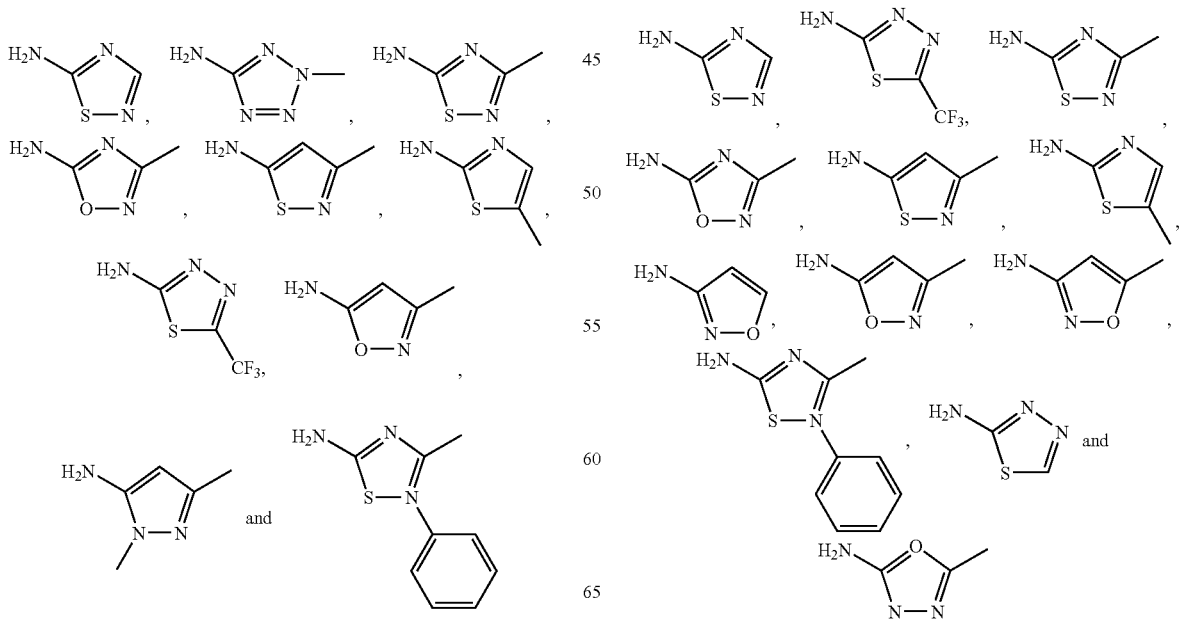

Scheme B-2 outlines an exemplary synthetic route to aminopyrazoles.

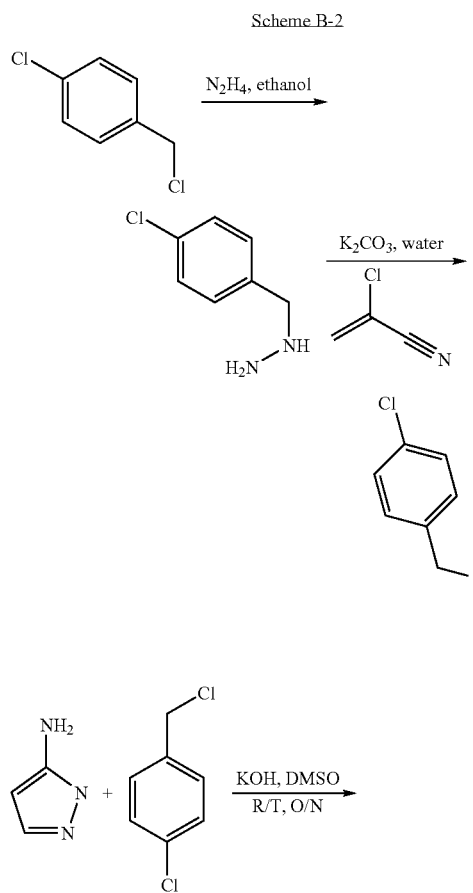

Mixture of isomers obtained which can be seperable by trituration with TBME.

Another route to sulfone/sulfonamide-containing compounds of the invention is set forth in Scheme C:

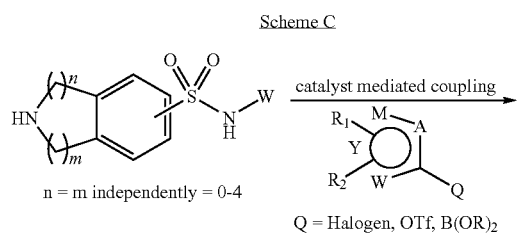

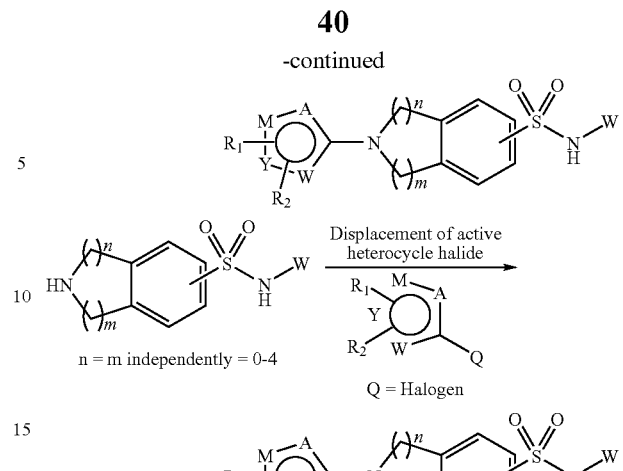

Another route to the compounds of the invention is set forth in Scheme D:

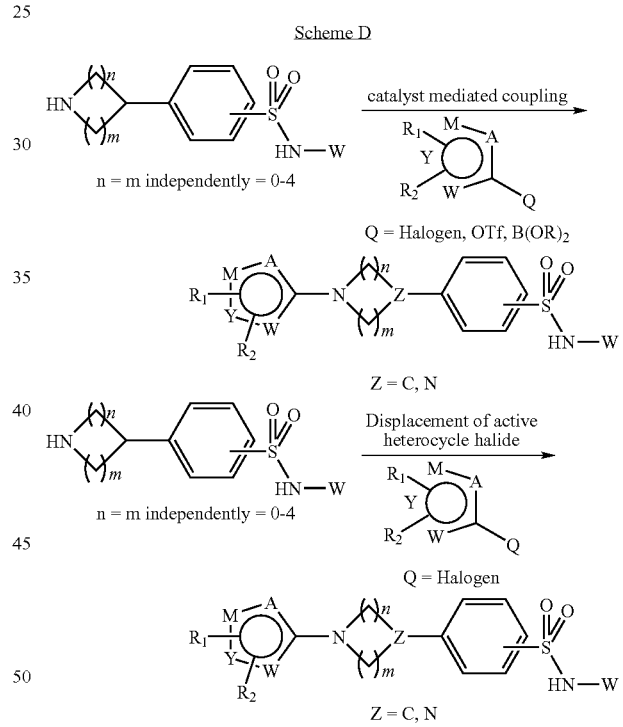

A further route to the compounds of the invention is set forth in Scheme E:

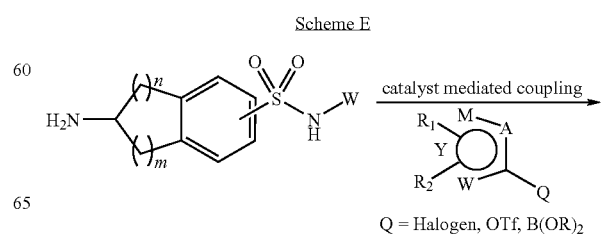

41

-continued

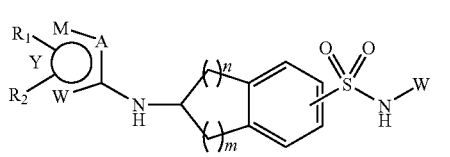

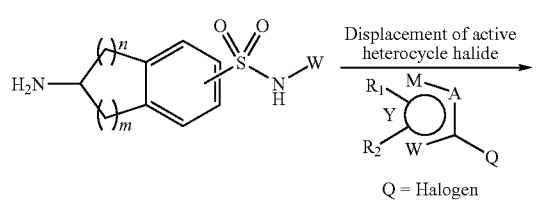

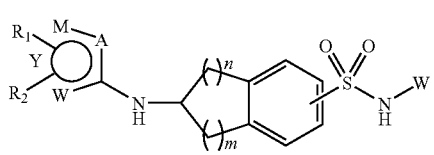

Another route to compounds of the invention is set forth in Scheme F:

Scheme F

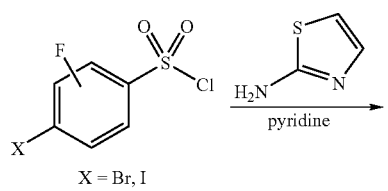

Another route to compounds of the invention is set forth in Scheme G:

Scheme G

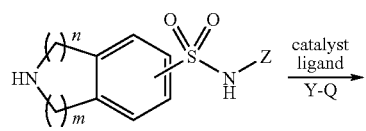

42

-continued

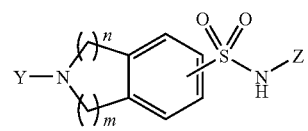

n = m independently = 0-5
Q = Halogen, OTf, B(OR)$_2$

Another route to compounds of the invention is set forth in Scheme H:

Scheme H

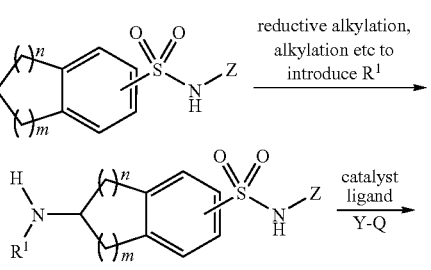

n = m independently = 0-5
Q = halogen, OTf, B(OR)$_2$

Another route to compounds of the invention is set forth in Scheme I:

Scheme I

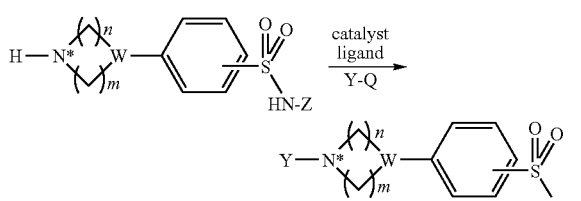

n = m independently = 0-5
Q = Halogen, OTf, B(OR)$_2$

Another route to compounds of the invention is set forth in Scheme J:

Scheme J

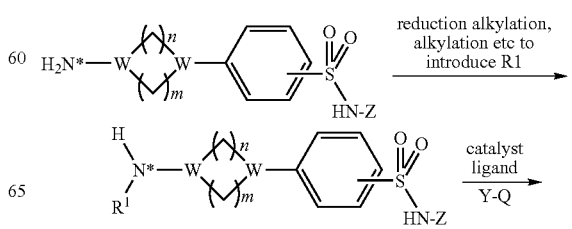

-continued

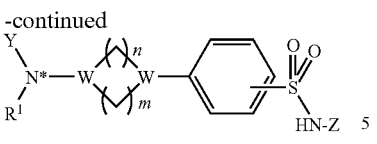

Still other compounds of the present invention, having formula I, IA or II, consisting of compounds, pharmaceutically acceptable salts, hydrates or solvates thereof, as set forth in Table II.

TABLE II 1. 4-Bromo-2-fluoro-N-thiazol-2-yl-benzenesulfonamide
2. 4-(4-Benzhydrylthiazol-2-ylamino)-N-(thiazol-2-yl)benzenesulfonamide
3. 2-Fluoro-4-[4-(4-methoxy-benzyl)-thiazol-2-ylamino]-N-thiazol-2-yl-benzenesulfonamide
4. 2-Fluoro-4-[4-(4-methanesulfonyl-benzyl)-thiazol-2-ylamino]-N-thiazol-2-yl-benzenesulfonamide
5. 4-[4-(4-Cyano-benzyl)-thiazol-2-ylamino]-2-fluoro-N-thiazol-2-yl-benzenesulfonamide
6. 4-[4-(4-Chloro-benzyl)-thiazol-2-yl]-methyl-amino-2-fluoro-N-thiazol-2-yl-benzenesulfonamide
7. 4-(4-Tert-butyl-thiazol-2-ylamino)-2-fluoro-N-thiazol-2-yl-benzenesulfonamide
8. 4-(5-Tert-butyl-4-methylthiazol-2-ylamino)-N-(thiazol-2-yl)benzenesulfonamide
9. 4-(5-Acetyl-4-methyl-thiazol-2-ylamino)-2-fluoro-N-thiazol-2-yl-benzenesulfonamide
10. 4-(4-Tert-butyl-thiazol-2-ylamino)-2-chloro-N-thiazol-2-yl-benzenesulfonamide
11. 4-(4-tert-Butyl-thiazol-2-ylamino)-N-thiazol-2-yl-2-trifluoromethoxy-benzenesulfonamide
12. 4-(4-tert-Butyl-thiazol-2-ylamino)-naphthalene-1-sulfonic acid thiazol-2-ylamide
13. 4-(5-tert-butyl-4-methylthiazol-2-ylamino)-2-fluoro-N-(thiazol-2-yl)benzenesulfonamide
14. 4-(4-Tert-butyl-thiazol-2-ylamino)-N-thiazol-2-yl-benzenesulfonamide
15. 4-(1-tert-butyl-3-(4-chlorobenzyl)-1H-pyrazol-5-ylamino)-N-(thiazol-2-yl)benzenesulfonamide
16. 4-(3-(4-Chlorobenzyl)-1H-pyrazol-5-ylamino)-N-(thiazol-2-yl)benzenesulfonamide
17. 4-(3-Tert-butyl-1-methyl-1H-pyrazol-5-ylamino)-N-(thiazol-2-yl)benzenesulfonamide
18. 4-(3-Tert-butylisoxazol-3-ylamino)-N-(thiazol-2-yl)benzenesulfonamide
19. 4-(5-Amino-1-tert-butyl-1H-1,2,4-triazol-3-ylamino)-N-(thiazol-2-yl)benzenesulfonamide
20. 4-(3-methyl-1-phenyl-1H-pyrazol-5-ylamino)-N-(thiazol-2-yl)benzenesulfonamide
21. 4-(3-(4-Chlorobenzyl)-1-methyl-1H-pyrazol-5-ylamino)-N-(thiazol-2-yl)benzenesulfonamide
22. 4-(1,3-di-tert-butyl-1H-pyrazol-5-ylamino)-N-(thiazol-2-yl)benzenesulfonamide
23. 4-(3-tert-butyl-1H-pyrazol-5-ylamino)-N-(thiazol-2-yl)benzenesulfonamide
24. 4-(5-amino-1-(4-chlorobenzyl)-1H-1,2,4-triazol-3-ylamino)-N-(thiazol-2-yl)benzenesulfonamide
25. 4-(1-(3-chloro-4-fluorophenyl)-4-cyano-1H-pyrazol-5-ylamino)-N-(thiazol-2-yl)benzenesulfonamide
26. 4-(1-tert-butyl-3-(4-chlorobenzyl)-1H-pyrazol-5-ylamino)-2-fluoro-N-(thiazol-2-yl)benzenesulfonamide
27. N-(thiazol-2-yl)-4-(5-(4-(trifluoromethyl)benzyl)-1,3,4-thiadiazol-2-ylamino)benzenesulfonamide
28. N-(thiazol-2-yl)-4-(5-(4-(trifluoromethyl)benzyl)-1,3,4-oxadiazol-2-ylamino)benzenesulfonamide
29. 4-(3-(cyclohexylmethyl)-1-methyl-1H-pyrazol-5-ylamino)-N-(thiazol-2-yl)benzenesulfonamide
30. 2-fluoro-4-(3-methyl-1-phenyl-1H-pyrazol-5-ylamino)-N-(thiazol-2-yl)benzenesulfonamide
31. 4-(1-(4-chlorobenzyl)-1H-pyrazol-3-ylamino)-2-fluoro-N-(thiazol-2-yl)benzenesulfonamide
32. 4-(3-cyclopropyl-1-phenyl-1H-pyrazol-5-ylamino)-2-fluoro-N-(thiazol-2-yl)benzenesulfonamide
33. 4-(1-(4-chlorobenzyl)-1H-pyrazol-4-ylamino)-2-fluoro-N-(thiazol-2-yl)benzenesulfonamide
34. 2-fluoro-4-(1-methyl-3-neopentyl-1H-pyrazol-5-ylamino)-N-(thiazol-2-yl)benzenesulfonamide
35. 3-fluoro-4-(3-methyl-1-phenyl-1H-pyrazol-5-ylamino)-N-(thiazol-2-yl)benzenesulfonamide
36. 4-(3-cyclopropyl-1-phenyl-1H-pyrazol-5-ylamino)-3-fluoro-N-(thiazol-2-yl)benzenesulfonamide
37. 4-(Biphenyl-2-ylamino)-2-fluoro-N-thiazol-2-yl-benzenesulfonamide
43. 4-(4-phenylthiazol-2-ylamino)-N-(thiazol-2-yl)benzenesulfonamide
44. 4-(pyrimidin-2-ylamino)-N-(thiazol-2-yl)benzenesulfonamide
45. 4-(4-(benzyloxy)pyrimidin-2-ylamino)-N-(thiazol-2-yl)benzenesulfonamide
46. 4-(4-(2,2-diphenylethoxy)pyrimidin-2-ylamino)-N-(thiazol-2-yl)benzenesulfonamide
47. 4-(4,5-diphenylthiazol-2-ylamino)-N-(thiazol-2-yl)benzenesulfonamide
48. 4-(4-(phenoxymethyl)thiazol-2-ylamino)-N-(thiazol-2-yl)benzenesulfonamide
49. 4-(4-(2,2-diphenylethyl)thiazol-2-ylamino)-N-(thiazol-2-yl)benzenesulfonamide
50. 4-(4-(3-phenoxypropyl)thiazol-2-ylamino)-N-(thiazol-2-yl)benzenesulfonamide

TABLE II-continued 51. 4-(4-(2-cyclopentylethyl)thiazol-2-ylamino)-N-(thiazol-2-yl)benzenesulfonamide
52. 4-(4-((4-chlorophenoxy)methyl)thiazol-2-ylamino)-N-(thiazol-2-yl)benzenesulfonamide
53. 4-(4-(2-phenylcyclopropyl)thiazol-2-ylamino)-N-(thiazol-2-yl)benzenesulfonamide
54. 4-(4-(2-fluorobenzyloxy)pyrimidin-2-ylamino)-N-(thiazol-2-yl)benzenesulfonamide
55. N-(thiazol-2-yl)-4-(4-(4-(trifluoromethyl)benzyloxy)pyrimidin-2-ylamino)benzenesulfonamide
56. 4-(4-((2,2-diphenylethylamino)methyl)thiazol-2-ylamino)-N-(thiazol-2-yl)benzenesulfonamide
57. 4-(4-((2-phenoxyethylamino)methyl)thiazol-2-ylamino)-N-(thiazol-2-yl)benzenesulfonamide
58. (S)-4-(4-((2-(pyrrolidin-1-ylmethyl)pyrrolidin-1-yl)methyl)thiazol-2-ylamino)-N-(thiazol-2-yl)benzenesulfonamide
59. 4-(4-(3-chloropropyl)thiazol-2-ylamino)-N-(thiazol-2-yl)benzenesulfonamide
60. 4-(4-((benzhydrylamino)methyl)thiazol-2-ylamino)-N-(thiazol-2-yl)benzenesulfonamide
61. 4-(4-((3,3-diphenylpropylamino)methyl)thiazol-2-ylamino)-N-(thiazol-2-yl)benzenesulfonamide
62. 4-(4-((4-tert-butylphenoxy)methyl)thiazol-2-ylamino)-N-(thiazol-2-yl)benzenesulfonamide
63. 4-(4-(1-phenoxyethyl)thiazol-2-ylamino)-N-(thiazol-2-yl)benzenesulfonamide
64. 4-(4-(1-(4-chlorophenyl)cyclopentyl)thiazol-2-ylamino)-N-(thiazol-2-yl)benzenesulfonamide
65. 4-(4-((4-chlorobenzylamino)methyl)thiazol-2-ylamino)-N-(thiazol-2-yl)benzenesulfonamide
66. 4-(4-((3,4-dimethoxyphenethylamino)methyl)thiazol-2-ylamino)-N-(thiazol-2-yl)benzenesulfonamide
67. 4-(4-((methyl(phenethyl)amino)methyl)thiazol-2-ylamino)-N-(thiazol-2-yl)benzenesulfonamide
68. 4-(4-((diethylamino)methyl)thiazol-2-ylamino)-N-(thiazol-2-yl)benzenesulfonamide
69. 4-(4-((4-phenylbutylamino)methyl)thiazol-2-ylamino)-N-(thiazol-2-yl)benzenesulfonamide
70. 4-(4-((benzhydryl(methyl)amino)methyl)thiazol-2-ylamino)-N-(thiazol-2-yl)benzenesulfonamide
71. N-(thiazol-2-yl)-4-(4-((4-(trifluoromethyl)benzylamino)methyl)thiazol-2-ylamino)benzenesulfonamide
72. 4-(4-((4-nitrobenzylamino)methyl)thiazol-2-ylamino)-N-(thiazol-2-yl)benzenesulfonamide
73. 4-(4-((4-(dimethylamino)benzylamino)methyl)thiazol-2-ylamino)-N-(thiazol-2-yl)benzenesulfonamide
74. 4-(4-((cycloheptylamino)methyl)thiazol-2-ylamino)-N-(thiazol-2-yl)benzenesulfonamide
75. 4-(4-((methyl(2-(pyridin-4-yl)ethyl)amino)methyl)thiazol-2-ylamino)-N-(thiazol-2-yl)benzenesulfonamide
76. 4-(4-((2,4-dimethoxybenzylamino)methyl)thiazol-2-ylamino)-N-(thiazol-2-yl)benzenesulfonamide
77. methyl 4-methyl-2-(4-(N-thiazol-2-ylsulfamoyl)phenylamino)thiazole-5-carboxylate
78. 4-(4-methylthiazol-2-ylamino)-N-(thiazol-2-yl)benzenesulfonamide
79. 4-(4-(2,4-difluorobenzyl)thiazol-2-ylamino)-N-(thiazol-2-yl)benzenesulfonamide
80. 4-(4,5-dimethylthiazol-2-ylamino)-N-(thiazol-2-yl)benzenesulfonamide
81. 4-(4-(cyclohexylmethoxy)pyrimidin-2-ylamino)-N-(thiazol-2-yl)benzenesulfonamide
82. 4-(4-((4-fluorophenylthio)methyl)thiazol-2-ylamino)-N-(thiazol-2-yl)benzenesulfonamide
83. N-(thiazol-2-yl)-4-(4-(trifluoromethyl)thiazol-2-ylamino)benzenesulfonamide
84. N-(thiazol-2-yl)-4-(4-(4-(trifluoromethyl)phenyl)thiazol-2-ylamino)benzenesulfonamide
85. 4-(4-methoxypyrimidin-2-ylamino)-N-(thiazol-2-yl)benzenesulfonamide
86. 4-(4-methoxypyrimidin-2-ylamino)-N-(5-methylisoxazol-3-yl)benzenesulfonamide
87. N-(5-methylisoxazol-3-yl)-4-(4-(4-(trifluoromethyl)benzyloxy)pyrimidin-2-ylamino)benzenesulfonamide
88. N-(5-methylisoxazol-3-yl)-4-(2-(4-(trifluoromethyl)benzyloxy)pyrimidin-4-ylamino)benzenesulfonamide
89. 4-(4-((4-fluorophenylsulfinyl)methyl)thiazol-2-ylamino)-N-(thiazol-2-yl)benzenesulfonamide
90. 4-(4-(2-fluoro-4-(trifluoromethyl)phenyl)thiazol-2-ylamino)-N-(thiazol-2-yl)benzenesulfonamide
91. 4-(4-(4-chlorobenzyl)thiazol-2-ylamino)-N-(thiazol-2-yl)benzenesulfonamide
92. 4-(6-benzhydrylpyrazin-2-ylamino)-N-(thiazol-2-yl)benzenesulfonamide
93. 4-(6-benzhydrylpyridin-2-ylamino)-N-(thiazol-2-yl)benzenesulfonamide
94. 4-(4-(3-(4-chlorophenoxy)propyl)thiazol-2-ylamino)-N-(thiazol-2-yl)benzenesulfonamide
95. 4-(4-((2,4-dichlorophenoxy)methyl)thiazol-2-ylamino)-N-(thiazol-2-yl)benzenesulfonamide
96. 4-(4-((4-chloro-2-methylphenoxy)methyl)thiazol-2-ylamino)-N-(thiazol-2-yl)benzenesulfonamide
97. 4-(4-(2-(4-chlorophenoxy)propan-2-yl)thiazol-2-ylamino)-N-(thiazol-2-yl)benzenesulfonamide
98. 4-(6-(3,5-difluorobenzyl)pyrazin-2-ylamino)-N-(thiazol-2-yl)benzenesulfonamide TABLE II-continued 99. 4-(5-chloro-1H-benzo[d]imidazol-2-ylamino)-N-(thiazol-2-yl)benzenesulfonamide
100. 4-(5-chloro-1-methyl-1H-benzo[d]imidazol-2-ylamino)-N-(thiazol-2-yl)benzenesulfonamide
101. 4-(6-chloro-1-methyl-1H-benzo[d]imidazol-2-ylamino)-N-(thiazol-2-yl)benzenesulfonamide
102. 4-(4-((4-tert-butylphenoxy)methyl)thiazol-2-ylamino)-2-fluoro-N-(thiazol-2-yl)benzenesulfonamide
103. 4-(4-(4-chlorobenzyl)thiazol-2-ylamino)-N-(pyridin-2-yl)benzenesulfonamide
104. 4-(4-(4-chlorophenyl)thiazol-2-ylamino)-2-fluoro-N-(thiazol-2-yl)benzenesulfonamide
105. 4-(5-(4-chlorophenylsulfonyl)thiazol-2-ylamino)-2-fluoro-N-(thiazol-2-yl)benzenesulfonamide
106. 6-(4-tert-butylthiazol-2-ylamino)-N-(thiazol-2-yl)pyridine-3-sulfonamide
107. 6-(4-(4-chlorobenzyl)thiazol-2-ylamino)-N-(thiazol-2-yl)pyridine-3-sulfonamide
108. 4-(4-(4-chlorobenzyl)thiazol-2-ylamino)-2-fluoro-N-(5-methylthiazol-2-yl)benzenesulfonamide
109. 4-(4-(4-chlorobenzyl)thiazol-2-ylamino)-2-fluoro-N-(4-methylthiazol-2-yl)benzenesulfonamide
110. 4-(1-tert-butyl-3-(4-chlorobenzyl)-1H-pyrazol-5-ylamino)-N-(pyridin-2-yl)benzenesulfonamide
111. 4-(1-tert-butyl-3-(4-chlorobenzyl)-1H-pyrazol-5-ylamino)-N-(1,3,4-thiadiazol-2-yl)benzenesulfonamide
112. 1-(3-chloro-4-fluorophenyl)-5-(4-(N-thiazol-2-ylsulfamoyl)phenylamino)-1H-pyrazole-4-carboxamide
113. 4-(4-tert-butylthiazol-2-ylamino)-2-cyano-N-(thiazol-2-yl)benzenesulfonamide
114. 4-(benzo[d]oxazol-2-ylamino)-N-(thiazol-2-yl)benzenesulfonamide
115. 4-(3-(4-chlorobenzyl)-1H-pyrazol-5-ylamino)-2-fluoro-N-(thiazol-2-yl)benzenesulfonamide
116. 5-(4-tert-butylthiazol-2-ylamino)-N-(thiazol-2-yl)pyridine-2-sulfonamide
117. 4-(benzo[d]thiazol-2-ylamino)-N-(thiazol-2-yl)benzenesulfonamide
118. 4-(5-(4-chlorobenzyl)-1,3,4-oxadiazol-2-ylamino)-N-(thiazol-2-yl)benzenesulfonamide
119. 4-(3-(4-chlorobenzyl)-4-cyano-1-methyl-1H-pyrazol-5-ylamino)-N-(thiazol-2-yl)benzenesulfonamide
120. 4-(5-(4-chlorobenzyl)-1,3,4-thiadiazol-2-ylamino)-N-(thiazol-2-yl)benzenesulfonamide
121. 3-(4-chlorobenzyl)-1-methyl-5-(4-(N-thiazol-2-ylsulfamoyl)phenylamino)-1H-pyrazole-4-carboxamide
122. 4-(1,3-dimethyl-4-phenyl-1H-pyrazol-5-ylamino)-N-(thiazol-2-yl)benzenesulfonamide
123. 4-(1-tert-butyl-3-methyl-4-phenyl-1H-pyrazol-5-ylamino)-N-(thiazol-2-yl)benzenesulfonamide
124. 4-(3-methyl-4-phenyl-1H-pyrazol-5-ylamino)-N-(thiazol-2-yl)benzenesulfonamide
125. 4-(1-methyl-3-neopentyl-1H-pyrazol-5-ylamino)-N-(thiazol-2-yl)benzenesulfonamide
126. 4-(3-(4-methoxybenzyl)-1-methyl-1H-pyrazol-5-ylamino)-N-(thiazol-2-yl)benzenesulfonamide
127. 4-(3-(2-methoxybenzyl)-1-methyl-1H-pyrazol-5-ylamino)-N-(thiazol-2-yl)benzenesulfonamide
128. 4-(1-(4-chlorobenzyl)-3-methyl-1H-pyrazol-5-ylamino)-N-(thiazol-2-yl)benzenesulfonamide
129. 4-(3-(1-(4-chlorophenyl)cyclopropyl)-1-methyl-1H-pyrazol-5-ylamino)-N-(thiazol-2-yl)benzenesulfonamide
130. 2-fluoro-N-(thiazol-2-yl)-4-(1-(2,2,2-trifluoroethyl)-1H-pyrazol-4-ylamino)benzenesulfonamide
131. 4-(3-methyl-1-(pyridin-4-ylmethyl)-1H-pyrazol-5-ylamino)-N-(thiazol-2-yl)benzenesulfonamide
132. 4-(1-(cyclohexylmethyl)-3-methyl-1H-pyrazol-5-ylamino)-N-(thiazol-2-yl)benzenesulfonamide
133. 4-(3-(cyclohexylmethyl)-1-methyl-1H-pyrazol-5-ylamino)-2-fluoro-N-(thiazol-2-yl)benzenesulfonamide
134. 4-(3-(cyclohexylmethyl)-1-methyl-1H-pyrazol-5-ylamino)-2-hydroxy-N-(thiazol-2-yl)benzenesulfonamide
135. 4-(7-oxo-5-phenyl-4,5,6,7-tetrahydrobenzo[d]thiazol-2-ylamino)-N-(thiazol-2-yl)benzenesulfonamide
136. 4-(5,5-dimethyl-7-oxo-4,5,6,7-tetrahydrobenzo[d]thiazol-2-ylamino)-N-(thiazol-2-yl)benzenesulfonamide
137. 4-(1-(4-chlorophenyl)-3-methyl-1H-pyrazol-5-ylamino)-N-(thiazol-2-yl)benzenesulfonamide
138. 4-(1-methyl-3-(4-(trifluoromethyl)benzyl)-1H-pyrazol-5-ylamino)-N-(thiazol-2-yl)benzenesulfonamide
139. 4-(3-(2,4-difluorobenzyl)-1-methyl-1H-pyrazol-5-ylamino)-N-(thiazol-2-yl)benzenesulfonamide
140. 4-(1-(4-chlorophenyl)-3-methyl-1H-pyrazol-5-ylamino)-2-fluoro-N-(thiazol-2-yl)benzenesulfonamide
141. 4-(3-(4-chlorobenzyl)-1-methyl-1H-pyrazol-5-ylamino)-2-fluoro-N-(thiazol-2-yl)benzenesulfonamide
142. 4-(3-(1-(4-chlorophenyl)cyclopropyl)-1-methyl-1H-pyrazol-5-ylamino)-3-fluoro-N-(thiazol-2-yl)benzenesulfonamide TABLE II-continued 143. 4-(3-(4-chlorobenzyl)-1-methyl-1H-pyrazol-5-ylamino)-3-fluoro-N-(thiazol-2-yl)benzenesulfonamide
144. 4-(3-cyclopropyl-1-phenyl-1H-pyrazol-5-ylamino)-N-(thiazol-2-yl)benzenesulfonamide
145. 2-fluoro-4-(3-isopropyl-1-phenyl-1H-pyrazol-5-ylamino)-N-(thiazol-2-yl)benzenesulfonamide
146. 2-fluoro-4-(3-methyl-1-o-tolyl-1H-pyrazol-5-ylamino)-N-(thiazol-2-yl)benzenesulfonamide
147. 2-fluoro-4-(3-methyl-1-p-tolyl-1H-pyrazol-5-ylamino)-N-(thiazol-2-yl)benzenesulfonamide
148. 2-fluoro-4-(1-methyl-4-phenyl-1H-pyrazol-5-ylamino)-N-(thiazol-2-yl)benzenesulfonamide
149. 4-(1-(2-chlorophenyl)-3-methyl-1H-pyrazol-5-ylamino)-2-fluoro-N-(thiazol-2-yl)benzenesulfonamide
150. 2-fluoro-N-(thiazol-2-yl)-4-(1-(4-(trifluoromethyl)benzyl)-1H-pyrazol-4-ylamino)benzenesulfonamide
151. 4-(1-phenyl-1H-pyrazol-5-ylamino)-N-(thiazol-2-yl)benzenesulfonamide
152. 4-(1-(3-chlorophenyl)-3-methyl-1H-pyrazol-5-ylamino)-2-fluoro-N-(thiazol-2-yl)benzenesulfonamide
153. 4-(3-(4-chlorophenyl)-1-methyl-1H-pyrazol-5-ylamino)-2-fluoro-N-(thiazol-2-yl)benzenesulfonamide
154. 4-(1,3-diphenyl-1H-pyrazol-5-ylamino)-2-fluoro-N-(thiazol-2-yl)benzenesulfonamide
155. 2-(3-(4-chlorobenzyl)-5-(4-(N-thiazol-2-ylsulfamoyl)phenylamino)-1H-pyrazol-1-yl)acetamide
156. 4-(3-tert-butyl-1-phenyl-1H-pyrazol-5-ylamino)-2-fluoro-N-(thiazol-2-yl)benzenesulfonamide
157. 4-(1-tert-butyl-3-(4-methylbenzyl)-1H-pyrazol-5-ylamino)-2-fluoro-N-(thiazol-2-yl)benzenesulfonamide
158. 4-(1-tert-butyl-3-(4-methylbenzyl)-1H-pyrazol-5-ylamino)-3-fluoro-N-(thiazol-2-yl)benzenesulfonamide
159. 2-fluoro-4-(1-methyl-3-(4-methylbenzyl)-1H-pyrazol-5-ylamino)-N-(thiazol-2-yl)benzenesulfonamide
160. 3-fluoro-4-(1-methyl-3-(4-methylbenzyl)-1H-pyrazol-5-ylamino)-N-(thiazol-2-yl)benzenesulfonamide
161. 2-chloro-4-(3-methyl-1-phenyl-1H-pyrazol-5-ylamino)-N-(thiazol-2-yl)benzenesulfonamide
162. N-(5-chlorothiazol-2-yl)-2-fluoro-4-(3-methyl-1-phenyl-1H-pyrazol-5-ylamino)benzenesulfonamide
163. N-(5-chlorothiazol-2-yl)-4-(3-methyl-1-phenyl-1H-pyrazol-5-ylamino)benzenesulfonamide
164. 4-(1-tert-butyl-3-(3-chlorobenzyl)-1H-pyrazol-5-ylamino)-2-fluoro-N-(thiazol-2-yl)benzenesulfonamide
165. 2-fluoro-4-(3-(4-methylbenzyl)-1H-pyrazol-5-ylamino)-N-(thiazol-2-yl)benzenesulfonamide
166. 4-(1-tert-butyl-3-(4-chloro-3-fluorobenzyl)-1H-pyrazol-5-ylamino)-2-fluoro-N-(thiazol-2-yl)benzenesulfonamide
167. 3-fluoro-4-(3-(4-methylbenzyl)-1H-pyrazol-5-ylamino)-N-(thiazol-2-yl)benzenesulfonamide
168. 2-fluoro-4-(1-phenyl-1H-pyrazol-5-ylamino)-N-(thiazol-2-yl)benzenesulfonamide
169. 4-(1-cyclopentyl-3-methyl-1H-pyrazol-5-ylamino)-2-fluoro-N-(thiazol-2-yl)benzenesulfonamide
170. 2-fluoro-4-(3-methyl-1-(4-(trifluoromethyl)phenyl)-1H-pyrazol-5-ylamino)-N-(thiazol-2-yl)benzenesulfonamide
171. 4-(1-benzhydryl-1H-pyrazol-4-ylamino)-2-fluoro-N-(thiazol-2-yl)benzenesulfonamide
172. 4-(biphenyl-2-ylamino)-2-fluoro-N-(thiazol-2-yl)benzenesulfonamide
173. 2-fluoro-4-(1-(2-fluorophenyl)-3-methyl-1H-pyrazol-5-ylamino)-N-(thiazol-2-yl)benzenesulfonamide
174. 2-fluoro-4-(2-phenyl-2,4,5,6-tetrahydrocyclopenta[c]pyrazol-3-ylamino)-N-(thiazol-2-yl)benzenesulfonamide
175. 4-(1-(1-cyclopropylethyl)-3-methyl-1H-pyrazol-5-ylamino)-2-fluoro-N-(thiazol-2-yl)benzenesulfonamide
176. 2-fluoro-4-(3-methyl-1-m-tolyl-1H-pyrazol-5-ylamino)-N-(thiazol-2-yl)benzenesulfonamide
177. 2-fluoro-4-(1-(3-fluorophenyl)-3-methyl-1H-pyrazol-5-ylamino)-N-(thiazol-2-yl)benzenesulfonamide
178. 2-fluoro-4-(1-(4-fluorophenyl)-3-methyl-1H-pyrazol-5-ylamino)-N-(thiazol-2-yl)benzenesulfonamide
179. 2-fluoro-4-(3-methyl-1-(2-(trifluoromethyl)phenyl)-1H-pyrazol-5-ylamino)-N-(thiazol-2-yl)benzenesulfonamide
180. 4-(4-cyano-1-phenyl-1H-pyrazol-3-ylamino)-2-fluoro-N-(thiazol-2-yl)benzenesulfonamide
181. 2-fluoro-4-(3-methyl-1-(3-(trifluoromethyl)phenyl)-1H-pyrazol-5-ylamino)-N-(thiazol-2-yl)benzenesulfonamide
182. 4-(1-(2-chloro-4-fluorophenyl)-3-methyl-1H-pyrazol-5-ylamino)-2-fluoro-N-(thiazol-2-yl)benzenesulfonamide
183. 2-fluoro-N-(thiazol-2-yl)-4-(1-(4-(trifluoromethyl)benzyl)-1H-pyrazol-3-ylamino)benzenesulfonamide

TABLE II-continued 184. 4-(1-(4-chlorobenzyl)-1H-pyrazol-3-ylamino)-3-fluoro-N-(thiazol-2-yl)benzenesulfonamide
185. 3-fluoro-N-(thiazol-2-yl)-4-(1-(4-(trifluoromethyl)benzyl)-1H-pyrazol-3-ylamino)benzenesulfonamide
186. 2-fluoro-4-(1-(5-fluoro-2-methylphenyl)-3-methyl-1H-pyrazol-5-ylamino)-N-(thiazol-2-yl)benzenesulfonamide
187. 2-fluoro-4-(1-(4-fluoro-2-(trifluoromethyl)phenyl)-3-methyl-1H-pyrazol-5-ylamino)-N-(thiazol-2-yl)benzenesulfonamide
188. 2-fluoro-4-(1-(2-methoxyphenyl)-3-methyl-1H-pyrazol-5-ylamino)-N-(thiazol-2-yl)benzenesulfonamide
189. 4-(1-(2,6-dichlorophenyl)-3-methyl-1H-pyrazol-5-ylamino)-2-fluoro-N-(thiazol-2-yl)benzenesulfonamide
190. 4-(1-(2,6-difluorophenyl)-3-methyl-1H-pyrazol-5-ylamino)-2-fluoro-N-(thiazol-2-yl)benzenesulfonamide
191. 4-(1-(2,6-dimethylphenyl)-3-methyl-1H-pyrazol-5-ylamino)-2-fluoro-N-(thiazol-2-yl)benzenesulfonamide
192. 4-(1-tert-butyl-3-methyl-1H-pyrazol-5-ylamino)-2-fluoro-N-(thiazol-2-yl)benzenesulfonamide
193. 4-(3-tert-butyl-1-methyl-1H-pyrazol-5-ylamino)-2-fluoro-N-(thiazol-2-yl)benzenesulfonamide
194. 4-(1-tert-butyl-3-(3-chlorobenzyl)-1H-pyrazol-5-ylamino)-N-(thiazol-2-yl)benzenesulfonamide
195. 4-(1-tert-butyl-3-(3-chlorobenzyl)-1H-pyrazol-5-ylamino)-3-fluoro-N-(thiazol-2-yl)benzenesulfonamide
196. 4-(3-(4-chloro-3-fluorobenzyl)-1-methyl-1H-pyrazol-5-ylamino)-N-(thiazol-2-yl)benzenesulfonamide
197. 4-(1-(4-chloro-2-fluorobenzyl)-1H-pyrazol-3-ylamino)-2-fluoro-N-(thiazol-2-yl)benzenesulfonamide
198. 4-(1-(4-chloro-2-fluorobenzyl)-1H-pyrazol-3-ylamino)-3-fluoro-N-(thiazol-2-yl)benzenesulfonamide
199. 4-(1-(4-chlorobenzyl)-1H-1,2,4-triazol-3-ylamino)-3-fluoro-N-(thiazol-2-yl)benzenesulfonamide
200. 3-fluoro-N-(thiazol-2-yl)-4-(1-(3-(trifluoromethyl)benzyl)-1H-1,2,4-triazol-3-ylamino)benzenesulfonamide
201. 4-(1-(3-chlorobenzyl)-1H-1,2,4-triazol-3-ylamino)-3-fluoro-N-(thiazol-2-yl)benzenesulfonamide
202. 2-fluoro-4-(3-methyl-1-(1-methylpiperidin-4-yl)-1H-pyrazol-5-ylamino)-N-(thiazol-2-yl)benzenesulfonamide
203. 3-fluoro-4-(1-(2-fluorophenyl)-3-methyl-1H-pyrazol-5-ylamino)-N-(thiazol-2-yl)benzenesulfonamide
204. 2-fluoro-4-(1-(2-fluorophenyl)-3-(2,2,2-trifluoroethyl)-1H-pyrazol-5-ylamino)-N-(thiazol-2-yl)benzenesulfonamide
205. 3-chloro-4-(1-(4-chlorobenzyl)-1H-pyrazol-3-ylamino)-N-(thiazol-2-yl)benzenesulfonamide
206. 4-(1-(4-chlorobenzyl)-1H-pyrazol-3-ylamino)-2,5-difluoro-N-(thiazol-2-yl)benzenesulfonamide
207. 4-(1-(2-chloro-4-fluorobenzyl)-1H-1,2,4-triazol-3-ylamino)-3-fluoro-N-(thiazol-2-yl)benzenesulfonamide
208. 4-(1-(2-chlorobenzyl)-1H-1,2,4-triazol-3-ylamino)-3-fluoro-N-(thiazol-2-yl)benzenesulfonamide
209. 4-(3-(4-chloro-3-fluorobenzyl)-1-methyl-1H-pyrazol-5-ylamino)-3-fluoro-N-(thiazol-2-yl)benzenesulfonamide
210. 4-(3-(4-chloro-3-fluorobenzyl)-1-methyl-1H-pyrazol-5-ylamino)-2-fluoro-N-(thiazol-2-yl)benzenesulfonamide
211. 4-(1-benzyl-1H-pyrazol-3-ylamino)-2-fluoro-N-(thiazol-2-yl)benzenesulfonamide
212. 4-(1-(4-chlorobenzyl)-1H-pyrazol-3-ylamino)-N-(thiazol-2-yl)-2-(trifluoromethyl)benzenesulfonamide
213. 2-(5-(3-fluoro-4-(N-thiazol-2-ylsulfamoyl)phenylamino)-1-phenyl-1H-pyrazol-3-yl)-N,N-dimethylethanamide
214. 4-(3-tert-butyl-1-(2-methoxyphenyl)-1H-pyrazol-5-ylamino)-2-fluoro-N-(thiazol-2-yl)benzenesulfonamide
215. 3-fluoro-4-(1-(2-methoxyphenyl)-3-methyl-1H-pyrazol-5-ylamino)-N-(thiazol-2-yl)benzenesulfonamide
216. N,N-diethyl-2-(5-(3-fluoro-4-(N-thiazol-2-ylsulfamoyl)phenylamino)-1-phenyl-1H-pyrazol-3-yl)ethanamide
217. 2-fluoro-4-(1-(4-fluorobenzyl)-1H-pyrazol-3-ylamino)-N-(thiazol-2-yl)benzenesulfonamide
218. 4-(3-(3-chlorobenzyl)-1-methyl-1H-pyrazol-5-ylamino)-N-(thiazol-2-yl)benzenesulfonamide
219. 4-(3-(3-chlorobenzyl)-1-methyl-1H-pyrazol-5-ylamino)-3-fluoro-N-(thiazol-2-yl)benzenesulfonamide
220. 2-fluoro-4-(1-(3-methoxyphenyl)-3-methyl-1H-pyrazol-5-ylamino)-N-(thiazol-2-yl)benzenesulfonamide
221. 1-(4-chlorobenzyl)-3-(3-fluoro-4-(N-thiazol-2-ylsulfamoyl)phenylamino)-1H-pyrazole-4-carboxamide
222. 4-(3-(4-chloro-2-methoxyphenyl)-1-methyl-1H-pyrazol-5-ylamino)-2-fluoro-N-(thiazol-2-yl)benzenesulfonamide
223. 2-fluoro-4-(3-(2-methoxyphenyl)-1-methyl-1H-pyrazol-5-ylamino)-N-(thiazol-2-yl)benzenesulfonamide TABLE II-continued 224. 2-fluoro-4-(1-(4-methoxybenzyl)-1H-pyrazol-3-ylamino)-N-(thiazol-2-yl)benzenesulfonamide
225. 4-(1-(4-chlorobenzyl)-3,5-dimethyl-1H-pyrazol-4-ylamino)-2-fluoro-N-(thiazol-2-yl)benzenesulfonamide
226. 3-fluoro-4-(1-(4-fluorobenzyl)-1H-pyrazol-3-ylamino)-N-(thiazol-2-yl)benzenesulfonamide
227. 6-(1-(4-chlorobenzyl)-1H-pyrazol-3-ylamino)-N-(thiazol-2-yl)pyridine-3-sulfonamide
228. 6-(1-(4-chlorobenzyl)-1H-pyrazol-4-ylamino)-N-(thiazol-2-yl)pyridine-3-sulfonamide
229. 4-(1-(4-chloro-3-(trifluoromethyl)benzyl)-1H-pyrazol-4-ylamino)-2-fluoro-N-(thiazol-2-yl)benzenesulfonamide
230. 2-fluoro-4-(1-(2-methoxy-5-(trifluoromethoxy)benzyl)-1H-pyrazol-4-ylamino)-N-(thiazol-2-yl)benzenesulfonamide
231. 5-(1-(4-chlorobenzyl)-1H-pyrazol-4-ylamino)-N-(thiazol-2-yl)pyridine-2-sulfonamide
232. 4-(1-(4-chlorobenzyl)-1H-pyrazol-3-ylamino)-2-fluoro-N-(1,3,4-thiadiazol-2-yl)benzenesulfonamide
234. 5-(3-methyl-1-phenyl-1H-pyrazol-5-ylamino)-N-(thiazol-2-yl)pyridine-2-sulfonamide
235. 5-(1-(4-chlorobenzyl)-1H-pyrazol-3-ylamino)-N-(thiazol-2-yl)pyridine-2-sulfonamide
236. 2-fluoro-N-(3-methyl-1,2,4-thiadiazol-5-yl)-4-(3-methyl-1-phenyl-1H-pyrazol-5-ylamino)benzenesulfonamide
237. 2-fluoro-N-(5-methyl-1,3,4-oxadiazol-2-yl)-4-(3-methyl-1-phenyl-1H-pyrazol-5-ylamino)benzenesulfonamide
238. 2-fluoro-4-(3-methyl-1-phenyl-1H-pyrazol-5-ylamino)-N-(1,3,4-thiadiazol-2-yl)benzenesulfonamide
239. 2-fluoro-4-(3-methyl-1-phenyl-1H-pyrazol-5-ylamino)-N-(5-methylthiazol-2-yl)benzenesulfonamide
240. 2-fluoro-4-(3-methyl-1-phenyl-1H-pyrazol-5-ylamino)-N-(1,2,4-thiadiazol-5-yl)benzenesulfonamide
241. 2-fluoro-4-(3-methyl-1-phenyl-1H-pyrazol-5-ylamino)-N-(5-phenyl-1,3,4-thiadiazol-2-yl)benzenesulfonamide
243. 4-(1-(4-chlorobenzyl)-1H-pyrazol-3-ylamino)-2-fluoro-N-(5-(trifluoromethyl)-1,3,4-thiadiazol-2-yl)benzenesulfonamide
244. 4-(1-(4-chlorobenzyl)-1H-pyrazol-3-ylamino)-2-fluoro-N-(1,2,4-thiadiazol-5-yl)benzenesulfonamide
245. N-(5-cyanothiazol-2-yl)-2-fluoro-4-(3-methyl-1-phenyl-1H-pyrazol-5-ylamino)benzenesulfonamide
246. N-(5-ethyl-1,3,4-thiadiazol-2-yl)-2-fluoro-4-(3-methyl-1-phenyl-1H-pyrazol-5-ylamino)benzenesulfonamide
247. 2-fluoro-N-(5-methyl-1,3,4-thiadiazol-2-yl)-4-(3-methyl-1-phenyl-1H-pyrazol-5-ylamino)benzenesulfonamide
248. N-(5-(difluoromethyl)-1,3,4-thiadiazol-2-yl)-2-fluoro-4-(3-methyl-1-phenyl-1H-pyrazol-5-ylamino)benzenesulfonamide
249. 2-fluoro-N-(5-(methoxymethyl)-1,3,4-thiadiazol-2-yl)-4-(3-methyl-1-phenyl-1H-pyrazol-5-ylamino)benzenesulfonamide
250. N-(5-cyclopropyl-1,3,4-thiadiazol-2-yl)-2-fluoro-4-(3-methyl-1-phenyl-1H-pyrazol-5-ylamino)benzenesulfonamide
251. 4-(1-(4-chlorobenzyl)-1H-pyrazol-3-ylamino)-2-fluoro-N-(5-methyl-1,3,4-thiadiazol-2-yl)benzenesulfonamide
252. 2-fluoro-N-(5-isopropyl-1,3,4-thiadiazol-2-yl)-4-(3-methyl-1-phenyl-1H-pyrazol-5-ylamino)benzenesulfonamide
253. 4-(1-(4-chlorobenzyl)-1H-pyrazol-3-ylamino)-N-(5-cyclopropyl-1,3,4-thiadiazol-2-yl)-2-fluorobenzenesulfonamide
254. 4-(1-(4-chlorobenzyl)-1H-pyrazol-3-ylamino)-2-fluoro-N-(5-(methoxymethyl)-1,3,4-thiadiazol-2-yl)benzenesulfonamide
255. 4-(1-(4-chlorobenzyl)-1H-pyrazol-3-ylamino)-N-(5-ethyl-1,3,4-thiadiazol-2-yl)-2-fluorobenzenesulfonamide
256. 4-(1-(4-chlorobenzyl)-1H-pyrazol-3-ylamino)-2-fluoro-N-(5-isopropyl-1,3,4-thiadiazol-2-yl)benzenesulfonamide
257. 4-(4-(4-chlorobenzyl)thiazol-2-ylamino)-N-(4-(trifluoromethyl)thiazol-2-yl)benzenesulfonamide
258. 4-(4-(4-chlorobenzyl)thiazol-2-ylamino)-N-(4-(trifluoromethyl)oxazol-2-yl)benzenesulfonamide
259. 4-(1-(4-chlorobenzyl)-1H-pyrazol-3-ylamino)-2-fluoro-N-(6-methylpyridin-2-yl)benzenesulfonamide
260. 4-(1-(4-chlorobenzyl)-1H-pyrazol-3-ylamino)-2-fluoro-N-(pyridazin-3-yl)benzenesulfonamide
261. 4-(1-(4-chlorobenzyl)-1H-pyrazol-3-ylamino)-2-fluoro-N-(5-methyl-1,3,4-oxadiazol-2-yl)benzenesulfonamide
262. 4-(1-(4-chlorobenzyl)-1H-pyrazol-3-ylamino)-2-fluoro-N-(pyrimidin-4-yl)benzenesulfonamide
263. 2-chloro-4-(1-(4-chlorobenzyl)-1H-pyrazol-3-ylamino)-N-(thiazol-2-yl)benzenesulfonamide
264. 4-(1-(4-chlorobenzyl)-1H-pyrazol-3-ylamino)-2-cyano-N-(thiazol-2-yl)benzenesulfonamide
265. 4-(1-(4-chlorobenzyl)-1H-pyrazol-3-ylamino)-N-(1,3,4-thiadiazol-2-yl)-2-(trifluoromethyl)benzenesulfonamide

TABLE II-continued 266. 4-(1-(4-chlorobenzyl)-1H-pyrazol-3-ylamino)-N-(thiazol-2-yl)-2-(trifluoromethoxy)benzenesulfonamide
267. 2,5-difluoro-4-(3-methyl-1-phenyl-1H-pyrazol-5-ylamino)-N-(thiazol-2-yl)benzenesulfonamide
268. 2-methyl-4-(3-methyl-1-phenyl-1H-pyrazol-5-ylamino)-N-(thiazol-2-yl)benzenesulfonamide
269. 4-(1-(4-chlorobenzyl)-1H-pyrazol-3-ylamino)-2-fluoro-5-methyl-N-(thiazol-2-yl)benzenesulfonamide
270. 4-(3-methyl-1-phenyl-1H-pyrazol-5-ylamino)-N-(thiazol-2-yl)-2-(trifluoromethoxy)benzenesulfonamide
271. 4-(1-(4-chlorobenzyl)-1H-pyrazol-3-ylamino)-2-methyl-N-(thiazol-2-yl)benzenesulfonamide
272. 4-(3-methyl-1-phenyl-1H-pyrazol-5-ylamino)-N-(thiazol-2-yl)-2-(trifluoromethyl)benzenesulfonamide
273. 3-cyano-4-(5-hydroxy-6-phenyl-1,2,4-triazin-3-ylamino)-N-(1,2,4-thiadiazol-5-yl)benzenesulfonamide
274. N-(thiazol-2-yl)-1-(4-(trifluoromethoxy)benzyl)-1H-indazole-5-sulfonamide
275. N-(thiazol-2-yl)-2-(4-(trifluoromethoxy)benzyl)-2H-indazole-5-sulfonamide
276. 1-(2-(2,4-dimethoxyphenyl)-2-oxoethyl)-N-(thiazol-2-yl)-1H-indazole-5-sulfonamide
277. 2-(2-(2,4-dimethoxyphenyl)-2-oxoethyl)-N-(thiazol-2-yl)-2H-indazole-5-sulfonamide
278. 1-(4-phenylbutyl)-N-(thiazol-2-yl)-1H-indazole-5-sulfonamide
279. 2-(4-phenylbutyl)-N-(thiazol-2-yl)-2H-indazole-5-sulfonamide
280. 1-(2-(4-fluorophenyl)-2-oxoethyl)-N-(thiazol-2-yl)-1H-indazole-5-sulfonamide The compounds set forth in Table II can be prepared by the methods described in Schemes A, A-1, B, B-1, B-2 and C to J.

Excluded from the above generic formula, as well as each of the formulae below, are those compounds are either commercially available or known in the literature, including: ethyl 2-methyl-5-oxo-1-phenyl-4-(4-(N-thiazol-2-ylsulfamoyl)phenylamino)-2,5-dihydro-1H-pyrrole-2-carboxylate (38); 4-(4-methylphthalazin-1-ylamino)-N-(thiazol-2-yl)benzenesulfonamide (39); 4-(4-(4-chlorophenyl)phthalazin-1-ylamino)-N-(thiazol-2-yl)benzenesulfonamide (40); N-(thiazol-2-yl)-4-(4-p-tolylphthalazin-1-ylamino)benzenesulfonamide (41); and 4-(4-phenylphthalazin-1-ylamino)-N-(thiazol-2-yl)benzenesulfonamide (42).

Accordingly, in a first set of embodiments, the invention provides a compound of formula II:

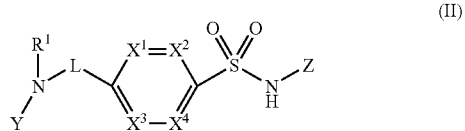

(II)

or a pharmaceutically acceptable salt or solvate thereof;
Z is selected from the group consisting of 5-membered heteroaryl having from 1 to 4 heteroatoms as ring members selected from N, O or S and 6-membered heteroaryl having from 1 to 3 nitrogen heteroatoms as ring members;
Y is selected from the group consisting of 5-membered heteroaryl having from 1 to 4 heteroatoms as ring members selected from N, O or S, 6-membered heteroaryl having from 1 to 3 nitrogen heteroatoms as ring members, and aryl optionally fused with a 5-membered heteroaryl having 1 to 2 heteroatoms as ring members selected from O, N or S; or Y and $X^1$ are taken together to form a 5-membered fused heteroaryl ring having from 0-2 additional nitrogen atoms as ring members and $R^1$ is a lone pair, wherein the fused heteroaryl ring is optionally substituted with a $R^b$ group; wherein the heteroaryl and aryl of Y and Z substituents are each optionally substituted with from 1 to 3 $R^a$ substituents, at each occurrence, each $R^a$ is independently selected from the group consisting of $C_{1-8}$alkyl-NH—, $(C_{1-8}$alkyl$)_2$N—, aryl, $R^b$, $C_{1-8}$haloalkyl, aryl-$C_{3-8}$cycloalkyl, $C_{3-8}$cycloalkyl, heterocycloalkyl, arylsulfonyl, arylsulfinyl and $R^f$, wherein $R^b$ is $C_{1-8}$alkyl optionally substituted with from 1-3 members independently selected from the group consisting of aryl, aryl-(CO)—, aryloxy, $(R^c)(R^d)$N—, $C_{3-5}$cycloalkyl, hetero-$C_{4-5}$cycloalkyl, arylthio and heteroaryl; wherein $R^c$ is —H or $C_{1-6}$alkyl and $R^d$ is $C_{3-7}$cycloalkyl or $C_{1-8}$alkyl optionally substituted with from 1-2 aryl groups, or optionally $R^c$ and $R^d$ together with the nitrogen atom to which they are attached form a 5 or 6-membered ring having 0-2 additional heteroatoms as ring members selected from N, O or S; wherein the aryl portion of each $R^a$ substituent is further optionally substituted with from 1-3 substituents independently selected from the group consisting of $C_{1-4}$haloalkyl, $C_{1-4}$haloalkoxy and $R^f$, and the heterocycloalkyl of the $R^b$ group is further optionally substituted with a hetero-$C_{4-5}$cycloalkyl-$C_{1-6}$alkyl; or any two adjacent $R^a$ substituents together with the atoms to which they are attached form a 5- or 6-membered carbocyclic ring, wherein 1-2 ring carbon atoms of the carbocyclic ring are optionally replaced by a carbonyl and the carbocyclic ring is optionally substituted with 1-2 members independently selected from an halogen, aryl or $C_{1-8}$alkyl; wherein $R^f$ is halogen, —OH, —$OR^g$, —OC(O)O—$R^g$, —OC(O)$R^g$, —OC(O)NH$R^g$, —OC(O)N($R^g$)$_2$, —SH, —S$R^g$, —S(O)$R^g$, —S(O)$_2R^g$, —SO$_2$NH$_2$, —S(O)$_2$NH$R^g$, —S(O)$_2$N($R^g$)$_2$, —NHS(O)$_2R^g$, —$R^g$S(O)$_2R^g$, —C(O)NH$_2$, —C(O)NH$R^g$, —C(O)N($R^g$)$_2$, —C(O)$R^g$, —C(O)H, —C(=S)$R^g$, —NHC(O)$R^g$, —$NR^g$C(O)$R^g$, —NHC(O)NH$_2$, —$NR^g$C(O)NH$_2$, —$NR^g$C(O)NH$R^g$, —NHC(O)NH$R^g$, —$NR^g$C(O)N($R^g$)$_2$, —NHC(O)N($R^g$)$_2$, —CO$_2$H, —CO$_2R^g$, —NHCO$_2R^g$, —$NR^g$CO$_2R^g$, —CN, —NO$_2$, —NH$_2$, —$NR^g$S(O)NH$_2$, —$NR^g$S(O)$_2$NH$R^g$, —NHC(=$NR^g$)NH$_2$, —N=C(NH$_2$)NH$_2$, —C(=$NR^g$)NH$_2$, —NH—OH, —$NR^g$—OH, —$NR^g$—$OR^g$, —N=C=O and —N=C=S; wherein each $R^g$ is independently a $C_{1-8}$alkyl;
$X^1$, $X^2$, $X^3$ and $X^4$ are each independently —N=, or C($R^2$)=, wherein $R^2$ is selected from the group consisting of —H, halogen, $C_{1-8}$alkyl, —CN, —OH, $C_{1-6}$haloalkyl and $C_{1-6}$haloalkoxy; or any two adjacent $R^2$ substituents together with the atoms to which they are attached form a fused benzene ring, optionally substituted with a $C_{1-6}$alkyl, with the proviso that not more than three of $X^1$, $X^2$, $X^3$ and $X^4$ are —N=;
L is a bond or i) L, the aromatic carbon atom to which L is attached, and $X^1$ taken together form a fused 5- or 6-membered carbocyclic ring, wherein 1-2 ring carbon atoms of the fused carbocyclic ring are optionally replaced with —C(O)— or —S(O)$_2$— group; or ii) L, the two atoms to which L is attached, and $X^1$ taken together form a 5- or 6-membered fused heterocyclic ring having from 0-2 additional heteroatoms selected from N, O or S, wherein 1-2 ring carbon atoms of the fused heterocyclic ring are optionally replaced with —C(O)— or —S(O)$_2$— group;
$R^1$ is —H, a lone pair or $C_{1-8}$alkyl; with the proviso that the compound is other than 4-(4-methylphthalazin-1-ylamino)-N-(thiazol-2-yl)benzenesulfonamide; 4-(4-(4-chlorophenyl) phthalazin-1-ylamino)-N-(thiazol-2-yl)benzenesulfonamide; N-(thiazol-2-yl)-4-(4-p-tolylphthalazin-1-ylamino) benzenesulfonamide; and 4-(4-phenylphthalazin-1-ylamino)-N-(thiazol-2-yl)benzenesulfonamide; and
at each occurrence, alkyl by itself or as part of another substituent, is an unsubstituted, fully saturated, straight or branched chain hydrocarbon radical; at each occurrence, cycloalkyl by itself or as part of another substituent is an unsubstituted, fully saturated, cyclic hydrocarbon radical; and at each occurrence, aryl by itself or as part of another substituent is a monovalent monocyclic, bicyclic or polycyclic polyunsaturated aromatic hydrocarbon radical.

In a second set of embodiments, the invention provides compounds of the first set, wherein Z is selected from the group consisting of: i) 5-membered heteroaryl having from 1-3 heteroatoms as ring members selected from N, O or S, wherein the heteroaryl is optionally substituted with from 1 to 2 substituents selected from the group consisting of $C_{1-8}$haloalkyl, —CN, halogen, $C_{3-7}$cycloalkyl, aryl, $C_{1-8}$alkyl, aryl-NH—$C_{1-6}$alkyl and $C_{1-8}$alkoxy-$C_{1-4}$alkyl; and ii) 6-membered heteroaryl having from 1-2 nitrogen atoms as ring members, wherein the heteroaryl is optionally substituted with 1-3 $C_{1-8}$alkyl; and $X^1$, $X^2$, $X^3$ and $X^4$ are each independently —N=, or C($R^2$)=, wherein $R^2$ is selected from the group consisting of —H, halogen, $C_{1-8}$alkyl, —CN, —OH, $C_{1-6}$haloalkyl and $C_{1-6}$haloalkoxy; or any two adjacent $R^2$ substituents together with the atoms to which they are attached form a fused benzene ring, optionally substituted with a $C_{1-6}$alkyl, with the proviso that not more than three of $X^1$, $X^2$, $X^3$ and $X^4$ are —N=; L is a bond or i) L, the aromatic carbon atom to which L is attached, and $X^1$ taken together form a fused 5- or 6-membered carbocyclic ring, wherein 1-2 ring carbon atoms of the fused carbocyclic ring are optionally replaced with —C(O)— or —S(O)$_2$— group; or ii) L, the two atoms to which L is attached, and $X^1$ taken together form a 5- or 6-membered fused heterocyclic ring having from 0-2 additional heteroatoms selected from N, O or S, wherein the fused heterocyclic ring is optionally substituted with a $R^b$ group and 1-2 ring carbon atoms of the fused heterocyclic ring are optionally replaced with —C(O)— or —S(O)$_2$— group; Y is selected from the group consisting of: i) 5-membered heteroaryl having from 1-4 heteroatoms as ring members selected from N, O or S, wherein the heteroaryl is optionally substituted with 1-3 $R^a$ members, at each occurrence, each $R^a$ is independently selected from the group consisting of $C_{1-8}$alkyl-NH—, ($C_{1-8}$alkyl)$_2$N—, aryl, $R^b$, $C_{1-8}$haloalkyl, aryl-$C_{3-8}$cycloalkyl, $C_{3-5}$cycloalkyl, heterocycloalkyl, arylsulfonyl, arylsulfinyl and $R^f$, wherein $R^b$ is $C_{1-8}$alkyl optionally substituted with from 1-3 members independently selected from the group consisting of aryl, aryl-(CO)—, aryloxy, ($R^c$)($R^d$)N—, $C_{3-5}$cycloalkyl, hetero-$C_{4-5}$cycloalkyl, arylthio and heteroaryl; wherein $R^c$ is —H or $C_{1-6}$alkyl and $R^d$ is $C_{3-7}$cycloalkyl or $C_{1-8}$alkyl optionally substituted with from 1-2 aryl groups; wherein the aryl portion of each $R^a$ substituent is further optionally substituted with from 1-3 substituents independently selected from the group consisting of $C_{1-4}$haloalkyl, $C_{1-4}$haloalkoxy and $R^f$, and the heterocycloalkyl of the $R^b$ group is further optionally substituted with a hetero-$C_{4-5}$cycloalkyl-$C_{1-6}$alkyl; or any two adjacent $R^a$ substituents together with the atoms to which they are attached form a 5- or 6-membered carbocyclic ring, wherein 1-2 ring carbon atoms of the carbocyclic ring are optionally replaced by a carbonyl and the carbocyclic ring is optionally substituted with 1-2 members independently selected from an halogen, aryl or $C_{1-8}$alkyl; wherein $R^f$ is halogen, —OH, —O$R^g$, —OC(O)O—$R^g$, —OC(O)$R^g$, —OC(O)NH$R^g$, —OC(O)N($R^g$)$_2$, —SH, —S$R^g$, —S(O)$R^g$, —S(O)$_2R^g$, —SO$_2$NH$_2$, —S(O)$_2$NH$R^g$, —S(O)$_2$N($R^g$)$_2$, —NHS(O)$_2R^g$, —N$R^g$S(O)$_2R^g$, —C(O)NH$_2$, —C(O)NH$R^g$, —C(O)N($R^g$)$_2$, —C(O)$R^g$, —C(O)H, —C(=S)$R^g$, —NHC(O)$R^g$, —N$R^g$C (O)$R^g$, —NHC(O)NH$_2$, —N$R^g$C(O)NH$_2$, —N$R^g$C(O) NH$R^g$, —NHC(O)NH$R^g$, —N$R^g$C(O)N($R^g$)$_2$, —NHC(O)N ($R^g$)$_2$, —CO$_2$H, —CO$_2R^g$, —NHCO$_2R^g$, —N$R^g$CO$_2R^g$, —CN, —NO$_2$, —NH$_2$, —N$R^g$S(O)NH$_2$, —N$R^g$S(O)$_2$NH$R^g$, —NH$_2$C(=N$R^g$)NH$_2$, —N=C(NH$_2$)NH$_2$, —C(=N$R^g$)NH$_2$, —NH—OH, —N$R^g$—OH, —N$R^g$—O$R^g$, —N=C=O and —N=C=S; wherein each $R^g$ is independently a $C_{1-8}$alkyl. ii) 6-member heteroaryl having from 1-3 nitrogen atoms as ring members, wherein the heteroaryl is optionally substituted with 1-3 $R^e$ substituents independently selected from the group consisting of —OH, aryl, aryl-$C_{1-6}$alkyl, aryl-$C_{1-6}$alkoxy, $C_{3-6}$cycloalkyl-$C_{1-6}$alkoxy and $C_{1-8}$alkoxy, wherein the aliphatic portion of the $R^e$ group is further optionally substituted with an aryl and the aromatic portion of the $R^e$ group is further optionally substituted with from 1-2 members independently selected from $C_{1-6}$haloalkyl, halogen or $C_{1-6}$alkyl; or any two adjacent $R^e$ substituents together with the atoms to which they are attached form a 6-membered fused benzene ring, optionally substituted with a halogen or $C_{1-6}$ alkyl; and iii) aryl optionally substituted with an aryl or $C_{1-6}$alkyl; and $R^1$ is —H or $C_{1-6}$alkyl.

In a third set of embodiments, the invention provides compounds of the second set wherein L is a bond and Y is selected from the group consisting of:
i) 5-membered heteroaryl having from 1-4 heteroatoms as ring members selected from N, O or S, wherein the heteroaryl is optionally substituted with 1-3 $R^a$ members, at each occurrence, each $R^a$ is independently selected from the group consisting of —NH$_2$, $C_{1-8}$alkyl-NH—, ($C_{1-8}$alkyl)$_2$N—, aryl, $R^b$, $C_{1-8}$haloalkyl, aryl-$C_{3-8}$cycloalkyl, $C_{3-5}$cycloalkyl, heterocycloalkyl, arylsulfonyl, arylsulfinyl, NH$_2$C(O)—, ($C_{1-8}$alkyl) (H)NC(O)—, ($C_{1-8}$alkyl)$_2$NC(O)—, $C_{1-8}$alkylcarbonyl and $C_{1-8}$alkoxycarbonyl, wherein $R^b$ is $C_{1-8}$alkyl optionally substituted with from 1-2 members independently selected from the group consisting of aryl, aryl-(CO)—, aryloxy, ($R^c$)($R^d$) N—, $C_{3-5}$cycloalkyl, hetero-$C_{4-5}$cycloalkyl, arylthio and heteroaryl; wherein $R^c$ is —H or $C_{1-6}$alkyl and $R^d$ is $C_{3-7}$cycloalkyl or $C_{1-8}$alkyl optionally substituted with from 1-2 aryl groups; wherein the aryl portion of each $R^a$ substituent is further optionally substituted with from 1-3 substituents independently selected from the group consisting of halogen, $C_{1-4}$haloalkyl, $C_{1-4}$haloalkoxy, $C_{1-4}$alkoxy, —CN, $C_{1-4}$alkylsulfonyl, OH and —NO$_2$; and the heterocycloalkyl of the $R^b$ group is further optionally substituted with a hetero-$C_{4-5}$cycloalkyl-$C_{1-6}$alkyl; or any two adjacent $R^a$ substituents together with the atoms to which they are attached form a 5- or 6-membered carbocyclic ring, wherein one of the ring carbon atom of the carbocyclic ring is optionally replaced by a carbonyl and the carbocyclic ring is optionally substituted with 1-2 members independently selected from an halogen, aryl or $C_{1-8}$alkyl;

ii) 6-member heteroaryl having from 1-3 nitrogen atoms as ring members, wherein the heteroaryl is optionally substituted with 1-3 $R^e$ substituents independently selected from the group consisting of —OH, aryl, aryl-$C_{1-6}$alkyl, aryl-$C_{1-6}$alkoxy, $C_{3-6}$cycloalkyl-$C_{1-6}$alkoxy and $C_{1-8}$alkoxy, wherein the aliphatic portion of the $R^e$ group is further optionally substituted with an aryl and the aromatic portion of the $R^e$ group is further optionally substituted with from 1-2 members independently selected from $C_{1-6}$haloalkyl, halogen or $C_{1-6}$alkyl; or any two adjacent $R^e$ substituents together with the atoms to which they are attached form a 6-membered fused benzene ring, optionally substituted with a halogen or $C_{1-6}$ alkyl; and iii) aryl optionally substituted with an aryl or $C_{1-6}$alkyl.

In a fourth set of embodiments, the invention provides compounds of the first, second or third sets wherein $R^1$ is —H.

In a fifth set of embodiments, the invention provides compounds of the first, second, third or fourth sets wherein Z is a 5-membered heteroaryl having from 1-3 heteroatoms as ring members selected from N, O or S, wherein the heteroaryl is optionally substituted with a member selected from the group consisting of $C_{1-8}$haloalkyl, —CN, halogen, $C_{3-7}$cycloalkyl, aryl, $C_{1-8}$alkyl, aryl-NH—$C_{1-6}$alkyl and $C_{1-8}$alkoxy-$C_{1-4}$alkyl.

In a further sixth set of embodiments, the invention provides a compound of the fourth set wherein Z is selected from the group consisting of thiazolyl, isothiazolyl, isoxazoly, oxazolyl, 1,3,4-thiadiazoly, 1,2,3-thiadiazoly, 1,2,4-thiadiazoly, 1,3,4-oxadiazoly, 1,2,3-oxadiazoly, 1,2,4-oxadiazoly, 1,2,5-thiadiazolyl, pyrazolyl, 1,2,5-oxadiazolyl, 1,2,3,5-thiatriazolyl, 1,2,3,4-thiatriazolyl, 1,2,3,5-oxatriazolyl, 1,2,3,4-oxatriazolyl and imidazoly, each of which is optionally substituted with a member selected from the group consisting of $C_{1-8}$haloalkyl, —CN, halogen, $C_{3-7}$cycloalkyl, aryl, $C_{1-8}$alkyl, aryl-NH—$C_{1-6}$alkyl and $C_{1-8}$alkoxy-$C_{1-4}$alkyl.

In a 7th set of embodiments, the invention provides a compound of the fourth set wherein Z is selected from the group consisting of thiazol-2-yl, 4-thiazolyl, 5-thiazolyl, isoxazol-3-yl, 2-oxazolyl, 1,3,4-thiadiazol-2-yl, 1,2,3-thiadiazol-4-yl, 1,2,3-thiadiazol-5-yl, 1,2,4-thiazol-3-yl, 1,2,4-thiadiazol-5-yl, 1,3,4-oxadiazol-2yl, 1,2,5-thiadiazol-4-yl, pyrazolyl, 1,2,5-oxadiazol-4-yl, 1,2,3,5-thiatriazol-4-yl, 1,2,3,4-thiatriazol-5-yl, 1,2,3,5-oxatriazol-4-yl, 1,2,3,4-oxatriazol-5-yl and 2-imidazolyl, each of which is optionally substituted with a member selected from the group consisting of $C_{1-8}$haloalkyl, —CN, halogen, $C_{3-7}$cycloalkyl, aryl, $C_{1-8}$alkyl, aryl-NH— $C_{1-6}$alkyl and $C_{1-8}$alkoxy-$C_{1-4}$alkyl.

In an 8th set of embodiments, the invention provides a compound of the fourth set, wherein Z is substituted with a member selected from the group consisting of 3-chloropropyl, phenylaminomethyl, —CH₃, CH₂CH₃, —Cl, —CF₃, —CF₂H, CH₃OCH₂—, cyclopropyl, isopropyl and —CN.

In a 9th set of embodiments, the invention provides a compound of the fourth set, wherein Z is 6-membered heteroaryl having from 1-2 nitrogen atoms as ring members, wherein the heteroaryl is optionally substituted with 1-3 $C_{1-8}$alkyl.

In a 10th set of embodiments, the invention provides a compound of the ninth set wherein Z is selected from the group consisting of pyridyl, pyridazinyl, primidinyl or pyrizinyl, each of which is optionally substituted with from 1-3 $C_{1-6}$alkyl.

In an 11th set of embodiments, the invention provides a compound of the fourth set, wherein Z is selected from the group consisting of 2-pyridyl, 3-pyridazinyl, 4-primidinyl and 2-pyrizinyl, each of which is optionally substituted with from 1-3 $C_{1-6}$alkyl.

In a 12th set of embodiments, the invention provides a compound of the fourth set, the invention provides a compound of any one of sets 1, 2, 3, 4, 5, 6, 7, 8, 9, 10, and 11, wherein Y is 5-membered heteroaryl having from 1-3 heteroatoms as ring members selected from N, O or S, wherein the heteroaryl is optionally substituted with 1-3 $R^a$ members, at each occurrence, each $R^a$ is independently selected from the group consisting of —NH₂, $C_{1-8}$alkyl-NH—, ($C_{1-8}$alkyl)₂N—, aryl, $R^b$, $C_{1-8}$haloalkyl, aryl-$C_{3-8}$cycloalkyl, $C_{3-5}$cycloalkyl, heterocycloalkyl, arylsulfonyl, arylsulfinyl, NH₂C(O)—, ($C_{1-8}$alkyl)(H)NC(O)—, ($C_{1-8}$alkyl)₂NC(O)—, $C_{1-8}$alkylcarbonyl and $C_{1-8}$alkoxycarbonyl, wherein $R^b$ is $C_{1-8}$alkyl optionally substituted with from 1-2 members independently selected from the group consisting of aryl, aryloxy, ($R^c$)($R^d$)N—, $C_{3-5}$cycloalkyl, hetero-$C_{4-5}$cycloalkyl, arylthio and heteroaryl; wherein $R^c$ is —H or $C_{1-6}$alkyl and $R^d$ is $C_{3-7}$cycloalkyl or $C_{1-8}$alkyl optionally substituted with from 1-2 aryl groups; wherein the aryl portion of each $R^a$ substituent is further optionally substituted with from 1-3 substituents independently selected from the group consisting of halogen, $C_{1-4}$haloalkyl, $C_{1-4}$haloalkoxy, $C_{1-4}$alkoxy, —CN, $C_{1-4}$alkylsulfonyl, OH and —NO₂; and the heterocycloalkyl of the $R^b$ group is further optionally substituted with a hetero-$C_{4-5}$cycloalkyl-$C_{1-6}$alkyl; or any two adjacent $R^a$ substituents together with the atoms to which they are attached form a 5- or 6-membered carbocyclic ring, wherein one of the ring carbon atom is optionally replaced by a carbonyl and the carbocyclic ring is optionally substituted with 1-2 members independently selected from an halogen, aryl or $C_{1-8}$alkyl.

In a 13th set of embodiments, the invention provides a compound of any one of sets 1, 2, 3, 4, 5, 6, 7, 8, 9, 10, 11 and 12, wherein Y is selected from the group consisting of thiazolyl, pyrazolyl, isoxazolyl, imidazolyl, 1,2,4-triazolyl, 1,2,3-thiadiazolyl, 1,3,4-thiadiazolyl, 1,3,4-oxadiazolyl, 1,2,5-thiadiazol-4-yl, 1,2,5-oxadiazol-4-yl, 1,2,3,5-thiatriazol-4-yl, 1,2,3,4-thiatriazol-5-yl, 1,2,3,5-oxatriazol-4-yl, 1,2,3,4-oxatriazol-5-yl, benzimidazolyl, benzoxazolyl, benzthiazolyl, tetrahydrobenzothiazolyl and dihydrobenzothiazolone, each of which is optionally substituted with 1-3 $R^a$ members.

In a 14th set of embodiments, the invention provides a compound of the 12th set wherein Y is selected from the group consisting of thiazol-2-yl, pyrazol-3-yl, pyrazol-4-yl, pyrazol-5-yl, isoxazol-3-yl, 1,2,4-triazol-1yl, 1,2,4-triazol-3-yl, 1,3,4-thiadiazol-2-yl, 1,3,4-oxadiazol-2-yl, benzimidazol-2-yl, benzoxazol-2-yl, benzthiazol-2-yl, tetrahydrobenzothiazol-2-yl and dihydrobenzothiazol-2-yl-7-one, each of which is optionally substituted with 1-3 $R^a$ members.

In a 15th set of embodiments, the invention provides a compound of any one of sets any one of sets 1, 2, 3, 4, 5, 6, 7, 8, 9, 10, 11, 12, 13 and 14, wherein $R^a$ is selected from the group consisting of -Ph, Ph₂CH—, PhOCH₂—, Ph₂CHCH₂—, Ph-O(CH₂)₃—, cyclopentylethyl, 4-chlorophenoxymethyl, 2-phenylcyclopropyl, Ph₂CHCH₂NHCH₂—, PhOCH₂CH₂NHCH₂—, 2-(pyrrolidin-1-ylmethyl)pyrrolidin-1-yl, (S)-2-(pyrrolidin-1-ylmethyl)pyrrolidin-1-yl, Ph₂NHCH₂—, Ph₂CHCH₂CH₂NHCH₂—, 4-t-butyl-phenoxymethyl, PhO(CH₃)CH—, 1-(4-chlorophenyl)cyclopentyl, 4-chlorophenyl-CH₂NHCH₂—, 3,4-dimethoxyphenyl-(CH₂)₂NHCH₂—, Ph(CH₂)₂N(CH₃)CH₂—, (CH₃CH₂)₂NCH₂—, Ph(CH₂)₄NHCH₂—, Ph₂CHN(CH₃)CH₂—, 4-CF₃-Ph-CH₂NHCH₂—, 4-NO₂-Ph-CH₂NHCH₂—, 4-dimethylaminophenyl-CH₂NHCH₂—, 4-pyridyl-CH₂CH₂N(CH₃)

CH$_2$—, 3,5-dimethoxyphenyl-CH$_2$NH—CH$_2$—, —CH$_3$, CH$_3$OC(O)—, 2,4-difluorobenzyl, 4-fluoro-Ph-SCH$_2$—, —CF$_3$, 4-trifluoromethylphenyl, 4-fluorophenylsulfinylmethyl, 4-chlorophenylsulfinylmethyl, 2-fluoro-4-trifluoromethylphenyl, 4-chlorobenzyl, 4-chlorophenoxypropyl, 2,4-dichlorophenoxymethyl, 2-methyl-4-chlorophenoxymethyl, 4-chlorophenoxy-C(CH$_3$)$_2$—, t-butoxyphenoxymethyl, 4-chlorophenyl, t-butyl, 4-methoxybenzyl, 4-methylsulfonylbenzyl, 4-cyanobenzyl, 4-chlorophenylsulfonyl, acetyl, —NH$_2$, 3-chloro-4-fluoro-phenyl, 4-trifluoromethylbenzyl, neopentyl, 4-methoxybenzyl, 2-methoxybenzyl, 1-(4-chlorophenyl)cyclopropyl, CF$_3$CH$_2$—, —CN, —NO$_2$, 4-pyridylmethyl, cyclohexylmethyl, cyclopropyl, isopropyl, 2-methylphenyl, 4-methylphenyl, 2-chlorophenyl, 3-chlorophenyl, 4-methylbenzyl, 2-fluoro-4-chlorobenzyl, cylopentyl, 2-fluorophenyl, cyclopropyl-(CH$_3$)CH—, 3-methylphenyl, 3-fluorophenyl, 4-fluorophenyl, 2-trifluoromethylphenyl, 2-chloro-4-fluorophenyl, 2-methyl-4-fluoro-phenyl, 2-trifluoromethyl-4-fluorophenyl, 2-methoxyphenyl, 2,6-dichlorophenyl, 2,6-difluororophenyl, 2,6-dimethylphenyl, 2,4-difluorobenzyl, 3-trifluoromethylphenyl, 1-methypiperidinyl, 2-chloro-4-fluorobenzyl, 2-chlorobenzyl, 3-fluoro-4-chlorobenzyl, benzyl, (CH$_3$CH$_2$)$_2$NC(O)—CH$_2$—, 4-fluorobenzyl, 3-chlorobenzyl, 2-methoxy-4-chlorophenyl, 2-methoxyphenyl, 4-methoxybenzyl, 3-trifluoromethyl-4-chlorobenzyl, 2-methoxy-4-chlorophenyl, 3-methoxyphenyl, 4-methoxybenzyl, 3-trifluormethyl-4-chlorobenzyl, 2-methoxy-5-trifluoromethoxybenzyl and NH$_2$C(O)—.

In a 16th set of embodiments, the invention provides a compound of any of sets 1, 2, 3, 4, 5, 6, 7, 8, 9, 10, 11 and 12 wherein Y is a 6-member heteroaryl having from 1-3 nitrogen atoms as ring members, wherein the heteroaryl is optionally substituted with 1-3 R$^e$ substituents independently selected from the group consisting of —OH, aryl, aryl-C$_{1-6}$alkyl, aryl-C$_{1-6}$alkoxy, C$_{3-6}$cycloalkyl-C$_{1-8}$alkoxy and C$_{1-8}$alkoxy, wherein the aliphatic portion of the R$^e$ group is further optionally substituted with an aryl and the aromatic portion of the R$^e$ group is further optionally substituted with from 1-2 members independently selected from C$_{1-6}$haloalkyl, halogen or C$_{1-6}$alkyl; or any two adjacent R$^e$ substituents together with the atoms to which they are attached form a 6-membered fused benzene ring, optionally substituted with a halogen or C$_{1-6}$alkyl.

In a seventh set of embodiments, the invention provides a compound of any of sets 1, 2, 3, 4, 5, 6, 7, 8, 9, 10, 11, 12 and 16, wherein Y is selected from the group consisting of primidinyl, pyridazinyl, prazinyl, triazinyl and phthalazinyl, each of which is optionally substituted with from 1-3 R$^e$ substituents.

In a 18th set of embodiments, the invention provides a compound of any of sets 1, 2, 3, 4, 5, 6, 7, 8, 9, 10, 11, 12 and 16, 17, wherein Y is selected from the group consisting of 2-primidinyl, 4-pyrimidinyl, pyridazinyl, 3-prazinyl, 1,2,4-triazin-3-yl and 1-phthalazinyl, each of which is optionally substituted with from 1-3 R$^e$ substituents.

In a 19th set of embodiments, the invention provides a compound of any of sets 1, 2, 3, 4, 5, 6, 7, 8, 9, 10, 11, 12, 16, 17 and 18, wherein R$^e$ is selected from the group consisting of 4-chlorophenyl, 4-methylphenyl, Ph-, benzyloxy, Ph$_2$CHCH$_2$O—, 4-trifluoromethylbenzyloxy, cyclohexylmethyloxy, methoxy, Ph$_2$CH—, —OH, and 3,5-difluorobenzyl.

In a 20th set of embodiments, the invention provides a compound of any of sets 1, 2, 3, 4, 5, 6, 7, 8, 9, 10, 11 and 12, wherein Y is an aryl, optionally substituted with an aryl or C$_{1-6}$alkyl.

In a 21st set of embodiments, the invention provides a compound of any of sets 1, 2, 3, 4, 5, 6, 7, 8, 9, 10, 11, 12 and 20, wherein Y is an aryl, optionally substituted with phenyl or —CH$_3$ In a 22nd set of embodiments, the invention provides a compound of any of sets 1, 2, 3, 4, 5, 6, 7, 8, 9, 10, 11, 12, 20 and 21, wherein Y is phenyl.

In a 23rd set of embodiments, the invention provides a compound of any of sets 1 to 22, wherein $X^1$, $X^2$, $X^3$ and $X^4$ are =CH—.

In a 24th set of embodiments, the invention provides a compound of any of sets 1 to 22, wherein $X^1$ is —N=, and $X^2$, $X^3$ and $X^4$ are =CH—.

In a 25th set of embodiments, the invention provides a compound of any of sets 1 to 22, wherein $X^2$ is —N=, and $X^1$, $X^3$ and $X^4$ are =CH—.

In a 26th set of embodiments, the invention provides a compound of any of sets 1 to 22, wherein $X^1$ is =CF—, =CCl—, =C(OCF$_3$)—, =C(CH$_3$)— or —C(CH)= and $X^2$, $X^3$ and $X^4$ are =CH—.

In a 27th set of embodiments, the invention provides a compound of any of sets 1 to 22, wherein $X^2$ is =CF—, =CCl—, =C(OCF$_3$)—, =C(CH$_3$)—, —C(CN)=, —C(CF$_3$)= or —C(CH)= and $X^1$, $X^3$ and $X^4$ are =CH— or =C(CH$_3$)—.

In a 28th set of embodiments, the invention provides a compound of any of sets 1 to 22, wherein $X^2$ and $X^3$ are =CH—.

In a 29th set of embodiments, the invention provides a compound of any of sets 1 to 22, wherein $X^3$ and $X^4$ are =CH—.

In a 30th set of embodiments, the invention provides a compound of any of sets 1 to 22, wherein $X^2$, $X^3$ and $X^4$ are =CH—.

In a 31st set of embodiments, the invention provides a compound of any of sets 1 to 22, wherein $X^1$, $X^2$ and $X^3$ are =CH—.

In a 32nd set of embodiments, the invention provides a compound of any of sets 1 to 31, wherein $R^2$ is selected from the group consisting of —H, halogen, C$_{1-8}$alkyl, —CN, C$_{1-6}$haloalkyl and C$_{1-6}$haloalkyoxy; or any two adjacent $R^2$ substituents together with the atoms to which they are attached form a fused benzene ring, optionally substituted with a C$_{1-6}$alkyl.

In a 33rd set of embodiments, the invention provides a compound of any of sets 1 to 31, wherein $R^2$ is selected from the group consisting of —H, —Cl, —F, —CF$_3$, —OCF$_3$, —CH$_3$ and —CN.

In a 34th set of embodiments, the invention provides a compound of any of sets 1 to 31, wherein two adjacent $R^2$ substituents together with the atoms to which they are attached form a fused benzene ring, optionally substituted with a halogen or C$_{1-6}$alkyl.

In a 35th set of embodiments, the invention provides a compound of any of sets 1 to 4, wherein the compound has a Formula (IIa):

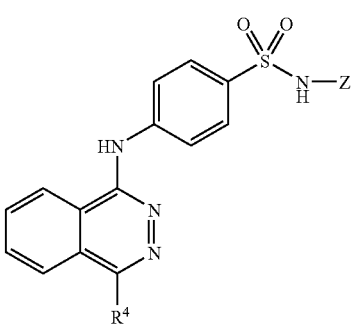

wherein Z is 2-thiazoly, 4-thiazolyl, 5-thiazolyl, 1,2,3-thiadiazol-4-yl, 1,2,3-thiadiazol-5-yl, 1,3,4-thiadiazol-2-yl, 1,2,5-thiadiazol-4-yl, 1,2,4-thiazol-3-yl or 1,2,4-thiazol-5-yl, each of which is optionally substituted with from 1-2 $R^3$ substituents selected from the group consisting of $C_{1-8}$haloalkyl, —CN, halogen, $C_{3-7}$cycloalkyl, aryl, $C_{1-8}$alkyl, aryl-NH—$C_{1-6}$alkyl and $C_{1-8}$alkoxy-$C_{1-4}$alkyl; and $R^4$ is selected from the group consisting of —H, —OH, $C_{0-6}$alkylaryl, aryl-$C_{1-6}$alkyl, aryl-$C_{1-6}$alkoxy, $C_{3-6}$cycloalkyl-$C_{1-6}$alkoxy and $C_{1-6}$alkoxy, wherein the aryl group is optionally substituted with from 1-3 $R^f$ substituents.

In a 36th set of embodiments, the invention provides a compound of any of sets 1 to 4, wherein the compound has a Formula (IIb):

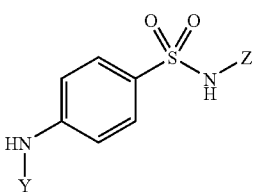

wherein Y is 2-pyrimidinyl, 4-pyrimidinyl, 2-pyrazinyl, pyridyl or 1,2,4-triazin-3-yl, each of which is optionally substituted with a member selected from the group consisting of —H, $C_{1-8}$haloalkyl, —CN, halogen, $C_{3-7}$cycloalkyl, aryl, $C_{1-8}$alkyl, aryl-NH—$C_{1-6}$alkyl and $C_{1-8}$alkoxy-$C_{1-4}$alkyl; and Z is 2-thiazolyl or 3-isoxazolyl, each of which is optionally substituted with a member selected from the group consisting of —H, —OH, aryl, aryl-$C_{1-6}$alkyl, aryl-$C_{1-6}$alkoxy, $C_{3-6}$cycloalkyl-$C_{1-6}$alkoxy and $C_{1-6}$alkoxy.

In a 37th set of embodiments, the invention provides a compound of any of sets 1 to 4, wherein the compound has a Formula (IIc):

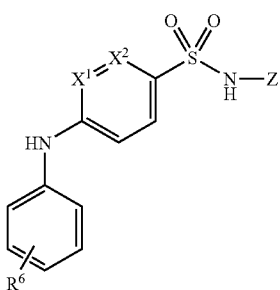

wherein Z is 2-thiazoly, 4-thiazolyl, 5-thiazolyl, 1,2,3-thiadiazol-4-yl, 1,2,3-thiadiazol-5-yl, 1,3,4-thiadiazol-2-yl, 1,2,5-thiadiazol-4-yl, 1,2,4-thiazol-3-yl or 1,2,4-thiazol-5-yl, each of which is optionally substituted with from 1-2 $R^5$ substituents selected from the group consisting of —H, $C_{1-8}$haloalkyl, —CN, halogen, —OH, $C_{3-7}$cycloalkyl, aryl, $C_{1-8}$alkyl, aryl-NH—$C_{1-6}$alkyl and $C_{1-8}$alkoxy-$C_{1-4}$alkyl; $R^6$ is —H, aryl or $C_{1-6}$alkyl; and $X^1$ and $X^2$ are each independently —CH=, —C(CF$_3$)=, =C(OH)— or —C(halo)=.

In a 38th set of embodiments, the invention provides a compound of any of sets 1 to 4, wherein Z is selected from the group consisting of 2-thiazolyl and 3-isoxazolyl, each of which is optionally substituted with a member selected from the group consisting of $C_{1-8}$haloalkyl, —CN, halogen, $C_{3-7}$cycloalkyl, aryl, $C_{1-8}$alkyl, aryl-NH—$C_{1-6}$alkyl and $C_{1-8}$alkoxy-$C_{1-4}$alkyl; and Y is selected from the group consisting of 3-pyrazolyl, 4-pyrazolyl, 5-pyrazolyl, 2-thiazolyl, imidazoly and 1,2,4-triazol-3-yl, each of which is optionally substituted with from 1-3 $R^a$ groups, wherein any two adjacent $R^a$ substituents together with the atoms to which they are attached optionally form a 5- or 6-membered carbocyclic ring, wherein one of the ring carbon atom is optionally replaced by a carbonyl and the carbocyclic ring is optionally substituted with 1-2 members independently selected from an halogen, aryl or $C_{1-8}$alkyl.

In a 39th set of embodiments, the invention provides a compound of any of sets 1 to 4 and 38, wherein Z is 2-thiazolyl, optionally substituted with a member selected from the group consisting of $C_{1-8}$haloalkyl, —CN, halogen, $C_{3-7}$cycloalkyl, aryl, $C_{1-8}$alkyl, aryl-NH—$C_{1-6}$alkyl and $C_{1-8}$alkoxy-$C_{1-4}$alkyl.

In a 40th set of embodiments, the invention provides a compound of any of sets 1 to 4 and 39, wherein the carbocyclic ring is a benzene ring, a cyclopentane ring or cyclohexane ring.

In a 41st set of embodiments, the invention provides a compound of any of sets 1 to 4, wherein the compound has Formula (IId):

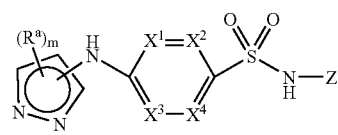

wherein Z is 2-thiazoly, 4-thiazolyl, 5-thiazolyl, 1,2,3-thiadiazol-4-yl, 1,2,3-thiadiazol-5-yl, 1,3,4-thiadiazol-2-yl, 1,2,5-thiadiazol-4-yl, 1,2,4-thiazol-3-yl or 1,2,4-thiazol-5-yl, each of which is optionally substituted with from 1-2 $R^7$ substituents selected from the group consisting of $C_{1-8}$haloalkyl, —CN, halogen, —OH, $C_{3-7}$cycloalkyl, aryl, $C_{1-8}$alkyl, aryl-NH—$C_{1-6}$alkyl and $C_{1-8}$alkoxy-$C_{1-4}$alkyl; and m is an integer of from 0-3.

In a 42nd set of embodiments, the invention provides a compound of any of sets 1 to 4, wherein the compound has Formula (IIe):

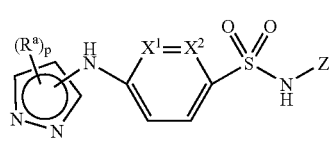

wherein Z is selected from the group consisting of pyridyl, pyridazinyl, primidinyl or pyrizinyl, each of which is optionally substituted with from 1-3 $C_{1-6}$alkyl; $X^1$ or $X^2$ is —CH= and the other is —CF=; and the subscript p is an integer of 0-3.

In a 43rd set of embodiments, the invention provides a compound of any of sets 1 to 4, wherein the compound has Formula (IIf):

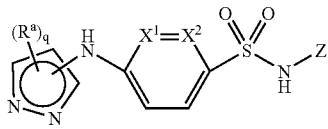

(IIf)

wherein Z is selected from the group consisting of 1,2,3,-thiadiazolyl, 1,2,4-thiadiazolyl, 1,2,5-thiadiazolyl, 1,3,4-thiadiazolyl, 1,3,4-triazolyl and 1,3,4-oxadiazolyl; and subscript q is an integer from 0-3.

In a 44th set of embodiments, the invention provides a compound of any of sets 1 to 4, wherein the compound has Formula (IIg):

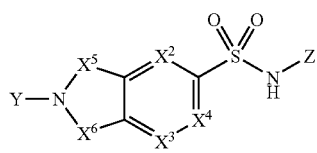

(IIg)

wherein $X^5$ and $X^6$ are each independently —S(O)$_2$—, —C(O)— or —CHR$^2$—.

In a 45th set of embodiments, the invention provides a compound of the first set, wherein the compound has Formula (IIh):

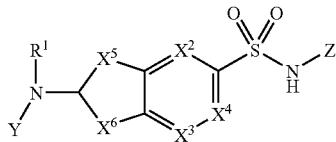

IIh wherein $X^5$ and $X^6$ are each independently —S(O)$_2$—, —C(O)— or —CHR$^2$—.

In a 46th set of embodiments, the invention provides a compound of the first set, wherein the compound has Formula (IIi):

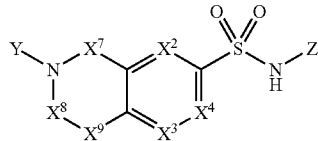

IIi wherein $X^7$, $X^8$ and $X^g$ are each independently CHR$^2$—, —S(O)$_2$— or —C(O)—.

In a 47th set of embodiments, the invention provides a compound of the first set, wherein the compound has Formula (IIj):

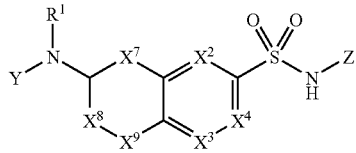

(IIj)

wherein $X^7$, $X^8$ and $X^g$ are each independently CHR$^2$—, —S(O)$_2$— or —C(O)—.

In a 48th set of embodiments, the invention provides a compound of any of sets 44-47, wherein $X^2$, $X^3$ and $X^4$ are each independently —CR$^2$=.

In a 49th set of embodiments, the invention provides a compound of any sets 1 to 48, wherein the compound has inhibitory activity against a voltage-gated sodium channel.

In another aspect, the invention provides a pharmaceutical formulation or composition comprising: a compound of any one of the above sets (i.e., sets 1 to 49) and a pharmaceutically acceptable excipient.

In another aspect, the present invention provides a pharmaceutical formulation comprising: a compound selected from 4-(4-methylphthalazin-1-ylamino)-N-(thiazol-2-yl) benzenesulfonamide; 4-(4-(4-chlorophenyl)phthalazin-1-ylamino)-N-(thiazol-2-yl)benzenesulfonamide; N-(thiazol-2-yl)-4-(4-p-tolylphthalazin-1-ylamino) benzenesulfonamide; or 4-(4-phenylphthalazin-1-ylamino)-N-(thiazol-2-yl)benzenesulfonamide and a pharmaceutically acceptable excipient.

In another aspect, the invention provides a method of modulating activity of a sodium channel in a subject, said method comprising: administering to said subject in need thereof an effective amount of a compound of any of sets 1 to 49 to modulate the activity of a sodium channel.

In a further aspect, the invention provides a method of ameliorating or alleviating a condition in a subject, wherein said condition is a member selected from pain, irritable bowel syndrome, Crohn's disease, epilepsy, seizures, multiple sclerosis, bipolar depression and tachy-arrhythmias, said method comprising: administering to said subject in need thereof an effective amount of a compound of any of sets 1 to 49 to ameliorate or alleviate said condition.

In a further aspect, the invention provides a method of ameliorating or alleviating a condition in a subject, wherein said condition is a member selected from pain, irritable bowel syndrome, Crohn's disease, epilepsy, seizures, multiple sclerosis, bipolar depression and tachy-arrhythmias, said method comprising: administering to said subject in need thereof an effective amount of 4-(4-methylphthalazin-1-ylamino)-N-(thiazol-2-yl)benzenesulfonamide; 4-(4-(4-chlorophenyl) phthalazin-1-ylamino)-N-(thiazol-2-yl)benzenesulfonamide; N-(thiazol-2-yl)-4-(4-p-tolylphthalazin-1-ylamino) benzenesulfonamide; or 4-(4-phenylphthalazin-1-ylamino)-N-(thiazol-2-yl)benzenesulfonamide to ameliorate or alleviate said condition. In one embodiment, the condition is pain, and said pain is a member selected from acute pain, chronic pain, visceral pain, inflammatory pain and neuropathic pain.

In some embodiments, the present invention provides a compound of any of sets 1-49, wherein Y is other than 4-$C_{1-8}$alkylphthalazin-1-yl or 4-arylphthalazin-1-yl, wherein the aryl is optionally substituted with halogen or $C_{1-8}$alkyl. In other embodiments, Y is other than 4-methylphthalazinyl or 4-phenylphthalazinyl, wherein the phenyl is optionally substituted with halogen or $C_{1-8}$alkyl. Exemplary halogen or $C_{1-8}$alkyl includes —Cl or —CH$_3$. In yet other embodiments, Y is other than 4-(4-chlorophenyl)phthalazin-1-yl, 4-(4-methylphenyl)phthalazin-1-yl or 4-phenyl)phthalazin-1-yl.

In some embodiments, the present invention provides a compound of any of sets 1-49, wherein $X^1$, $X^2$, $X^3$ and $X^4$ are other than —CH=. In other embodiments, Z is other than 2-thiazolyl, optionally substituted with a $C_{1-8}$alkyl.

In some embodiments, the present invention provides a compound of any of sets 1-49, wherein Y is other than 4-$C_{1-8}$alkylphthalazin-1-yl or 4-arylphthalazin-1-yl, wherein the aryl is optionally substituted with halogen or $C_{1-8}$alkyl and Z is other than 2-thiazolyl, optionally substituted with a $C_{1-8}$alkyl.

In some embodiments, the present invention provides a compound of any of sets 1-49, wherein Y is other than 4-(4-chlorophenyl)phthalazin-1-yl, 4-(4-methylphenyl)phthalazin-1-yl or 4-phenyl)phthalazin-1-yl, Z is other than 2-thiazolyl and $X^1$, $X^2$, $X^3$ and $X^4$ are other than —CH=.

In certain embodiments, the present invention provides a compound of any of sets 1-49, wherein the compound is other than 4-(4-methylphthalazin-1-ylamino)-N-(thiazol-2-yl) benzenesulfonamide; 4-(4-(4-chlorophenyl)phthalazin-1-ylamino)-N-(thiazol-2-yl)benzenesulfonamide; N-(thiazol-2-yl)-4-(4-(p-tolylphthalazin-1-ylamino) benzenesulfonamide; or 4-(4-phenylphthalazin-1-ylamino)-N-(thiazol-2-yl)benzenesulfonamide.

Included within the scope of the present invention are all stereoisomers, geometric isomers and tautomeric forms of the compounds of Formulas I, IA, Ib-Ie, II, IIa-IIj and IId-1 to IId-3, including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

III. Assays for Blockers of Voltage-Dependent TTX-Sensitive Sodium Channels

The activity of sodium channels can be assessed using a variety of in vitro assays, including but not limited to, measuring ion flux, measuring transmembrane potential, and/or measuring ionic current. Measurement of ionic fluxes can be accomplished by measuring changes in the concentration of the permeant species or by tracking the movement of small amounts of an appropriately permeant radioactive tracer. Transmembrane potential can be assessed with voltage-sensitive fluorescent dyes or, more sensitively, with electrophysiological methods.

Determination of the effectiveness of compounds as ex vivo blockers of sodium channels can be assessed by the inhibition of compound action potential propagation in isolated nerve preparations (Kourtney and Stricharz, LOCAL ANESTHETICS, Springer-Verlag, New York, 1987). A number of experimental models in the rat are appropriate for assessing the in vivo efficacy of the compounds of the invention. For example, the neuropathic pain model produced by the tight ligation of spinal nerves, described by Kim et al., *Pain,* 50: 355-363 (1992), can be used to experimentally determine the effect of the compounds of the invention in an in vivo model of pain. Mechanical sensitivity can also be assessed using a procedure described by Chaplan et al., *J. Neurosci. Methods,* 53: 55-63 (1994). Other assays of use are known to those of skill in the art.

Modulators of TTX-sensitive sodium channels can be tested using biologically active recombinant channels, or naturally occurring TTX-sensitive sodium channels, or by using native cells, like neurons expressing a TTX-sensitive sodium current. TTX-sensitive sodium channels can be isolated, co-expressed or expressed in a cell, or expressed in a membrane derived from a cell. In such assays, TTX-sensitive sodium channels are generally expressed alone to form a homomeric sodium channel or may be co-expressed with a second subunit (e.g., an auxiliary beta subunit) so as to form a heteromeric sodium channel. The TTX-sensitive sodium channels are stably expressed in HEK-293 cells, an example of an effective mammalian expression system.

Modulation can be tested using one of the in vitro or in vivo assays described above. Samples or assays that are treated with a potential sodium channel inhibitor are compared to control samples without the test compound, to examine the extent of modulation. Control samples (untreated with inhibitors) are assigned a relative sodium channel activity value of 100. Inhibition of TTX-sensitive sodium channels is achieved when the sodium channel activity value relative to the control is less than 70%, preferably less than 40% and still more preferably, less than 30%. Compounds that decrease the flux of ions will cause a detectable decrease in the ion current density by decreasing the probability of a TTX-sensitive sodium channel being open, by decreasing conductance through the channel, decreasing the number of channels, or decreasing the expression of channels.

Changes in ion flux may be assessed by determining changes in polarization (i.e., electrical potential) of the cell or membrane expressing the sodium channel. A preferred means to determine changes in cellular polarization is by measuring changes in current or voltage with the voltage-clamp and patch-clamp techniques, using the "cell-attached" mode, the "inside-out" mode, the "outside-out" mode, the "perforated patch" mode, the "whole cell" mode or other means of controlling or measuring changes in transmembrane potential (see, e.g., Ackerman et al., *New Engl. J. Med.,* 336: 1575-1595 (1997)). Whole cell currents are conveniently determined using the standard methodology (see, e.g., Hamill et al., *Pflugers. Archiv.* 391: 85 (1981). Other known assays include: radiotracer flux assays and fluorescence assays using voltage-sensitive dyes (see, e.g., Vestergarrd-Bogind et al., *J. Membrane Biol.* 88: 67-75 (1988); Daniel et al., *J. Pharmacol. Meth.* 25: 185-193 (1991); Holevinsky et al., *J. Membrane Biology* 137: 59-70 (1994)). Assays for compounds capable of inhibiting or increasing sodium flux through the channel proteins can be performed by application of the compounds to a bath solution in contact with and comprising cells having a channel of the present invention (see, e.g., Blatz et al., *Nature* 323: 718-720 (1986); Park, *J. Physiol.* 481: 555-570 (1994)). Generally, the compounds to be tested are present in the range from about 1 nM to about 100 mM, preferably from about 1 nM to about 30 μM. In an exemplary embodiment, the compounds to be tested are present in the range from about 1 nM to about 3 μM.

The effects of the test compounds upon the function of the channels can be measured by changes in the electrical currents or ionic flux or by the consequences of changes in currents and flux. Changes in electrical current or ionic flux are measured by either increases or decreases in flux of ions such as sodium or guanidinium ions (see U.S. Pat. No. 5,688, 830). The cations can be measured in a variety of standard ways. They can be measured directly by concentration changes of the ions or indirectly by membrane potential or by using radioactive ions. Consequences of the test compound on ion flux can be quite varied. Accordingly, any suitable physiological change can be used to assess the influence of a test compound on the channels of this invention. The effects of a test compound can be measured by a toxin-binding assay. When the functional consequences are determined using intact cells or animals, one can also measure a variety of effects such as transmitter release, hormone release, transcriptional changes to both known and uncharacterized genetic markers, changes in cell metabolism such as cell growth or pH changes, and changes in intracellular second messengers such as $Ca^{2+}$, or cyclic nucleotides.

High throughput screening (HTS) is of use in identifying promising candidate compounds of the invention. Physiologically, sodium channels open and close on a millisecond timescale. To overcome the short time in which channels are open the HTS assay can be run in the presence of an agent that modifies the gating of the channel, (e.g., pyrethroids, alpha-scorpion toxins, beta-scorpion toxins, batrachotoxin, etc). These agents modify the gating of sodium channels and keep the pore open for extended periods of time. In addition, while sodium channels are primarily selective for sodium, other ionic species can permeate the channel.

The specificity and effect of the TTX-sensitive sodium channel blocking agents of the invention can also be assayed against non-specific blockers of sodium channels, such as tetracaine, mexilitine, and flecamide.

IV. Pharmaceutical Compositions of VGSC Inhibitors

In another aspect, the present invention provides pharmaceutical compositions comprising/including a pharmaceutically acceptable excipient and a compound of the invention described herein or a pharmaceutically acceptable salt or solvate thereof. In an exemplary embodiment, the present invention provides a pharmaceutical formulation comprising/including a compound as described herein. In one embodiment, the compound has any of Formulas I, IA, Ib-Ie, II, IIa-IIj and IId-1 to IId-3. In another embodiments, the present invention provides a pharmaceutical formulation comprising/including 4-(4-methylphthalazin-1-ylamino)-N-(thiazol-2-yl)benzenesulfonamide; 4-(4-(4-chlorophenyl)phthalazin-1-ylamino)-N-(thiazol-2-yl)benzenesulfonamide; N-(thiazol-2-yl)-4-(4-p-tolylphthalazin-1-ylamino) benzenesulfonamide; or 4-(4-phenylphthalazin-1-ylamino)-N-(thiazol-2-yl)benzenesulfonamide.

Formulation of the Compounds (Compositions)

The compounds of the present invention can be prepared and administered in a wide variety of oral, parenteral and topical dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. Accordingly, the present invention also provides pharmaceutical compositions comprising/including a pharmaceutically acceptable carrier or excipient and either a compound described herein, or a pharmaceutically acceptable salt of a compound described herein.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

V. Methods for Inhibiting Ion Flow in VGSC

In yet another aspect, the present invention provides methods for decreasing ion flow through voltage gated sodium channels in a cell, comprising/including contacting a cell containing the target ion channels with a sodium channel-inhibiting amount of a compound described herein. In one embodiment, the method includes contacting a cell containing the target ion channels with a sodium channel-inhibiting amount of a compound of any of Formulas I, IA, Ib-Ie, II, IIa-IIj and IId-1 to IId-3. In another embodiments, the method includes contacting a cell containing the target ion channels with a sodium channel-inhibiting amount of a compound selected from 4-(4-methylphthalazin-1-ylamino)-N-(thiazol-2-yl)benzenesulfonamide; 4-(4-(4-chlorophenyl)phthalazin-1-ylamino)-N-(thiazol-2-yl)benzenesulfonamide; N-(thiazol-2-yl)-4-(4-p-tolylphthalazin-1-ylamino)

benzenesulfonamide; or 4-(4-phenylphthalazin-1-ylamino)-N-(thiazol-2-yl)benzenesulfonamide.

The methods provided in this aspect of the invention are useful for the diagnosis of conditions that can be treated by inhibiting ion flux through voltage gated sodium channels, or for determining if a patient will be responsive to therapeutic agents, which act by inhibiting sodium channels.

In a still another aspect, the present invention provides a method of modulating the activity of a sodium channel in a subject. This method comprises administering to a subject an amount of a compound according a formula described herein sufficient to modulate said activity. In an exemplary embodiment, the method comprises administering to a subject an amount of a compound described herein sufficient to modulate said activity. This method comprises administering to a subject an amount of a compound according to a formula described herein sufficient to modulate said activity. In an exemplary embodiment, the method comprises administering to a subject an amount of a compound selected from 4-(4-methylphthalazin-1-ylamino)-N-(thiazol-2-yl)benzenesulfonamide; 4-(4-(4-chlorophenyl)phthalazin-1-ylamino)-N-(thiazol-2-yl)benzenesulfonamide; N-(thiazol-2-yl)-4-(4-p-tolylphthalazin-1-ylamino)benzenesulfonamide; or 4-(4-phenylphthalazin-1-ylamino)-N-(thiazol-2-yl)benzenesulfonamide sufficient to modulate the activity. In another embodiment, the method includes administering to a subject an amount of sufficient to modulate the activity. Methods of detecting and amplifying modulation of a sodium channel are generally known in the art.

VI. Methods for Treating Conditions Mediated by VGSC

The compounds of formula (II), being sodium channel modulators, are potentially useful in the treatment of a range of disorders. The treatment of pain, particularly acute pain, chronic pain, visceral pain, inflammatory pain and neuropathic pain, is a preferred use.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a heightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:
pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;

heart and vascular pain, including pain caused by angina, myocardical infarction, mitral stenosis, pericarditis, Raynaud's phenomenon, scleredoma and skeletal muscle ischemia;

head pain, such as migraine (including migraine with aura and migraine without aura), cluster headache, tension-type headache mixed headache and headache associated with vascular disorders; and orofacial pain, including dental pain, otic pain, burning mouth syndrome and temporomandibular myofascial pain.

In one aspect, the present invention provides a method of ameliorating or alleviating a condition in a subject. The condition can be a member selected from pain, irritable bowel syndrome, Crohn's disease, epilepsy, seizures multiple sclerosis, bipolar depression and tachy-arrhythmias. The method includes administering to the subject an amount of the compound described herein sufficient to ameliorate or alleviate the condition. In one embodiment, the compound has any of Formulas I, IA, Ib-Ie, II, IIa-IIj and IId-1 to IId-3. In another embodiment, the compound is selected from 4-(4-methylphthalazin-1-ylamino)-N-(thiazol-2-yl)benzenesulfonamide; 4-(4-(4-chlorophenyl)phthalazin-1-ylamino)-N-(thiazol-2-yl)benzenesulfonamide; N-(thiazol-2-yl)-4-(4-p-tolylphthalazin-1-ylamino)benzenesulfonamide; or 4-(4-phenylphthalazin-1-ylamino)-N-(thiazol-2-yl) benzenesulfonamide. In an exemplary embodiment, the condition is pain, and the pain can be a member selected from acute pain, chronic pain, visceral pain, inflammatory pain and neuropathic pain. Exemplary aspects of this method are described in greater detail herein.

In another aspect, the present invention provides a method for the treatment of a disorder or condition through inhibition of a voltage gated sodium channel. In this method, a subject in need of such treatment is administered an effective amount of a compound described herein and/or according to a formula described herein or any of sets 1-49. In one embodiment, the compound has any of Formulas I, IA, Ib-Ie, II, IIa-IIj and IId-1 to IId-3. In another embodiment, the compound is selected from 4-(4-methylphthalazin-1-ylamino)-N-(thiazol-2-yl)benzenesulfonamide; 4-(4-(4-chlorophenyl)phthalazin-1-ylamino)-N-(thiazol-2-yl)benzenesulfonamide; N-(thiazol-2-yl)-4-(4-p-tolylphthalazin-1-ylamino) benzenesulfonamide; or 4-(4-phenylphthalazin-1-ylamino)-N-(thiazol-2-yl)benzenesulfonamide. In a preferred embodiment, the compounds provided herein are used to treat a disorder or condition by inhibiting an ion channel of the VGSC family.

The compounds provided herein are useful as sodium channel inhibitors and find therapeutic utility via inhibition of VGSCs in the treatment of diseases or conditions. The sodium channels that are typically inhibited are described herein as VGSCs such as the $Na_v1.1$ channel.

The compounds of the invention are particularly preferred for use in the treating, preventing or ameliorating pain or seizures. The method includes administering to a patient in need of such treatment, a therapeutically effective amount of a compound described herein and/or according to a formula described herein, or a pharmaceutically acceptable salt or solvate thereof. In one embodiment, the compound has any of Formulas I, IA, Ib-Ie, II, IIa-IIj and IId-1 to IId-3.

The compounds, compositions and methods of the present invention are of particular use in treating pain, comprising/including both inflammatory and neuropathic pain. Exemplary forms of pain treated by a compound of the invention include, postoperative pain, osteoarthritis pain, pain associated with metastatic cancer, neuropathy secondary to metastatic inflammation, trigeminal neuralgia, glossopharangyl neuralgia, adiposis dolorosa, burn pain, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, pain following stroke, thalamic lesions, radiculopathy, and other forms of neuralgic, neuropathic, and idiopathic pain syndromes.

Idiopathic pain is pain of unknown origin, for example, phantom limb pain. Neuropathic pain is generally caused by injury or infection of the peripheral sensory nerves. It includes, but is not limited to pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies.

Moreover, any VGSC inhibitory substance possessed of satisfactory VGSC modulating activity coupled with favorable intracranial transfer kinetics and metabolic stability is expected to show efficacy in central nervous system (CNS) diseases and disorders such as central nervous system ischemia, central nervous system trauma (e.g. brain trauma, spinal cord injury, whiplash injury, etc.), epilepsy, seizures, neurodegenerative diseases (e.g. amyotrophic lateral sclerosis (ALS), Alzheimer's disease, Huntington's chorea, Parkinson's disease, diabetic neuropathy, etc.), vascular dementia (e.g. multi-infarct dementia, Binswanger's disease, etc.), manic-depressive psychosis, depression, schizophrenia, chronic pain, trigeminal neuralgia, migraine, ataxia, bipolar disorder, spasticity, mood disorders, psychotic disorders, hearing and vision loss, age-related memory loss, learning deficiencies, anxiety and cerebral edema.

In treatment of the above conditions, the compounds utilized in the method of the invention are administered at the initial dosage of about 0.001 mg/kg to about 1000 mg/kg daily. A daily dose range of about 0.1 mg/kg to about 100 mg/kg is more typical. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages, which are less than the optimum dose of the compound. Thereafter, the dosage is increased by small increments until the optimum effect under the circumstances is reached. For convenience, the total daily dosage may be divided and administered in portions during the day, if desired.

In one embodiment, the present invention provides a compound as described herein or a compound of any of sets 1-49 above, or a pharmaceutically acceptable salt or solvate thereof, for use as a medicament. In one embodiment, the compound has any of Formulas I, IA, Ib-Ie, II, IIa-IIj and IId-1 to IId-3. The present invention further provides 4-(4-methylphthalazin-1-ylamino)-N-(thiazol-2-yl)benzenesulfonamide; 4-(4-(4-chlorophenyl)phthalazin-1-ylamino)-N-(thiazol-2-yl)benzenesulfonamide; N-(thiazol-2-yl)-4-(4-p-tolylphthalazin-1-ylamino)benzenesulfonamide; or 4-(4-phenylphthalazin-1-ylamino)-N-(thiazol-2-yl) benzenesulfonamide or pharmaceutically acceptable salts or solvates thereof, for use as a medicament.

In another embodiment, the present invention provides a compound as described herein or a compound of any of sets 1-49 above, or a pharmaceutically acceptable salt or solvate thereof, for use in the treatment of pain, irritable bowel syndrome, Crohn's disease, epilepsy, seizures, multiple sclerosis, bipolar depression and tachy-arrhythmias. In one embodiment, the compound has any of Formulas I, IA, Ib-Ie, II, IIa-IIj and IId-1 to IId-3. In certain instances, the pain includes, but are not limited to, acute pain, chronic pain, visceral pain, inflammatory pain and neuropathic pain. The present invention further provides 4-(4-methylphthalazin-1-ylamino)-N-(thiazol-2-yl)benzenesulfonamide; 4-(4-(4-chlorophenyl)phthalazin-1-ylamino)-N-(thiazol-2-yl)benzenesulfonamide; N-(thiazol-2-yl)-4-(4-p-tolylphthalazin-1-ylamino)benzenesulfonamide; or 4-(4-phenylphthalazin-1-ylamino)-N-(thiazol-2-yl)benzenesulfonamide or pharmaceutically acceptable salts or solvates thereof, for use in the treatment of pain, irritable bowel syndrome, Crohn's disease, epilepsy, seizures, multiple sclerosis, bipolar depression and tachy-arrhythmias. The pain includes, but are not limited to, acute pain, chronic pain, visceral pain, inflammatory pain and neuropathic pain.

In yet another embodiment, the present invention provides a use of a compound as described herein or a compound of any of sets 1-49 above, or a pharmaceutically acceptable salt or solvate thereof, in the manufacture of a medicament for the treatment of pain, irritable bowel syndrome, Crohn's disease, epilepsy, seizures, multiple sclerosis, bipolar depression and tachy-arrhythmias. In certain instances, the pain includes, but are not limited to, acute pain, chronic pain, visceral pain, inflammatory pain and neuropathic pain. In one embodiment, the compound has any of Formulas I, IA, Ib-Ie, II, IIa-IIj and IId-1 to IId-3. The present invention further provides a use of 4-(4-methylphthalazin-1-ylamino)-N-(thiazol-2-yl)benzenesulfonamide; 4-(4-(4-chlorophenyl)phthalazin-1-ylamino)-N-(thiazol-2-yl)benzenesulfonamide; N-(thiazol-2-yl)-4-(4-p-tolylphthalazin-1-ylamino) benzenesulfonamide; or 4-(4-phenylphthalazin-1-ylamino)-N-(thiazol-2-yl)benzenesulfonamide or pharmaceutically acceptable salts or solvates thereof, in the manufacture of a medicament for the treatment of pain, irritable bowel syndrome, Crohn's disease, epilepsy, seizures, multiple sclerosis, bipolar depression and tachy-arrhythmias. The pain includes, but are not limited to, acute pain, chronic pain, visceral pain, inflammatory pain and neuropathic pain.

Combination Therapy

Sodium channel modulators may be usefully combined with another pharmacologically active compound, or with two or more other pharmacologically active compounds, particularly in the treatment of pain. For example, a sodium channel modulator, particularly a compound of formula (I), or a pharmaceutically acceptable salt or solvate thereof, as defined above, may be administered simultaneously, sequentially or separately in combination with one or more agents selected from:

(1) an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

(2) a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

(3) a barbiturate sedative, e.g. amobarbital, aprobarbital, butabarbital, butabital, mephobarbital, metharbital, methohexital, pentobarbital, phenobarbital, secobarbital, talbutal, theamylal or thiopental;

(4) a benzodiazepine having a sedative action, e.g. chlordiazepoxide, clorazepate, diazepam, flurazepam, lorazepam, oxazepam, temazepam or triazolam;

(5) an $H_1$ antagonist having a sedative action, e.g. diphenhydramine, pyrilamine, promethazine, chlorpheniramine or chlorcyclizine;

(6) a sedative such as glutethimide, meprobamate, methaqualone or dichloralphenazone;

(7) a skeletal muscle relaxant, e.g. baclofen, carisoprodol, chlorzoxazone, cyclobenzaprine, methocarbamol or orphrenadine;

(8) an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

(9) an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl) quinazoline;

(10) a tricyclic antidepressant, e.g. desipramine, imipramine, amitriptyline or nortriptyline;

(11) an anticonvulsant, e.g. carbamazepine, lamotrigine, topiratmate or valproate;

(21) a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

(13) a muscarinic antagonist, e.g oxybutynin, tolterodine, propiverine, tropsium chloride, darifenacin, solifenacin, temiverine and ipratropium;

(14) a COX-2 selective inhibitor, e.g. celecoxib, rofecoxib, parecoxib, valdecoxib, deracoxib, etoricoxib, or lumiracoxib;

(15) a coal-tar analgesic, in particular paracetamol;

(16) a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

(17) a vanilloid receptor agonist (e.g. resinferatoxin) or antagonist (e.g. capsazepine);

(18) a beta-adrenergic such as propranolol;

(19) a local anaesthetic such as mexiletine;

(20) a corticosteroid such as dexamethasone;

(21) a 5-HT receptor agonist or antagonist, particularly a 5-$HT_{1B/1D}$ agonist such as eletriptan, sumatriptan, naratriptan, zolmitriptan or rizatriptan;

(22) a 5-$HT_{2A}$ receptor antagonist such as R(+)-alpha-(2,3-dimethoxy-phenyl)-1-[2-(4-fluorophenylethyl)]-4-piperidinemethanol (MDL-100907);

(23) a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

(24) Tramadol®;

(25) a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl) pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

(z) an alpha-2-delta ligand such as gabapentin, pregabalin, 3-methylgabapentin, (1α,3α,5α)(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl] acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

(26) a cannabinoid;

(27) metabotropic glutamate subtype 1 receptor (mGluR1) antagonist;

(28) a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

(29) a noradrenaline (norepinephrine) reuptake inhibitor, such as maprotiline, lofepramine, mirtazepine, oxaprotiline, fezolamine, tomoxetine, mianserin, buproprion, buproprion metabolite hydroxybuproprion, nomifensine and viloxazine (Vivalan®), especially a selective noradrenaline reuptake inhibitor such as reboxetine, in particular (S,S)-reboxetine;

(30) a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

(31) an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

(32) an acetylcholinesterase inhibitor such as donepezil;

(33) a prostaglandin $E_2$ subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methylbenzenesulfonamide or 4-[(1S)-1-({[5-chloro-2-(3-fluorophenoxy)pyridin-3-yl]carbonyl}amino)ethyl]benzoic acid;

(34) a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870,

(35) a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl),1,4-benzoquinone (CV-6504);

(36) a sodium channel blocker, such as lidocaine;

(37) a 5-HT3 antagonist, such as ondansetron;

and the pharmaceutically acceptable salts and solvates thereof.

EXAMPLES

The following examples are offered to illustrate, but not to limit the claimed invention. In the examples below, unless otherwise stated, temperatures are given in degrees Celsius ° C.); operations were carried out at room or ambient temperature (typically a range of from about 18-25° C.; evaporation of solvent was carried out using a rotary evaporator under reduced pressure (typically, 4.5-30 mmHg) with a bath temperature of up to 60° C.; the course of reactions was typically followed by TLC and reaction times are provided for illustration only; melting points are uncorrected; products exhibited satisfactory $^1$H-NMR and/or LC/MS data and yields are provided for illustration only. The following conventional abbreviations are also used: mp (melting point), L (liter(s)), mL (milliliters), mmol (millimoles), g (grams), mg (milligrams), min (minutes), LC-MS (liquid chromatography-mass spectrometry) and h (hours), PS (polystyrene), DIE (diisopropylethylamine).

Example 1

General Procedure 1

Compound 1

4-Bromo-2-fluoro-N-thiazol-2-yl-benzenesulfonamide

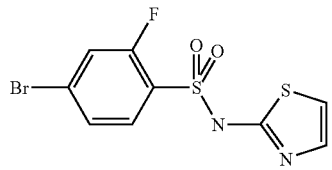

To a solution of 2-aminothiazole (4.51 g, 0.0450 mol) and pyridine (24.26 mL, 0.3000 mol) in methylene chloride (40 mL, 0.6 mol) at 0° C. was added portionwise 4-bromo-2-fluorobenzenesulfonyl chloride (8.2 g, 0.030 mol). The reaction mixture was stirred at room temperature overnight. The reaction mixture was concentrated under reduced pressure, diluted with EtOAc, washed with 1N HCl solution, H₂O and brine. The organic phase was dried with anhydrous sodium sulfate, filtered and concentrated to give the crude product that was purified via automated flash chromatography (silica gel, 25% EtOAc in hexanes to 100% EtOAc) to give the product as a light brown solid (3.6 g, 36%).

General Procedure 2

4-(2,4-Dimethoxy-benzylamino)-2-fluoro-N-thiazol-2-yl-benzenesulfonamide

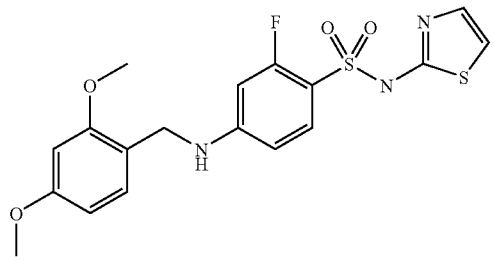

Into a vial was added the 4-bromo-2-fluoro-N-thiazol-2-yl-benzenesulfonamide (2.60 g, 0.00771 mol), sodium tert-butoxide (1.78 g, 0.0185 mol), 9,9-dimethyl-4,5-bis(diphenylphosphino)xanthene (0.27 g, 0.00046 mol), tris(dibenzylideneacetone)dipalladium(0) (0.14 g, 0.00015 mol) and 1,4-dioxane (24.1 mL, 0.308 mol). Argon was bubbled for 15 minutes. 2,4-Dimethoxybenzylamine (1.40 mL, 0.00925 mol) was added and the reaction mixture was heated at 100° C. overnight. The reaction mixture was cooled to room temperature then filtered over Celite. The filtrate was concentrated to give the crude product that was purified via automated flash chromatography (silica gel, 50% EtOAc in hexanes to 100% EtOAc) to give the product as a yellow solid (2.59 g, 79.3%).

General Procedure 3

4-Amino-2-fluoro-N-thiazol-2-yl-benzenesulfonamide

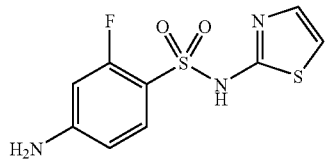

Trifluoroacetic acid (8 mL, 0.1 mol) was added to the mixture of the [A] 4-(2,4-dimethoxy-benzylamino)-2-fluoro-N-thiazol-2-yl-benzenesulfonamide (2.59 g, 0.00612 mol) in methylene chloride (33 mL). The reaction mixture was stirred for one hour (turned into a purple solution) then concentrated to give the crude product, which was purified using Gilson preparative HPLC (reverse phase, Phenomenex 250×30 mm, 15 micron C18 column, 40 mL/min. Gradient, 85% A to 100% B over 25 min. Solvent A: 7800 water/200 acetonitrile/8 TFA. Solvent B: 7200 acetonitrile/800 water/8) to give the product as a yellow solid (0.92 g, 55%).

General Procedure 4

2-Fluoro-N-thiazol-2-yl-4-thioureido-benzene-sulfonamide

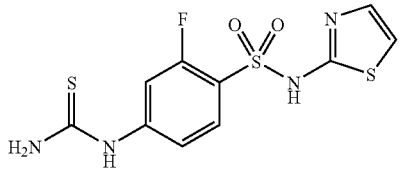

Carbonothioic dichloride (25 uL, 0.00032 mol) was added to a mixture of the 4-amino-2-fluoro-N-thiazol-2-yl-benzenesulfonamide (105 mg, 0.000271 mol) and N,N-diisopropylethylamine (0.14 mL, 0.00081 mol) in tetrahydrofuran (1.5 mL, 0.018 mol) at 0° C. and stirred for 40 min. Sat'd NH$_4$OH solution was added to the reaction mixture and stirred for a few min. The reaction mixture was rotovaped to remove THF. The aq phase was acidified with 1.0 N HCl (pH 6), extracted with EtOAc (3×), dried, and was concentrated to give the crude product, which was purified via automated flash chromatography (silica gel, 25% EtOAc in hexanes to 100% EtOAc). 32 mg (36%) of the product was obtained as a yellow solid.

General Procedure 5

4-[4-(4-Chloro-benzyl)-thiazol-2-ylamino]-2-fluoro-N-thiazol-2-yl-benzenesulfonamide

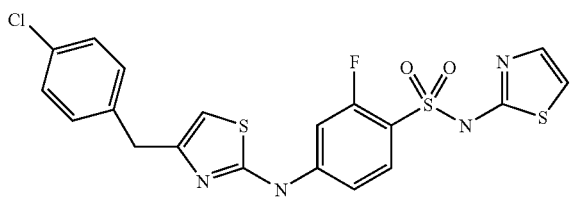

The mixture of the 2-fluoro-N-thiazol-2-yl-4-thioureido-benzenesulfonamide (32 mg, 0.000048 mol) and 1-bromo-3-(4-chloro-phenyl)-propan-2-one (14 mg, 0.000058 mol) in DMF/AcOH (1:1) was heated at 95° C. for 20 min. The crude product was purified using Gilson preparative HPLC (reverse phase, Phenomenex 250×30 min, 15 micron C18 column, 40 mL/min. Gradient, 85% A to 100% B over 25 min. Solvent A: 7800 water/200 acetonitrile/8 TFA. Solvent B: 7200 acetonitrile/800 water/8). Fractions were checked by LC/MS. The appropriate fractions were combined and dried on a lyophilizer to give the desired product as a light yellow powder (10.8 mg, 47%).

Compound 2

4-(4-Benzhydrylthiazol-2-ylamino)-N-(thiazol-2-yl)benzenesulfonamide

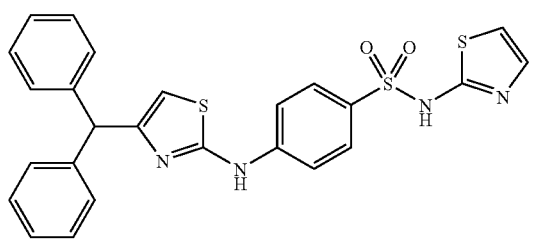

Synthesized according to General Procedure 5.

Compound 3

2-Fluoro-4-[4-(4-methoxy-benzyl)-thiazol-2-ylamino]-N-thiazol-2-yl-benzenesulfonamide

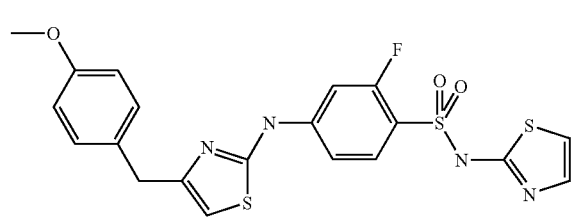

Synthesized according to General Procedure 5.

Compound 4

2-Fluoro-4-[4-(4-methanesulfonyl-benzyl)-thiazol-2-ylamino]-N-thiazol-2-yl-benzenesulfonamide

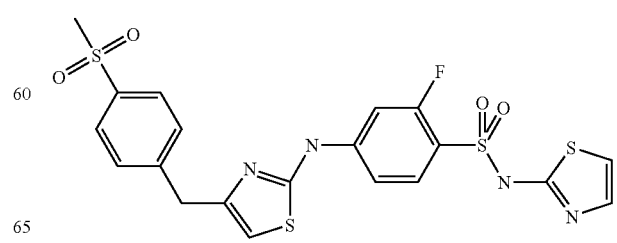

Synthesized according to General Procedure 5.

Compound 5

4-[4-(4-Cyano-benzyl)-thiazol-2-ylamino]-2-fluoro-N-thiazol-2-yl-benzenesulfonamide

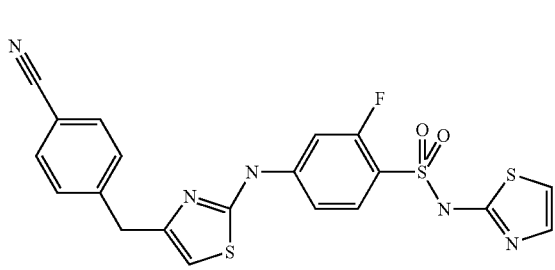

Synthesized according to General Procedure 5.

Compound 6

Synthesis of 4-[(2,4-Dimethoxy-benzyl)-methyl-amino]-2-fluoro-N-thiazol-2-yl-benzenesulfonamide N-(2,4-Dimethoxy-benzyl)-formamide

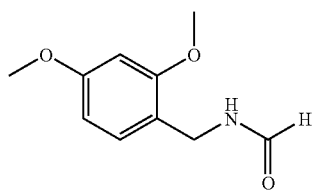

2,4-Dimethoxybenzylamine (2.00 mL, 12.3 mmol) and the ethyl formate (4.96 mL, 61.4 mmol) were stirred at rt. After 18 h, the reaction mixture was concentrated in vacuo. The resulting solid was washed with ether and collected by filtration to afford the product as an off-white solid (1.5 g, 59%).

(2,4-Dimethoxy-benzyl)-methyl-amine

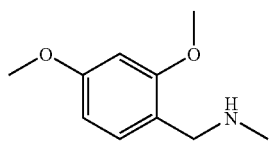

N-(2,4-Dimethoxy-benzyl)-formamide (0.50 g, 2.6 mmol) was added slowly to a suspension of the lithium tetrahydroaluminate (0.19 g, 5.1 mmol) in ether (30 mL, 200 mmol) at −78° C. The reaction mixture was warmed slowly to rt and stirred at rt under an atmosphere of Argon over night. The reaction was quenched at 0° C. by the sequential addition of 0.19 ml of $H_2O$, 0.19 ml of 15% aq NaOH solution, and 0.57 ml of the $H_2O$. The inorganic solids were removed by filtration and washed with ether. The ether filtrate was washed with water and brine, dried over $Na_2SO_4$. Evaporation of the solvent gave the product as a pale yellow oil (0.38 g, 82%).

4-[(2,4-Dimethoxy-benzyl)-methyl-amino]-2-fluoro-N-thiazol-2-yl-benzenesulfonamide

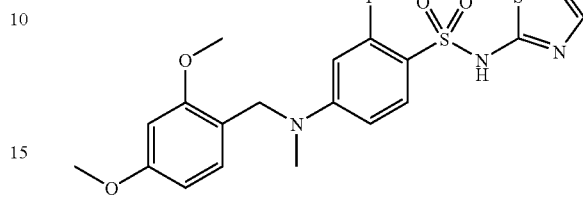

Into a vial was added the [B] 4-bromo-2-fluoro-N-thiazol-2-yl-benzenesulfonamide (170 mg, 0.00050 mol), sodium tert-butoxide (117 mg, 0.00121 mol), 9,9-dimethyl-4,5-bis(diphenylphosphino)xanthene (18 mg, 0.000030 mol), Tris(dibenzylideneacetone)dipalladium(0) (9.3 mg, 0.000010 mol) and 1,4-dioxane (1.58 mL, 0.0202 mol). Argon was bubbled for 15 minutes. Into the reaction was added the [2,4-dimethoxy-benzyl)-methyl-amine (110 mg, 0.00061 mol) and the reaction mixture was heated at 100° C. overnight. The reaction mixture was cooled to room temperature then filtered over Celite. The filtrate was concentrated to give the crude compound as a yellow solid that was used in the next step without purification.

Synthesis of 4-[4-(4-Chloro-benzyl)-thiazol-2-yl]-methyl-amino-2-fluoro-N-thiazol-2-yl-benzenesulfonamide 2-Fluoro-4-methylamino-N-thiazol-2-yl-benzenesulfonamide

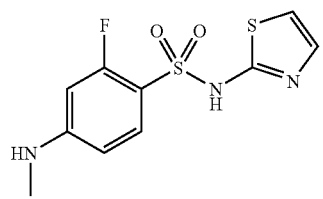

Trifluoroacetic acid (1 mL, 0.01 mol) was added to a solution of the 4-[(2,4-dimethoxy-benzyl)-methyl-amino]-2-fluoro-N-thiazol-2-yl-benzenesulfonamide (0.22 g, 0.00050 mol) in methylene chloride (5.0 mL, 0.078 mol). The reaction solution was stirred for one hour then concentrated. The residue was partitioned between sat'd $NaHCO_3$ and EtOAc. Organic layer was separated and the aq phase was extracted with EtOAc (2×). The combined organic layers were washed with water and brine, dried over $Na_2SO_4$. Evaporation of the solvent gave the crude product that was purified using Gilson preparative HPLC (reverse phase, Phenomenex 250×30 mm, 15 micron C18 column, 40 mL/min. Gradient, 85% A to 100% B over 25 min. Solvent A: 7800 water/200 acetonitrile/8 TFA. Solvent B: 7200 acetonitrile/800 water/8). Fractions were checked by LC/MS. The appropriate fractions were combined and dried on a lyophilizer to give the desired product as a pale yellow powder (62 mg, 43%).

2-Fluoro-4-(1-methyl-thioureido)-N-thiazol-2-yl-benzenesulfonamide

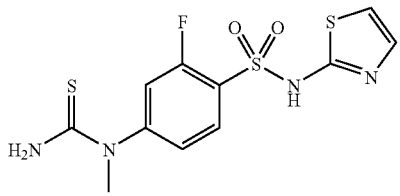

The mixture of the 2-fluoro-4-methylamino-N-thiazol-2-yl-benzenesulfonamide (15 mg, 0.000052 mol) and the potassium thiocyanate (23 mg, 0.00024 mol) was heated at 90° C. in 1.0 N HCl for 7 h. The reaction solution was extracted with EtOAc, washed with water and brine, dried and was concentrated to give the product as a brown solid (15 mg, 83%) that was used in the next step without further purification.

4-[4-(4-Chloro-benzyl)-thiazol-2-yl]-methyl-amino-2-fluoro-N-thiazol-2-yl-benzenesulfonamide

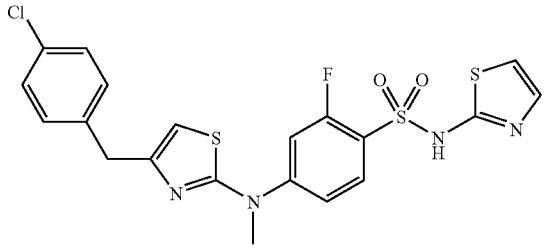

The mixture of the 2-fluoro-4-(1-methyl-thioureido)-N-thiazol-2-yl-benzenesulfonamide (15 mg, 0.000043 mol) and 1-bromo-3-(4-chloro-phenyl)-propan-2-one (13 mg, 0.000052 mol) in DMF/AcOH (1:1) was heated at 95° C. for 20 min. The crude product was purified using Gilson preparative HPLC (reverse phase, Phenomenex 100×21.2 mm 10 micron C18 column, 20 mL/min, Gradient 85% A to 100% B over 25 min. Solvent A: 7800 water/200 acetonitrile/8 TFA. Solvent B: 7200 acetonitrile/800 water/8 TFA). Fractions were checked by LC/MS. The appropriate fractions were combined and dried on a lyophilizer to give the product as a yellow powder (3.5 mg, 16%).

General Procedure 6

Compound 7

4-(4-Tert-butyl-thiazol-2-ylamino)-2-fluoro-N-thiazol-2-yl-benzenesulfonamide

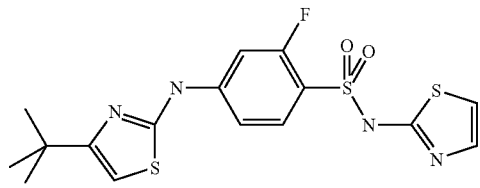

Into a vial was added the 4-bromo-2-fluoro-N-thiazol-2-yl-benzenesulfonamide (50 mg, 0.0001 mol), sodium tert-butoxide (43 mg, 0.00044 mol), 9,9-dimethyl-4,5-bis(diphenylphosphino)xanthene (1.0E1 mg, 0.000018 mol), tris(dibenzylideneacetone)dipalladium(0) (5.4 mg, 0.0000059 mol), 2-amino-4-(4-chlorophenyl)thiazole and the de-gassed anhydrous 1,4-dioxane (2.0 mL, 0.026 mol). The reaction mixture was heated at 150° C. for 1 h in microwave. The reaction mixture was filtered through celite and the filtrate was concentrated. The residue was diluted with EtOAc and washed with 1.0 N HCl, dried and was concentrated to give the crude product that was purified using Gilson preparative HPLC (reverse phase, Phenomenex 250×30 mm, 15 micron C18 column, 40 mL/min. Gradient, 85% A to 100% B over 25 min. Solvent A: 7800 water/200 acetonitrile/8 TFA. Solvent B: 7200 acetonitrile/800 water/8). Fractions were checked by LC/MS, then combined, and dried on a lyophilizer to give the product as a yellow solid (24.5 mg, 40%).

Compound 8

4-(5-Tert-butyl-4-methylthiazol-2-ylamino)-N-(thiazol-2-yl)benzenesulfonamide

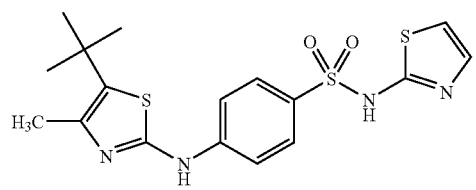

Synthesized according to General Procedure 6.

Compound 9

4-(5-Acetyl-4-methyl-thiazol-2-ylamino)-2-fluoro-N-thiazol-2-yl-benzenesulfonamide

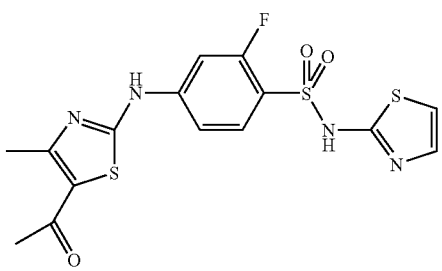

Synthesized according to General Procedure 6.

Compound 10

4-(4-Tert-butyl-thiazol-2-ylamino)-2-chloro-N-thiazol-2-yl-benzenesulfonamide

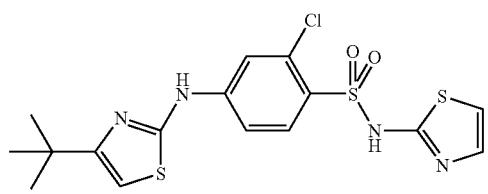

87

Synthesized according to General Procedure 6.

Compound 11

Synthesis of 4-(4-tert-Butyl-thiazol-2-ylamino)-N-thiazol-2-yl-2-trifluoromethoxy-benzenesulfonamide 4-Bromo-N-thiazol-2-yl-2-trifluoromethoxy-benzenesulfonamide

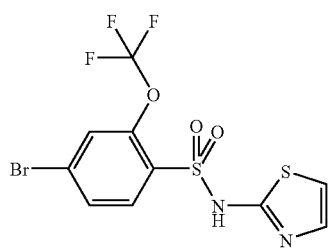

Synthesized according to General Procedure 1.

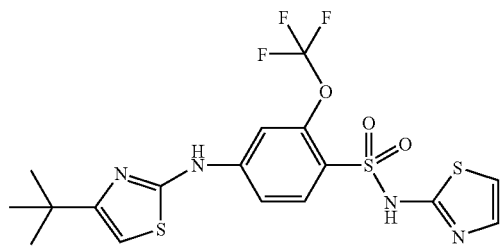

Synthesized according to General Procedure 6.

Compound 12

Synthesis of 4-(4-tert-Butyl-thiazol-2-ylamino)-naphthalene-1-sulfonic acid thiazol-2-ylamide 4-Bromo-naphthalene-1-sulfonic acid thiazol-2-ylamide

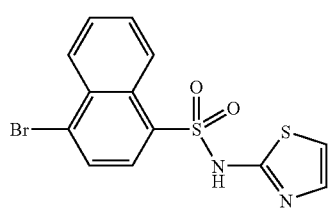

88

Synthesized according to General Procedure 1.

4-(4-tert-Butyl-thiazol-2-ylamino)-naphthalene-1-sulfonic acid thiazol-2-ylamide

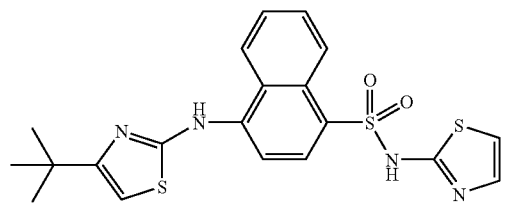

Synthesized according to General Procedure 6.

Compound 13

4-(5-tert-butyl-4-methylthiazol-2-ylamino)-2-fluoro-N-(thiazol-2-yl)benzenesulfonamide

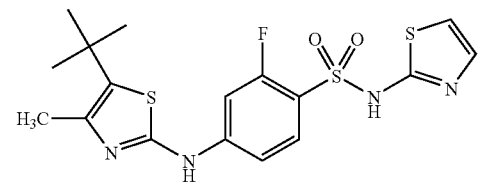

Synthesized according to General Procedure 6.

Compound 14

Synthesis of 4-(4-Tert-butyl-thiazol-2-ylamino)-N-thiazol-2-yl-benzenesulfonamide 4-Iodo-N-thiazol-2-yl-benzenesulfonamide

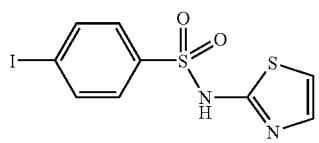

2-Aminothiazole (1.32 g, 0.0132 mol) was added to a solution of 4-iodobenzenesulfonyl chloride (4.00 g, 0.0132 mol) in Pyridine (10 mL, 0.1 mol) and methylene chloride (36 mL, 0.56 mol). After stirring 4 d, the reaction mixture was concentrated in vacuo. The resulting oil was taken up in 1:1 methylene chloride-methanol and stirred. A white precipitate formed. The solid was collected by filtration. 2.65 g (49%) of the product was obtained as an off-white solid.

4-(4-Tert-butyl-thiazol-2-ylamino)-N-thiazol-2-yl-benzenesulfonamide

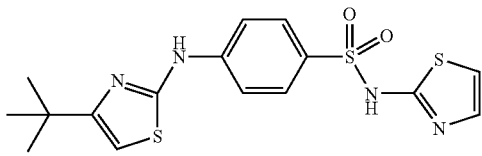

Synthesized according to General Procedure 6.

Compound 15

4-Iodo-N-(thiazol-2-yl)benzenesulfonamide

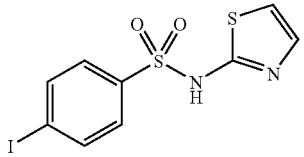

4-Iodobenzenesulfonyl chloride (1.8 g, 6.0 mmol, 1.0 equiv) was added portion-wise to a 0° C. solution of 2-aminothiazole (654 mg, 6.53 mmol, 1.1 equiv) in 4.91 mL of anhydrous pyridine. After addition was complete, the reaction mixture was warmed to ambient temperature. After 3 d, the reaction mixture was concentrated in vacuo. The residue was treated with methanol and ether to precipitate the product. The solid was collected by filtration, washing with ether, to afford the product as a light brown solid (1.18 g, 49%).

4-(4-Chlorophenyl)-3-oxobutanenitrile

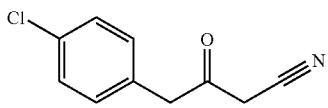

Isopropylmagnesium chloride (24.6 mL, 2 M solution in THF, 50 mmol, 5 equiv) was added to a −78° C. solution of cyanoacetic acid (2.52 g, 29.6 mmol, 2.96 equiv) in 80 mL of anhydrous tetrahydrofuran. After 1 h, a solution of 4-chlorophenylacetic acid (1.7 g, 10 mmol, 1.0 equiv) and N,N-carbonyldiimidazole (1.93 g, 11.9 mmol, 1.19 equiv) in 20 mL of anhydrous tetrahydrofuran was added to the reaction mixture, and the reaction mixture was warmed to ambient temperature. After 16 h, the reaction mixture was poured into 300 mL of water. The mixture was adjusted to pH 4 with glacial acetic acid. Gas evolution was evident during addition of the acetic acid. The mixture was extracted with ethyl acetate (4×100 mL). The combined organic layers were washed with brine, dried over sodium sulfate, filtered, and concentrated in vacuo. The residue was purified via automated flash chromatography (80 g SiO$_2$, gradient from hexanes to ethyl acetate) to afford the product as a white solid (1.17 g, 57%).

1-Tert-butyl-3-(4-chlorobenzyl)-1H-pyrazol-5-amine

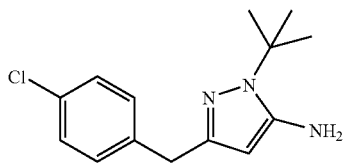

A solution of 4-(4-chloro-phenyl)-3-oxo-butyronitrile (500 mg, 2 mmol, 1.0 equiv), triethylamine (1.16 mL, 8.3 mmol, 3.2 equiv), and tert-butylhydrazine hydrochloride (1.03 g, 8.3 mmol, 3.2 equiv) in 10 mL of ethanol was heated at 100° C. in a sealed tube. After 4 d, the reaction mixture was cooled to ambient temperature and concentrated in vacuo. The residue was purified via automated flash chromatography (40 g SiO$_2$, gradient from hexanes to ethyl acetate) to afford the product as a yellow oil (610 mg, 70%).

General Procedure 7

4-(1-tert-butyl-3-(4-chlorobenzyl)-1H-pyrazol-5-ylamino)-N-(thiazol-2-yl)benzenesulfonamide

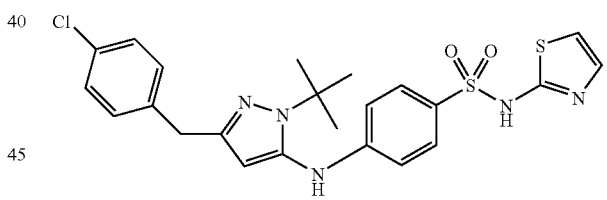

To a mixture of 4-iodo-N-thiazol-2-yl-benzenesulfonamide (100 mg, 0.3 mmol, 1.0 equiv), tris(dibenzylideneacetone)dipalladium(0) (10 mg, 0.01 mmol, 0.04 equiv), 9,9-dimethyl-4,5-bis(diphenylphosphino)xanthene (19 mg, 0.033 mmol, 0.12 equiv) and 2-tert-butyl-5-(4-chloro-benzyl)-2H-pyrazole-3-ylamine (86 mg, 0.33 mmol, 1.2 equiv) in 3.7 mL of anhydrous 1,4-dioxane was added sodium tert-butoxide (79 mg, 0.82 mmol, 3.0 equiv). The vial was capped, and the reaction mixture was heated 30 min at 150° C. in the microwave. The crude reaction mixture was filtered through celite then concentrated in vacuo. The residue was taken up in chloroform-methanol, concentrated onto celite, and purified via automated flash chromatography (12 g SiO$_2$, gradient from hexanes to ethyl acetate). The appropriate fractions were collected, concentrated in vacuo, then lyophilized from water-acetonitrile to afford the product as an off-white solid (60 mg, 40%).

Compound 16

4-(3-(4-Chlorobenzyl)-1H-pyrazol-5-ylamino)-N-(thiazol-2-yl)benzenesulfonamide

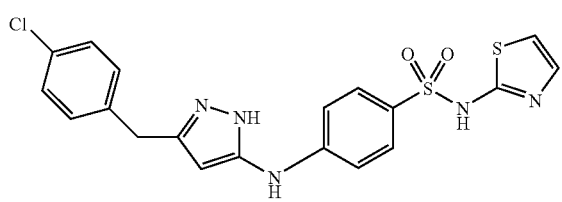

A solution of 4-[2-tert-butyl-5-(4-chloro-benzyl)-2H-pyrazol-3-ylamino]-N-thiazol-2-yl-benzenesulfonamide (20 mg, 0.04 mmol, 1.0 equiv) was heated in 1.0 mL of formic acid at 95° C. After 16 h, the reaction mixture was concentrated in vacuo. The residue was purified via automated flash chromatography (4 g $SiO_2$, gradient from chloroform to 12% methanol in chloroform) to afford the product as an off-white solid (7 mg, 40%).

Compound 17

4-(3-Tert-butyl-1-methyl-1H-pyrazol-5-ylamino)-N-(thiazol-2-yl)benzenesulfonamide

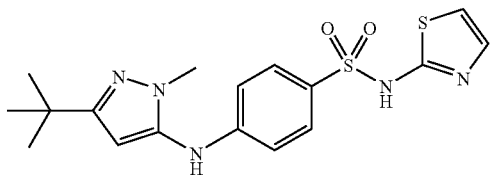

To a mixture of 4-iodo-N-thiazol-2-yl-benzenesulfonamide (50 mg, 0.1 mmol, 1.0 equiv), tris(dibenzylideneacetone)dipalladium(0) (5 mg, 0.005 mmol, 0.04 equiv), 9,9-dimethyl-4,5-bis(diphenylphosphino)xanthene (10 mg, 0.0016 mmol, 0.12 equiv) and 5-amino-3-tert-butyl-1-methylpyrazole (25 mg, 0.16 mmol, 1.2 equiv) in 1.8 mL of anhydrous 1,4-dioxane was added sodium tert-butoxide (39 mg, 0.41 mmol, 3.0 equiv). The vial was capped, and the reaction mixture was heated 30 min at 150° C. in the microwave. The crude reaction mixture was filtered through celite then concentrated in vacuo. The residue was taken up in chloroform-methanol, concentrated onto celite, and purified via automated flash chromatography (12 g $SiO_2$, gradient from hexanes to ethyl acetate). The appropriate fractions were collected, concentrated in vacuo, then lyophilized from water-acetonitrile to afford the product as an off-white solid (30 mg, 50%).

Compound 18

4-(3-Tert-butylisoxazol-3-ylamino)-N-(thiazol-2-yl)benzenesulfonamide

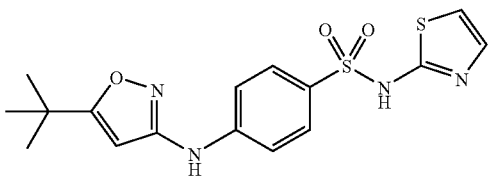

To a mixture of 4-iodo-N-thiazol-2-yl-benzenesulfonamide (50 mg, 0.1 mmol, 1.0 equiv), tris(dibenzylideneacetone)dipalladium(0) (5 mg, 0.005 mmol, 0.04 equiv), 9,9-dimethyl-4,5-bis(diphenylphosphino)xanthene (10 mg, 0.0016 mmol, 0.12 equiv) and 3-amino-5-tert-butylisoxazole (23 mg, 0.16 mmol, 1.2 equiv) in 1.8 mL of anhydrous 1,4-dioxane was added sodium tert-butoxide (39 mg, 0.41 mmol, 3.0 equiv). The vial was capped, and the reaction mixture was heated 30 min at 150° C. in the microwave. The crude reaction mixture was filtered through celite then concentrated in vacuo. The residue was taken up in chloroform-methanol, concentrated onto celite, and purified via automated flash chromatography (12 g $SiO_2$, gradient from hexanes to ethyl acetate). The appropriate fractions were collected, concentrated in vacuo, then purified further via reverse phase HPLC. The solvent was removed by lyophilization to afford the product as a white solid (9 mg, 20%).

Compound 19

4-(5-Amino-1-tert-butyl-1H-1,2,4-triazol-3-ylamino)-N-(thiazol-2-yl)benzenesulfonamide

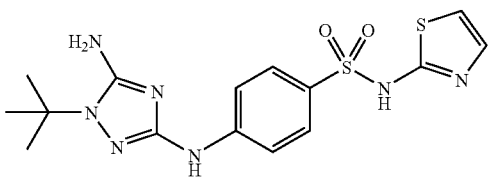

Sodium hydrogencyanamide (222 mg, 0.34 mmol, 1.02 equiv) was added to a solution of 4-isothiocyanato-N-thiazol-w-yl-benzenesulfonamide (100 mg, 0.3 mmol, 1.0 equiv) in 1.0 mL of ethanol. After 22 h, the reaction mixture was concentrated in vacuo. The residue was taken up in 1.0 mL of N,N-dimethylformamide. To this mixture was added N,N'-dicyclohexylcarbodiimide (71 mg, 0.34 mmol, 1.02 equiv), tert-butylhydrazine hydrochloride (46 mg, 0.37 mmol, 1.1 equiv) and N,N-diisopropylethylamine (82 µL, 0.47 mmol, 1.4 equiv). The reaction mixture was heated at 50° C. After 16 h, the reaction mixture was cooled to ambient temperature, filtered, and purified via reverse phase HPLC. The solvent was removed by lyophilization to afford the product as an off-white solid (37 mg, 30%).

Compound 20

4-(3-methyl-1-phenyl-1H-pyrazol-5-ylamino)-N-(thiazol-2-yl)benzenesulfonamide

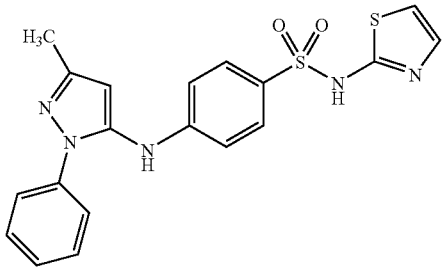

To a mixture of 4-iodo-N-thiazol-2-yl-benzenesulfonamide (100 mg, 0.3 mmol, 1.0 equiv), tris(dibenzylideneacetone)dipalladium(0) (10 mg, 0.01 mmol, 0.04 equiv), 9,9-dimethyl-4,5-bis(diphenylphosphino)xanthene (21 mg, 0.036 mmol, 0.12 equiv) and 5-amino-3-methyl-1-phenylpyrazole (62 mg, 0.36 mmol, 1.2 equiv) in 4.0 mL of anhydrous 1,4-dioxane was added sodium tert-butoxide (100 mg, 0.90 mmol, 3.0 equiv). The vial was capped, and the reaction mixture was heated 30 min at 150° C. in the microwave. The crude reaction mixture was filtered through celite then concentrated in vacuo. The residue was taken up in chloroform-methanol, concentrated onto celite, and purified via automated flash chromatography (12 g SiO$_2$, gradient from hexanes to ethyl acetate). The appropriate fractions were collected, concentrated in vacuo, then lyophilized from water-acetonitrile to afford the product as an off-white solid (60 mg, 40%).

Compound 21

Synthesis of 4-(3-(4-Chlorobenzyl)-1-methyl-1H-pyrazol-5-ylamino)-N-(thiazol-2-yl)benzenesulfonamide 3-(4-Chlorobenzyl)-1-methyl-1H-pyrazol-5-ylamine

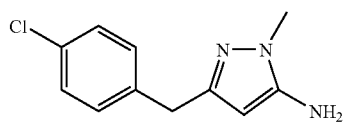

A solution of 4-(4-chloro-phenyl)-3-oxo-butyronitrile (200 mg, 1 mmol, 1.0 equiv) and N-methylhydrazine (153 mg, 3.32 mmol, 3.2 equiv) in 4 mL of ethanol was heated at 100° C. in a sealed tube. After 4 d, the reaction mixture was cooled to ambient temperature and concentrated in vacuo. The residue was purified via automated flash chromatography (40 g SiO$_2$, gradient from hexanes to ethyl acetate) to afford the product as a yellow solid (188 mg, 80%).

4-(3-(4-Chlorobenzyl)-1-methyl-1H-pyrazol-5-ylamino)-N-(thiazol-2-yl)benzenesulfonamide

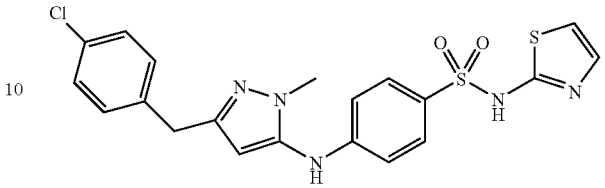

To a mixture of 4-iodo-N-thiazol-2-yl-benzenesulfonamide (100 mg, 0.3 mmol, 1.0 equiv), tris(dibenzylideneacetone)dipalladium(0) (10 mg, 0.01 mmol, 0.04 equiv), 9,9-dimethyl-4,5-bis(diphenylphosphino)xanthene (19 mg, 0.033 mmol, 0.12 equiv) and 5-(4-chloro-benzyl)-2-methyl-2H-pyrazole-3-ylamine (80 mg, 0.36 mmol, 1.2 equiv) in 4.0 mL of anhydrous 1,4-dioxane was added sodium tert-butoxide (100 mg, 0.90 mmol, 3.0 equiv). The vial was capped, and the reaction mixture was heated 30 min at 150° C. in the microwave. The crude reaction mixture was filtered through celite then concentrated in vacuo. The residue was taken up in chloroform-methanol, concentrated onto celite, and purified via automated flash chromatography (12 g SiO$_2$, gradient from hexanes to ethyl acetate). The appropriate fractions were collected, concentrated in vacuo, then purified further via reverse phase HPLC. The appropriate fractions were lyophilized from water-acetonitrile to afford the product as a white solid (9 mg, 6%).

Compound 22

Synthesis of 4-(1,3-di-tert-butyl-1H-pyrazol-5-ylamino)-N-(thiazol-2-yl)benzenesulfonamide 1,3-di-tert-butyl-1H-pyrazol-5-amine

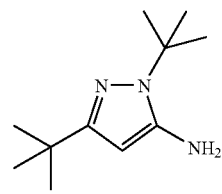

A solution of pivaloylacetonitrile (300 mg, 2 mmol, 1.0 equiv), triethylamine (1.16 mL, 8.3 mmol, 3.2 equiv), and tert-butylhydrazine hydrochloride (1.03 g, 8.3 mmol, 3.2 equiv) in 10 mL of ethanol was heated at 100° C. in a sealed tube. After 4 days, the reaction mixture was cooled to ambient temperature and concentrated in vacuo. The residue was purified via automated flash chromatography (40 g SiO$_2$, ethyl acetate to 20% methanol in ethyl acetate) to afford the product as an off-white solid (123 mg, 20%).

4-(1,3-di-tert-butyl-1H-pyrazol-5-ylamino)-N-(thiazol-2-yl)benzenesulfonamide

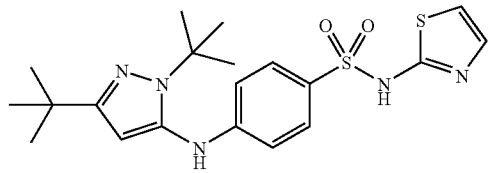

To a mixture of 4-iodo-N-thiazol-2-yl-benzenesulfonamide (100 mg, 0.3 mmol, 1.0 equiv), tris(dibenzylideneacetone)dipalladium(0) (10 mg, 0.01 mmol, 0.04 equiv), 9,9-dimethyl-4,5-bis(diphenylphosphino)xanthene (19 mg, 0.033 mmol, 0.12 equiv) and 2,5-di-tert-butyl-2H-pyrazole-3-ylamine (70 mg, 0.36 mmol, 1.2 equiv) in 4.0 mL of anhydrous 1,4-dioxane was added sodium tert-butoxide (100 mg, 0.90 mmol, 3.0 equiv). The vial was capped, and the reaction mixture was heated 30 min at 150° C. in the microwave. The crude reaction mixture was filtered through celite then concentrated in vacuo. The residue was dissolved in 0.5 mL of 1:1 dimethyl sulfoxide-acetonitrile then purified further via reverse phase HPLC. The appropriate fractions were lyophilized from water-acetonitrile to afford the product as an off-white solid (32 mg, 20%).

Compound 23

4-(3-tert-butyl-1H-pyrazol-5-ylamino)-N-(thiazol-2-yl)benzenesulfonamide

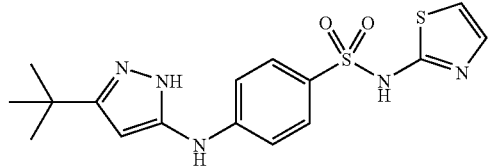

A solution of 4-(2,5-di-tert-butyl-2H-pyrazol-3-ylamino)-N-thiazol-2-yl-benzenesulfonamide (20 mg, 0.04 mmol, 1.0 equiv) was heated in 1.0 mL of formic acid at 95° C. After 16 h, the reaction mixture was concentrated in vacuo. The residue was purified via automated flash chromatography (4 g $SiO_2$, gradient from chloroform to 12% methanol in chloroform) to afford the product as an off-white solid (9 mg, 60%).

Compound 24

4-(5-amino-1-(4-chlorobenzyl)-1H-1,2,4-triazol-3-ylamino)-N-(thiazol-2-yl)benzenesulfonamide

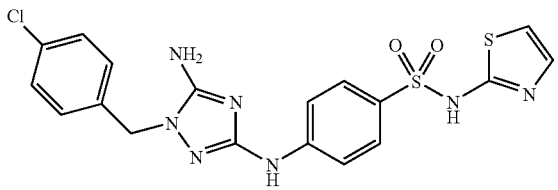

Sodium hydrogencyanamide (22 mg, 0.34 mmol, 1.02 equiv) was added to a solution of 4-isothiocyanato-N-thiazol-w-yl-benzenesulfonamide (100 mg, 0.3 mmol, 1.0 equiv) in 1.0 mL of ethanol. After 16 h, the reaction mixture was concentrated in vacuo. The residue was taken up in 1.0 mL of N,N-dimethylformamide. To this mixture was added N,N'-dicyclohexylcarbodiimide (71 mg, 0.34 mmol, 1.02 equiv), tert-butylhydrazine hydrochloride (46 mg, 0.37 mmol, 1.1 equiv) and N,N-diisopropylethylamine (82 µL, 0.47 mmol, 1.4 equiv). The reaction mixture was heated at 50° C. After 16 h, the reaction mixture was diluted with water and extracted with ethyl acetate (3×). The combined organic layers were washed successively with water, aqueous lithium chloride, then brine, dried over sodium sulfate, filtered and concentrated in vacuo. The residue was taken up in methylene chloride-methanol and concentrated onto celite. The residue was purified via automated flash chromatography (12 g $SiO_2$, chloroform to 20% methanol in chloroform) to afford the product as an off-white solid (7 mg, 4%).

Compound 25

4-(1-(3-chloro-4-fluorophenyl)-4-cyano-1H-pyrazol-5-ylamino)-N-(thiazol-2-yl)benzenesulf

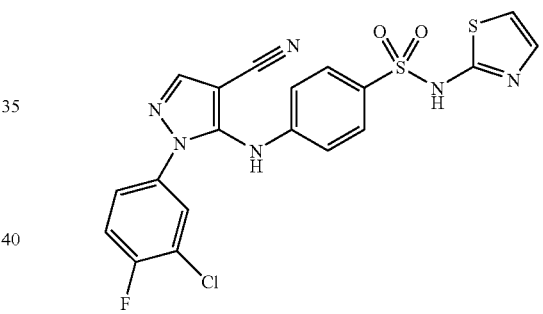

To a mixture of 4-iodo-N-thiazol-2-yl-benzenesulfonamide (200 mg, 0.5 mmol, 1.0 equiv), tris(dibenzylideneacetone)dipalladium(0) (20 mg, 0.02 mmol, 0.04 equiv), 9,9-dimethyl-4,5-bis(diphenylphosphino)xanthene (38 mg, 0.066 mmol, 0.12 equiv) and 5-amino-1-(3-chloro-4-fluorophenyl)-4-cyanopyrazole (160 mg, 1.6 mmol, 1.2 equiv) in 7.4 mL of anhydrous 1,4-dioxane was added sodium tert-butoxide (160 mg, 1.6 mmol, 3.0 equiv). The vial was capped, and the reaction mixture was heated 30 min at 150° C. in the microwave. The crude reaction mixture was filtered through celite then concentrated in vacuo. The residue was taken up in chloroform-methanol and concentrated onto celite, and purified via automated flash chromatography (12 g $SiO_2$, hexanes to ethyl acetate). The appropriate fractions were concentrated in vacuo. The residue was dissolved in 0.5 mL of 1:1 dimethyl sulfoxide-acetonitrile then purified further via reverse phase HPLC. The appropriate fractions were lyophilized from water-acetonitrile to afford the product as an off-white solid (68 mg, 20%).

Compound 26

4-(L-tert-butyl-3-(4-chlorobenzyl)-1H-pyrazol-5-ylamino)-2-fluoro-N-(thiazol-2-yl)benzenesulfonamide

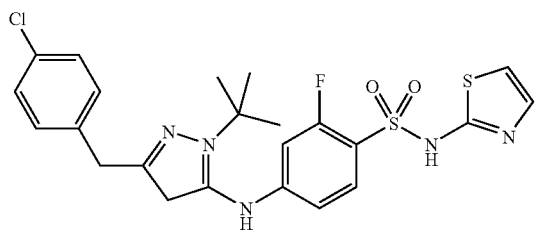

Synthesized according to General Procedure 7.

Compound 27

N-(thiazol-2-yl)-4-(5-(4-(trifluoromethyl)benzyl)-1,3,4-thiadiazol-2-ylamino)benzenesulfonamide

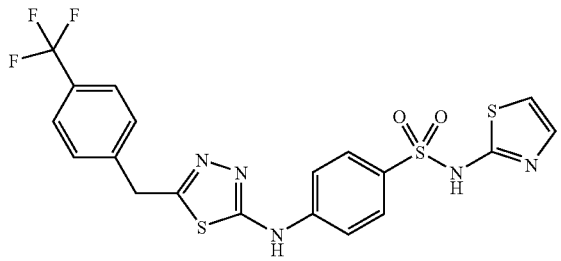

A mixture of (4-trifluoromethyl-phenyl)-acetic acid hydrazide (55 mg, 0.25 mmol, 1.5 equiv), 4-isothiocyanato-N-thiazol-2-yl-benzenesulfonamide (50 mg, 0.2 mmol, 1.0 equiv) and sodium carbonate (20 mg, 0.18 mmol, 1.1 equiv) in 1.0 mL of ethanol was heated at 85° C. After 16 h, the heterogeneous reaction mixture was concentrated in vacuo, diluted with 500 µL of acetonitrile, filtered, and purified via reverse phase HPLC. The fraction containing product was lyophilized to afford the product as an off-white solid (15 mg, 20%).

Compound 28

N-(thiazol-2-yl)-4-(5-(4-(trifluoromethyl)benzyl)-1,3,4-oxadiazol-2-ylamino)benzenesulfonamide

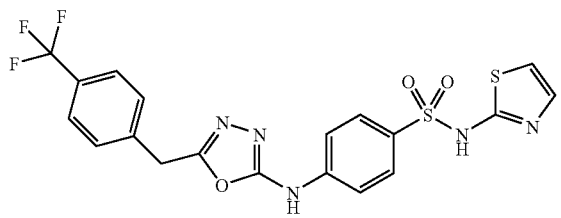

A mixture of (4-trifluoromethyl-phenyl)-acetic acid hydrazide (200 mg, 0.9 mmol, 1.0 equiv) and 4-isothiocyanato-N-thiazol-2-yl-benzenesulfonamide (273 mg, 0.9 mmol, 1.0 equiv) in 3 mL of anhydrous tetrahydrofuran was stirred at ambient temperature. After 18 h, p-toluenesulfonyl chloride (210 mg, 1.1 mmol, 1.2 equiv) and pyridine (156 mL, 1.93 mmol, 2.10 equiv) were added, and the reaction mixture was heated at reflux. After 4 h, the reaction mixture was cooled to ambient temperature. Ethyl acetate (3 mL) and 1 N hydrochloric acid (3 mL) were added. After stirring vigorously for 5 min, the layers were separated. The aqueous layer was extracted with ethyl acetate (3 mL). The combined organic layers were dried over sodium sulfate, filtered and concentrated in vacuo. The residue was triturated with hot acetonitrile to afford the product as a light yellow solid (295 mg, 60%).

Compound 29

4-(3-(cyclohexylmethyl)-1-methyl-1H-pyrazol-5-ylamino)-N-(thiazol-2-yl)benzenesulfonamide

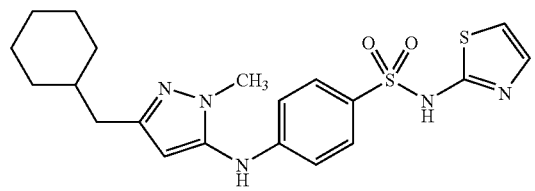

Synthesized according to General Procedure 7.

Compound 30

2-fluoro-4-(3-methyl-1-phenyl-1H-pyrazol-5-ylamino)-N-(thiazol-2-yl)benzenesulfonamide

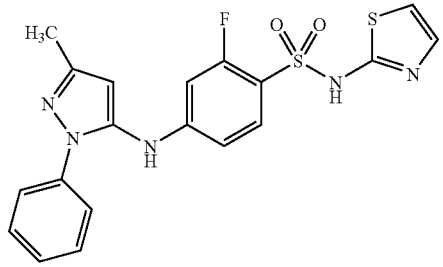

Synthesized according to General Procedure 7.

Compound 31

4-(1-(4-chlorobenzyl)-1H-pyrazol-3-ylamino)-2-fluoro-N-(thiazol-2-yl)benzenesulfonamide

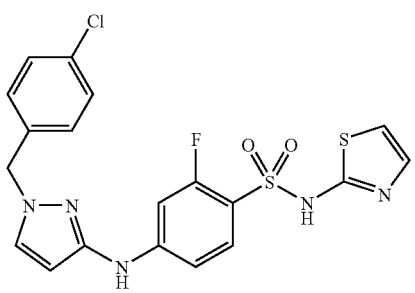

Synthesized according to General Procedure 7.

Compound 32

4-(3-cyclopropyl-1-phenyl-1H-pyrazol-5-ylamino)-2-fluoro-N-(thiazol-2-yl)benzenesulfonamide

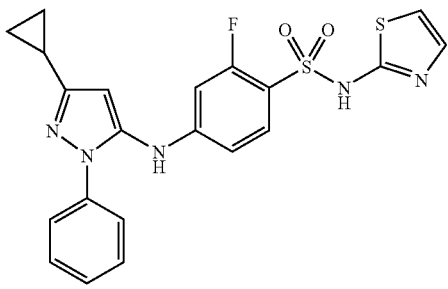

Synthesized according to General Procedure 7.

Compound 33

4-(1-(4-chlorobenzyl)-1H-pyrazol-4-ylamino)-2-fluoro-N-(thiazol-2-yl)benzenesulfonamide

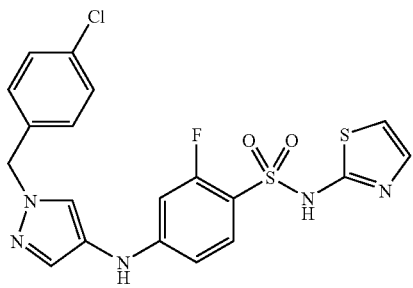

Synthesized according to General Procedure 7.

Compound 34

2-fluoro-4-(1-methyl-3-neopentyl-1H-pyrazol-5-ylamino)-N-(thiazol-2-yl)benzenesulfonamide

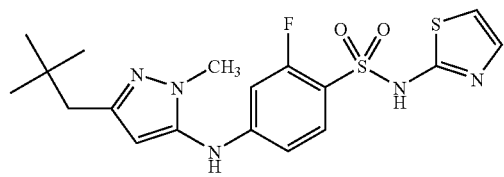

Synthesized according to General Procedure 7.

Compound 35

3-fluoro-4-(3-methyl-1-phenyl-1H-pyrazol-5-ylamino)-N-(thiazol-2-yl)benzenesulfonamide

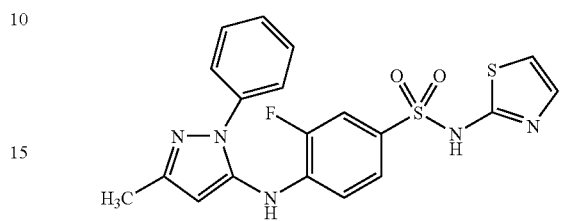

Synthesized according to General Procedure 7.

Compound 36

4-(3-cyclopropyl-1-phenyl-1H-pyrazol-5-ylamino)-3-fluoro-N-(thiazol-2-yl)benzenesulfonamide

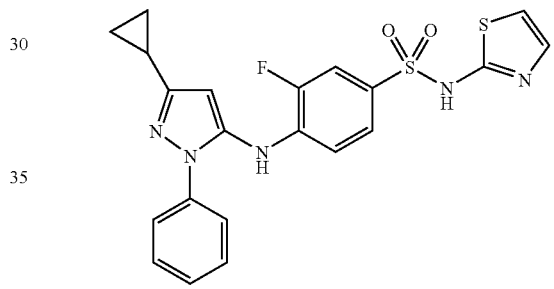

Synthesized according to General Procedure 7.

Compound 37

4-(Biphenyl-2-ylamino)-2-fluoro-N-thiazol-2-yl-benzenesulfonamide

Into a vial was added 4-bromo-2-fluoro-N-thiazol-2-yl-benzenesulfonamide (100 mg, 0.3 mmol), 9,9-dimethyl-4,5-bis(diphenylphosphino)xanthene (2.0 µl mg, 0.036 mmol), tris(dibenzylideneacetone)dipalladium(0) (11 mg, 0.012 mmol), [1,1'-Biphenyl]-2-amine (50.2 mg, 0.296 mmol), sodium tert-butoxide (86 mg, 0.89 mmol) and anhydrous tert-butyl alcohol (4.1 mL, 43 mmol). The reaction mixture was sparged with argon for ~5 min. The septum was replaced with a microwave vial cap, and the reaction mixture was heated for 5 min at 120° C. The reaction mixture was then filtered through a syringe filter and the filtrate concentrated in vacuo. The vial and syringe were washed with 3 mL of DMSO and this was combined with the concentrated filtrate. The resulting solution was filtered through a plug of cotton then purified by reverse phase HPLC (Prep: Phenomenex 250×30.0 mm 15 micron C18 column. 40 mL/min. Gradient 15% B to 100% B over 25 min. Solvent A: 7800 water/200 acetonitrile/8 TFA. Solvent B: 7200 acetonitrile/800 water/8 TFA). The clean fractions were concentrated in vacuo to afford the product as an off-white solid. LC/MS analysis: Retention time: 1.52 minutes, M+H=426.

Compound 113

4-(4-tert-butylthiazol-2-ylamino)-2-cyano-N-(thiazol-2-yl)benzenesulfonamide 4-bromo-2-cyanobenzene-1-sulfonyl chloride

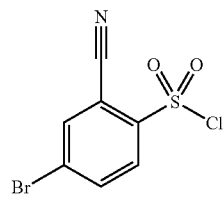

2-AMINO-5-BROMOBENZONITRILE (1.0 g, 5.1 mmol) was added in Acetonitrile (17 mL, 330 mmol) at room temperature and Acetic acid (3 mL, 50 mmol) was added. Concentrated 37% hydrochloric acid (37:63, Hydrogen chloride:Water, 5.7 mL) was added slowly. The reaction was chilled to 0° C. and Sodium nitrite (0.38 g, 5.6 mmol) in 2 mL of water was added over 1 min. The reaction was stirred at 0° C. for 20 minutes. Then Sulfur dioxide (10 mL, 200 mmol) in acetic acid was added followed by a solution of Copper(II) Chloride Dihydrate (0.86 g, 5.1 mmol) in 3 ml of water. Rxn warmed to rt and stirred for 2 hours. Rxn poured into water and was extracted with Ethyl acetate, dried over sodium sulfate, concentrated under reduced pressure to yield crude product (1.2 g, light brown solid) that was used in the next step without further purification.

4-bromo-2-cyano-N-(thiazol-2-yl)benzenesulfonamide

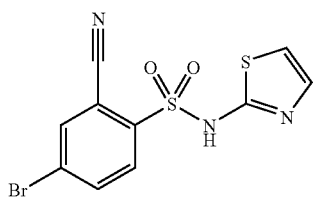

To 2-AMINOTHIAZOLE (0.21 g, 0.0021 mol) in Pyridine (1 mL, 0.01 mol) was added portion-wise the crude 4-Bromo-2-cyano-benzenesulfonyl chloride (0.40 g, 0.0014 mol). The reaction mixture was stirred at room temperature overnight. The reaction mixture was concentrated under reduced pressure, diluted with Ethyl acetate, washed with 1.0 N HCl, H2O and brine, dried with anhydrous sodium sulfate, filtered and concentrated to give the crude product, which was purified on ISCO (25% to 100% Ethyl acetate in hexanes). 35 mg of the product was obtained as a light yellow solid.

4-(4-tert-butylthiazol-2-ylamino)-2-cyano-N-(thiazol-2-yl)benzenesulfonamide

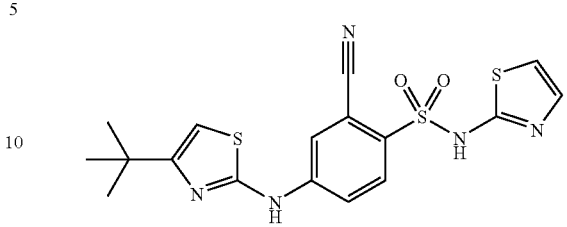

Into a Vial was added the 4-Bromo-2-cyano-N-thiazol-2-yl-benzenesulfonamide (35 mg, 0.00010 mol), Sodium tert-butoxide (29 mg, 0.00030 mol), 9,9-DIMETHYL-4,5-BIS(DIPHENYLPHOSPHINO)XANTHENE (7.1 mg, 0.000012 mol), Tris(dibenzylideneacetone)dipalladium(0) (3.7 mg, 0.0000041 mol), 2-AMINO-4-(4-CHLOROPHENYL)THIAZOLE and the de-gassed anhydrous 1,4-Dioxane (1.4 mL, 0.018 mol). The reaction mixture was heated at 150° C. for 1 h in microwave. The reaction mixture was filtered through celite and the filtrate was concentrated. The residue was diluted with ethyl acetate and washed with 1.0 N HCl, dried and was concentrated to give the crude product that was purified on ISCO twice (10% methanol in chloroform for first run, 25% Ethyl acetate to 100% Ethyl acetate for second run). Product was lyophilized from acetonitrile-water to afford a light orange powder.

Compound 150

2-fluoro-N-(thiazol-2-yl)-4-(1-(4-(trifluoromethyl)benzyl)-1H-pyrazol-4-ylamino)benzenesulfonamide 4-nitro-1-(4-(trifluoromethyl)benzyl)-1H-pyrazole

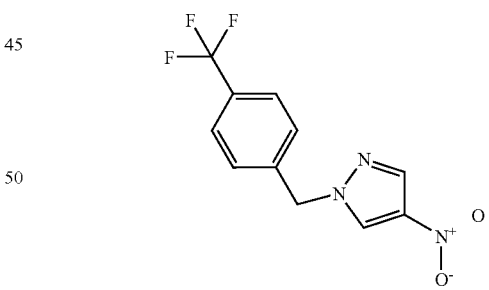

To a solution of ART-CHEM-BB B001469 (1.33 g, 0.0115 mol) and 4-(Bromomethyl)trifluoromethylbenzene (2.39 g, 0.0100 mol) in N,N-Dimethylformamide (10 mL, 0.1 mol) was added Cesium Carbonate (5.00 g, 0.0153 mol). The exothermic reaction was stirred for 10 min then heated in the microwave at 100° C. for 10 minutes. The cooled reaction was diluted with water, and the resultant precipitate was collected by filtration. The white solid was dissolved in ethyl ether and washed with 1N NaOH, water then brine. The organic phase was dried over magnesium sulfate. Concentration in vacuo gave 2.50 g of product as a white solid.

1-(4-(trifluoromethyl)benzyl)-1H-pyrazol-4-amine

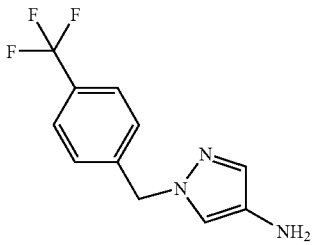

4-Nitro-1-(4-trifluoromethyl-benzyl)-1H-pyrazole (2.40 g, 0.00867 mol) was dissolved in Methanol (3.0E1 mL, 0.74 mol) and 10% Palladium on carbon (0.180 g) was added. The reaction was hydrogenated under balloon pressure for 2 days. The reaction was filtered through celite and concentrated in vacuo to give 2.08 g of product as a red oil.

2-fluoro-N-(thiazol-2-yl)-4-(1-(4-(trifluoromethyl)benzyl)-1H-pyrazol-4-ylamino)benzenesulfonamide

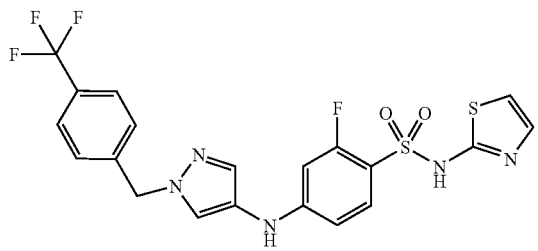

4-Bromo-2-fluoro-N-thiazol-2-yl-benzenesulfonamide (0.337 g, 1.00 mmol), 1-(4-Trifluoromethyl-benzyl)-1H-pyrazol-4-ylamine (0.242 g, 1.00 mmol), Tris(dibenzylideneacetone)dipalladium(0) (0.037 g, 0.040 mmol), and 9,9-DIMETHYL-4,5-BIS(DIPHENYLPHOSPHINO)XANTHENE (0.069 g, 0.12 mmol), were mixed in anhydrous N,N-Dimethylacetamide (10 mL, 100 mmol). The solution was sparged with argon for 10 minutes. Sodium tert-butoxide (0.290 g, 3.02 mmol) was added and the reaction was heated in the microwave for 5 minutes at 120° C. The crude reaction was partitioned between 1N HCl and chloroform. The organic phase was separated and the aqueous phase washed a second time with chloroform. The combined organic phase was washed with brine and dried over magnesium sulfate, then evaporated onto celite. The product was purified by column chromatography, chloroform to 10% methanol-chloroform gradient elution. Product fractions were combined and evaporated to a residue. The product was purified by reverse phase HPLC. (Phenomenex 100×21.2 mm 10 micron C18 column. 20 mL/min. Gradient 85% A to 100% B over 25 min. Solvent A: 7800 water/200 acetonitrile/8 TFA.).

Compound 155

2-(3-(4-chlorobenzyl)-5-(4-(N-thiazol-2-ylsulfamoyl)phenylamino)-1H-pyrazol-1-yl)acetamide

Ethyl 2-(5-amino-3-(4-chlorobenzyl)-1H-pyrazol-1-yl)acetate

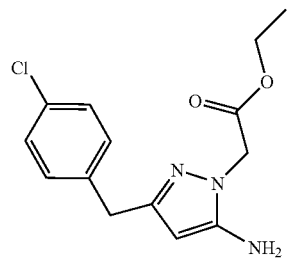

To a 40 mL vial equipped with a magnetic stir bar was added 4-(4-Chloro-phenyl)-3-oxo-butyronitrile (0.99 g, 5.1 mmol) in ethanol (20 mL, 400 mmol) followed by the addition of ETHYL HYDRAZINO ACETATE HYDROCHLORIDE (2.54 g, 16.4 mmol). The reaction was heated at 100° C. overnight. The reaction mixture was cooled to ambient temperature and concentrated in vacuo. The residue was partitioned between ethyl acetate and water. The aqueous phase was extracted with ethyl acetate. The organic layers were combined and washed with water and brine, dried, and was concentrated to give the crude product that was purified on the ISCO (hexanes to 50% ethyl acetate in hexanes) to give the product as a light pink solid.

2-(3-(4-chlorobenzyl)-5-(4-(N-thiazol-2-ylsulfamoyl)phenylamino)-1H-pyrazol-1-yl)acetic acid

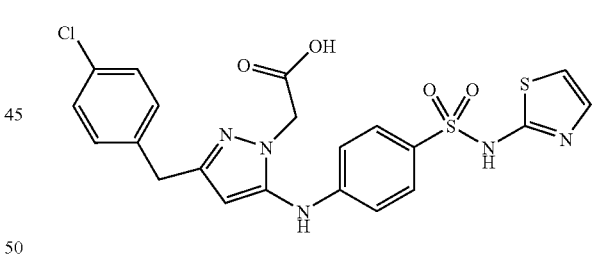

Into a Vial was added the 4-Iodo-N-thiazol-2-yl-benzenesulfonamide (108 mg, 0.000295 mol), 9,9-DIMETHYL-4,5-BIS(DIPHENYLPHOSPHINO)XANTHENE (2.0E1 mg, 0.000035 mol), Tris(dibenzylideneacetone)dipalladium(0) (11 mg, 0.000012 mol), 2-AMINO-4-(4-CHLOROPHENYL)THIAZOLE and the de-gassed anhydrous N,N-Dimethylacetamide (6.0 mL, 0.064 mol). The mixture was sparged with argon for 1 min. Sodium tert-butoxide (85 mg, 0.00088 mol) was added. The vial was capped immediately and reaction mixture was heated at 120° C. for 15 min in microwave. LC/MS showed the reaction was complete and only hydrolyzed product was detected. The reaction mixture was filtered through celite and diluted with ethyl acetate, washed with 1.0 N HCl solution, water (2×) and brine, dried over sodium sulfate, filtered, and was concentrated to give the crude product that was purified on ISCO (25% ethyl acetate in hexanes to 100% ethyl acetate, then 5% methanol in ethyl acetate). 30 mg of the product was obtained as a yellow oil.

2-(3-(4-chlorobenzyl)-5-(4-(N-thiazol-2-ylsulfa-
moyl)phenylamino)-1H-pyrazol-1-yl)acetamide

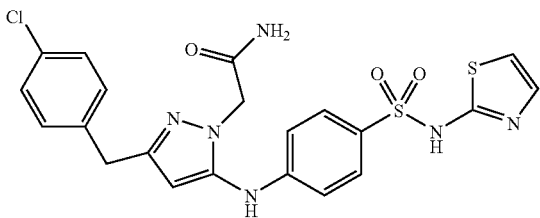

2-(3-(4-Chlorobenzyl)-5-(4-(N-thiazol-2-ylsulfamoyl)
phenylamino)-1H-pyrazol-1-yl)acetic acid (30 mg, 0.00006
mol) was dissolved in N,N-Dimethylformamide (0.4 uL,
0.000005 mol) and methylene chloride (0.2 mL, 0.003 mol).
Oxalyl chloride (7.6 uL, 0.000089 mol) was added and the
reaction stirred 1 hour. The reaction was quenched by pouring
it into 1.0 mL satd. ammonium hydroxide solution, neutralized with 1.0 N HCl, and extracted 2× with ethyl acetate. The
combined extracts were washed with brine, dried over magnesium sulfate and evaporated to give the desired product,
which was lyophilized from acetonitrile-water to provide a
yellow powder.

Compound 184

4-(1-(4-chlorobenzyl)-1H-pyrazol-3-ylamino)-3-
fluoro-N-(thiazol-2-yl)benzenesulfonamide

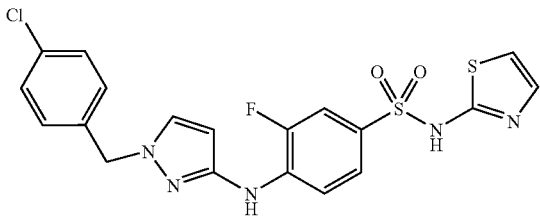

4-bromo-3-fluoro-N-(thiazol-2-yl)benzenesulfonamide
(0.136 g, 0.405 mmol), ART-CHEM-BB B001304 (0.0842 g,
0.406 mmol), Tris(dibenzylideneacetone)dipalladium(0)
(0.015 g, 0.016 mmol), 9,9-DIMETHYL-4,5-BIS(DIPHE-
NYLPHOSPHINO)XANTHENE (0.028 g, 0.049 mmol),
and Sodium tert-butoxide (0.117 g, 1.22 mmol) were mixed
in tert-Butyl alcohol (5 mL, 50 mmol). The solution was
sparged with argon for 5 minutes. The reaction was heated in
the microwave for 8 minutes at 120° C. The reaction was
diluted with 3 volumes of water and filtered through a celite
pad. The t-butanol was removed by rotory evaporation and the
solution acidified with 6N HCl. The precipitate was collected
by filtration. The product was purified by reverse phase
HPLC. Phenomenex 100×21.2 mm 10 micron C18 column.
20 mL/min. Gradient 85% A to 100% B over 25 min. Solvent
A: 7800 water/200 acetonitrile/8 TFA. Solvent B: 7200 acetonitrile/800 water/8 TFA. 254 nM UV detection. Product fractions were combined and evaporated to give product. The
product was purified a second time via column chromatography (ISCO, 4 g silica gel column, 20% ethyl acetate-hexanes
to 100% ethyl acetate gradient elution). Product fractions
were combined and evaporated. Vacuum drying yielded 65.9
mg of product as a white glass.

Compound 205

3-chloro-4-(1-(4-chlorobenzyl)-1H-pyrazol-3-
ylamino)-N-(thiazol-2-yl)benzenesulfonamide 4-bromo-3-chloro-N-(thiazol-2-yl)benzenesulfona-
mide

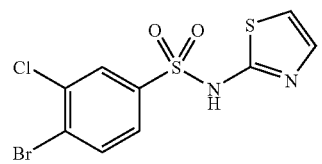

4-BROMO-3-CHLOROBENZENESULFONYL CHLORIDE (10.0 g, 0.0345 mol) and 2-AMINOTHIAZOLE (3.80
g, 0.0379 mol) were mixed in Pyridine (40 mL, 0.5 mol). The
reaction was allowed to stir at room temperature for 9 days.
The reaction was concentrated in vacuo to a total volume of
approximately 40 mL. The residue was triturated with acetonitrile and the solid collected by filtration. The filtrate was
concentrated in vacuo and the residue triturated with 1N HCl.
The solid was collected by filtration and rinsed with acetonitrile then ethyl ether. The combined solid from steps 4 and 5
was dissolved in boiling acetonitrile and treated with activated carbon then filtered through a celite pad. The filtrate
was reduced to ⅓ its original volume by distillation. The
mixture was cooled to room temperature. The crystals were
collected by filtration and rinsed with ethyl ether. Vacuum
drying gave 7.73 g of yellow solid.

3-chloro-4-(1-(4-chlorobenzyl-1H-pyrazol-3-
ylamino)-N-(thiazol-2-yl)benzenesulfonamide

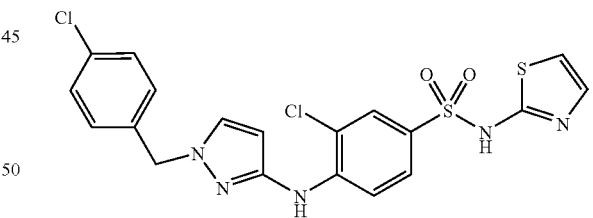

4-Bromo-3-chloro-N-thiazol-2-yl-benzenesulfonamide
(0.354 g, 1.00 mmol), ART-CHEM-BB B001304 (0.208 g,
1.00 mmol), Tris(dibenzylideneacetone)dipalladium(0)
(0.0742 g, 0.0810 mmol), 9,9-DIMETHYL-4,5-BIS(DIPHE-
NYLPHOSPHINO)XANTHENE (0.141 g, 0.243 mmol),
and Sodium tert-butoxide (0.288 g, 3.00 mmol) were mixed
in tert-Butyl alcohol (6.17 mL, 64.5 mmol). The solution was
sparged with argon for 5 minutes. The reaction was heated in
the microwave for 10 minutes at 120° C. The reaction was
diluted with acetonitrile and filtered through a celite pad. The
filtrate was evaporated in vacuo and the crude material purified by reverse phase HPLC. (Phenomenex 100×21.2 mm 10
micron C18 column. 20 mL/min. Gradient 85% A to 100% B
over 25 min. Solvent A: 7800 water/200 acetonitrile/8 TFA.

Solvent B: 7200 acetonitrile/800 water/8 TFA. 254 nM UV detection.) Product fractions were combined and evaporated in vacuo. The residue was purified a second time via column chromatography (10% ethyl acetate/hexanes to ethyl acetate gradient elution through a 12 g silica gel column). Product fractions were combined and evaporated to a residue. The residue was crystallized from acetonitrile-ethyl ether. The product was collected by filtration and vacuum dried to give 166 mg of white solid.

Compound 206

4-(1-(4-chlorobenzyl)-1H-pyrazol-3-ylamino)-2,5-difluoro-N-(thiazol-2-yl)benzenesulfonamide 4-bromo-2,5-difluoro-N-(thiazol-2-yl)benzenesulfonamide

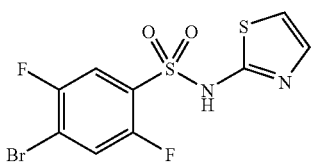

4-BROMO-2,5-DIFLUOROBENZENESULFONYL CHLORIDE (10.0 g, 0.0345 mol) and 2-AMINOTHIAZOLE (3.80 g, 0.0379 mol) were mixed in Pyridine (40 mL, 0.5 mol). The reaction was allowed to stir at room temperature for 9 days. The reaction was concentrated in vacuo to a total volume of approximately 40 mL. The residue was triturated with 1N HCl (aq). Acetonitrile was added until the precipitate became free-flowing. The solid was collected by filtration and rinsed with acetonitrile then ethyl ether. The solid was dissolved in boiling acetonitrile and treated with activated carbon then filtered through a celite pad. The filtrate was reduced to ⅓ its original volume by distillation. The mixture was cooled to room temperature. The crystals were collected by filtration and rinsed with ethyl ether. Vacuum drying gave 2.66 g of off-white solid.

4-(1-(4-chlorobenzyl)-1H-pyrazol-3-ylamino)-2,5-difluoro-N-(thiazol-2-yl)benzenesulfonamide

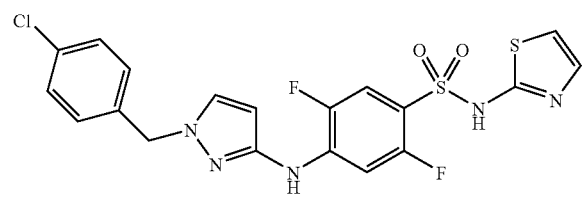

4-bromo-2,5-difluoro-N-(thiazol-2-yl)benzenesulfonamide (0.355 g, 1.00 mmol), ART-CHEM-BB B001304 (0.208 g, 1.00 mmol), Tris(dibenzylideneacetone)dipalladium(0) (0.0742 g, 0.0810 mmol), 9,9-DIMETHYL-4,5-BIS(DIPHENYLPHOSPHINO)XANTHENE (0.141 g, 0.243 mmol), and Sodium tert-butoxide (0.288 g, 3.00 mmol) were mixed in tert-Butyl alcohol (6.17 mL, 64.5 mmol). The solution was sparged with argon for 5 minutes. The reaction was heated in the microwave for 10 minutes at 120° C. The reaction was diluted with acetonitrile and filtered through a celite pad. The filtrate was evaporated in vacuo and the crude material purified by reverse phase HPLC. (Phenomenex 100×21.2 mm 10 micron C18 column. 20 mL/min. Gradient 85% A to 100% B over 25 min. Solvent A: 7800 water/200 acetonitrile/8 TFA. Solvent B: 7200 acetonitrile/800 water/8 TFA. 254 nM UV detection.) Product fractions were combined and evaporated in vacuo. The residue was crystallized from methylene chloride. The product was collected by filtration and vacuum dried to give 138 mg of off-white powder.

Compound 106

6-(4-tert-butylthiazol-2-ylamino)-N-(thiazol-2-yl)pyridine-3-sulfonamide 6-chloro-N-(thiazol-2-yl)pyridine-3-sulfonamide

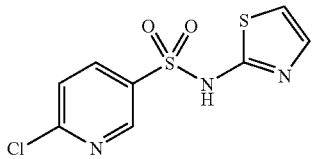

To 2-AMINOTHIAZOLE (1.80 g, 0.0179 mol) in Pyridine (6 mL, 0.08 mol) at 0° C. was added 2-Chloropyridine-5-sulfonyl chloride (1.55 g, 0.00717 mol) portion-wise. The reaction mixture was stirred overnight at room temperature. The reaction mixture was concentrated under reduced pressure, diluted with ethyl acetate (150 mL), washed with water and brine. The organic phase was dried over anhydrous sodium sulfate, filtered and concentrated. The crude product was purified on ISCO companion (silica gel, 10% to 100% ethyl acetate in hexanes) to give product as a brown solid.

6-(4-tert-butylthiazol-2-ylamino)-N-(thiazol-2-yl)pyridine-3-sulfonamide

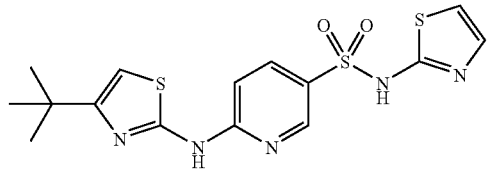

Into a Vial was added the 6-Chloro-pyridine-3-sulfonic thiazol-2-ylamide (35 mg, 0.00013 mol), Sodium tert-butoxide (36 mg, 0.00038 mol), 9,9-DIMETHYL-4,5-BIS(DIPHENYLPHOSPHINO)XANTHENE (8.8 mg, 0.000015 mol), Tris(dibenzylideneacetone)dipalladium(0) (4.6 mg, 0.0000051 mol), 2-AMINO-4-(4-CHLOROPHENYL)THIAZOLE and the de-gassed anhydrous 1,4-Dioxane (1.7 mL, 0.022 mol). The reaction mixture was heated at 150° C. for 1 h in microwave. The reaction mixture was filtered through celite and the filtrate was concentrated to give the crude product that was purified on Gilson (semi-prep, reverse phase, Phenomenex 100×21.2 mm 10 micron C18 column, 20 mL/min, Gradient 85% A to 100% B over 25 min. Solvent A: 7800 water/200 acetonitrile/8 TFA. Solvent B: 7200 acetoni-

Compound 107

6-(4-(4-chlorobenzyl)thiazol-2-ylamino)-N-(thiazol-2-yl)pyridine-3-sulfonamide 6-amino-N-(thiazol-2-yl)pyridine-3-sulfonamide

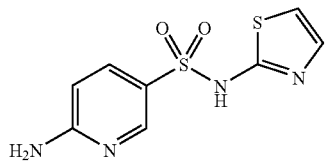

6-Chloro-pyridine-3-sulfonic thiazol-2-ylamide (200 mg, 0.0007 mol) in 7 M of Ammonia in methanol (5.00 mL) was heated at 160° C. in a pressure bottle for ~6 h. The reaction had to be stopped because the pressure was too high and some of the reaction solution was leaking. By LC/MS, reaction show ~30% conversion. The reaction solution was concentrated and then purified on Gilson (Prep LC, reverse phase, Phenomenex 250×30 mm, 15 micron C18 column, 40 mL/min. Gradient, 85% A to 100% B over 25 min. Solvent A: 7800 water/200 acetonitrile/8 TFA. Solvent B: 7200 acetonitrile/800 water/8). Fractions were checked by LC/MS and dried on a lyophilizer to give the product as a brown oil.

N-(THIAZOL-2-YL)-6-THIOUREIDOPYRIDINE-3-SULFONAMIDE

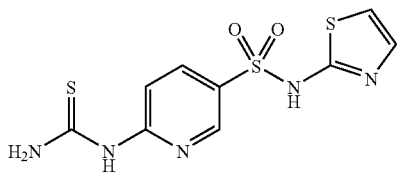

Carbonothioic dichloride (2.0E1 uL, 0.00026 mol) was added to a solution of the 6-Amino-pyridine-3-sulfonic acid thiazol-2-ylamide (45 mg, 0.00018 mol) and N,N-Diisopropylethylamine (0.092 mL, 0.00053 mol) in Tetrahydrofuran (1.2 mL, 0.014 mol) at 0° C. under an atmosphere of Argon and was stirred for 40 min at 0° C. Saturated ammonium hydroxide solution was added to the reaction mixture and stirred for a few min, then warmed to ambient temperature. The reaction mixture was concentrated and then dried on a lyophilizer to give the crude product that was used in the next step without purification. Note: The starting material, 6-Amino-pyridine-3-sulfonic acid thiazol-2-ylamide, was TFA salts.

6-(4-(4-chlorobenzyl)thiazol-2-ylamino)-N-(thiazol-2-yl)pyridine-3-sulfonamide

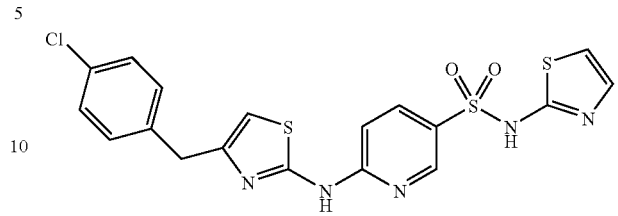

The mixture of the 6-Thioureido-pyridine-3-sulfonic acid thiazol-2-ylamide (27 mg, 0.000086 mol) and 1-Bromo-3-(4-chloro-phenyl)-propan-2-one (25 mg, 0.00010 mol) in DMF/AcOH (1:1) was heated at 95° C. for 20 min. The reaction solution was directly purified on Gilson (semi-prep, reverse phase, Phenomenex 100×21.2 mm 10 micron C18 column, 20 mL/min, Gradient 85% A to 100% B over 25 min. Solvent A: 7800 water/200 acetonitrile/8 TFA. Solvent B: 7200 acetonitrile/800 water/8 TFA). Fractions were checked by LC/MS and found no pure desired product was isolated. Fractions with the desired product were combined and then dried on a lyophilizer to give the product (1126-8-P1) as a yellow powder. The product (a mixture) was purified again by chromatography (silica gel, 5% Ethyl acetate in hexanes to 100% Ethyl acetate) to give a cleaner product (1126-8-P2), which was purified by Prep TLC (25% Ethyl acetate in hexanes, then 100% Ethyl acetate) to give the final pure product (1126-8-P-3) as a yellow solid.

Compound 116

5-iodopyridine-2-thiol 5-(4-tert-butylthiazol-2-ylamino)-N-(thiazol-2-yl)pyridine-2-sulfonamide

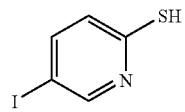

2-CHLORO-5-IODOPYRIDINE (2.0 g, 8.4 mmol) was added to a warm solution of Thiourea (662 mg, 8.70 mmol) in Ethanol (10 mL, 200 mmol). The mixture was heated 1 h at reflux. LC/MS indicated mostly SM. 1 additional equivalent of thiourea was added, and the reaction mixture was heated at reflux. After 16 h, LC/MS shows conversion to the intermediate along with a small amount of product. The reaction mixture was concentrated in vacuo. To the intermediate 6-Carbamimidoylsulfanyl-N-(4-trifluoromethyl-benzyl)-nicotinamide; hydrochloride in Water (21 mL, 1200 mmol) was added Sodium carbonate (706 mg, 6.66 mmol). After stirring for 15 minutes, Sodium hydroxide (1060 mg, 26.5 mmol) in Water (13 mL, 740 mmol) was added. The reaction mixture was filtered then acidified with 6 N HCl. The resulting bright yellow solid was collected by filtration, washed with water, and dried under vacuum.

5-iodopyridine-2-sulfonyl chloride

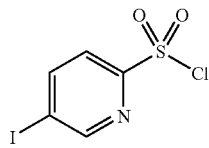

To a 0° C. mixture of 5-Iodo-pyridine-2-thiol (904 mg, 3.81 mmol) in Methylene chloride (17 mL, 270 mmol) and Water (8.6 mL, 480 mmol) was added 37% hydrochloric acid (37:63, Hydrogen chloride:Water, 2.6 mL). 10% NaOCl (1:9, Sodium hypochlorite:Water, 2.0E1 mL) was then added dropwise over 10 min to the vigorously stirred reaction mixture. After stirring 20 min, the reaction mixture was partitioned, and the aqueous layer was extracted with methylene chloride (2×). The combined organic layers were washed with aqueous sodium bisulfite, dried over sodium sulfate, filtered and concentrated in vacuo to afford a light yellow crystalline solid.

N-(2,4-dimethoxybenzyl)-5-iodo-N-(thiazol-2-yl) pyridine-2-sulfonamide

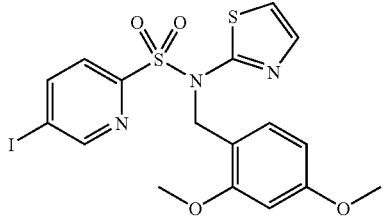

(2,4-Dimethoxy-benzyl)-thiazol-2-yl-amine (0.453 g, 1.81 mmol) was dissolved in Tetrahydrofuran (5 mL, 70 mmol) and cooled in an ice bath. 1.0 M of Lithium hexamethyldisilazide in Tetrahydrofuran (2.0 mL) was added dropwise to the reaction. After addition was complete, the reaction mixture was warmed to ambient temperature. After 30 min, the reaction was cooled to at 0° C. and a solution of 5-Iodo-pyridine-2-sulfonyl chloride (0.50 g, 1.6 mmol) in Tetrahydrofuran (4 mL, 50 mmol) was added dropwise. The reaction mixture was stirred 4 h then quenched with saturated aqueous ammonium chloride. The reaction mixture was concentrated in vacuo. The residue was taken up in ethyl acetate and additional saturated aqueous ammonium chloride was added. The layers were separated, and the aqueous layer was extracted with ethyl acetate. The combined organic layers were washed with brine, dried over sodium sulfate, filtered through celite, and concentrated in vacuo. The residue was purified on the ISCO twice (hexanes to ethyl acetate) to afford the product as a yellow solid.

5-(4-tert-butylthiazol-2-ylamino)-N-(2,4-dimethoxy-benzyl)-N-(thiazol-2-yl)pyridine-2-sulfonamide

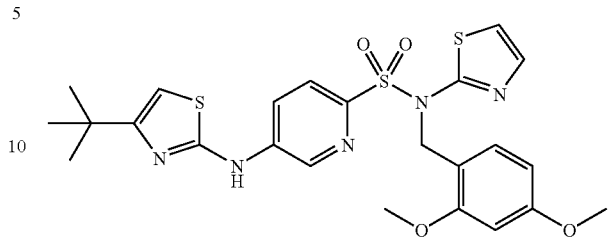

Into a Vial was added the 5-Iodo-pyridine-2-sulfonic acid (2,4-dimethoxy-benzyl)-thiazol-2-yl-amide (80 mg, 0.0001 mol), Sodium tert-butoxide (43 mg, 0.00044 mol), 9,9-DIMETHYL-4,5-BIS(DIPHENYLPHOSPHINO)XANTHENE (1.0E1 mg, 0.000018 mol), Tris(dibenzylideneacetone)dipalladium(0) (5.4 mg, 0.0000059 mol), 2-AMINO-4-(4-CHLOROPHENYL)THIAZOLE and the de-gassed anhydrous 1,4-Dioxane (2.0 mL, 0.026 mol). The reaction mixture was heated at 150° C. for 1 h in microwave. The reaction mixture was filtered through Celite and the filtrate was concentrated to give the crude product that was purified on ISCO twice (10% to 100% E/H) to give the product as a light brown solid.

5-(4-tert-butylthiazol-2-ylamino)-N-(thiazol-2-yl) pyridine-2-sulfonamide

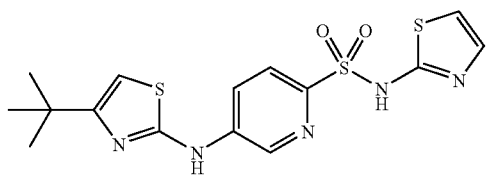

Trifluoroacetic Acid (49.4 uL, 0.641 mmol) was added to a solution of 5-(4-tert-Butyl-thiazol-2-ylamino)-pyridine-2-sulfonic acid (2,4-dimethoxy-benzyl)-thiazol-2-yl-amide (35 mg, 0.064 mmol) in Methylene chloride (0.39 mL, 6.1 mmol). After 30 min, the reaction mixture was concentrated in vacuo. The residue was dissolved in DMSO and purified on Gilson (semi-prep, reverse phase, Phenomenex 100×21.2 mm 10 micron C18 column, 20 mL/min, Gradient 85% A to 100% B over 25 min. Solvent A: 7800 water/200 acetonitrile/8 TFA. Solvent B: 7200 acetonitrile/800 water/8 TFA). Fractions were checked by LC/MS and then dried on a lyophilizer to give the desired product as a pale yellow powder.

Compound 227

6-(1-(4-chlorobenzyl)-1H-pyrazol-3-ylamino)-N-(thiazol-2-yl)pyridine-3-sulfonamide

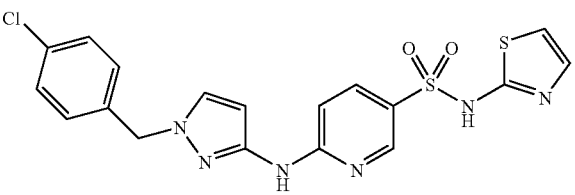

Into a Vial was added the 6-Chloro-pyridine-3-sulfonic thiazol-2-ylamide (82 mg, 0.00030 mol), Sodium tert-butoxide (86 mg, 0.00089 mol), 9,9-DIMETHYL-4,5-BIS(DIPHENYLPHOSPHINO)XANTHENE (21 mg, 0.000036 mol), Tris(dibenzylideneacetone)dipalladium(0) (11 mg, 0.000012 mol), ART-CHEM-BB B001304 (74 mg, 0.00036 mol) and Isopropyl alcohol (4.0 mL, 0.052 mol). The reaction mixture was heated at 150° C. for 40 min in microwave. LC/MS showed the reaction was not complete. Additional amount of the 9,9-DIMETHYL-4,5-BIS(DIPHENYLPHOSPHINO)XANTHENE and Tris(dibenzylideneacetone)dipalladium(0) were added and the reaction was heated again at 150° C. for 1 h. LC/MS showed no improvement of the reaction. The reaction mixture was filtered through Celite and washed with acetonitrile. The combined filtrate and washing was concentrated to give the crude product that was purified on Gilson (Prep LC, reverse phase, Phenomenex 250×30 mm, 15 micron C18 column, 40 mL/min. Gradient, 85% A to 100% B over 25 min. Solvent A: 7800 water/200 acetonitrile/8 TFA. Solvent B: 7200 acetonitrile/800 water/8). Fractions were checked by LC/MS and then dried on a lyophilizer to give the desired product as TFA salt (pale yellow powder).

Compound 228

6-(1-(4-chlorobenzyl)-1H-pyrazol-4-ylamino)-N-(thiazol-2-yl)pyridine-3-sulfonamide

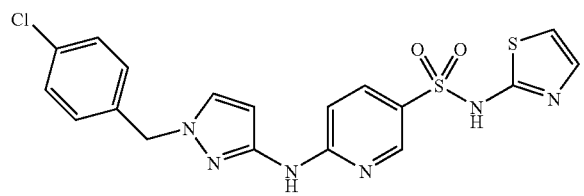

Into a Vial was added the 6-Chloro-pyridine-3-sulfonic thiazol-2-ylamide (82 mg, 0.00030 mol), 9,9-DIMETHYL-4,5-BIS(DIPHENYLPHOSPHINO)XANTHENE (21 mg, 0.000036 mol), Tris(dibenzylideneacetone)dipalladium(0) (11 mg, 0.000012 mol), [B] 1-(4-chlorobenzyl)-1H-pyrazol-4-amine dihydrochloride (1.0E2 mg, 0.00036 mol) and N,N-Dimethylacetamide (4.0 mL, 0.043 mol). The mixture was sparged with argon for ~5 min. Sodium tert-butoxide (140 mg, 0.0015 mol) was added and the reaction mixture was heated at 120° C. for 30 min in microwave. The reaction mixture was filtered through celite. The filtrate was diluted with Ethyl acetate and washed with 0.1 N HCl solution. The aqueous phase was neutralized with 1.0 N NaOH solution, extracted with Ethyl acetate. The combined organic phase was washed with water (3×) and brine, dried over Na2SO4, filtered and was concentrated to give the crude product that was purified on Gilson (Prep LC, reverse phase, Phenomenex 250×30 mm, 15 micron C18 column, 40 mL/min. Gradient, 85% A to 100% B over 25 min. Solvent A: 7800 water/200 acetonitrile/8 TFA. Solvent B: 7200 acetonitrile/800 water/8). Fractions were checked by LC/MS and combined accordingly. LC/MS showed the product was only ~90% pure. The combined product solution was concentrated to remove the acetonitrile, neutralized with 1.0 N NaOH solution and then extracted with Ethyl acetate (3×). The combined organic layers were dried over sodium sulfate, filtered and was concentrated to give the product as free base, which was purified again on ISCO (0% to 100% Ethyl acetate in DCM). 48 mg of the product was obtained as a pale yellow solid.

Compound 231

5-(1-(4-chlorobenzyl)-1H-pyrazol-4-ylamino)-N-(thiazol-2-yl)pyridine-2-sulfonamide 5-bromo-N-(thiazol-2-yl)pyridine-2-sulfonamide

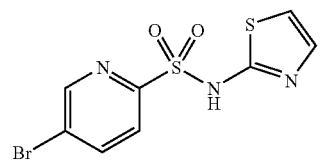

To 2-AMINOTHIAZOLE (0.29 g, 0.0029 mol) in Pyridine (2 mL, 0.02 mol) was added portionwise 5-Bromo-pyridine-2-sulfonyl chloride (0.50 g, 0.0019 mol). The reaction mixture was stirred at room temperature for 24 h. The reaction mixture was concentrated under reduced pressure, diluted with Ethyl acetate, washed with 1.0 N HCl, H₂O and brine, dried with anhydrous sodium sulfate, filtered and concentrated to give the product was obtained as a yellow solid.

5-(1-(4-chlorobenzyl)-1H-pyrazol-4-ylamino)-N-(thiazol-2-yl)pyridine-2-sulfonamide

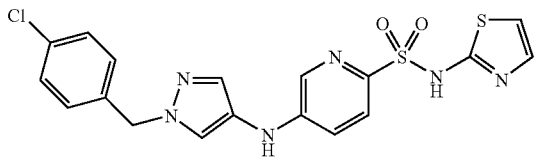

Into a Vial was added the 5-Bromo-pyridine-2-sulfonic acid thiazol-2-ylamide (50 mg, 0.0002 mol), 9,9-DIMETHYL-4,5-BIS(DIPHENYLPHOSPHINO)XANTHENE (11 mg, 0.000019 mol), Tris(dibenzylideneacetone)dipalladium(0) (5.7 mg, 0.0000062 mol), 1-(4-Chloro-benzyl)-1H-pyrazol-4-ylamine (39 mg, 0.00019 mol) and N,N-Dimethylacetamide (2.1 mL, 0.022 mol). The mixture was sparged with argon for ~5 min. Sodium tert-butoxide (75 mg, 0.00078 mol) was added and the reaction mixture was heated at 120° C. for 30 min in microwave. The reaction mixture was filtered through celite. The filtrate was diluted with Ethyl acetate and washed with 0.1 N HCl solution, water (3×) and brine, dried over sodium sulfate, filtered and was concentrated to give the crude product that was purified on ISCO (40% to 100% Ethyl acetate). 16.8 mg of the product was obtained as a light tan solid.

Compound 234

5-(3-methyl-1-phenyl-1H-pyrazol-5-ylamino)-N-(thiazol-2-yl)pyridine-2-sulfonamide

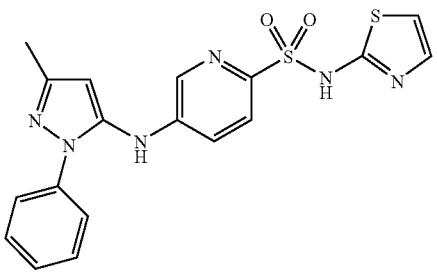

Into a Vial was added the 5-Bromo-pyridine-2-sulfonic acid thiazol-2-ylamide (75 mg, 0.00023 mol), 9,9-DIM-ETHYL-4,5-BIS(DIPHENYLPHOSPHINO)XANTHENE (16 mg, 0.000028 mol), Tris(dibenzylideneacetone)dipalladium(0) (8.6 mg, 0.0000094 mol), 5-AMINO-3-METHYL-1-PHENYLPYRAZOLE (49 mg, 0.00028 mol) and N,N-Dimethylacetamide (3.0 mL, 0.032 mol). The mixture was sparged with argon for ~5 min. Sodium tert-butoxide (68 mg, 0.00070 mol) was added and the reaction mixture was heated at 120° C. for 30 min in microwave. The reaction mixture was filtered through celite. The filtrate was diluted with Ethyl acetate and washed with 0.1 N HCl solution, water (3×) and brine, dried over sodium sulfate, filtered and was concentrated to give the crude product that was purified on ISCO (0% to 100% Ethyl acetate in CHCl3). 58 mg of the product was obtained as a light brown solid.

Compound 235

5-(1-(4-chlorobenzyl)-1H-pyrazol-3-ylamino)-N-(thiazol-2-yl)pyridine-2-sulfonamide

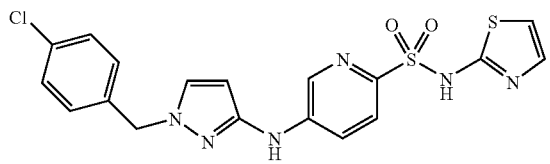

Into a Vial was added the 5-Bromo-pyridine-2-sulfonic acid thiazol-2-ylamide (150 mg, 0.00047 mol), 9,9-DIM-ETHYL-4,5-BIS(DIPHENYLPHOSPHINO)XANTHENE (32 mg, 0.000056 mol), Tris(dibenzylideneacetone)dipalladium(0) (17 mg, 0.000019 mol), ART-CHEM-BB B001304 (120 mg, 0.00056 mol) and N,N-Dimethylacetamide (6.0 mL, 0.064 mol). The mixture was sparged with argon for ~5 min. Sodium tert-butoxide (140 mg, 0.0014 mol) was added and the reaction mixture was heated at 120° C. for 30 min in microwave. The reaction mixture was filtered through celite. The filtrate was diluted with Ethyl acetate and washed with 0.1 N HCl solution, water (3×) and brine, dried over sodium sulfate, filtered and was concentrated to give the crude product that was purified on ISCO (0% to 100% Ethyl acetate in CHCl3). 125 mg of the product was obtained as a light tan solid.

Compound 278

1-(4-phenylbutyl)-N-(thiazol-2-yl)-1H-indazole-5-sulfonamide

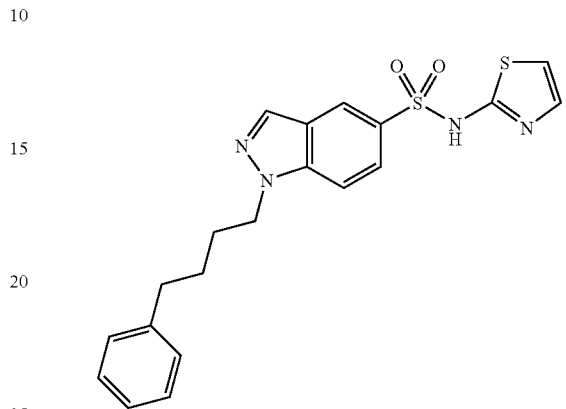

A suspension of 5-nitroindazole (1.098 g, 0.006731 mol), 1-bromo-4-phenylbutane (1.52 g, 0.00713 mol) and cesium carbonate (2.70 g, 0.00829 mol) in N,N-dimethylformamide (15 mL) was degassed with Ar for 10 min and then heated at 120° C. in a microwave for 50 min. The reaction was poured into water and extracted with methylene chloride (3×). The combined organics were washed with water and brine and then dried over MgSO$_4$, filtered, and concentrated. The residue was purified by flash column chromatography to give the two regioisomers 5-nitro-1-(4-phenylbutyl)-1H-indazole and 5-nitro-2-(4-phenylbutyl)-2H-indazole as an inseparable mixture.

To this mixture (756 mg, 0.00256 mol) dissolved in methanol (30 mL) was added 10% palladium on carbon (260 mg, 0.0024 mol). The reaction was fitted with a H$_2$ filled balloon and stirred for 2 hrs. The reaction was filtered through celite and concentrated to give the two regioisomeric anilines as a clear oil that was used without further purification.

The mixture (675 mg, 0.00254 mol) was dissolved in acetonitrile (20 mL) and acetic acid (3 mL, 0.05 mol) was added. Concentrated 12.0 M hydrogen chloride in water (2.5 mL) was added slowly. The resulting orange/red reaction was chilled in an ice water bath and a solution of sodium nitrite (457 mg, 0.00662 mol) in 1 mL of water was added over 1 min. After stirring at 5° C. for 50 minutes, 50% sulfur dioxide in acetic acid (7 mL) was added followed by copper(II) chloride dihydrate (1065 mg, 0.006247 mol). After stirring for 30 min, the reaction was taken out of the bath and stirred at room temp for an additional 16 hours. The reaction was poured into water and extracted with methylene chloride (2×). The combined organics were dried over MgSO$_4$, filtered, and concentrated to yield the sulfonyl chloride as a black oil. The sulfonyl chloride was dissolved in pyridine (35 mL, 0.43 mol) and then 2-aminothiazole (1.001 g, 0.009996 mol) was added. After stirring at room temp for 3 days, the reaction was concentrated and redissolved in methylene chloride. This was washed with saturated NH$_4$Cl and the aqueous layer extracted with methylene chloride. The combined organics were dried over MgSO$_4$, filtered, and concentrated. Purification using a Gilson preparatory HPLC separated the title compound and its regioisomer, providing both products as white solids.

Compounds 274-277 and 279-280 were synthesized according to the procedure for compound 278 above.

Compounds 38-105, 108-112, 114-115, 117-149, 151-154, 156-204, 207-226, 229-230, 232-233 and 236-273 were synthesized according to the general procedures 1-7 above and the synthetic Schemes A, A-1, B, B-1, B-2, and C-J.

Additional compounds of the invention, which have been synthesized according to the methods described herein are set forth below and listed in Table IV: 4-(5-tert-butyl-4-methylthiazol-2-ylamino)-N-(thiazol-2-yl)benzenesulfonamide; 4-(5-tert-butyl-4-methylthiazol-2-ylamino)-2-fluoro-N-(thiazol-2-yl)benzenesulfonamide; 4-(1-tert-butyl-3-(4-chlorobenzyl)-1H-pyrazol-5-ylamino)-2-fluoro-N-(thiazol-2-yl)benzenesulfonamide; 2-oxo-N-(thiazol-2-yl)-1-(4-(4-(trifluoromethyl)benzyl)thiazol-2-yl)indoline-5-sulfonamide; 4-(4-cyclopropylpyrimidin-2-ylamino)-2-fluoro-N-(thiazol-2-yl)benzenesulfonamide; 5-(3-(4-chlorobenzyl)-1-methyl-1H-pyrazol-5-ylamino)-N-(thiazol-2-yl)pyrimidine-2-sulfonamide; 2-(4-tert-butylthiazol-2-ylamino)-4-fluoro-N-(thiazol-2-yl)-2,3-dihydro-1H-indene-5-sulfonamide; 4-fluoro-2-(4-neopentylthiazol-2-ylamino)-3-oxo-N-(thiazol-2-yl)-2,3-dihydro-1H-indene-5-sulfonamide; 2-(3-(4-fluorobenzyl)isoxazol-5-yl)-N-(thiazol-2-yl)-1,2,3,4-tetrahydroisoquinoline-7-sulfonamide; 2-(3-(4-fluorobenzyl)isoxazol-5-yl)-4-oxo-N-(thiazol-2-yl)-1,2,3,4-tetrahydroisoquinoline-7-sulfonamide; 2-((4-cyclopropylthiazol-2-yl)(4-(N-thiazol-2-ylsulfamoyl)phenyl)amino)acetamide.

Additional characterization data for certain compounds of the present invention are set forth in Table III, below.

TABLE III

| Compound No. | MZ | m/z (M + H)+ | Retention Time (min) HPLC |
|---|---|---|---|
| 1 | 480 | 481 | 1.67 |
| 6 | 494 | 495 | 1.70 |
| 7 | 412 | 413 | 1.63 |
| 3 | 476 | 477 | 1.50 |
| 4 | 524 | 525 | 1.34 |
| 5 | 471 | 472 | 1.42 |
| 15 | 501 | 502 | 1.61 |
| 16 | 445 | 446 | 1.47 |
| 9 | 412 | 413 | 1.37 |
| 10 | 428 | 429 | 1.55 |
| 17 | 391 | 392 | 1.38 |
| 18 | 378 | 379 | 1.41 |
| 19 | 393 | 394 | 1.26 |
| 11 | 478 | 479 | 1.72 |
| 12 | 444 | 445 | 1.68 |
| 14 | 394 | 395 | 1.65 |
| 20 | 411 | 412 | 1.38 |
| 21 | 459 | 460 | 1.58 |
| 23 | 377 | 378 | 1.39 |
| 22 | 433 | 434 | 1.73 |
| 24 | 461 | 462 | 1.41 |
| 25 | 474 | 475 | 1.48 |
| 8 | 408 | 409 | 1.63 |
| 13 | 426 | 427 | 1.67 |
| 26 | 519 | 520 | 1.70 |
| 27 | 497 | 498 | 1.45 |
| 28 | 481 | 482 | 1.52 |
| 29 | 431 | 432 | 1.61 |
| 30 | 429 | 430 | 1.40 |
| 31 | 463 | 464 | 1.54 |
| 32 | 455 | 456 | 1.47 |
| 33 | 463 | 464 | 1.51 |
| 34 | 423 | 424 | 1.57 |
| 35 | 429 | 430 | 1.43 |
| 36 | 455 | 456 | 1.54 |
| 37 | 425 | 426 | 1.52 |

Additional characterization data for certain compounds of the present invention are set forth in Table IV, below.

TABLE IV

| Compound No. | MZ | Mass Spec m/z [MH]+ | Retention time (min) HPLC |
|---|---|---|---|
| 43 | 414 | 415 | 1.56 |
| 44 | 333 | 334 | 1.12 |
| 45 | 439 | 440 | 1.56 |
| 46 | 529 | 530 | 1.61 |
| 47 | 490 | 491 | 1.79 |
| 48 | 444 | 445 | 1.56 |
| 49 | 518 | 519 | 1.59 |
| 50 | 472 | 473 | 1.67 |
| 51 | 434 | 435 | 1.33 |
| 52 | 478 | 479 | 1.66 |
| 53 | 454 | 455 | 1.69 |
| 54 | 457 | 458 | 1.44 |
| 55 | 507 | 508 | 1.51 |
| 56 | 547 | 548 | 1.34 |
| 57 | 487 | 488 | 1.14 |
| 58 | 504 | 505 | 1.18 |
| 59 | 414 | 415 | 1.5 |
| 60 | 533 | 534 | 1.32 |
| 61 | 561 | 562 | 1.56 |
| 62 | 500 | 501 | 1.78 |
| 63 | 458 | 459 | 1.42 |
| 64 | 516 | 517 | 1.86 |
| 65 | 491 | 492 | 1.25 |
| 66 | 531 | 532 | 1.1 |
| 67 | 485 | 486 | 1.1 |
| 68 | 423 | 424 | 0.86 |
| 69 | 499 | 500 | 1.22 |
| 70 | 547 | 548 | 1.34 |
| 71 | 525 | 526 | 1.3 |
| 72 | 502 | 503 | 1.07 |
| 73 | 500 | 501 | 1.25 |
| 74 | 463 | 464 | 1.18 |
| 75 | 486 | 487 | 0.94 |
| 76 | 517 | 518 | 1.2 |
| 77 | 410 | 411 | 1.42 |
| 78 | 352 | 353 | 1.25 |
| 79 | 464 | 465 | 1.62 |
| 80 | 366 | 366 | 1.45 |
| 81 | 445 | 446 | 1.78 |
| 82 | 478 | 478 | 1.42 |
| 83 | 406 | 407 | 0.76 |
| 84 | 482 | 483 | 1.73 |
| 85 | 363 | 364 | 1.22 |
| 86 | 361 | 362 | 1.41 |
| 87 | 505 | 506 | 1.78 |
| 88 | 505 | 506 | 1.69 |
| 89 | 494 | 494 | 1.21 |
| 90 | 500 | 501 | 1.7 |
| 91 | 462 | 463 | 1.63 |
| 92 | 499 | 500 | 1.71 |
| 93 | 498 | 499 | 1.78 |
| 94 | 506 | 507 | 1.83 |
| 95 | 512 | 514 | 1.5 |
| 96 | 492 | 493 | 1.59 |
| 97 | 506 | 507 | 1.83 |
| 98 | 459 | 460 | 1.5 |
| 99 | 405 | 406 | 1.37 |
| 100 | 419 | 420 | 1.37 |
| 101 | 419 | 420 | 1.37 |
| 102 | 518 | 519 | 1.77 |
| 103 | 456 | 457 | 1.68 |
| 104 | 466 | 467 | 1.65 |
| 105 | 530 | 531 | 1.58 |
| 106 | 395 | 396 | 1.60 |
| 107 | 463 | 464 | 1.66 |
| 108 | 494 | 495 | 1.77 |
| 109 | 494 | 495 | 1.76 |
| 110 | 495 | 496 | 1.72 |
| 111 | 502 | 503 | 1.71 |
| 112 | 492 | 493 | 1.37 |
| 113 | 419 | 420 | 1.64 |
| 114 | 372 | 373 | 1.32 |
| 115 | 463 | 464 | 1.56 |

TABLE IV-continued

| Compound No. | MZ | Mass Spec m/z [MH]+ | Retention time (min) HPLC |
|---|---|---|---|
| 116 | 395 | 396 | 1.60 |
| 117 | 388 | 389 | 1.50 |
| 118 | 447 | 448 | 1.5 |
| 119 | 484 | 485 | 1.56 |
| 120 | 463 | 464 | 1.44 |
| 121 | 502 | 503 | 1.47 |
| 122 | 425 | 426 | 1.45 |
| 123 | 467 | 468 | 1.56 |
| 124 | 411 | 412 | 1.43 |
| 125 | 405 | 406 | 1.51 |
| 126 | 455 | 456 | 1.42 |
| 127 | 455 | 456 | 1.45 |
| 128 | 459 | 460 | 1.49 |
| 129 | 485 | 486 | 1.64 |
| 130 | 421 | 422 | 1.29 |
| 131 | 426 | 427 | 1.20 |
| 132 | 431 | 432 | 1.49 |
| 133 | 449 | 450 | 1.66 |
| 134 | 447 | 448 | 1.64 |
| 135 | 482 | 483 | 1.35 |
| 136 | 434 | 435 | 1.49 |
| 137 | 445 | 446 | 1.56 |
| 138 | 493 | 494 | 1.62 |
| 139 | 461 | 462 | 1.51 |
| 140 | 463 | 464 | 1.49 |
| 141 | 477 | 478 | 1.60 |
| 142 | 503 | 504 | 1.67 |
| 143 | 477 | 478 | 1.62 |
| 144 | 437 | 438 | 1.5 |
| 145 | 457 | 458 | 1.52 |
| 146 | 443 | 444 | 1.44 |
| 147 | 443 | 444 | 1.42 |
| 148 | 429 | 430 | 1.39 |
| 149 | 463 | 464 | 1.38 |
| 150 | 497 | 498 | 1.50 |
| 151 | 397 | 398 | 1.36 |
| 152 | 463 | 464 | 1.45 |
| 153 | 463 | 464 | 1.58 |
| 154 | 491 | 492 | 1.59 |
| 155 | 502 | 503 | 1.54 |
| 156 | 471 | 472 | 1.62 |
| 157 | 499 | 500 | 1.6 |
| 158 | 499 | 500 | 1.74 |
| 159 | 457 | 458 | 1.59 |
| 160 | 457 | 458 | 1.58 |
| 161 | 445 | 446 | 1.41 |
| 162 | 463 | 464 | 1.50 |
| 163 | 445 | 446 | 1.59 |
| 164 | 519 | 520 | 1.66 |
| 165 | 443 | 444 | 1.51 |
| 166 | 537 | 538 | 1.69 |
| 167 | 443 | 444 | 1.53 |
| 168 | 415 | 416 | 1.41 |
| 169 | 421 | 422 | 1.42 |
| 170 | 497 | 498 | 1.52 |
| 171 | 505 | 506 | 1.59 |
| 172 | 425 | 426 | 1.52 |
| 173 | 447 | 448 | 1.33 |
| 174 | 455 | 456 | 1.44 |
| 175 | 421 | 422 | 1.42 |
| 176 | 443 | 444 | 1.42 |
| 177 | 447 | 448 | 1.40 |
| 178 | 447 | 448 | 1.39 |
| 179 | 497 | 498 | 1.39 |
| 180 | 440 | 441 | 1.36 |
| 181 | 497 | 498 | 1.52 |
| 182 | 481 | 482 | 1.40 |
| 183 | 497 | 498 | 1.48 |
| 184 | 463 | 464 | 1.57 |
| 185 | 497 | 498 | 1.55 |
| 186 | 461 | 462 | 1.39 |
| 187 | 515 | 516 | 1.49 |
| 188 | 459 | 460 | 1.31 |
| 189 | 497 | 498 | 1.39 |
| 190 | 465 | 466 | 1.31 |
| 191 | 457 | 458 | 1.41 |
| 192 | 409 | 410 | 1.33 |
| 193 | 409 | 410 | 1.42 |
| 194 | 501 | 502 | 1.57 |
| 195 | 519 | 520 | 1.64 |
| 196 | 477 | 478 | 1.55 |
| 197 | 481 | 482 | 1.55 |
| 198 | 481 | 482 | 1.57 |
| 199 | 464 | 465 | 1.49 |
| 200 | 498 | 499 | 1.48 |
| 201 | 464 | 465 | 1.49 |
| 202 | 450 | 451 | 1.06 |
| 203 | 447 | 448 | 1.37 |
| 204 | 515 | 516 | 1.4 |
| 205 | 479 | 480 | 1.59 |
| 206 | 481 | 482 | 1.50 |
| 207 | 482 | 483 | 1.46 |
| 208 | 464 | 465 | 1.45 |
| 209 | 495 | 496 | 1.6 |
| 210 | 495 | 496 | 1.57 |
| 211 | 429 | 430 | 1.41 |
| 212 | 513 | 514 | 1.47 |
| 213 | 500 | 501 | 1.31 |
| 214 | 501 | 502 | 1.53 |
| 215 | 459 | 460 | 1.39 |
| 216 | 528 | 529 | 1.39 |
| 217 | 447 | 448 | 1.45 |
| 218 | 459 | 460 | 1.53 |
| 219 | 477 | 478 | 1.55 |
| 220 | 459 | 460 | 1.35 |
| 221 | 506 | 507 | 1.52 |
| 222 | 493 | 494 | 1.6 |
| 223 | 459 | 460 | 1.55 |
| 224 | 459 | 460 | 1.41 |
| 225 | 491 | 492 | 1.48 |
| 226 | 447 | 448 | 1.48 |
| 227 | 446 | 447 | 1.49 |
| 228 | 446 | 447 | 1.42 |
| 229 | 531 | 532 | 1.53 |
| 230 | 543 | 544 | 1.51 |
| 231 | 446 | 447 | 1.39 |
| 232 | 464 | ES+ 465 ES− 463 | AP3 RT 2.24 min 100% ELSD |
| 234 | 412 | 413 | 1.35 |
| 235 | 446 | 447 | 1.46 |
| 236 | 444 | ES+ 445 | AP3 RT 2.46 min 100% ELSD |
| 237 | 428 | ES+ 429 | AP3 RT 2.31 min 100% ELSD |
| 238 | 430 | ES+ 431 | AP3 RT 2.0 min 100% ELSD |
| 239 | 443 | ES+ 444 | AP3 RT 2.46 min 100% ELSD |
| 240 | 430 | ES+ 429 | AP3 RT 2.04 min 100% ELSD |
| 241 | 506 | ES+ 507 | AP3 RT 2.7 min 100% ELSD |
| 243 | 532 | ES+ 533 ES− 531 | AP3 RT 2.54 min 100% ELSD |
| 244 | 464 | ES+ 465 ES− 463 | AP3 RT 2.27 min 100% ELSD |
| 245 | 454 | ES+ 455 | AP3 RT 2.27 min 100% ELSD |
| 246 | 458 | ES+ 459 | AP3 RT 3.21 min 100% ELSD |
| 247 | 444 | ES+ 445 | AP3 RT 3.11 min 100% ELSD |
| 248 | 480 | ES+ 481 | AP3 RT 3.4 min 100% ELSD |
| 249 | 474 | ES+ 475 | AP3 RT 3.15 min 100% ELSD |
| 250 | 470 | ES+ 471 | AP3 RT 2.3 min 100% ELSD |
| 251 | 478 | ES+ 479 ES− 477 | AP3 RT 2.20 min 100% ELSD |
| 252 | 472 | ES+ 473 | AP3 RT 3.45 min 100% ELSD |
| 253 | 504 | ES+ 505 ES− 503 | AP3 RT 3.51 min 100% ELSD |
| 254 | 508 | ES+ 509 ES− 507 | AP3 RT 3.45 min 100% ELSD |
| 255 | 492 | ES+ 493 ES− 491 | AP3 RT 3.50 min 100% ELSD |
| 256 | 506 | ES+ 507 ES− 505 | AP3 RT 2.33 min 100% ELSD |
| 257 | 530 | 531 | 1.86 |
| 258 | 514 | 515 | 1.49 |
| 259 | 471 | 472 | 3.27 |
| 260 | 458 | 459 | 3.24 |
| 261 | 462 | 463 | 3.27 |
| 262 | 458 | 459 | 3.15 |
| 263 | 479 | 482 | 20 min LC run = 10.03 |
| 264 | 470 | 471 | 3.33 |
| 265 | 514 | 515 | 3.45 |
| 266 | 529 | 530 | RT = 3.43 mins. |
| 267 | 447 | 448 | RT = 3.14 mins. |
| 268 | 425 | 426 | RT = 3.05 mins. |
| 269 | 477 | 478 | RT = 3.34 mins. |
| 270 | 495 | 496 | RT = 3.17 mins. |
| 271 | 459 | 460 | RT = 3.31 mins |

TABLE IV-continued

| Compound No. | MZ | Mass Spec m/z [MH]+ | Retention time (min) HPLC |
|---|---|---|---|
| 272 | 479 | 480 | RT = 3.20 mins. |
| 273 | 452 | AP+ 453 AP− and ES− 451 | system2__2ndfl RT 1.19 min 100% ELSD |
| 274 | 454 | 455.0 | 1.7 |
| 275 | 454 | 455.0 | 1.6 |
| 276 | 458 | 459.1 | 1.4 |
| 277 | 458 | 459.2 | 1.4 |
| 278 | 412 | 413.0 | 1.6 |
| 279 | 412 | 413.0 | 1.5 |
| 280 | 416 | 417.0 | 1.3 |

Example 2 provides methods for testing the efficacy of the compounds of the invention.

Example 2

2.a. Cell Line Construction and Maintenance

Human Embryonic Kidney (HEK) cells were transfected with hSCN3A or hSCN9A constructs using lipofectamine reagent (Invitrogen), using standard techniques. Cells stably expressing the hSCN3A or hSCN9A constructs were identified by their resistance to G-418 (400 µg/ml). Clones were screened for expression using the whole-cell voltage-clamp technique.

2.b. Cell Culture

HEK cells stably transfected with hSCN3A or hSCN9A were maintained in DMEM medium supplemented with 10% heat-inactivated fetal bovine serum and 400 µg/ml G418 sulfate in an incubator at 37° C. with a humidified atmosphere of 10% $CO_2$. For HTS, cells were harvested from flasks by trypsinization and replated in an appropriate multi-well plate (typically 96 or 384 wells/plate) such that confluence would be achieved within 24 hours of plating. For electrophysiological studies, cells were removed from the culture flask by brief trypsinization and replated at low density onto glass cover slips. Cells were typically used for electrophysiological experiments within 24 to 72 h after plating.

2.c. Electrophysiological Recording

Cover slips containing HEK cells expressing hSCN3A or hSCN9A were placed in a bath on the stage of an inverted microscope and perfused (approximately 1 ml/min) with extracellular solution of the following composition: 138 mM NaCl, 2 mM $CaCl_2$, 5.4 mM KCl, 1 mM $MgCl_2$, 10 mM glucose, and 10 mM HEPES, pH 7.4, with NaOH. Pipettes were filled with an intracellular solution of the following composition: 135 mM CsF, 5 mM CsCl, 2 mM $MgCl_2$, 10 mM EGTA, 10 mM HEPES, pH 7.3 to 7.4, and had a resistance of 1 to 2 mega ohms. The osmolarity of the extracellular and intracellular solutions was 300 mmol/kg and 295 mmol/kg, respectively. All recordings were made at room temperature (22-24° C.) using AXOPATCH 200B amplifiers and PCLAMP software (Axon Instruments, Burlingame, Calif.) or PatchXpress 7000 hardware and associated software (Axon Instruments, Burlingame, Calif.).

hSCN3A or hSCN9A currents in HEK cells were measured using the whole-cell configuration of the patch-clamp technique (Hamill et al., 1981). Uncompensated series resistance was typically 2 to 5 mega ohms and >85% series resistance compensation (50% for PatchXpress) was routinely achieved. As a result, voltage errors were negligible and no correction was applied. Current records were acquired at 20 to 50 KHz and filtered at 5 to 10 KHz.

HEK cells stably transfected with hSCN3A or hSCN9A were viewed under Hoffman contrast optics and placed in front of an array of flow pipes emitting either control or compound-containing extracellular solutions. All compounds were dissolved in dimethyl sulfoxide to make 10 mM stock solutions, which were then diluted into extracellular solution to attain the final concentrations desired. The final concentration of dimethyl sulfoxide (<0.3% dimethyl sulfoxide) was found to have no significant effect on hSCN3A or hSCN9A sodium currents.

The voltage-dependence of inactivation was determined by applying a series of depolarizing prepulses (8 sec long in 10 mV increments) from a negative holding potential. The voltage was then immediately stepped to 0 mV to assess the magnitude of the sodium current. Currents elicited at 0 mV were plotted as a function of prepulse potential to allow estimation of the voltage midpoint of inactivation ($V_{1/2}$). Cells were then voltage clamped at the empirically determined $V_{1/2}$.

Compounds were tested for their ability to inhibit hSCN3A or hSCN9A sodium channels by activating the channel with a 20 msec voltage step to 0 mV following an 8 second conditioning prepulse to the empirically determined $V_{1-2}$ (Table B). Compound effect (% inhibition) was determined by difference in current amplitude before and after application of test compounds. For ease of comparison, "estimated IC-50" (EIC-50) values were calculated from single point electrophysiology data by the following equation, (tested concentration, uM)×(100-% inhibition/% inhibition). Inhibition values <20% and >80% were excluded from the calculation.

In some cases electrophysiological assays were conducted with PatchXpress 7000 hardware and associated software (Molecular Devices Corp) (Table B). All assay buffers and solutions were identical to those used in conventional whole-cell voltage clamp experiments described above. hSCN3A or hSCN9A containing cells were grown as above to 50%-80% confluency and harvested by trypsinization. Trypsinized cells were washed and resuspended in extracellular buffer at a concentration of $1\times10^6$ cells/ml. The onboard liquid handling facility of the PatchXpress was used for dispensing cells and application of test compounds. Determination of the voltage midpoint of inactivation was as described for conventional whole-cell recordings. Cells were then voltage-clamped to the empirically determined $V_{1/2}$ and current was activated by a 20 msec voltage step to 0 mV.

Electrophysiological assays were also conducted using the Ionworks Quattro automated electrophysiological platform (Molecular Devices Corp) (Table C). Intracellular and extracellular solutions were as described above with the following changes, 100 µg/ml amphotericin was added to the intracellular solution to perforate the membrane and allow electrical access to the cells. hSCN3A or hSCN9A containing cells were grown and harvested as for PatchXpress and cells were resuspended in extracellular solution at a concentration of $3-4\times10^6$ cells/ml. The onboard liquid handling facility of the Ionworks Quattro was used for dispensing cells and application of test compounds. A voltage protocol was then applied that comprised of a voltage step to fully inactivate the sodium channels, followed by a brief hyperpolarized recovery period to allow partial recovery from inactivation for unblocked sodium channels, followed by a test depolarized voltage step to assess magnitude of inhibition by test compound. Compound effect was determined based on current amplitude difference between the pre-compound addition and post-compound addition scans.

2.d. High-Throughput Screening Assays

Confluent cells in multi-well plates were incubated with a permeant radioactive ion ($^{22}$Na, $^{14}$C-guanidinium, etc) for 4-16 hours to allow uptake of the radiotracer. Excess radioactive ions were removed by washing with prewarmed buffer of the following composition: 138 mM NaCl, 2 mM $CaCl_2$, 5.4 mM KCl, 1 mM $MgCl_2$, 10 mM glucose, and 10 mM HEPES, pH 7.4, with NaOH. Efflux was initiated by addition of buffer containing any necessary chemical activators (e.g., 100 μM veratridine, 10-20 μg/ml Lqh scorpion venom, etc.). Various concentrations of test compounds or reference sodium channel blockers were added concurrently with the initiation of efflux. Efflux was allowed to progress for a defined period of time, typically 30-90 minutes, at 37° C. in a humidified 10% $CO_2$ atmosphere. Stimulated efflux was determined by collecting the extracellular solution and transferring to a multiwell plate for scintillation counting. Residual intracellular radioactivity was also determined by scintillation counting following lysis of the cells in the assay plate. Inhibition of efflux was determined by comparing efflux in the presence of test compounds to efflux in untreated control cells.

The activity of certain compounds of the present invention is set forth in Table V, below.

TABLE V

| Compound No. | SCN3A EIC-50 | SCN9A EIC-50 |
|---|---|---|
| 1 | +++ | +++ |
| 2 | +++ | ++ |
| 6 | ++ | ++ |
| 7 | +++ | ++ |
| 3 | +++ | + |
| 4 | +++ | ++ |
| 5 | +++ | ++ |
| 15 | +++ | +++ |
| 16 | +++ | +++ |
| 9 | ++ | ++ |
| 10 | +++ | ++ |
| 17 | +++ | ++ |
| 18 | +++ | + |
| 19 | +++ | + |
| 11 | ++ | ++ |
| 12 | +++ | ++ |
| 14 | +++ | ++ |
| 20 | +++ | ++ |
| 21 | +++ | +++ |
| 23 | ++ | ++ |
| 22 | ++ | ++ |
| 24 | ++ | + |
| 25 | +++ | + |
| 8 | +++ | +++ |
| 13 | +++ | +++ |
| 26 | +++ | +++ |
| 27 | +++ | + |
| 28 | +++ | + |
| 29 | +++ | +++ |
| 30 | +++ | +++ |
| 31 | +++ | +++ |
| 32 | +++ | +++ |
| 33 | +++ | +++ |
| 34 | +++ | +++ |
| 35 | +++ | +++ |
| 36 | +++ | +++ |
| 37 | +++ | +++ |

"+++" <2 μM;
"++" 2-10 μM;
"+" >10 μM

The activity of certain compounds of the present invention is set forth in Table VI, below.

TABLE VI

| Compound No. | SCN3A EIC-50 (μM) | SCN9A EIC-50 (μM) |
|---|---|---|
| 43 | >1 | ++ |
| 44 | >1 | >3 |
| 45 | +++ | + |
| 46 | +++ | >10 |
| 47 | +++ | >3 |
| 48 | +++ | >1 |
| 49 | +++ | +++ |
| 50 | +++ | ++ |
| 51 | +++ | ++ |
| 52 | +++ | +++ |
| 53 | +++ | >1 |
| 54 | ++ | >1 |
| 55 | +++ | >1 |
| 56 | +++ | +++ |
| 57 | ++ | >1 |
| 58 | >1 | ++ |
| 59 | +++ | |
| 60 | +++ | ++ |
| 61 | +++ | +++ |
| 62 | +++ | ++ |
| 63 | +++ | ++ |
| 64 | +++ | >1 |
| 65 | +++ | +++ |
| 66 | >1 | >3 |
| 67 | +++ | ++ |
| 68 | >1 | ++ |
| 69 | +++ | +++ |
| 70 | +++ | >1 |
| 71 | +++ | ++ |
| 72 | +++ | ++ |
| 73 | +++ | ++ |
| 74 | ++ | ++ |
| 75 | +++ | >1 |
| 76 | ++ | ++ |
| 77 | +++ | >3 |
| 78 | ++ | >1 |
| 79 | +++ | +++ |
| 80 | ++ | >1 |
| 81 | +++ | + |
| 82 | +++ | +++ |
| 83 | +++ | ++ |
| 84 | +++ | +++ |
| 85 | >1 | >3 |
| 86 | >1 | |
| 87 | >1 | |
| 88 | ++ | |
| 89 | ++ | >1 |
| 90 | +++ | >1 |
| 91 | +++ | +++ |
| 92 | +++ | ++ |
| 93 | +++ | >1 |
| 94 | +++ | +++ |
| 95 | +++ | +++ |
| 96 | +++ | +++ |
| 97 | +++ | >1 |
| 98 | +++ | ++ |
| 99 | +++ | ++ |
| 100 | +++ | ++ |
| 101 | +++ | ++ |
| 102 | | +++ |
| 103 | + | >1 |
| 104 | | >1 |
| 105 | +++ | + |
| 106 | ++ | >1 |
| 107 | +++ | ++ |
| 108 | ++ | ++ |
| 109 | +++ | ++ |
| 110 | +++ | + |
| 111 | +++ | ++ |
| 112 | >1 | >1 |
| 113 | ++ | >1 |
| 114 | | ++ |
| 115 | +++ | +++ |
| 116 | | >1 |
| 117 | | >1 |
| 118 | | >1 |
| 119 | | ++ |

TABLE VI-continued

| Compound No. | SCN3A EIC-50 (μM) | SCN9A EIC-50 (μM) |
|---|---|---|
| 120 | | ++ |
| 121 | | >1 |
| 122 | | >1 |
| 123 | | >1 |
| 124 | | >1 |
| 125 | | ++ |
| 126 | | >1 |
| 127 | | ++ |
| 128 | | ++ |
| 129 | +++ | +++ |
| 130 | +++ | ++ |
| 131 | | >1 |
| 132 | | >1 |
| 133 | +++ | +++ |
| 134 | +++ | +++ |
| 135 | | >1 |
| 136 | | >1 |
| 137 | | ++ |
| 138 | | +++ |
| 139 | | +++ |
| 140 | | +++ |
| 141 | | +++ |
| 142 | | +++ |
| 143 | | +++ |
| 144 | | +++ |
| 145 | +++ | +++ |
| 146 | +++ | +++ |
| 147 | +++ | +++ |
| 148 | | ++ |
| 149 | +++ | +++ |
| 150 | +++ | +++ |
| 151 | +++ | ++ |
| 152 | +++ | +++ |
| 153 | +++ | +++ |
| 154 | +++ | +++ |
| 155 | +++ | +++ |
| 156 | +++ | +++ |
| 157 | | +++ |
| 158 | | +++ |
| 159 | | +++ |
| 160 | | +++ |
| 161 | +++ | +++ |
| 162 | +++ | +++ |
| 163 | | ++ |
| 164 | | +++ |
| 165 | | +++ |
| 166 | | +++ |
| 167 | | +++ |
| 168 | | +++ |
| 169 | | +++ |
| 170 | | +++ |
| 171 | | +++ |
| 172 | +++ | +++ |
| 173 | +++ | +++ |
| 174 | | +++ |
| 175 | | +++ |
| 176 | | +++ |
| 177 | | +++ |
| 178 | | +++ |
| 179 | | +++ |
| 180 | | ++ |
| 181 | | +++ |
| 182 | +++ | +++ |
| 183 | +++ | +++ |
| 184 | +++ | +++ |
| 185 | +++ | +++ |
| 186 | | +++ |
| 187 | | +++ |
| 188 | +++ | +++ |
| 189 | | +++ |
| 190 | | +++ |
| 191 | +++ | +++ |
| 192 | | ++ |
| 193 | +++ | +++ |
| 194 | | ++ |
| 195 | | +++ |
| 196 | | +++ |
| 197 | | +++ |
| 198 | +++ | +++ |
| 199 | | +++ |
| 200 | | +++ |
| 201 | ++ | +++ |
| 202 | | ++ |
| 203 | | +++ |
| 204 | +++ | +++ |
| 205 | +++ | +++ |
| 206 | +++ | +++ |
| 207 | | +++ |
| 208 | | +++ |
| 209 | | +++ |
| 210 | | +++ |
| 211 | | ++ |
| 212 | | ++ |
| 213 | | ++ |
| 214 | | +++ |
| 215 | | +++ |
| 216 | >1 | +++ |
| 217 | | +++ |
| 218 | | +++ |
| 219 | | +++ |
| 220 | | +++ |
| 221 | | ++ |
| 222 | +++ | +++ |
| 223 | | +++ |
| 224 | | +++ |
| 225 | | ++ |
| 226 | | +++ |
| 227 | +++ | ++ |
| 228 | +++ | ++ |
| 229 | | +++ |
| 230 | | +++ |
| 231 | | ++ |
| 232 | | +++ |
| 234 | | ++ |
| 235 | +++ | ++ |
| 236 | | ++ |
| 237 | | ++ |
| 238 | | ++ |
| 239 | | ++ |
| 240 | | ++ |
| 241 | | ++ |
| 243 | | ++ |
| 244 | +++ | +++ |
| 245 | ++ | >1 |
| 246 | | >1 |
| 247 | | >1 |
| 248 | | ++ |
| 249 | | >1 |
| 250 | | >1 |
| 251 | | >1 |
| 252 | | >1 |
| 253 | | >1 |
| 254 | | >1 |
| 255 | | >1 |
| 256 | | >1 |
| 257 | | ++ |
| 258 | | >1 |
| 259 | | >3 |
| 260 | | >1 |
| 261 | | >1 |
| 262 | | ++ |
| 263 | +++ | +++ |
| 264 | +++ | +++ |
| 265 | | +++ |
| 266 | ++ | >1 |
| 267 | | +++ |
| 268 | | ++ |
| 269 | +++ | +++ |
| 270 | | >1 |
| 271 | | ++ |
| 272 | | >1 |
| 273 | | >1 |
| 274 | | +++ |
| 275 | | ++ |

TABLE VI-continued

| Compound No. | SCN3A EIC-50 (µM) | SCN9A EIC-50 (µM) |
|---|---|---|
| 276 | +++ | >1 |
| 277 | >1 | +++ |
| 278 |  | +++ |
| 279 |  | ++ |
| 280 | ++ | ++ |

"+++" <2 µM;
"++" 2-10 µM;
"+" >10 µM

The activity of certain commercial compounds is set forth in Table VI, below.

TABLE VI

| Compound No. | SCN3A EIC-50 (µM) | SCN9A EIC-50 (µM) |
|---|---|---|
| 38 | >1 | >3 |
| 39 | >1 | >3 |
| 40 | 1.32 | 3.49 |
| 41 | 1.61 | >3 |
| 42 | 2.03 | >3 |

While this invention has been disclosed with reference to specific embodiments, it is apparent that other embodiments and variations of this invention may be devised by others skilled in the art without departing from the true spirit and scope of the invention. All patents, patent applications, and other publications cited in this application are incorporated by reference in their entirety.

What is claimed is:

1. A compound having Formula (II):

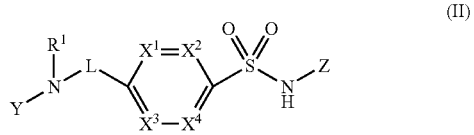

(II)

or a pharmaceutically acceptable salt thereof;
wherein
Z is selected from the group consisting of thiazolyl, isothiazolyl, isoxazolyl, oxazolyl, 1,3,4-thiadiazolyl, 1,2,3-thiadiazolyl, 1,2,4-thiadiazolyl, 1,3,4-oxadiazolyl, 1,2,3-oxadiazolyl, 1,2,4-oxadiazolyl, 1,2,5-thiadiazolyl, pyrazolyl, 1,2,5-oxadiazolyl, and imidazolyl, each of which is optionally substituted with from 1 to 2 substituents selected from the group consisting of $C_{1-8}$haloalkyl, —CN, halogen, $C_{3-7}$cycloalkyl, aryl, $C_{1-8}$alkyl, aryl-NH—$C_{1-6}$alkyl and $C_{1-8}$alkoxy-$C_{1-4}$alkyl;
Y is selected from the group consisting of:
i) 5-membered heteroaryl having from 1 to 4 heteroatoms as ring members selected from N, O or S, wherein the heteroaryl of Y is optionally substituted with from 1 to 3 $R^a$ substituents, at each occurrence, each $R^a$ is independently selected from the group consisting of $C_{1-8}$alkyl-NH—, $(C_{1-8}$alkyl$)_2$N—, aryl, $R^b$, $C_{1-8}$haloalkyl, aryl-$C_{3-8}$cycloalkyl, $C_{3-5}$cycloalkyl, heterocycloalkyl, arylsulfonyl, arylsulfinyl and $R^f$, wherein $R^b$ is $C_{1-8}$alkyl optionally substituted with from 1-3 members independently selected from the group consisting of aryl, aryl-C(O)—, aryloxy, $(R^c)(R^d)$N—, $C_{3-5}$cycloalkyl, hetero-$C_{4-5}$cycloalkyl, arylthio and heteroaryl; wherein $R^c$ is —H or $C_{1-6}$alkyl and $R^d$ is $C_{3-7}$cycloalkyl or $C_{1-8}$alkyl optionally substituted with from 1-2 aryl groups; wherein the aryl portion of each $R^a$ substituent is further optionally substituted with from 1-3 substituents independently selected from the group consisting of $C_{1-4}$haloalkyl, $C_{1-4}$haloalkoxy and $R^f$, and the heterocycloalkyl of the $R^b$ group is further optionally substituted with a hetero-$C_{4-5}$cycloalkyl-$C_{1-6}$alkyl;
wherein $R^f$ is halogen, —OH, —OR$^g$, —OC(O)O—R$^g$, —OC(O)R$^g$, —OC(O)NHR$^g$, —OC(O)N(R$^g$)$_2$, —SH, —SR$^g$, —S(O)R$^g$, —S(O)$_2$R$^g$, —SO$_2$NH$_2$, —S(O)$_2$NHR$^g$, —S(O)$_2$N(R$^g$)$_2$, —NHS(O)$_2$R$^g$, —NR$^g$S(O)$_2$R$^g$, —C(O)NH$_2$, —C(O)NHR$^g$, —C(O)N(R$^g$)$_2$, —C(O)R$^g$, —C(O)H, —C(=S)R$^g$, —NHC(O)R$^g$, —NR$^g$C(O)R$^g$, —NHC(O)NH$_2$, —NR$^g$C(O)NH$_2$, —NR$^g$C(O)NHR$^g$, —NHC(O)NHR$^g$, —NR$^g$C(O)N(R$^g$)$_2$, —NHC(O)N(R$^g$)$_2$, —CO$_2$H, —CO$_2$R$^g$, —NHCO$_2$R$^g$, —NR$^g$CO$_2$R$^g$, —CN, —NH$_2$, —NR$^g$S(O)NH$_2$, —NR$^g$S(O)$_2$NHR$^g$, —NHC(=NR$^g$)NH$_2$, —N=C(NH$_2$)NH$_2$, —C(=NR$^g$)NH$_2$, —NH—OH, —NR$^g$—OH, —NR$^g$—OR$^g$, —N=C=O and —N=C=S; wherein each R$^g$ is independently a $C_{1-8}$alkyl; and
ii) 6-member heteroaryl having from 1-3 nitrogen atoms as ring members, wherein the heteroaryl is optionally substituted with 1-3 R$^e$ substituents independently selected from the group consisting of —OH, aryl, aryl-$C_{1-6}$alkyl, aryl-$C_{1-6}$alkoxy, $C_{3-6}$cycloalkyl-$C_{1-6}$alkoxy and $C_{1-8}$alkoxy, wherein the aliphatic portion of the R$^e$ group is optionally substituted with an aryl and the aromatic portion of the R$^e$ group is optionally substituted with from 1-2 members independently selected from $C_{1-6}$haloalkyl or $C_{1-6}$alkyl;
$X^1$, $X^2$, $X^3$ and $X^4$ are each independently C(R$^2$)=, wherein R$^2$ is selected from the group consisting of —H, halogen, —OH, $C_{1-8}$alkyl, —CN, $C_{1-6}$haloalkyl and $C_{1-6}$haloalkoxy; or any two adjacent R$^2$ substituents together with the atoms to which they are attached form a fused benzene ring, optionally substituted with a $C_{1-6}$alkyl;
L is a bond;
$R^1$ is —H, a lone pair or $C_{1-6}$alkyl;
and
at each occurrence, "alkyl" by itself or as part of another substituent, is an unsubstituted, fully saturated, straight or branched chain hydrocarbon radical;
at each occurrence, "cycloalkyl" by itself or as part of another substituent is an unsubstituted, fully saturated, cyclic hydrocarbon radical; and
at each occurrence, "aryl" by itself or as part of another substituent is a monovalent monocyclic, bicyclic or polycyclic polyunsaturated aromatic hydrocarbon radical.

2. The compound of claim 1, wherein Y is selected from the group consisting of:
i) 5-membered heteroaryl having from 1-4 heteroatoms as ring members selected from N, O or S, wherein the heteroaryl is optionally substituted with 1-3 R$^a$ members, at each occurrence, each R$^a$ is independently selected from the group consisting of —NH$_2$, $C_{1-8}$alkyl-NH—, $(C_{1-8}$alkyl$)_2$N—, aryl, R$^b$, $C_{1-8}$haloalkyl, aryl-$C_{3-8}$cycloalkyl, $C_{3-5}$cycloalkyl, heterocycloalkyl, arylsulfonyl, arylsulfinyl, NH$_2$C(O)—, (C$_{1-8}$alkyl)(H)NC(O)—, (C$_{1-8}$alkyl)$_2$NC(O)—, $C_{1-8}$alkylcarbonyl and $C_{1-8}$alkoxycarbonyl, wherein $R^b$ is $C_{1-8}$alkyl optionally substituted with from 1-2 members independently selected from the group consisting of aryl, aryl-(CO)—, aryloxy, $(R^c)(R^d)N$—, $C_{3-5}$cycloalkyl, hetero-$C_{4-5}$cycloalkyl, arylthio and heteroaryl; wherein $R^c$ is —H or $C_{1-6}$alkyl and $R^d$ is $C_{3-7}$cycloalkyl or $C_{1-8}$alkyl optionally substituted with from 1-2 aryl groups;

wherein the aryl portion of each $R^a$ substituent is further optionally substituted with from 1-3 substituents independently selected from the group consisting of halogen, $C_{1-4}$-haloalkyl, $C_{1-4}$-haloalkoxy, $C_{1-4}$alkoxy, —CN, $C_{1-4}$-alkylsulfonyl, OH and —NO$_2$; and the heterocycloalkyl of the $R^b$ group is further optionally substituted with a hetero-$C_{4-5}$cycloalkyl-$C_{1-6}$alkyl; and ii) 6-member heteroaryl having from 1-3 nitrogen atoms as ring members, wherein the heteroaryl is optionally substituted with 1-3 $R^e$ substituents independently selected from the group consisting of —OH, aryl, aryl-$C_{1-6}$alkyl, aryl-$C_{1-6}$alkoxy, $C_{3-6}$cycloalkyl-$C_{1-6}$alkoxy and $C_{1-8}$alkoxy, wherein the aliphatic portion of the $R^e$ group is optionally substituted with an aryl and the aromatic portion of the $R^e$ group is optionally substituted with from 1-2 members independently selected from $C_{1-6}$haloalkyl or $C_{1-6}$alkyl.

3. The compound of claim 1, wherein $R^1$ is —H.

4. The compound of claim 1, wherein Z is optionally substituted with a member selected from the group consisting of $C_{1-8}$haloalkyl, —CN, halogen, $C_{3-7}$cycloalkyl, aryl, $C_{1-8}$alkyl, aryl-NH—$C_{1-6}$alkyl and $C_{1-8}$alkoxy-$C_{1-4}$alkyl.

5. The compound of claim 4, wherein Z is selected from the group consisting of thiazol-2yl, 4-thiazolyl, 5-thiazolyl, isoxazol-3yl, 2-oxazolyl, 1,3,4-thiadiazol-2yl, 1,2,3-thiadiazol-4-yl, 1,2,3-thiadiazol-5yl, 1,2,4-thiadiazol-3yl, 1,2,4-thiadiazol-5yl, 1,3,4-oxadiazol-2yl, 1,2,5-thiadiazol-4-yl, pyrazolyl, 1,2,5-oxadiazol-4-yl, and 2-imidazolyl.

6. The compound of claim 5, wherein Z is substituted with a member selected from the group consisting of 3-chloropropyl, phenylaminomethyl, —CH$_3$, CH$_2$CH$_3$, —Cl, —CF$_3$, —CF$_2$H, CH$_3$OCH$_2$—, cyclopropyl, isopropyl and —CN.

7. The compound of claim 1, wherein Y is 5-membered heteroaryl having from 1-4 heteroatoms as ring members selected from N, O or S, wherein the heteroaryl is optionally substituted with 1-3 $R^a$ members, at each occurrence, each $R^a$ is independently selected from the group consisting of —NH$_2$, $C_{1-8}$alkyl-NH—, $(C_{1-8}$alkyl)$_2$N—, aryl, $R^b$, $C_{1-8}$haloalkyl, aryl-$C_{3-8}$cycloalkyl, $C_{3-5}$cycloalkyl, heterocycloalkyl, arylsulfonyl, arylsulfinyl, NH$_2$C(O)—, $(C_{1-8}$alkyl)(H)NC(O)—, $(C_{1-8}$alkyl)$_2$NC(O)—, $C_{1-8}$alkylcarbonyl and $C_{1-8}$alkoxycarbonyl, wherein $R^b$ is $C_{1-8}$alkyl optionally substituted with from 1-2 members independently selected from the group consisting of aryl, aryloxy, $(R^c)(R^d)N$—, $C_{3-5}$cycloalkyl, hetero-$C_{4-5}$cycloalkyl, arylthio and heteroaryl;

wherein $R^c$ is —H or $C_{1-6}$alkyl and $R^d$ is $C_{3-7}$cycloalkyl or $C_{1-8}$alkyl optionally substituted with from 1-2 aryl groups; wherein the aryl portion of each $R^a$ substituent is further optionally substituted with from 1-3 substituents independently selected from the group consisting of halogen, $C_{1-4}$-haloalkyl, $C_{1-4}$-haloalkoxy, $C_{1-4}$alkoxy, —CN, $C_{1-4}$-alkylsulfonyl, OH and —NO$_2$; and the heterocycloalkyl of the $R^b$ group is further optionally substituted with a hetero-$C_{4-5}$cycloalkyl-$C_{1-6}$alkyl.

8. The compound of claim 7, wherein Y is selected from the group consisting of thiazolyl, pyrazolyl, isoxazolyl, imidazolyl, 1,2,4-triazolyl, 1,2,3-thiadiazolyl, 1,3,4-thiadiazolyl, 1,3,4-oxadiazolyl, 1,2,5-thiadiazol-4-yl, 1,2,5-oxadiazol-4-yl, 1,2,3,5-thiatriazol-4-yl, 1,2,3,4-thiatriazol-5yl, 1,2,3,5-oxatriazol4-yl, and 1,2,3,4-oxatriazol-5yl, each of which is optionally substituted with 1-3 $R^a$ members.

9. The compound of claim 8, wherein Y is selected from the group consisting of thiazol-2yl, pyrazol-3yl, pyrazol-4-yl, pyrazol-5-yl, isoxazol-3yl, 1,2,4-triazol-1yl, 1,2,4-triazol-3yl, 1,3,4-thiadiazol-2yl, and 1,3,4-oxadiazol-2yl, each of which is optionally substituted with 1-3 $R^a$ members.

10. The compound of claim 9, wherein $R^a$ is selected from the group consisting of -Ph, Ph$_2$CH—, PhOCH$_2$—, Ph$_2$CHCH$_2$—, Ph-O(CH$_2$)$_3$—, cyclopentylethyl, 4-chlorophenoxymethyl, 2-phenylcyclopropyl, Ph$_2$CHCH$_2$NHCH$_2$—, PhOCH$_2$CH$_2$NHCH$_2$—, 2-(pyrrolidin-1-ylmethyl)pyrrolidin-1-yl, (S)-2-(pyrrolidin-1-ylmethyl)pyrrolidin-1-yl, Ph$_2$NHCH$_2$—, Ph$_2$CHCH$_2$CH$_2$NHCH$_2$—, 4-t-butyl-phenoxymethyl, PhO(CH$_3$)CH—, 1-(4-chlorophenyl)cyclopentyl, 4-chlorophenyl-CH$_2$NHCH$_2$—, 3,4-dimethoxyphenyl-(CH$_2$)$_2$NHCH$_2$—, Ph(CH$_2$)$_2$N(CH$_3$)CH$_2$—, (CH$_3$CH$_2$)$_2$NCH$_2$—, Ph(CH$_2$)$_4$NHCH$_2$—, Ph$_2$CHN(CH$_3$)CH$_2$—, 4-CF$_3$-Ph-CH$_2$NHCH$_2$—, 4-NO$_2$-Ph-CH$_2$NHCH$_2$—, 4-dimethylaminophenyl-CH$_2$NHCH$_2$—, 4-pyridyl-CH$_2$CH$_2$N(CH$_3$)CH$_2$—, 3,5-dimethoxyphenyl-CH$_2$NH—CH$_2$—, —CH$_3$, CH$_3$OC(O)—, 2,4-difluorobenzyl, 4-fluoro-Ph-SCH$_2$—, —CF$_3$, 4-trifluoromethylphenyl, 4-fluorophenylsulfinylmethyl, 4-chlorophenylsulfinylmethyl, 2-fluoro-4-trifluoromethylphenyl, 4-chlorobenzyl, 4-chlorophenoxypropyl, 2,4-dichlorophenoxymethyl, 2-methyl-4-chlorophenoxymethyl, 4-chlorophenoxy-C(CH$_3$)$_2$—, t-butoxyphenoxymethyl, 4-chlorophenyl, t-butyl, 4-methoxybenzyl, 4-methylsulfonylbenzyl, 4-cyanobenzyl, 4-chlorophenylsulfonyl, acetyl, —NH$_2$, 3-chloro-4-fluoro-phenyl, 4-trifluoromethylbenzyl, neopentyl, 4-methoxybenzyl, 2-methoxybenzyl, 1-(4-chlorophenyl)cyclopropyl, CF$_3$CH$_2$—, —CN, 4-pyridylmethyl, cyclohexylmethyl, cyclopropyl, isopropyl, 2-methylphenyl, 4-methylphenyl, 2-chlorophenyl, 3-chlorophenyl, 4-methylbenzyl, 2-fluoro-4-chlorobenzyl, cyclopentyl, 2-fluorophenyl, cyclopropyl-(CH$_3$)CH—, 3-methylphenyl, 3-fluorophenyl, 4-fluorophenyl, 2-trifluoromethylphenyl, 2-chloro-4-fluorophenyl, 2-methyl-4-fluoro-phenyl, 2-trifluoromethyl-4-fluorophenyl, 2-methoxyphenyl, 2,6-dichlorophenyl, 2,6-difluororophenyl, 2,6-dimethylphenyl, 2,4-difluorobenzyl, 3-trifluoromethylphenyl, 1-methylpiperidinyl, 2-chloro-4-fluorobenzyl, 2-chlorobenzyl, 3-fluoro-4-chlorobenzyl, benzyl, (CH$_3$CH$_2$)$_2$NC(O)—CH$_2$—, 4-fluorobenzyl, 3-chlorobenzyl, 2-methoxy-4-chlorophenyl, 2-methoxyphenyl, 4-methoxybenzyl, 3-trifluoromethyl-4-chlorobenzyl, 2-methoxy-4-chlorophenyl, 3-methoxyphenyl, 4-methoxybenzyl, 3-trifluormethyl-4-chlorobenzyl, 2-methoxy-5-trifluoromethoxybenzyl and NH$_2$C(O)—.

11. The compound of claim 1, wherein Y is a 6-member heteroaryl having from 1-3 nitrogen atoms as ring members, wherein the heteroaryl is optionally substituted with 1-3 $R^e$ substituents independently selected from the group consisting of —OH, aryl, aryl-$C_{1-6}$alkyl, aryl-$C_{1-6}$alkoxy, $C_{3-6}$cycloalkyl-$C_{1-6}$alkoxy and $C_{1-8}$alkoxy, wherein the aliphatic portion of the $R^e$ group is optionally substituted with an aryl and the aromatic portion of the $R^e$ group is optionally substituted with from 1-2 members independently selected from $C_{1-6}$haloalkyl or $C_{1-6}$alkyl.

12. The compound of claim 11, wherein Y is selected from the group consisting of pyrimidinyl, pyridazinyl, pyrazinyl, and triazinyl, each of which is optionally substituted with from 1-3 $R^e$ substituents.

13. The compound of claim 12, wherein Y is selected from the group consisting of 2-pyrimidinyl, 4-pyrimidinyl, pyridazinyl, 3-pyrazinyl, and 1,2,4-triazin-3yl, each of which is optionally substituted with from 1-3 $R^e$ substituents.

14. The compound of claim 13, wherein $R^e$ is selected from the group consisting of 4-methylphenyl, Ph-, benzyloxy, Ph$_2$CHCH$_2$O—, 4-trifluoromethylbenzyloxy, cyclohexylmethyloxy, methoxy, Ph$_2$CH—, and —OH.

15. The compound of claim 1, wherein $X^1$, $X^2$, $X^3$ and $X^4$ are =CH—.

16. The compound of claim 1, wherein $X^1$ is =CF—, =CCl—, =C(OCF$_3$)—, =C(CH$_3$)— or —C(CH)= and $X^2$, $X^3$ and $X^4$ are =CH—.

17. The compound of claim 1, wherein $X^2$ is =CF—, =CCl—, =C(OCF$_3$)—, =C(CH$_3$)—, —C(CN)=, —C(CF$_3$)= or —C(CH)= and $X^1$, $X^3$ and $X^4$ are =CH— or =C(CH$_3$)—.

18. The compound of claim 1, wherein $X^2$ and $X^3$ are =CH—.

19. The compound of claim 1, wherein $X^3$ and $X^4$ are =CH—.

20. The compound of claim 1, wherein $X^2$, $X^3$ and $X^4$ are =CH—.

21. The compound of claim 1, wherein $X^1$, $X^2$ and $X^3$ are =CH—.

22. The compound of claim 1, wherein $R^2$ is selected from the group consisting of —H, halogen, $C_{1-8}$alkyl, —CN, $C_{1-6}$haloalkyl and $C_{1-6}$haloalkyoxy;
or any two adjacent $R^2$ substituents together with the atoms to which they are attached form a fused benzene ring, optionally substituted with a $C_{1-6}$alkyl.

23. The compound of claim 22, wherein $R^2$ is selected from the group consisting of —H, —Cl, —F, —CF$_3$, —OCF$_3$, —CH$_3$ and —CN.

24. The compound of claim 22, wherein two adjacent $R^2$ substituents together with the atoms to which they are attached form a fused benzene ring, optionally substituted with a halogen or $C_{1-6}$alkyl.

25. A compound having Formula (IIa):

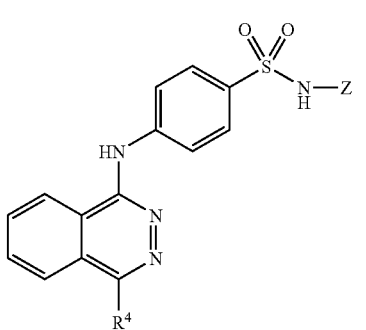

wherein
Z is 2-thiazolyl, 4-thiazolyl, 5-thiazolyl, 1,2,3-thiadiazol-4-yl, 1,2,3-thiadiazol-5yl, 1,3,4-thiadiazol-2yl, 1,2,5-thiadiazol-4-yl, 1,2,4-thiadiazol-3yl or 1,2,4-thiadiazol-5yl, each of which is optionally substituted with from 1-2 $R^3$ substituents selected from the group consisting of $C_{1-8}$haloalkyl, —CN, halogen, $C_{3-7}$cycloalkyl, aryl, $C_{1-8}$alkyl, aryl-NH—$C_{1-6}$alkyl and $C_{1-8}$alkoxy-$C_{1-4}$alkyl; and
$R^4$ is selected from the group consisting of —H, —OH, $C_{0-6}$alkylaryl, aryl-$C_{1-6}$alkyl, aryl-$C_{1-6}$alkoxy, $C_{3-6}$cycloalkyl-$C_{1-6}$alkoxy and $C_{1-6}$alkoxy;
with the proviso that the compound is other than N-(thiazol-2-yl)-4-(4-p-tolylphthalazin-1-ylamino)benzenesulfonamide; and 4-(4-phenylphthalazin-1-ylamino)-N-(thiazol-2-yl)benzenesulfonamide; and at each occurrence, "alkyl" by itself or as part of another substituent, is an unsubstituted, fully saturated, straight or branched chain hydrocarbon radical;

at each occurrence, "cycloalkyl" by itself or as part of another substituent is an unsubstituted, fully saturated, cyclic hydrocarbon radical; and at each occurrence, "aryl" by itself or as part of another substituent is a monovalent monocyclic, bicyclic or polycyclic polyunsaturated aromatic hydrocarbon radical.

26. The compound of claim 1, having Formula (IIb):

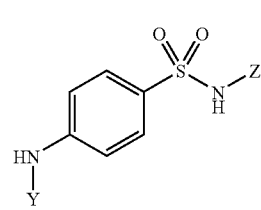

wherein

Y is 2-pyrimidinyl, 4-pyrimidinyl, 2-pyrazinyl, pyridyl or 1,2,4-triazin-3yl, each of which is optionally substituted with a member selected from the group consisting of —H, and aryl; and Z is 2-thiazolyl or 3-isoxazolyl, each of which is optionally substituted with a member selected from the group consisting of —H and aryl.

27. The compound of claim 1, wherein Z is selected from the group consisting of 2-thiazolyl and 3-isoxazolyl, each of which is optionally substituted with a member selected from the group consisting of $C_{1-8}$haloalkyl, —CN, halogen, $C_{3-7}$cycloalkyl, aryl, $C_{1-8}$alkyl, aryl-NH—$C_{1-6}$alkyl and $C_{1-8}$alkoxy-$C_{1-4}$alkyl; and Y is selected from the group consisting of 3-pyrazolyl, 4-pyrazolyl, 5-pyrazolyl, 2-thiazolyl, imidazolyl and 1,2,4-triazol-3yl, each of which is optionally substituted with from 1-3 $R^a$ groups.

28. The compound of claim 27, wherein Z is 2-thiazolyl, optionally substituted with a member selected from the group consisting of $C_{1-8}$haloalkyl, —CN, halogen, $C_{3-7}$cycloalkyl, aryl, $C_{1-8}$alkyl, aryl-NH—$C_{1-6}$alkyl and $C_{1-8}$alkoxy-$C_{1-4}$alkyl.

29. The compound of claim 1, having Formula (IId)

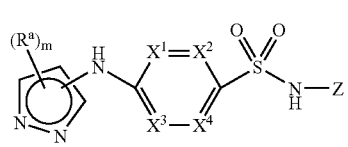

wherein Z is 2-thiazolyl, 4-thiazolyl, 5-thiazolyl, 1,2,3-thiadiazol-4yl, 1,2,3-thiadiazol-5yl, 1,3,4-thiadiazol-2yl, 1,2,5-thiadiazol-4yl, 1,2,4-thiadiazol-3yl or 1,2,4-thiadiazol-5yl, each of which is optionally substituted with from 1-2 $R^7$ substituents selected from the group consisting of $C_{1-8}$haloalkyl, —CN, halogen, $C_{3-7}$cycloalkyl, aryl, $C_{1-8}$alkyl, aryl-NH—$C_{1-6}$alkyl and $C_{1-8}$alkoxy-$C_{1-4}$alkyl; and m is an integer of from 0-3.

30. The compound of claim 1, having Formula (IIf):

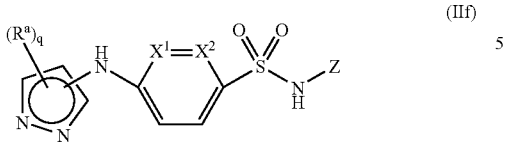

wherein Z is selected from the group consisting of 1,2,3-thiadiazolyl, 1,2,4-thiadiazolyl, 1,2,5-thiadiazolyl, 1,3,4-thiadiazolyl, and 1,3,4-oxadiazolyl; and subscript q is an integer from 0-3.

31. The compound of claim 1, wherein the compound has inhibitory activity against a voltage-gated sodium channel.

32. A compound selected from:
4-Bromo-2-fluoro-N-thiazol-2-yl-benzenesulfonamide;
4-(4-Benzhydrylthiazol-2-ylamino)-N-(thiazol-2-yl)benzenesulfonamide;
2-Fluoro-4-[4-(4-methoxy-benzyl)-thiazol-2-ylamino]-N-thiazol-2-yl-benzenesulfonamide;
2-Fluoro-4-[4-(4-methanesulfonyl-benzyl)-thiazol-2-ylamino]-N-thiazol-2-yl-benzenesulfonamide;
4-[4-(4-Cyano-benzyl)-thiazol-2-ylamino]-2-fluoro-N-thiazol-2-yl-benzenesulfonamide;
4-[4-(4-Chloro-benzyl)-thiazol-2-yl]-methyl-amino-2-fluoro-N-thiazol-2-yl-benzenesulfonamide;
4-(4-Tert-butyl-thiazol-2-ylamino)-2-fluoro-N-thiazol-2-yl-benzenesulfonamide;
4-(5-Tert-butyl-4-methylthiazol-2-ylamino)-N-(thiazol-2-yl)benzenesulfonamide;
4-(5-Acetyl-4-methyl-thiazol-2-ylamino)-2-fluoro-N-thiazol-2-yl-benzenesulfonamide;
4-(4-Tert-butyl-thiazol-2-ylamino)-2-chloro-N-thiazol-2-yl-benzenesulfonamide;
4-(4-tert-Butyl-thiazol-2-ylamino)-N-thiazol-2-yl-2-trifluoromethoxy-benzenesulfonamide;
4-(4-tert-Butyl-thiazol-2-ylamino)-naphthalene-1-sulfonic acid thiazol-2-ylamide;
4-(5-tert-butyl-4-methylthiazol-2-ylamino)-2-fluoro-N-(thiazol-2-yl)benzenesulfonamide;
4-(4-Tert-butyl-thiazol-2-ylamino)-N-thiazol-2-yl-benzenesulfonamide;
4-(1-tert-butyl-3-(4-chlorobenzyl)-1H-pyrazol-5-ylamino)-N-(thiazol-2-yl)benzenesulfonamide;
4-(3-(4-Chlorobenzyl)-1H-pyrazol-5-ylamino)-N-(thiazol-2-yl)benzenesulfonamide;
4-(3-Tert-butyl-1-methyl-1H-pyrazol-5-ylamino)-N-(thiazol-2-yl)benzenesulfonamide;
4-(3-Tert-butylisoxazol-3-ylamino)-N-(thiazol-2-yl)benzenesulfonamide;
4-(5-Amino-1-tert-butyl-1H-1,2,4-triazol-3-ylamino)-N-(thiazol-2-yl)benzenesulfonamide;
4-(3-methyl-1-phenyl-1H-pyrazol-5-ylamino)-N-(thiazol-2-yl)benzenesulfonamide;
4-(3-(4-Chlorobenzyl)-1-methyl-1H-pyrazol-5-ylamino)-N-(thiazol-2-yl)benzenesulfonamide;
4-(1,3-di-tert-butyl-1H-pyrazol-5-ylamino)-N-(thiazol-2-yl)benzenesulfonamide;
4-(3-tert-butyl-1H-pyrazol-5-ylamino)-N-(thiazol-2-yl)benzenesulfonamide;
4-(5-amino-1-(4-chlorobenzyl)-1H-1,2,4-triazol-3-ylamino)-N-(thiazol-2-yl)benzenesulfonamide;
4-(1-(3-chloro-4-fluorophenyl)-4-cyano-1H-pyrazol-5-ylamino)-N-(thiazol-2-yl)benzenesulfonamide;
4-(1-tert-butyl-3-(4-chlorobenzyl)-1H-pyrazol-5-ylamino)-2-fluoro-N-(thiazol-2-yl)benzenesulfonamide;
N-(thiazol-2-yl)-4-(5-(4-(trifluoromethyl)benzyl)-1,3,4-thiadiazol-2-ylamino)benzenesulfonamide;
N-(thiazol-2-yl)-4-(5-(4-(trifluoromethyl)benzyl)-1,3,4-oxadiazol-2-ylamino)benzenesulfonamide;
4-(3-(cyclohexylmethyl)-1-methyl-1H-pyrazol-5-ylamino)-N-(thiazol-2-yl)benzenesulfonamide;
2-fluoro-4-(3-methyl-1-phenyl-1H-pyrazol-5-ylamino)-N-(thiazol-2-yl)benzenesulfonamide;
4-(1-(4-chlorobenzyl)-1H-pyrazol-3-ylamino)-2-fluoro-N-(thiazol-2-yl)benzenesulfonamide;
4-(3-cyclopropyl-1-phenyl-1H-pyrazol-5-ylamino)-2-fluoro-N-(thiazol-2-yl)benzenesulfonamide;
4-(1-(4-chlorobenzyl)-1H-pyrazol-4-ylamino)-2-fluoro-N-(thiazol-2-yl)benzenesulfonamide;
2-fluoro-4-(1-methyl-3-neopentyl-1H-pyrazol-5-ylamino)-N-(thiazol-2-yl)benzenesulfonamide;
3-fluoro-4-(3-methyl-1-phenyl-1H-pyrazol-5-ylamino)-N-(thiazol-2-yl)benzenesulfonamide;
4-(3-cyclopropyl-1-phenyl-1H-pyrazol-5-ylamino)-3-fluoro-N-(thiazol-2-yl)benzenesulfonamide;
4-(biphenyl-2-ylamino)-2-fluoro-N-(thiazol-2-yl)benzenesulfonamide;
4-(4-phenylthiazol-2-ylamino)-N-(thiazol-2-yl)benzenesulfonamide;
4-(pyrimidin-2-ylamino)-N-(thiazol-2-yl)benzenesulfonamide;
4-(4-(benzyloxy)pyrimidin-2-ylamino)-N-(thiazol-2-yl)benzenesulfonamide;
4-(4-(2,2-diphenylethoxy)pyrimidin-2-ylamino)-N-(thiazol-2-yl)benzenesulfonamide;
4-(4,5-diphenylthiazol-2-ylamino)-N-(thiazol-2-yl)benzenesulfonamide;
4-(4-(phenoxymethyl)thiazol-2-ylamino)-N-(thiazol-2-yl)benzenesulfonamide;
4-(4-(2,2-diphenylethyl)thiazol-2-ylamino)-N-(thiazol-2-yl)benzenesulfonamide;
4-(4-(3-phenoxypropyl)thiazol-2-ylamino)-N-(thiazol-2-yl)benzenesulfonamide;
4-(4-(2-cyclopentylethyl)thiazol-2-ylamino)-N-(thiazol-2-yl)benzenesulfonamide;
4-(4-((4-chlorophenoxy)methyl)thiazol-2-ylamino)-N-(thiazol-2-yl)benzenesulfonamide;
4-(4-(2-phenylcyclopropyl)thiazol-2-ylamino)-N-(thiazol-2-yl)benzenesulfonamide;
4-(4-(2-fluorobenzyloxy)pyrimidin-2-ylamino)-N-(thiazol-2-yl)benzenesulfonamide;
N-(thiazol-2-yl)-4-(4-(4-(trifluoromethyl)benzyloxy)pyrimidin-2-ylamino)benzenesulfonamide;
4-(4-((2,2-diphenylethylamino)methyl)thiazol-2-ylamino)-N-(thiazol-2-yl)benzenesulfonamide;
4-(4-((2-phenoxyethylamino)methyl)thiazol-2-ylamino)-N-(thiazol-2-yl)benzenesulfonamide;
(S)-4-(4-((2-(pyrrolidin-1-ylmethyl)pyrrolidin-1-yl)methyl)thiazol-2-ylamino)-N-(thiazol-2-yl)benzenesulfonamide;
4-(4-(3-chloropropyl)thiazol-2-ylamino)-N-(thiazol-2-yl)benzenesulfonamide;
4-(4-((benzhydrylamino)methyl)thiazol-2-ylamino)-N-(thiazol-2-yl)benzenesulfonamide;
4-(4-((3,3-diphenylpropylamino)methyl)thiazol-2-ylamino)-N-(thiazol-2-yl)benzenesulfonamide;
4-(4-((4-tert-butylphenoxy)methyl)thiazol-2-ylamino)-N-(thiazol-2-yl)benzenesulfonamide;

4-(4-(1-phenoxyethyl)thiazol-2-ylamino)-N-(thiazol-2-yl)benzenesulfonamide;
4-(4-(1-(4-chlorophenyl)cyclopentyl)thiazol-2-ylamino)-N-(thiazol-2-yl)benzenesulfonamide;
4-(4-((4-chlorobenzylamino)methyl)thiazol-2-ylamino)-N-(thiazol-2-yl)benzenesulfonamide;
4-(4-((3,4-dimethoxyphenethylamino)methyl)thiazol-2-ylamino)-N-(thiazol-2-yl)benzenesulfonamide;
4-(4-((methyl(phenethyl)amino)methyl)thiazol-2-ylamino)-N-(thiazol-2-yl)benzenesulfonamide;
4-(4-((diethylamino)methyl)thiazol-2-ylamino)-N-(thiazol-2-yl)benzenesulfonamide;
4-(4-((4-phenylbutylamino)methyl)thiazol-2-ylamino)-N-(thiazol-2-yl)benzenesulfonamide;
4-(4-((benzhydryl(methyl)amino)methyl)thiazol-2-ylamino)-N-(thiazol-2-yl)benzenesulfonamide;
N-(thiazol-2-yl)-4-(4-(4-(trifluoromethyl)benzylamino)methyl)thiazol-2-ylamino)benzenesulfonamide;
4-(4-((4-nitrobenzylamino)methyl)thiazol-2-ylamino)-N-(thiazol-2-yl)benzenesulfonamide;
4-(4-((4-(dimethylamino)benzylamino)methyl)thiazol-2-ylamino)-N-(thiazol-2-yl)benzenesulfonamide;
4-(4-((cycloheptylamino)methyl)thiazol-2-ylamino)-N-(thiazol-2-yl)benzenesulfonamide;
4-(4-((methyl(2-(pyridin-4-yl)ethyl)amino)methyl)thiazol-2-ylamino)-N-(thiazol-2-yl)benzenesulfonamide;
4-(4-((2,4-dimethoxybenzylamino)methyl)thiazol-2-ylamino)-N-(thiazol-2-yl)benzenesulfonamide;
methyl 4-methyl-2-(4-(N-thiazol-2-ylsulfamoyl)phenylamino)thiazole-5-carboxylate;
4-(4-methylthiazol-2-ylamino)-N-(thiazol-2-yl)benzenesulfonamide;
4-(4-(2,4-difluorobenzyl)thiazol-2-ylamino)-N-(thiazol-2-yl)benzenesulfonamide;
4-(4,5-dimethylthiazol-2-ylamino)-N-(thiazol-2-yl)benzenesulfonamide;
4-(4-(cyclohexylmethoxy)pyrimidin-2-ylamino)-N-(thiazol-2-yl)benzenesulfonamide;
4-(4-((4-fluorophenylthio)methyl)thiazol-2-ylamino)-N-(thiazol-2-yl)benzenesulfonamide;
N-(thiazol-2-yl)-4-(4-(trifluoromethyl)thiazol-2-ylamino)benzenesulfonamide;
N-(thiazol-2-yl)-4-(4-(4-(trifluoromethyl)phenyl)thiazol-2-ylamino)benzenesulfonamide;
4-(4-methoxypyrimidin-2-ylamino)-N-(thiazol-2-yl)benzenesulfonamide;
4-(4-methoxypyrimidin-2-ylamino)-N-(5-methylisoxazol-3-yl)benzenesulfonamide;
N-(5-methylisoxazol-3-yl)-4-(4-(4-(trifluoromethyl)benzyloxy)pyrimidin-2-ylamino)benzenesulfonamide;
N-(5-methylisoxazol-3-yl)-4-(2-(4-(trifluoromethyl)benzyloxy)pyrimidin-4-ylamino)benzenesulfonamide;
4-(4-((4-fluorophenylsulfinyl)methyl)thiazol-2-ylamino)-N-(thiazol-2-yl)benzenesulfonamide;
4-(4-(2-fluoro-4-(trifluoromethyl)phenyl)thiazol-2-ylamino)-N-(thiazol-2-yl)benzenesulfonamide;
4-(4-(4-chlorobenzyl)thiazol-2-ylamino)-N-(thiazol-2-yl)benzenesulfonamide;
4-(6-benzhydrylpyrazin-2-ylamino)-N-(thiazol-2-yl)benzenesulfonamide;
4-(6-benzhydrylpyridin-2-ylamino)-N-(thiazol-2-yl)benzenesulfonamide;
4-(4-(3-(4-chlorophenoxy)propyl)thiazol-2-ylamino)-N-(thiazol-2-yl)benzenesulfonamide;
4-(4-((2,4-dichlorophenoxy)methyl)thiazol-2-ylamino)-N-(thiazol-2-yl)benzenesulfonamide;
4-(4-((4-chloro-2-methylphenoxy)methyl)thiazol-2-ylamino)-N-(thiazol-2-yl)benzenesulfonamide;
4-(4-(2-(4-chlorophenoxy)propan-2-yl)thiazol-2-ylamino)-N-(thiazol-2-yl)benzenesulfonamide;
4-(6-(3,5-difluorobenzyl)pyrazin-2-ylamino)-N-(thiazol-2-yl)benzenesulfonamide;
4-(5-chloro-1H-benzo[d]imidazol-2-ylamino)-N-(thiazol-2-yl)benzenesulfonamide;
4-(5-chloro-1-methyl-1H-benzo[d]imidazol-2-ylamino)-N-(thiazol-2-yl)benzenesulfonamide;
4-(6-chloro-1-methyl-1H-benzo[d]imidazol-2-ylamino)-N-(thiazol-2-yl)benzenesulfonamide;
4-(4-((4-tert-butylphenoxy)methyl)thiazol-2-ylamino)-2-fluoro-N-(thiazol-2-yl)benzenesulfonamide;
4-(4-(4-chlorobenzyl)thiazol-2-ylamino)-N-(pyridin-2-yl)benzenesulfonamide;
4-(4-(4-chlorophenyl)thiazol-2-ylamino)-2-fluoro-N-(thiazol-2-yl)benzenesulfonamide;
4-(5-(4-chlorophenylsulfonyl)thiazol-2-ylamino)-2-fluoro-N-(thiazol-2-yl)benzenesulfonamide;
6-(4-tert-butylthiazol-2-ylamino)-N-(thiazol-2-yl)pyridine-3-sulfonamide;
6-(4-(4-chlorobenzyl)thiazol-2-ylamino)-N-(thiazol-2-yl)pyridine-3-sulfonamide;
4-(4-(4-chlorobenzyl)thiazol-2-ylamino)-2-fluoro-N-(5-methylthiazol-2-yl)benzenesulfonamide;
4-(4-(4-chlorobenzyl)thiazol-2-ylamino)-2-fluoro-N-(4-methylthiazol-2-yl)benzenesulfonamide;
4-(1-tert-butyl-3-(4-chlorobenzyl)-1H-pyrazol-5-ylamino)-N-(pyridin-2-yl)benzenesulfonamide;
4-(1-tert-butyl-3-(4-chlorobenzyl)-1H-pyrazol-5-ylamino)-N-(1,3,4-thiadiazol-2-yl)benzenesulfonamide;
1-(3-chloro-4-fluorophenyl)-5-(4-(N-thiazol-2-ylsulfamoyl)phenylamino)-1H-pyrazole-4-carboxamide;
4-(4-tert-butylthiazol-2-ylamino)-2-cyano-N-(thiazol-2-yl)benzenesulfonamide;
4-(benzo[d]oxazol-2-ylamino)-N-(thiazol-2-yl)benzenesulfonamide;
4-(3-(4-chlorobenzyl)-1H-pyrazol-5-ylamino)-2-fluoro-N-(thiazol-2-yl)benzenesulfonamide;
5-(4-tert-butylthiazol-2-ylamino)-N-(thiazol-2-yl)pyridine-2-sulfonamide;
4-(benzo[d]thiazol-2-ylamino)-N-(thiazol-2-yl)benzenesulfonamide;
4-(5-(4-chlorobenzyl)-1,3,4-oxadiazol-2-ylamino)-N-(thiazol-2-yl)benzenesulfonamide;
4-(3-(4-chlorobenzyl)-4-cyano-1-methyl-1H-pyrazol-5-ylamino)-N-(thiazol-2-yl)benzenesulfonamide;
4-(5-(4-chlorobenzyl)-1,3,4-thiadiazol-2-ylamino)-N-(thiazol-2-yl)benzenesulfonamide;
3-(4-chlorobenzyl)-1-methyl-5-(4-(N-thiazol-2-ylsulfamoyl)phenylamino)-1H-pyrazole-4-carboxamide;
4-(1,3-dimethyl-4-phenyl-1H-pyrazol-5-ylamino)-N-(thiazol-2-yl)benzenesulfonamide;
4-(1-tert-butyl-3-methyl-4-phenyl-1H-pyrazol-5-ylamino)-N-(thiazol-2-yl)benzenesulfonamide;
4-(3-methyl-4-phenyl-1H-pyrazol-5-ylamino)-N-(thiazol-2-yl)benzenesulfonamide;
4-(1-methyl-3-neopentyl-1H-pyrazol-5-ylamino)-N-(thiazol-2-yl)benzenesulfonamide;
4-(3-(4-methoxybenzyl)-1-methyl-1H-pyrazol-5-ylamino)-N-(thiazol-2-yl)benzenesulfonamide;
4-(3-(2-methoxybenzyl)-1-methyl-1H-pyrazol-5-ylamino)-N-(thiazol-2-yl)benzenesulfonamide;
4-(1-(4-chlorobenzyl)-3-methyl-1H-pyrazol-5-ylamino)-N-(thiazol-2-yl)benzenesulfonamide;

4-(3-(1-(4-chlorophenyl)cyclopropyl)-1-methyl-1H-pyrazol-5-ylamino)-N-(thiazol-2-yl)benzenesulfonamide;
2-fluoro-N-(thiazol-2-yl)-4(1-(2,2,2-trifluoro ethyl)-1H-pyrazol-4-ylamino)benzenesulfonamide;
4-(3-methyl-1-(pyridin-4-ylmethyl)-1H-pyrazol-5-ylamino)-N-(thiazol-2-yl)benzenesulfonamide;
4-(1-(cyclohexylmethyl)-3-methyl-1H-pyrazol-5-ylamino)-N-(thiazol-2-yl)benzenesulfonamide;
4-(3-(cyclohexylmethyl)-1-methyl-1H-pyrazol-5-ylamino)-2-fluoro-N-(thiazol-2-yl)benzenesulfonamide;
4-(3-(cyclohexylmethyl)-1-methyl-1H-pyrazol-5-ylamino)-2-hydroxy-N-(thiazol-2-yl)benzenesulfonamide;
4-(7-oxo-5-phenyl-4,5,6,7-tetrahydrobenzo[d]thiazol-2-ylamino)-N-(thiazol-2-yl)benzenesulfonamide;
4-(5,5-dimethyl-7-oxo-4,5,6,7-tetrahydrobenzo[d]thiazol-2-ylamino)-N-(thiazol-2-yl)benzenesulfonamide;
4-(1-(4-chlorophenyl)-3-methyl-1H-pyrazol-5-ylamino)-N-(thiazol-2-yl)benzenesulfonamide;
4-(1-methyl-3-(4-(trifluoromethyl)benzyl)-1H-pyrazol-5-ylamino)-N-(thiazol-2-yl)benzenesulfonamide;
4-(3-(2,4-difluorobenzyl)-1-methyl-1H-pyrazol-5-ylamino)-N-(thiazol-2-yl)benzenesulfonamide;
4-(1-(4-chlorophenyl)-3-methyl-1H-pyrazol-5-ylamino)-2-fluoro-N-(thiazol-2-yl)benzenesulfonamide;
4-(3-(4-chlorobenzyl)-1-methyl-1H-pyrazol-5-ylamino)-2-fluoro-N-(thiazol-2-yl)benzenesulfonamide;
4-(3-(1-(4-chlorophenyl)cyclopropyl)-1-methyl-1H-pyrazol-5-ylamino)-3-fluoro-N-(thiazol-2-yl)benzenesulfonamide;
4-(3-(4-chlorobenzyl)-1-methyl-1H-pyrazol-5-ylamino)-3-fluoro-N-(thiazol-2-yl)benzenesulfonamide;
4-(3-cyclopropyl-1-phenyl-1H-pyrazol-5-ylamino)-N-(thiazol-2-yl)benzenesulfonamide;
2-fluoro-4-(3-isopropyl-1-phenyl-1H-pyrazol-5-ylamino)-N-(thiazol-2-yl)benzenesulfonamide;
2-fluoro-4-(3-methyl-1-o-tolyl-1H-pyrazol-5-ylamino)-N-(thiazol-2-yl)benzenesulfonamide;
2-fluoro-4-(3-methyl-1-p-tolyl-1H-pyrazol-5-ylamino)-N-(thiazol-2-yl)benzenesulfonamide;
2-fluoro-4-(1-methyl-4-phenyl-1H-pyrazol-5-ylamino)-N-(thiazol-2-yl)benzenesulfonamide;
4-(1-(2-chlorophenyl)-3-methyl-1H-pyrazol-5-ylamino)-2-fluoro-N-(thiazol-2-yl)benzenesulfonamide;
2-fluoro-N-(thiazol-2-yl)-4(1-(4-(trifluoromethyl)benzyl)-1H-pyrazol-4-ylamino)benzenesulfonamide;
4-(1-phenyl-1H-pyrazol-5-ylamino)-N-(thiazol-2-yl)benzenesulfonamide;
4-(1-(3-chlorophenyl)-3-methyl-1H-pyrazol-5-ylamino)-2-fluoro-N-(thiazol-2-yl)benzenesulfonamide;
4-(3-(4-chlorophenyl)-1-methyl-1H-pyrazol-5-ylamino)-2-fluoro-N-(thiazol-2-yl)benzenesulfonamide;
4-(1,3-diphenyl-1H-pyrazol-5-ylamino)-2-fluoro-N-(thiazol-2-yl)benzenesulfonamide;
2-(3-(4-chlorobenzyl)-5-(4-(N-thiazol-2-ylsulfamoyl)phenylamino)-1H-pyrazol-1-yl)acetamide;
4-(3-tert-butyl-1-phenyl-1H-pyrazol-5-ylamino)-2-fluoro-N-(thiazol-2-yl)benzenesulfonamide;
4-(1-tert-butyl-3-(4-methylbenzyl)-1H-pyrazol-5-ylamino)-2-fluoro-N-(thiazol-2-yl)benzenesulfonamide;
4-(1-tert-butyl-3-(4-methylbenzyl)-1H-pyrazol-5-ylamino)-3-fluoro-N-(thiazol-2-yl)benzenesulfonamide;
2-fluoro-4-(1-methyl-3-(4-methylbenzyl)-1H-pyrazol-5-ylamino)-N-(thiazol-2-yl)benzenesulfonamide;
3-fluoro-4-(1-methyl-3-(4-methylbenzyl)-1H-pyrazol-5-ylamino)-N-(thiazol-2-yl)benzenesulfonamide;
2-chloro-4-(3-methyl-1-phenyl-1H-pyrazol-5-ylamino)-N-(thiazol-2-yl)benzenesulfonamide;
N-(5-chlorothiazol-2-yl)-2-fluoro-4-(3-methyl-1-phenyl-1H-pyrazol-5-ylamino)benzenesulfonamide;
N-(5-chlorothiazol-2-yl)-4-(3-methyl-1-phenyl-1H-pyrazol-5-ylamino)benzenesulfonamide;
4-(1-tert-butyl-3-(3-chlorobenzyl)-1H-pyrazol-5-ylamino)-2-fluoro-N-(thiazol-2-yl)benzenesulfonamide;
2-fluoro-4-(3-(4-methylbenzyl)-1H-pyrazol-5-ylamino)-N-(thiazol-2-yl)benzenesulfonamide;
4-(1-tert-butyl-3-(4-chloro-3-fluorobenzyl)-1H-pyrazol-5-ylamino)-2-fluoro-N-(thiazol-2-yl)benzenesulfonamide;
3-fluoro-4-(3-(4-methylbenzyl)-1H-pyrazol-5-ylamino)-N-(thiazol-2-yl)benzenesulfonamide;
2-fluoro-4-(1-phenyl-1H-pyrazol-5-ylamino)-N-(thiazol-2-yl)benzenesulfonamide;
4-(1-cyclopentyl-3-methyl-1H-pyrazol-5-ylamino)-2-fluoro-N-(thiazol-2-yl)benzenesulfonamide;
2-fluoro-4-(3-methyl-1-(4-(trifluoromethyl)phenyl)-1H-pyrazol-5-ylamino)-N-(thiazol-2-yl)benzenesulfonamide;
4-(1-benzhydryl-1H-pyrazol-4-ylamino)-2-fluoro-N-(thiazol-2-yl)benzenesulfonamide;
2-fluoro-4-(1-(2-fluorophenyl)-3-methyl-1H-pyrazol-5-ylamino)-N-(thiazol-2-yl)benzenesulfonamide;
2-fluoro-4-(2-phenyl-2,4,5,6-tetrahydrocyclopenta[c]pyrazol-3-ylamino-)-N-(thiazol-2-yl)benzenesulfonamide;
4-(1-(1-cyclopropylethyl)-3-methyl-1H-pyrazol-5-ylamino)-2-fluoro-N-(thiazol-2-yl)benzenesulfonamide;
2-fluoro-4-(3-methyl-1-m-tolyl-1H-pyrazol-5-ylamino)-N-(thiazol-2-yl)benzenesulfonamide;
2-fluoro-4-(1-(3-fluorophenyl)-3-methyl-1H-pyrazol-5-ylamino)-N-(thiazol-2-yl)benzenesulfonamide;
2-fluoro-4-(1-(4-fluorophenyl)-3-methyl-1H-pyrazol-5-ylamino)-N-(thiazol-2-yl)benzenesulfonamide;
2-fluoro-4-(3-methyl-1-(2-(trifluoromethyl)phenyl)-1H-pyrazol-5-ylamino)-N-(thiazol-2-yl)benzenesulfonamide;
4-(4-cyano-1-phenyl-1H-pyrazol-3-ylamino)-2-fluoro-N-(thiazol-2-yl)benzenesulfonamide;
2-fluoro-4-(3-methyl-1-(3-(trifluoromethyl)phenyl)-1H-pyrazol-5-ylamino)-N-(thiazol-2-yl)benzenesulfonamide;
4-(1-(2-chloro-4-fluorophenyl)-3-methyl-1H-pyrazol-5-ylamino)-2-fluoro-N-(thiazol-2-yl)benzenesulfonamide;
2-fluoro-N-(thiazol-2-yl)-4(1-(4-(trifluoromethyl)benzyl)-1H-pyrazol-3-ylamino)benzenesulfonamide;
4-(1-(4-chlorobenzyl)-1H-pyrazol-3-ylamino)-3-fluoro-N-(thiazol-2-yl)benzenesulfonamide;
3-fluoro-N-(thiazol-2-yl)-4(1-(4-(trifluoromethyl)benzyl)-1H-pyrazol-3-ylamino)benzenesulfonamide;
2-fluoro-4-(1-(5-fluoro-2-methylphenyl)-3-methyl-1H-pyrazol-5-ylamino)-N-(thiazol-2-yl)benzenesulfonamide;
4-(1-(4-fluoro-2-(trifluoromethyl)phenyl)-3-methyl-1H-pyrazol-5-ylamino)-N-(thiazol-2-yl)benzenesulfonamide;
2-fluoro-4-(1-(2-methoxyphenyl)-3-methyl-1H-pyrazol-5-ylamino)-N-(thiazol-2-yl)benzenesulfonamide;

4-(1-(2,6-dichlorophenyl)-3-methyl-1H-pyrazol-5-ylamino)-2-fluoro-N-(thiazol-2-yl)benzenesulfonamide;
4-(1-(2,6-difluorophenyl)-3-methyl-1H-pyrazol-5-ylamino)-2-fluoro-N-(thiazol-2-yl)benzenesulfonamide;
4-(1-(2,6-dimethylphenyl)-3-methyl-1H-pyrazol-5-ylamino)-2-fluoro-N-(thiazol-2-yl)benzenesulfonamide;
4-(1-tert-butyl-3-methyl-1H-pyrazol-5-ylamino)-2-fluoro-N-(thiazol-2-yl)benzenesulfonamide;
4-(3-tert-butyl-1-methyl-1H-pyrazol-5-ylamino)-2-fluoro-N-(thiazol-2-yl)benzenesulfonamide;
4-(1-tert-butyl-3-(3-chlorobenzyl)-1H-pyrazol-5-ylamino)-N-(thiazol-2-yl)benzenesulfonamide;
4-(1-tert-butyl-3-(3-chlorobenzyl)-1H-pyrazol-5-ylamino)-3-fluoro-N-(thiazol-2-yl)benzenesulfonamide;
4-(3-(4-chloro-3-fluorobenzyl)-1-methyl-1H-pyrazol-5-ylamino)-N-(thiazol-2-yl)benzenesulfonamide;
4-(1-(4-chloro-2-fluorobenzyl)-1H-pyrazol-3-ylamino)-2-fluoro-N-(thiazol-2-yl)benzenesulfonamide;
4-(1-(4-chloro-2-fluorobenzyl)-1H-pyrazol-3-ylamino)-3-fluoro-N-(thiazol-2-yl)benzenesulfonamide;
4-(1-(4-chlorobenzyl)-1H-1,2,4-triazol-3-ylamino)-3-fluoro-N-(thiazol-2-yl)benzenesulfonamide;
3-fluoro-N-(thiazol-2-yl)-4-(1-(3-(trifluoromethyl)benzyl)-1H-1,2,4-triazol-3-ylamino)benzenesulfonamide;
4-(1-(3-chlorobenzyl)-1H-1,2,4-triazol-3-ylamino)-3-fluoro-N-(thiazol-2-yl)benzenesulfonamide;
2-fluoro-4-(3-methyl-1-(1-methylpiperidin-4-yl)-1H-pyrazol-5-ylamino)-N-(thiazol-2-yl)benzenesulfonamide;
3-fluoro-4-(1-(2-fluorophenyl)-3-methyl-1H-pyrazol-5-ylamino)-N-(thiazol-2-yl)benzenesulfonamide;
2-fluoro-4-(1-(2-fluorophenyl)-3-(2,2,2-trifluoroethyl)-1H-pyrazol-5-ylamino)-N-(thiazol-2-yl)benzenesulfonamide;
3-chloro-4-(1-(4-chlorobenzyl)-1H-pyrazol-3-ylamino)-N-(thiazol-2-yl)benzenesulfonamide;
4-(1-(4-chlorobenzyl)-1H-pyrazol-3-ylamino)-2,5-difluoro-N-(thiazol-2-yl)benzenesulfonamide;
4-(1-(2-chloro-4-fluorobenzyl)-1H-1,2,4-triazol-3-ylamino)-3-fluoro-N-(thiazol-2-yl)benzenesulfonamide;
4-(1-(2-chlorobenzyl)-1H-1,2,4-triazol-3-ylamino)-3-fluoro-N-(thiazol-2-yl)benzenesulfonamide;
4-(3-(4-chloro-3-fluorobenzyl)-1-methyl-1H-pyrazol-5-ylamino)-3-fluoro-N-(thiazol-2-yl)benzenesulfonamide;
4-(3-(4-chloro-3-fluorobenzyl)-1-methyl-1H-pyrazol-5-ylamino)-2-fluoro-N-(thiazol-2-yl)benzenesulfonamide;
4-(1-benzyl-1H-pyrazol-3-ylamino)-2-fluoro-N-(thiazol-2-yl)benzenesulfonamide;
4-(1-(4-chlorobenzyl)-1H-pyrazol-3-ylamino)-N-(thiazol-2-yl)-2-(trifluoromethyl)benzenesulfonamide;
2-(5-(3-fluoro-4-(N-thiazol-2-ylsulfamoyl)phenylamino)-1-phenyl-1H-pyrazol-3-yl)-N,N-dimethylethanamide;
4-(3-tert-butyl-1-(2-methoxyphenyl)-1H-pyrazol-5-ylamino)-2-fluoro-N-(thiazol-2-yl)benzenesulfonamide;
3-fluoro-4-(1-(2-methoxyphenyl)-3-methyl-1H-pyrazol-5-ylamino)-N-(thiazol-2-yl)benzenesulfonamide;
N,N-diethyl-2-(5-(3-fluoro-4-(N-thiazol-2-ylsulfamoyl)phenylamino)-1-phenyl-1H-pyrazol-3-yl)ethanamide;
2-fluoro-4-(1-(4-fluorobenzyl)-1H-pyrazol-3-ylamino)-N-(thiazol-2-yl)benzenesulfonamide;
4-(3-(3-chlorobenzyl)-1-methyl-1H-pyrazol-5-ylamino)-N-(thiazol-2-yl)benzenesulfonamide;
4-(3-(3-chlorobenzyl)-1-methyl-1H-pyrazol-5-ylamino)-3-fluoro-N-(thiazol-2-yl)benzenesulfonamide;
2-fluoro-4-(1-(3-methoxyphenyl)-3-methyl-1H-pyrazol-5-ylamino)-N-(thiazol-2-yl)benzenesulfonamide;
1-(4-chlorobenzyl)-3-(3-fluoro-4-(N-thiazol-2-ylsulfamoyl)phenylamino)-1H-pyrazole-4-carboxamide;
4-(3-(4-chloro-2-methoxyphenyl)-1-methyl-1H-pyrazol-5-ylamino)-2-fluoro-N-(thiazol-2-yl)benzenesulfonamide;
2-fluoro-4-(3-(2-methoxyphenyl)-1-methyl-1H-pyrazol-5-ylamino)-N-(thiazol-2-yl)benzenesulfonamide;
2-fluoro-4-(1-(4-methoxybenzyl)-1H-pyrazol-3-ylamino)-N-(thiazol-2-yl)benzenesulfonamide;
4-(1-(4-chlorobenzyl)-3,5-dimethyl-1H-pyrazol-4-ylamino)-2-fluoro-N-(thiazol-2-yl)benzenesulfonamide;
3-fluoro-4-(1-(4-fluorobenzyl)-1H-pyrazol-3-ylamino)-N-(thiazol-2-yl)benzenesulfonamide;
6-(1-(4-chlorobenzyl)-1H-pyrazol-3-ylamino)-N-(thiazol-2-yl)pyridine-3-sulfonamide;
6-(1-(4-chlorobenzyl)-1H-pyrazol-4-ylamino)-N-(thiazol-2-yl)pyridine-3-sulfonamide;
4-(1-(4-chloro-3-(trifluoromethyl)benzyl)-1H-pyrazol-4-ylamino)-2-fluoro-N-(thiazol-2-yl)benzenesulfonamide;
2-fluoro-4-(1-(2-methoxy-5-(trifluoromethoxy)benzyl)-1H-pyrazol-4-ylamino)-N-(thiazol-2-yl)benzenesulfonamide;
5-(1-(4-chlorobenzyl)-1H-pyrazol-4-ylamino)-N-(thiazol-2-yl)pyridine-2-sulfonamide;
4-(1-(4-chlorobenzyl)-1H-pyrazol-3-ylamino)-2-fluoro-N-(1,3,4-thiadiazol-2-yl)benzenesulfonamide;
5-(3-methyl-1-phenyl-1H-pyrazol-5-ylamino)-N-(thiazol-2-yl)pyridine-2-sulfonamide;
5-(1-(4-chlorobenzyl)-1H-pyrazol-3-ylamino)-N-(thiazol-2-yl)pyridine-2-sulfonamide;
2-fluoro-N-(3-methyl-1,2,4-thiadiazol-5-yl)-4-(3-methyl-1-phenyl-1H-pyrazol-5-ylamino)benzenesulfonamide;
2-fluoro-N-(5-methyl-1,3,4-oxadiazol-2-yl)-4-(3-methyl-1-phenyl-1H-pyrazol-5-ylamino)benzenesulfonamide;
2-fluoro-4-(3-methyl-1-phenyl-1H-pyrazol-5-ylamino)-N-(1,3,4-thiadiazol-2-yl)benzenesulfonamide;
2-fluoro-4-(3-methyl-1-phenyl-1H-pyrazol-5-ylamino)-N-(5-methylthiazol-2-yl)benzenesulfonamide;
2-fluoro-4-(3-methyl-1-phenyl-1H-pyrazol-5-ylamino)-N-(1,2,4-thiadiazol-5-yl)benzenesulfonamide;
2-fluoro-4-(3-methyl-1-phenyl-1H-pyrazol-5-ylamino)-N-(5-phenyl-1,3,4-thiadiazol-2-yl)benzenesulfonamide;
4-(1-(4-chlorobenzyl)-1H-pyrazol-3-ylamino)-2-fluoro-N-(5-(trifluoromethyl)-1,3,4-thiadiazol-2-yl)benzenesulfonamide;
4-(1-(4-chlorobenzyl)-1H-pyrazol-3-ylamino)-2-fluoro-N-(1,2,4-thiadiazol-5-yl)benzenesulfonamide;
N-(5-cyanothiazol-2-yl)-2-fluoro-4-(3-methyl-1-phenyl-1H-pyrazol-5-ylamino)benzenesulfonamide;
N-(5-ethyl-1,3,4-thiadiazol-2-yl)-2-fluoro-4-(3-methyl-1-phenyl-1H-pyrazol-5-ylamino)benzenesulfonamide;
2-fluoro-N-(5-methyl-1,3,4-thiadiazol-2-yl)-4-(3-methyl-1-phenyl-1H-pyrazol-5-ylamino)benzenesulfonamide;
N-(5-(difluoromethyl)-1,3,4-thiadiazol-2-yl)-2-fluoro-4-(3-methyl-1-phenyl-1H-pyrazol-5-ylamino)benzenesulfonamide;

2-fluoro-N-(5-(methoxymethyl)-1,3,4-thiadiazol-2-yl)-4-(3-methyl-1-phenyl-1H-pyrazol-5-ylamino)benzenesulfonamide;

N-(5-cyclopropyl-1,3,4-thiadiazol-2-yl)-2-fluoro-4-(3-methyl-1-phenyl-1H-pyrazol-5-ylamino)benzenesulfonamide;

4-(1-(4-chlorobenzyl)-1H-pyrazol-3-ylamino)-2-fluoro-N-(5-methyl-1,3,4-thiadiazol-2-yl)benzenesulfonamide;

2-fluoro-N-(5-isopropyl-1,3,4-thiadiazol-2-yl)-4-(3-methyl-1-phenyl-1H-pyrazol-5-ylamino)benzenesulfonamide;

4-(1-(4-chlorobenzyl)-1H-pyrazol-3-ylamino)-N-(5-cyclopropyl-1,3,4-thiadiazol-2-yl)-2-fluorobenzenesulfonamide;

4-(1-(4-chlorobenzyl)-1H-pyrazol-3-ylamino)-2-fluoro-N-(5-(methoxymethyl)-1,3,4-thiadiazol-2-yl)benzenesulfonamide;

4-(1-(4-chlorobenzyl)-1H-pyrazol-3-ylamino)-N-(5-ethyl-1,3,4-thiadiazol-2-yl)-2-fluorobenzenesulfonamide;

4-(1-(4-chlorobenzyl)-1H-pyrazol-3-ylamino)-2-fluoro-N-(5-isopropyl-1,3,4-thiadiazol-2-yl)benzenesulfonamide;

4-(4-(4-chlorobenzyl)thiazol-2-ylamino)-N-(4-(trifluoromethyl)thiazol-2-yl)benzenesulfonamide;

4-(4-(4-chlorobenzyl)thiazol-2-ylamino)-N-(4-(trifluoromethyl)oxazol-2-yl)benzenesulfonamide;

4-(1-(4-chlorobenzyl)-1H-pyrazol-3-ylamino)-2-fluoro-N-(6-methylpyridin-2-yl)benzenesulfonamide;

4-(1-(4-chlorobenzyl)-1H-pyrazol-3-ylamino)-2-fluoro-N-(pyridazin-3-yl)benzenesulfonamide;

4-(1-(4-chlorobenzyl)-1H-pyrazol-3-ylamino)-2-fluoro-N-(5-methyl-1,3,4-oxadiazol-2-yl)benzenesulfonamide;

4-(1-(4-chlorobenzyl)-1H-pyrazol-3-ylamino)-2-fluoro-N-(pyrimidin-4-yl)benzenesulfonamide;

2-chloro-4-(1-(4-chlorobenzyl)-1H-pyrazol-3-ylamino)-N-(thiazol-2-yl)benzenesulfonamide;

4-(1-(4-chlorobenzyl)-1H-pyrazol-3-ylamino)-2-cyano-N-(thiazol-2-yl)benzenesulfonamide;

4-(1-(4-chlorobenzyl)-1H-pyrazol-3-ylamino)-N-(1,3,4-thiadiazol-2-yl)-2-(trifluoromethyl)benzenesulfonamide;

4-(1-(4-chlorobenzyl)-1H-pyrazol-3-ylamino)-N-(thiazol-2-yl)-2-(trifluoromethoxy)benzenesulfonamide;

2,5-difluoro-4-(3-methyl-1-phenyl-1H-pyrazol-5-ylamino)-N-(thiazol-2-yl)benzenesulfonamide;

2-methyl-4-(3-methyl-1-phenyl-1H-pyrazol-5-ylamino)-N-(thiazol-2-yl)benzenesulfonamide;

4-(1-(4-chlorobenzyl)-1H-pyrazol-3-ylamino)-2-fluoro-5-methyl-N-(thiazol-2-yl)benzenesulfonamide;

4-(3-methyl-1-phenyl-1H-pyrazol-5-ylamino)-N-(thiazol-2-yl)-2-(trifluoromethoxy)benzenesulfonamide;

4-(1-(4-chlorobenzyl)-1H-pyrazol-3-ylamino)-2-methyl-N-(thiazol-2-yl)benzenesulfonamide;

4-(3-methyl-1-phenyl-1H-pyrazol-5-ylamino)-N-(thiazol-2-yl)-2-(trifluoromethyl)benzenesulfonamide;

3-cyano-4-(5-hydroxy-6-phenyl-1,2,4-triazin-3-ylamino)-N-(1,2,4-thiadiazol-5-yl)benzenesulfonamide;

N-(thiazol-2-yl)-1-(4-(trifluoromethoxy)benzyl)-1H-indazole-5-sulfonamide;

N-(thiazol-2-yl)-2-(4-(trifluoromethoxy)benzyl)-2H-indazole-5-sulfonamide;

1-(2-(2,4-dimethoxyphenyl)-2-oxoethyl)-N-(thiazol-2-yl)-1H-indazole-5-sulfonamide;

2-(2-(2,4-dimethoxyphenyl)-2-oxoethyl)-N-(thiazol-2-yl)-2H-indazole-5-sulfonamide;

1-(4-phenylbutyl)-N-(thiazol-2-yl)-1H-indazole-5-sulfonamide;

2-(4-phenylbutyl)-N-(thiazol-2-yl)-2H-indazole-5-sulfonamide; and 1-(2-(4-fluorophenyl)-2-oxoethyl)-N-(thiazol-2-yl)-1H-indazole-5-sulfonamide;

or a pharmaceutically acceptable salt thereof.

33. A pharmaceutical formulation comprising: a compound of claim 1 and a pharmaceutically acceptable excipient.

34. A pharmaceutical formulation comprising: a compound selected from the group consisting of 4-(4-methylphthalazin-1-ylamino)-N-(thiazol-2-yl)benzenesulfonamide; 4-(4-(4-chlorophenyl)phthalazin-1-ylamino)-N-(thiazol-2-yl)benzenesulfonamide; N-(thiazol-2-yl)-4-(4-p-tolylphthalazin-1-ylamino)benzenesulfonamide; or 4-(4-phenylphthalazin-1-ylamino)-N-(thiazol-2-yl) benzenesulfonamide and a pharmaceutically acceptable excipient.

35. A pharmaceutical formulation comprising: a compound of claim 32 and a pharmaceutically acceptable excipient.

36. A pharmaceutical formulation comprising: a compound of claim 25 and a pharmaceutically acceptable excipient.

37. A method of modulating activity of a sodium channel in a subject, said method comprising:
administering to said subject in need thereof an effective amount of a compound of claim 1 to modulate the activity of a sodium channel.

38. A method of modulating activity of a sodium channel in a subject, said method comprising:
administering to said subject in need thereof an effective amount of a pharmaceutical formulation of claim 34 to modulate the activity of a sodium channel.

39. A method of ameliorating or alleviating a condition in a subject, wherein said condition is a member selected from pain, irritable bowel syndrome, Crohn's disease, epilepsy, seizures, multiple sclerosis, bipolar depression and tachyarrhythmias, said method comprising:
administering to said subject in need thereof an effective amount of a compound of claim 1 to ameliorate or alleviate said condition.

40. A method of ameliorating or alleviating a condition in a subject, wherein said condition is a member selected from pain, irritable bowel syndrome, Crohn's disease, epilepsy, seizures, multiple sclerosis, bipolar depression and tachyarrhythmias, said method comprising:
administering to said subject in need thereof an effective amount of a pharmaceutical formulation of claim 34 to ameliorate or alleviate said condition.

41. The method according to claim 39, wherein said condition is pain, and said pain is a member selected from acute pain, chronic pain, visceral pain, inflammatory pain and neuropathic pain.

42. A method of modulating activity of a sodium channel in a subject, said method comprising:
administering to said subject in need thereof an effective amount of a compound of claim 32 to modulate the activity of a sodium channel.

43. A method of ameliorating or alleviating a condition in a subject, wherein said condition is a member selected from pain, irritable bowel syndrome, Crohn's disease, epilepsy, seizures, multiple sclerosis, bipolar depression and tachyarrhythmias, said method comprising:

administering to said subject in need thereof an effective amount of a compound of claim 32 to ameliorate or alleviate said condition.

44. The method according to claim 43, wherein said condition is pain, and said pain is a member selected from acute pain, chronic pain, visceral pain, inflammatory pain and neuropathic pain.

45. A method of modulating activity of a sodium channel in a subject, said method comprising:

administering to said subject in need thereof an effective amount of a compound of claim 25 to modulate the activity of a sodium channel.

46. A method of ameliorating or alleviating a condition in a subject, wherein said condition is a member selected from pain, irritable bowel syndrome, Crohn's disease, epilepsy, seizures, multiple sclerosis, bipolar depression and tachyarrhythmias, said method comprising:

administering to said subject in need thereof an effective amount of a compound of claim 25 to ameliorate or alleviate said condition.

47. The method according to claim 46, wherein said condition is pain, and said pain is a member selected from acute pain, chronic pain, visceral pain, inflammatory pain and neuropathic pain.

* * * * *